US007108968B2

(12) United States Patent
Gingeras et al.

(10) Patent No.: US 7,108,968 B2
(45) **Date of Patent: *Sep. 19, 2006**

(54) MYCOBACTERIAL RPOB SEQUENCES

(75) Inventors: Thomas R. Gingeras, Santa Clara, CA (US); Jorg Drenkow, Hollister, CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/285,306

(22) Filed: Apr. 2, 1999

(65) Prior Publication Data

US 2002/0187467 A1 Dec. 12, 2002

Related U.S. Application Data

(60) Provisional application No. 60/080,616, filed on Apr. 3, 1998.

(51) Int. Cl.
*C12Q 1/68* (2006.01)
*C07H 21/04* (2006.01)

(52) U.S. Cl. ........................ 435/6; 536/23.1; 536/24.3; 536/24.31; 536/24.32; 536/24.33

(58) Field of Classification Search .................... 435/6, 435/91.1, 91.2, 183, 283.1, 285.1; 436/164, 436/172; 536/22.1, 23.1, 24.3, 24.31, 24.32, 536/24.33

See application file for complete search history.

(56) References Cited

U.S. PATENT DOCUMENTS

| | | | | |
|---|---|---|---|---|
| 3,817,837 | A | 6/1974 | Rubenstein et al. | 195/103.5 R |
| 3,850,752 | A | 11/1974 | Schuurs et al. | 95/103.5 R |
| 3,939,350 | A | 2/1976 | Kronic et al. | 250/365 |
| 3,996,345 | A | 12/1976 | Ullman et al. | 424/12 |
| 4,275,149 | A | 6/1981 | Litman et al. | 435/7 |
| 4,277,437 | A | 7/1981 | Maggio | 422/61 |
| 4,366,241 | A | 12/1982 | Tom et al. | 435/7 |
| 5,143,854 | A | 9/1992 | Pirrung et al. | 436/518 |
| 5,384,261 | A | 1/1995 | Winkler et al. | 436/518 |
| 5,424,186 | A | 6/1995 | Fodor et al. | 435/6 |
| 5,429,807 | A | 7/1995 | Matson et al. | 422/131 |
| 5,436,327 | A | 7/1995 | Southern et al. | 536/25.34 |
| 5,445,934 | A | 8/1995 | Fodor et al. | 435/6 |
| 5,545,531 | A | 8/1996 | Rava et al. | 435/6 |
| 5,547,839 | A | 8/1996 | Dower et al. | |
| 5,700,637 | A | 12/1997 | Southern | 435/6 |
| 5,795,716 | A | 8/1998 | Chee et al. | 435/6 |
| 5,800,992 | A | 9/1998 | Fodor et al. | 435/6 |
| 5,837,832 | A | 11/1998 | Chee et al. | 536/22.1 |
| 5,861,242 | A | 1/1999 | Chee et al. | 435/5 |

FOREIGN PATENT DOCUMENTS

| | | |
|---|---|---|
| WO | 89/10977 | 11/1989 |
| WO | 90/15070 | 12/1990 |
| WO | 92/10092 | 6/1992 |
| WO | 94/10128 | 5/1994 |
| WO | 94/12305 | 6/1994 |
| WO | WO-9533851 A2 * | 12/1995 |

OTHER PUBLICATIONS

Telenti et al Detection of rifampicin-resistance mutaitons in *Mycobacterium tuberculosis*. Lancet, vol. 341 pp. 647-650.*

Miller et al The rpoB gene of *Mycobacterium tuberculosis*, Antimicrob. Agents Chemother. ovl. 38 (4) pp. 805-811 1994.*

Gingeras et al Simultaneous genotyping and species identification using hybridization pattern recognition analysis of generic mycobacterium DNA arrays, vol. 8, pp. 435-448 1998.*

Barringer, et al. "Blunt-end and single-strand ligations by *Escherichia coli* ligase: influence on an in vitro amplication scheme", *Gene*, vol. 89 (1990), pp. 117-122.

Beattie, et al., "Genosensor Technology", *Clinical Chemistry*, vol. 39, No. 4 (1993), pp. 719-722.

Bloch, et al., "Nationwide Survey of Drug Resistant Tuberculosis in the United States", *JAMA*, vol. 271, No. 9 (Mar. 2, 1994), pp. 665-671.

Chetverin, et al., "Oligonucleotide Arrays: New Concepts and Possibilities", *Bio/Technology*, vol. 12 (Nov. 1994), pp. 1093-1099.

Elder, "Analysis of DNA Oligonucleotide Hybridization Data by Maximum Entropy", Proceedings of the Twelfth International Workshop on Maximum Entropy and Bayesian Methods, Kluwer Academic Publishers, 1992.

Fodor, et al., "Light-Directed Spatially Addressable Parallel Chemical Synthesis", *Science*, vol. 251(1991), pp. 767-773.

Fodor, et al., "Multiplexed Biochemical Assays with Biological Chips", *Nature*, vol. 364 (Aug. 5, 1993), pp. 555-556.

Felmlee, et al., "Genotypic Detection of *Mycobacterium tuberculosis* Rifampin Resistance: Comparison of Single-Strand Conformation Polymorphism and Dideoxy Fingerprinting", *Jrnl. Clin. Microbiology*, vol. 33, No. 6 (1995), pp. 1617-1623.

Gingeras, et al., Simultaneous Genotyping and Species Identification Using Hybridization Pattern Recognition Analysis of Generic *Mycobacterium* DNA Arrays, *Genome Research*, vol. 8 (1998), pp. 435-448.

Guatelli, et al. "Isothermal, *in vitro* amplification of nucleic acids by a multienzyme reaction modeled after retroviral replication", *Porch. Natl. Acad. Sci. USA*, vol. 87 (Mar. 1990), pp. 1874-1878.

Hughes, et al., "Identification of Mycobacteria from Animals by Restriction Enzyme Analysis and Direct DNA Cycle Sequencing of Polymerase Chain Reaction-Amplified 16S rRNA Gene Sequences", *Jrnl. Clin. Microbiology* (Dec. 1993), pp. 3216-3222.

(Continued)

*Primary Examiner*—Kenneth R. Horlick
*Assistant Examiner*—Cynthia Wilder
(74) *Attorney, Agent, or Firm*—Cooley Godward LLP

(57) ABSTRACT

This invention provides polynucleotide probes, sequences and methods for speciating and phenotyping organisms, for example, using probes based on the *Mycobacterium tuberculosis* rpoB gene. The groups or species to which an organism belongs may be determined by comparing hybridization patterns of target nucleic acid from the organism to hybridization patterns in a database.

10 Claims, 1 Drawing Sheet

OTHER PUBLICATIONS

Hoffner, "Pulmonary Infections Caused by Less Frequently Encountered Slow-Growing Environmental Mycobacteria", *Euro. Jrnl. Clin. Microbial. Infect. Dis.*, vol. 13, No. 11 (Nov. 1994), pp. 937-941.

Hunt, et al., "Detection of a Genetic Locus Encoding Resistance to Rifampin in Mycobacterial Cultures and in Clinical Specimens", *Diagn. Microbiol. Infect. Dis.*, vol. 18 (1994), pp. 219-227.

Jonas, et al., "Detection and Identification of *Mycobacterium tuberculosis* Directly from Sputum Sediments by Amplification of rRNA", *Jrnl. Clin. Microbiology* (Sep. 1993), pp. 2410-2416.

Kanal, "Patterns in Pattern Recognition", *IEEE Trans. Info. Theory* (1974), pp. 697-722.

Kapur, et al., "Rapid *Mycobacterium* Species Assignment and Unambiguous Identification of Mutations Associated with Antimicrobial Resistance in *Mycobacterium tuberculosis* by Automated DNA Sequencing", *Arch. Pathol. Lab. Med.* (Feb. 1995), vol. 119, pp. 131-138.

Kox, et al., "PCR Assay Based on DNA Coding for 16S rRNA for Detection and Identification of Mycobacteria in Clinical Samples", *Jrnl. Clin. Microbiol.* (1995), pp. 3225-3233.

Kwoh, et al., "Transcription-based amplification system and detection of amplified human immunodeficiency virus type 1 with a bead-based sandwich hybridization format", *Proc. Natl. Acad. Sci. USA*, vol. 86 (Feb. 1989), pp. 1173-1177.

Landegren, et al., "A Ligase-Mediated Gene Detection Technique", *Science*, vol. 241 (Aug. 26, 1988), pp. 1077-1080.

Lipshutz, et al., "Using Olignucleotide Probe Arrays to Access Genetic Diversity", *Biotechniques*, vol. 19, No. 3 (1995), pp. 442-447.

Lipshutz, *Clin. Chem.*, vol. 40, No. 6 (1994 Abstract), p. 1173.

Pease, et al. "Light-Generated oligonucleotide arrays for rapid DNA sequence analysis", *Proc. Natl. Acad. Sci. USA*, vol. 91 (May 1994), pp. 5022-5026.

Plikaytis, et al., "Differentiation of Slowly Growing *Mycobacterium* Species, Including *Mycobacterium tuberculosis* by Gene Amplication and Restriction Fragment Length Polymorphism Analysis", *Jrnl. Clin. Microbiology* (Jul. 1992), pp. 1815-1822.

Salazar, et al., "Nucleic acid scanning-by-hybridization of enterohemorrhagic *Escherichia coli* isolates using oligodeoxynucleotide arrays", *Nucleic Acids Res.*, vol. 24, No. 24 (1996), pp. 5056-5057.

Schrim, et al., "Comparison of Amplicor, In-House PCR, and Conventional Culture for Detection of *Mycobacterium tuberculosis* in Clinical Samples", *Jrnl. Clin. Microbiology (1995), pp. 3221-3224.*

Sewell, et al., "Comparison of the Septi-Chek AFB and BACTEC Systems and Conventional Culture for Recovery of Mycobacteria", *Jrnl. Clin. Microbiology* (Oct. 1993), pp. 2689-2691.

Schafer, et al., "*Mycobacterium xenopi, Mycobacterium fortuitum, Mycobactgerium kansasii*, and Other Nontuberculous Mycobacteria in an Area of Endemicity fo AIDS", *Clin. Infect. Dis.* (1992), pp. 161-162.

Southern, et al., "Analyzing and Comparing Nucleic Acid Sequences by Hybridization to Arrays of Oligonucleotides: Evaluation Using Experimental Models", *Genomics* (1992), pp. 1008-1017.

Small, et al., "Molecular Epidemiology of Tuberculosis", *Tuberculosis: Pathogenesis, Protection and Control* (1994), pp. 569-582.

Stager, et al., "Role of Solid Media When Used in Conjunction with the BACTEC System for Mycobacterial Isolation and Identification", *Jrnl. Clin. Microbiol.* (Jan. 1991), pp. 154-157.

Talenti, et al., "Detection of rifampicin-resistance mutations in *Mycobacterium tuberculosis*", *The Lancet*, vol. 341 (Mar. 13, 1993), pp. 647-650.

Van der Vlliet, et al., "Nucleic acid sequence-based amplification (NASBA) for the identification of mycobacteria", *Journal of General Microbiology, vol. 139 (1993), pp. 2423-2429.*

Wolinsky, "Mycobacterial Diseases Other Than Tuberculosis", *Clinical Infectious Diseases*, vol. 15 (1992), pp. 1-12.

Wu, et al., "The Litigation Amplification Reaction (LAR)—Amplification of Specific DNA Sequences Using Sequential Rounds of Template-Dependant Ligation", *Genomics*, vol. 4 (1989), pp. 560-569.

Whelen, et al., "Direct Genotypic Detection of *Mycobacterium tuberculosis* Rifampin Resistance in Clinical Specimens by Using Single-tube Heminested PCR", *Jrnl. Clin. Microbiology*, vol. 33, No. 3 (1995), pp. 556-561.

* cited by examiner

MYCOBACTERIAL RPOB SEQUENCES

CROSS-REFERENCE TO RELATED APPLICATIONS

This application derives priority from U.S. Ser. No. 60/080,616, filed Apr. 3, 1998, and incorporated by reference. Applications U.S. Ser. No. 08/797,812, filed Feb. 7, 1997, now U.S. Pat. No. 6,228,575; U.S. Ser. No. 60/011,339, filed Feb. Feb. 8, 1996; U.S. Ser. No. 60/012,631, filed Mar. 1, 1996; U.S. Ser. No. 08/629,031, filed Apr. 8, 1996, now abandoned; and 60/017,765, filed 15 May 15, 1996 are directed to related subject matter. These applications are specifically incorporated by reference in their entirety for all purposes.

STATEMENT OF GOVERNMENT INTEREST

The work described in this application was supported in part by grant number 1R43a140400 by the NIAID. The Government may have certain rights in this invention.

BACKGROUND OF THE INVENTION

1. Field of the Invention

This invention is directed to polymorphisms in rpoB genes of mycobacteria and use of the same in the identification and characterization of microorganisms.

2. Background of the Invention

Multidrug resistance and human immunodeficiency virus (HIV-1) infections are factors which have had a profound impact on the tuberculosis problem. An increase in the frequency of *Mycobacterium tuberculosis* strains resistant to one or more anti-mycobacterial agents has been reported, Block, et al., (1994) *JAMA* 271:665–671. Immunocompromised HIV-1 infected patients not infected with *M. tuberculosis* are frequently infected with *M. avium* complex (MAC) or *M. avium-M. intracellulare* (MAI) complex. These mycobacteria species are often resistant to the drugs used to treat *M. tuberculosis*. These factors have re-emphasized the importance for the accurate determination of drug sensitivities and mycobacteria species identification.

In HIV-1 infected patients, the correct diagnosis of the mycobacterial disease is essential since treatment of *M. tuberculosis* infections differs from that called for by other mycobacteria infections, Hoffner, S. E. (1994) *Eur. J. Clin. Microbiol. Inf. Dis.* 13:937–941. Non-tuberculosis mycobacteria commonly associated with HIV-1 infections include *M. kansasii, M. xenopi, M. fortuitum, M. avium* and *M. intracellulare*, Wolinsky, E., (1992) *Clin. Infect. Dis.* 15:1–12, Shafer, R. W. and Sierra, M. F. 1992 *Clin. Infect. Dis.* 15:161–162. Additionally, 13% of new cases (HIV-1 infected and non-infected) of *M. tuberculosis* are resistant to one of the primary anti-tuberculosis drugs (isoniazid [INH], rifampin [RIF], streptomycin [STR], ethambutol [EMB] and pyrazinamide [PZA] and 3.2% are resistant to both RIF and INH, Block, et al., *JAMA* 271:665–671, (1994). Consequently, mycobacterial species identification and the determination of drug resistance have become central concerns during the diagnosis of mycobacterial diseases.

Methods used to detect, and to identify *Mycobacterium* species vary considerably. For detection of *Mycobacterium tuberculosis*, microscopic examination of acid-fast stained smears and cultures are still the methods of choice in most microbiological clinical laboratories. However, culture of clinical samples is hampered by the slow growth of mycobacteria. A mean time of four weeks is required before sufficient growth is obtained to enable detection and possible identification. Recently, two more rapid methods for culture have been developed involving a radiometric, Stager, C. E. et al., (1991) *J. Clin. Microbiol.* 29:154–157, and a biphasic (broth/agar) system Sewell, et al., (1993) *J. Clin. Microbiol.* 29:2689–2472. Once grown, cultured mycobacteria can be analyzed by lipid composition, the use of species specific antibodies, species specific DNA or RNA probes and PCR-based sequence analysis of 16S rRNA gene (Schirm, et al. (1995) *J. Clin. Microbiol.* 33:3221–3224; Kox, et al. (1995) *J. Clin. Microbiol.* 33:3225–3233) and IS6110 specific repetitive sequence analysis (For a review see, e.g., Small et al., P. M. and van Embden, J. D. A. (1994) *Am. Society for Microbiology*, pp. 569–582). The analysis of 16S rRNA sequences (RNA and DNA) has been the most informative molecular approach to identify *Mycobacteria* species (Jonas, et al., *J. Clin. Microbiol.* 31:2410–2416 (1993)). However, to obtain drug sensitivity information for the same isolate, additional protocols (culture) or alternative gene analysis is necessary.

To determine drug sensitivity information, culture methods are still the protocols of choice. *Mycobacteria* are judged to be resistant to particular drugs by use of either the standard proportional plate method or minimal inhibitory concentration (MIC) method. However, given the inherent lengthy times required by culture methods, approaches to determine drug sensitivity based on molecular genetics have been recently developed.

Because resistance to RIF in *E. coli* strains was observed to arise as a result of mutations in the rpoB gene, Telenti, et al., id., identified a 69 base pair (bp) region of the *M. tuberculosis* rpoB gene as the locus where RIF resistant mutations were focused. Kapur, et al., (1995) *Arch. Pathol. Lab. Med.* 119:131–138, identified additional novel mutations in the *M. tuberculosis* rpoB gene which extended this core region to 81 bp. In a detailed review on antimicrobial agent resistance in mycobacteria, Musser (*Clin. Microbiol. Rev.*, 8:496–514 (1995)), summarized all the characterized mutations and their relative frequency of occurrence in this 81 bp region of rpoB. Missense mutations comprise 88% of all known mutations while insertions (3 or 6 bp) and deletions (3, 6 and 9 bp) account for 4% and 8% of the remaining mutations, respectively. Approximately 90% of all RIF resistant tuberculosis isolates have been shown to have mutations in this 81 bp region. The remaining 10% are thought possibly to involve genes other than rpoB.

For the above reasons, it would be desirable to have simpler methods which identify and characterize microorganisms, such as *Mycobacteria*, both at the phenotypic and genotypic level. This invention fulfills that and related needs.

SUMMARY OF THE INVENTION

In one aspect, the invention provides isolated nucleic acids comprising at least 25, 50, 75, 100, or 200 contiguous bases from an rpoB sequence shown in Table 1 (SEQ ID NOS: 1–181). Some nucleic acid comprise a complete sequence shown in Table 1.

The invention further provides a set of probes perfectly complementary to and spanning such nucleic acids, preferably spanning one of the complete sequences shown in Table 1 (SEQ ID NOS: 1–181).

The invention further provides methods of classifying mycobacteria. Some such methods entail providing a sample comprising a mycobacterial rpoB target nucleic acid from a mycobacteria, determining the sequence of a segment of at least 50 contiguous bases from the target nucleic acid; comparing the determined sequence to at least one sequence shown in Table 1; and classifying the mycobacteria from the extent of similarity of the compared sequences. Preferably, at least 100 or 200 contiguous bases are determined from the target nucleic acid. Preferably, the determined sequence is compared with a plurality of sequences from Table 1, for example, 10, 20, 50 or all of the sequence from Table 1 (SEQ ID NOS: 1–181).

In other methods of classification, the identity of one or more bases in the target sequence at one or more positions corresponding to one or more of the highlighted positions in a sequence shown in Table 1 is determined. The identity of the one or more bases characterizing the species of mycobacteria that is present in the sample. In some methods, the identity of at least 10 bases in the target nucleic acid at positions corresponding to highlighted positions in a sequence shown in Table 1 is determined. In some methods, the identity of at least 20 bases in the target sequence at highlighted positions shown in Table 1 are identified. In some methods, at least 20 determined bases are compared with 20 bases occupying corresponding positions in each of at least ten sequences from Table 1.

In another aspect, the invention provides sequence-specific polynucleotide probes or primers that hybridizes to a segment of a mycobacterial rpoB sequence shown in Table 1 or its complement without hybridizing to the *M. tuberculosis* sequence designated ATCC9-Mtb in Table 1 or its complement, the segment including a highlighted nucleotide position shown in Table 1. In some such probes, a central position of the probe aligns with a highlighted nucleotide position shown in Table 1. In some such primers, the 3' end of the primer aligns with a highlighted nucleotide position shown in Table 1. Some probes and primers are between 10 and 50 bases long.

In another aspect, the invention provides a computer-readable storage medium for storing data for access by an application program being executed on a data processing system. Such a system comprises a data structure stored in the computer-readable storage medium. The data structure includes information resident in a database used by the application program and includes a plurality of records, each record comprising information identifying a polymorphism or sequence shown in Table 1. Some records have a field identifying a base occupying a polymorphic site and a field identifying location of the polymorphic site. Some records record a contiguous segment of at least 50, 100, or 200 bases from an rpoB sequence shown in Table 1. Some storage medium comprise at least ten records each recording a contiguous segment of at least 50 bases from at least ten rpoB sequences shown in Table 1.

DEFINITIONS

Figure 1:
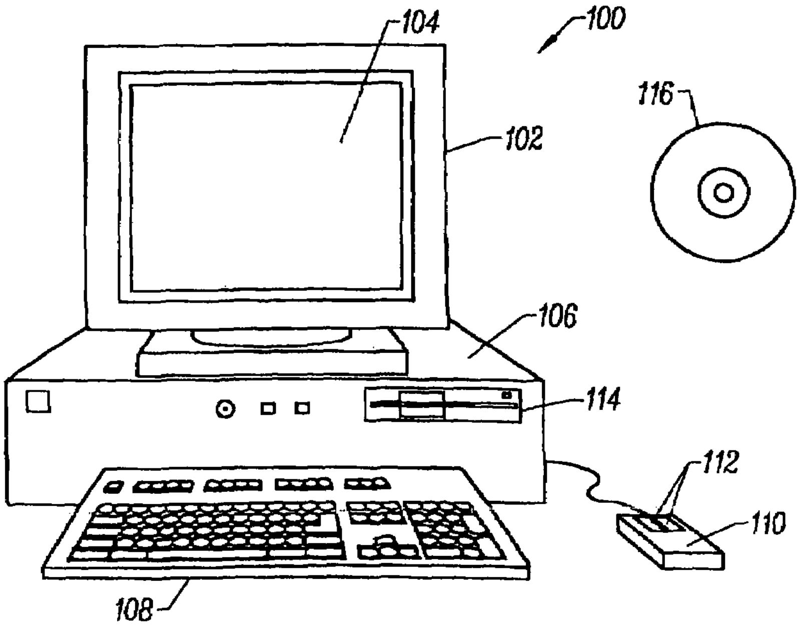
FIG. 1: Computer that may be utilized to execute software embodiments of the present invention.

A polynucleotide can be DNA or RNA, and single- or double-stranded. Polynucleotide can be naturally occurring or synthetic, and can be of any length. Preferred polynucleotide probes of the invention include contiguous segments of DNA, or their complements including any of the highlighted bases shown in Table 1. The segments are usually between 5 and 100 bases, and often between 5–10, 5–20, 10–20, 10–50, 20–50 or 20–100 bases. The highlighted site can occur within any position of the segment. Preferred polynucleotide probes are capable of binding in a base-specific manner to a complementary strand of nucleic acid. Such probes include peptide nucleic acids, as described in Nielsen et al., *Science* 254, 1497–1500 (1991), and probes having nonnaturally occurring bases.

The term primer refers to a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

A cDNA or cRNA is derived from an RNA if it produced by a process in which the RNA serves as a template for production of the cDNA or cRNA.

Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) and a temperature of 25–30° C. are suitable for allele-specific probe hybridizations.

An isolated nucleic acid means an object species invention that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "target nucleic acid" refers to a nucleic acid (often derived from a biological sample), to which the probe nucleic acid is designed to specifically hybridize. It is the presence or expression level of the target nucleic acid that is to be detected or quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g. gene or mRNA) whose expression level it is desired to detect. The difference in usage will be apparent from context.

"Subsequence" refers to a sequence of nucleic acids that comprise a part of a longer sequence of nucleic acids.

DETAILED DESCRIPTION

I. Mycobacterial Sequences of rpoB Genes

Table 1 shows a comparison of a substantial collection of mycobacterial strains of an about 700-nucleotide conserved region of an rpoB gene. The sequences shown in Table 1 are identified as follows: SEQ ID NOS: 1–56, respectively, are shown on pages 21, 25, 29, 33, 37, 41, 45, 49, 53, 57, 61 and 65; SEQ ID NOS: 57–112, respectively, are shown on pages 22, 26, 30, 34, 38, 42, 46, 50, 54, 58, 62 and 65; SEQ ID NOS: 113–168, respectively, are shown on pages 23, 27, 31, 35, 39, 43, 47, 51, 55, 59, 63 and 66; SEQ ID NOS: 169–181, respectively, are shown on pages 24, 28, 32, 36, 40, 44, 52, 56, 60, 64 and 68. The first sequence, designated as a reference sequence, is from *M. tuberculosis*. Nucleotides are numbered consecutively starting from the first nucleotide of the reference sequences. Other sequences are from other strains of mycobacteria. For example, the sequences designated ATCC-av, M29, M30 . . . M104 are from *M. avium*. Sequences designated from ATT-chelnew, M11, M13, and 17 are from *M. chelonae*. Sequences designated ATCC—for, M53, M55, M56, and M74 are from *M. fortuitum*, and so forth. Complete correspondence between strain designations and strain types is shown in Table 2. Nucleotides in a mycobacterial sequence are accorded the same number as the corresponding position of the reference sequence when the two are maximally aligned. Differences between a sequence and the reference sequences are shown in highlighted type. Many of the highlighted positions are common to all tested members of a species. Other highlighted positions vary among different isolates in a species. Both types of variation can be useful in speciation analysis.

II. Analysis of Species Variations

A. Preparation of Samples

An rpoB sequence is isolated from a sample of an unknown mycobacteria being tested. Nucleic acids can be isolated from myobacteria by standard methods as described in WO 97/29212 (incorporated by reference in its entirety for all purposes). The rpoB sequences to be analyzed can then be isolated and amplified by means of PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202 (each of which is incorporated by reference for all purposes). Primers for PCR preferably flank the regions of interest rpoB genes, although primers to internal sites can be used if it is intended to analyze only certain sites of potential species variation. Exemplary primers are described in WO 97/29212. If necessary, additional sequences flanking the sequences shown in Table 1 can be determined using probes based on the sequences in Table 1 to isolate full-length rpoB sequences from the appropriate mycobacterial species.

B. Detection of Species-Specific Variations in Target DNA

1. Sequence-Specific Probes

The design and use of sequence-specific probes for analyzing polymorphisms is described by e.g., Saiki et al., *Nature* 324, 163–166 (1986); Dattagupta, E P 235,726, Saiki, WO 89/11548. Sequence-specific probes can be designed that hybridize to a segment of target DNA in one isolate of mycobacteria that do not isolate to a corresponding isolate in another due to the presence of allelic or species variations in the respective segments from the two sequences. Hybridization conditions should be sufficiently stringent that there is a significant difference in hybridization intensity between alleles, and preferably an essentially binary response, whereby a probe hybridizes to only one of the sequences. Some probes are designed to hybridize to a segment of target DNA such that the site of potential sequence variation aligns with a central position (e.g., in a 15 mer at the 7 position; in a 16 mer, at either the 8 or 9 position) of the probe. This design of probe achieves good discrimination in hybridization between different allelic and species variants.

Sequence-specific probes are often used in pairs, one member of a pair showing a perfect match to a reference form of a target sequence and the other member showing a perfect match to a variant form. Several pairs of probes can then be immobilized on the same support for simultaneous analysis of multiple potential variations within the same target sequence.

2. Tiling Arrays

The bases occupying sites of potential variation can also be identified by hybridization to nucleic acid arrays, some example of which are described by WO 95/11995 (incorporated by reference in its entirety for all purposes). Such arrays contain a series of overlapping probes spanning a reference sequence. Any of the rpoB sequences shown in Table 1, or contiguous segments of, for example, at least 25, 50, 100 or 200 bases thereof, can serve as a reference sequence. WO 95/11995 also describes subarrays that are optimized for detection of a variant forms of a precharacterized polymorphism. Such a subarray contains probes designed to be complementary to a second reference sequence, which is a variant of the first reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Sequence-Specific Primers

A sequence-specific primer hybridizes to a site on target DNA overlapping a polymorphism and only primes amplification of a variant form to which the primer exhibits perfect complementarily. See Gibbs, *Nucleic Acid Res.* 17, 2427–2448 (1989). This primer is used in conjunction with a second primer which hybridizes at a distal site. Amplification proceeds from the two primers leading to a detectable product signifying the particular variant form is present. A control is usually performed with a second pair of primers, one of which shows a single base mismatch at the site of variation and the other of which exhibits perfect complementarily to a distal site. The single-base mismatch prevents amplification and no detectable product is formed. The method works best when the mismatch is included in the 3'-most position of the primer aligned with the point of variation because this position is most destabilizing to elongation from the primer. See, e.g., WO 93/22456.

4. Direct-Sequencing

The direct analysis of mycobacterial sequences can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

III. Methods of Use

The sequences and polymorphisms shown in Table 1 are useful for identifying the presence of myobacteria in samples, and optionally, classifying the mycobacteria. The sample can be obtained from a patient or from a biological source, such as a food product.

The sequences shown in Table 1 can be used for design of sequence-specific probes or primers encompassing polymorphic sites as described above. These probes or primers can then be used to determine the base occupying a corresponding position in an rpoB sequence from an isolate in a sample under test. A base in one sequence corresponds with a base in another when the two bases occupy the same position when the two sequences are maximally aligned by one of the criteria described in Definitions.

Alternatively, the sequences shown in Table 1 can be used for design of tiling arrays in which one or more of the sequences serves as a reference sequence. At least one set of overlapping probes is designed spanning a segment of the reference sequence, as described in WO95/11995 or EP 717,113. Target sequences from samples under test can be hybridized to such arrays, optionally in combination with controls of known rpoB sequences. The hybridization pattern of a target sequence to such an array can be analyzed to determine the identity of bases at which the target sequence differs from the reference sequence, as described in WO 95/11995.

One or more of the above methods, or direct sequencing, can be used to identify the base occupying at least one and usually several (e.g., 5, 10, 15, 25, 50 or 100) sites of potential variation between the 16S RNA and/or rpoB gene in an unknown mycobacteria relative to bases occupying corresponding sites in one or more known strains of mycobacteria, such as those shown in Table 1. This analysis results in a profile of bases occupying particular sites that characterizes the mycobacterial strain under test. The profile is compared with the corresponding profiles of different mycobacterial isolates shown in e.g., Table 1. In general, the unknown mycobacterium isolate is characterized as being from the same mycobacterial species as the precharacterized isolate with which it shares the greatest similarity in base profile.

In some methods, the sequence of a contiguous segment of the rpoB target nucleic acid is determined in a sample under test for comparison with one or more of the sequences shown in Table 1. The mycobacteria is classified by the extent of similarity. For example, if a target nucleic acid shows greater sequence identity to rpoB sequences from one species than any other, the sample from which the target was obtained is typically classified as arising from that species.

Alternatively, an array of tiled probes based on a reference sequence shown in Table 1 can be used for identifying and characterizing mycobacterial sequences based on comparison of hybridization patterns. Such an array is hybridized to a 16S RNA or rpoB target sequence from a sample, and the hybridization pattern compared with the hybridization pattern of one or more control sequences. The hybridization patterns of control sequences can be historic controls, stored, for example, in a computer database, or can be contemporaneous controls performed at or near the same time as the hybridization to the target sequence. Optionally, hybridization of target and reference sequence can be performed simultaneously using different labels.

Method of classifying unknown mycobacterial isolate by matching the hybridization pattern of a target sequence with those of control sequences from characterized species are described in more detail in WO 97/29212 (incorporated by reference in its entirety for all purposes). In an idealized case, the detection of a particular hybridization pattern in an isolate characterizes that isolate as belonging to a particular species. This can occur when the hybridization pattern detected in the isolate is uniquely associated with a specific species. More frequently however, such an unique one-to-one correspondence is not present. Instead, the hybridization pattern observed in an isolate does not bear a unique correspondence with a previously characterized species. However, the hybridization pattern detected is associated with a probability of the organism being screened belonging to a particular species (or not) or carrying a particular phenotypic trait (or not). As a result, analysis of an increasing number of polymorphic sites in an isolate, allows one to classify the isolated with an increasing level of confidence. Algorithms can be used to derive such composite probabilities from the comparison of multiple polymorphic forms between an isolate and references. Typically, the mathematical algorithm makes a call of the identity of the species and assign a confidence level to that call. One can determine the confidence level (>90%, >95% etc.) that one desires and the algorithm will analyze the hybridization pattern and either provide an identification or not. Occasionally, the call is that the sample may be one of two, three or more species, in which case a specific identification is not be possible. However, one of the strengths of this technique is that the rapid screening made possible by the chip-based hybridization allows one to continuously expand a database of patterns ultimately to enable the identification of species previously unidentifiable due to lack of sufficient information.

IV. Modified Polypeptides and Gene Sequences

The invention further provides variant forms of nucleic acids and corresponding proteins. The nucleic acids comprise one of the sequences described in Table 1. Some nucleic acid encode full-length variant forms of proteins. Variant proteins have the prototypical amino acid sequences of encoded by nucleic acid sequence shown in Table 1 (read so as to be in-frame with the full-length coding sequence of which it is a component).

Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like. The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice,* 2nd Edition, Springer-Verlag, New York (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one sequence-specific probe as described above. Often, the kits contain one or more pairs of sequence-specific probes hybridizing to different forms of a polymorphism. In some kits, the sequence-specific probes are provided immobilized to a substrate. For example, the same substrate can comprise sequence-specific probes for detecting at least 10, 100 or all of the variations shown in Table 1. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

VI. Computer Databases

Figure 2:
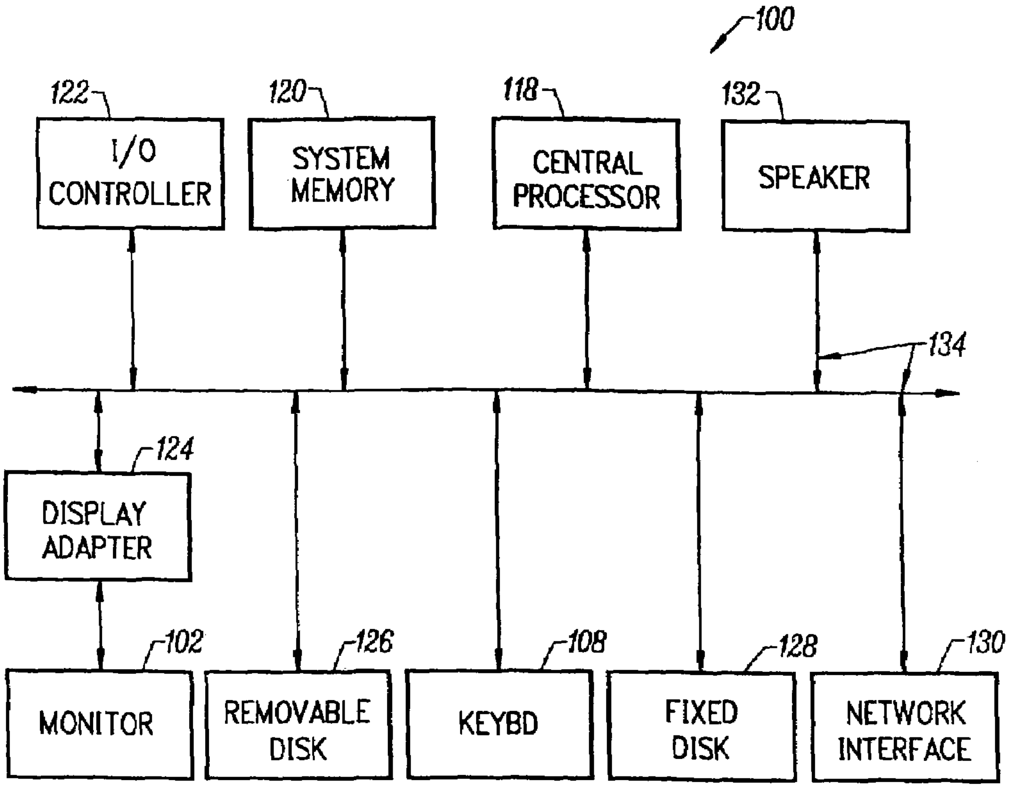
FIG. 2: A system block diagram of a typical computer system that may be used to execute software embodiments of the invention.

FIG. 1 illustrates an example of a computer system that can be used to store records relating to polymorphisms of the invention and perform algorithms comparing polymorphic profiles and to classify species. FIG. 2 shows a computer system 100 which includes a monitor 102, screen 104, cabinet 106, keyboard 108, and mouse 110. Mouse 110 may have one or more buttons such as mouse buttons 112. Cabinet 106 houses a CD-ROM drive 114, a system memory and a hard drive (see FIG. 2) which can be utilized to store and retrieve software programs incorporating code that implements the present invention, data for use with the present invention, and the like. Although a CD-ROM 116 is shown as an exemplary computer readable storage medium, other computer readable storage media including floppy disks, tape, flash memory, system memory, and hard drives may be utilized. Cabinet 106 also houses familiar computer components such as a central processor, system memory, hard disk, and the like.

FIG. 2 shows a system block diagram of computer system 100 that may be used to execute software embodiments of the present invention. As in FIG. 1, computer system 100 includes monitor 102 and keyboard 108. Computer system 100 further includes subsystems such as a central processor 102, system memory 120, I/O controller 122, display adapter 124, removable disk 126 (e.g., CD-ROM drive), fixed disk 128 (e.g., hard drive), network interface 130, and speaker 132. Other computer systems suitable for use with the present invention may include additional or fewer subsystems. For example, another computer system can include more than one processor 102 (i.e., a multi-processor system) or a cache memory.

Arrows such as 134 represent the system bus architecture of computer system 100. However, these arrows are illustrative of any interconnection scheme serving to link the subsystems. For example, a local bus can be utilized to connect the central processor to the system memory and display adapter. Computer system 100 shown in FIG. 1 is but an example of a computer system suitable for use with the present invention.

The computer stores records relating to the polymorphisms of the record. Some such records record a polymorphism by reference to the position of a polymorphic site and the identity of base(s) occupying that site in one or more species. Some databases include records for at least ten polymorphic sites in at least ten of the sequences shown in Table 1. Some databases include records for all of the polymorphic sites in at least one of the sequences shown in Table 1. Some databases includes records for at least 100, 1000, or 2000 polymorphic sites shown in Table 1. Some databases include records for all of the polymorphic sites shown in Table 1.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

TABLE 1

| | | BASE NOS 1–60 |
|---|---|---|
| ATCC9-Mtb.txt | SEQ ID NO 1 | CCCAGGACGTGGAGGCGATCACACCGCAGACGTTGATCAACATCCGGCCGGTGGTCGCCG |
| MY621.txt | SEQ ID NO 2 | TCCGTCCCGTCGTGGCGG |
| Atcc1-av.txt | SEQ ID NO 3 | CCCAGGACGTGGAGGCGATCACACCGCAGACCCTGATCAACATCCGTCCCGTCGTGGCGG |
| M29.txt | SEQ ID NO 4 | CCCAGGACGTGGAGGCGATCACACCGCAGACCCTGATCAACATCCGTCCAGTCGTGGCGG |
| M30.txt | SEQ ID NO 5 | CCCAGGACGTGGAGGCGATCACACCGCAGACCCTGATCAACATCCGTCCAGTCGTGGCGG |
| M31.txt | SEQ ID NO 6 | CCCAGGACGTGGAGGCGATCACACCGCAGACCCTGATCAACATCCGTCCAGTCGTGGCGG |
| M32.txt | SEQ ID NO 7 | CCCAGGACGTGGAGGCGATCACACCGCAGACCCTGATCAACATCCGTCCAGTCGTGGCGG |
| M33.txt | SEQ ID NO 8 | CCCAGGACGTGGAGGCGATCACACCGCAGACCCTGATCAACATCCGTCCAGTCGTGGCGG |
| M34.txt | SEQ ID NO 9 | CCCAGGACGTGGAGGCGATCACACCGCAGACCCTGATCAACATCCGTCCAGTCGTGGCGG |
| M48-new.txt | SEQ ID NO 10 | CCCAGGACGTGGAGGCGATCACACCGCAGACCCTGATCAACATCCGTCCRGTCGTGGCGG |
| M49.txt | SEQ ID NO 11 | CCCAGGACGTGGAGGCGATCACACCGCAGACCCTGATCAACATCCGTCCCGTCGTGGCGG |
| M64(Mav2).txt | SEQ ID NO 12 | CCCAGGACGTGGAGGCGATCACACCGCAGACCCTGATCAACATCCGTCCAGTCGTGGCGG |
| M65(Mav3).txt | SEQ ID NO 13 | CCCAGGACGTGGAGGCGATCACACCGCAGACCCTGATCAACATCCGTCCAGTCGTGGCGG |
| M67(Mav5).txt | SEQ ID NO 14 | CCCAGGACGTGGAGGCGATCACACCGCAGACCCTGATCAACATCCGTCCAGTCGTGGCGG |
| M69(Mav7).txt | SEQ ID NO 15 | TCCGTCCAGTCGTGGCGG |
| M71(Mav9).txt | SEQ ID NO 16 | CCCAGGACGTGGAGGCGATCACACCGCAGACCCTGATCAACATCCGTCCAGTCGTGGCGG |
| M91.txt | SEQ ID NO 17 | CCCAGGACGTGGAGGCGATCACACCGCAGACCCTGATCAACATCCGTCCAGTCGTGGCGG |
| M94.txt | SEQ ID NO 18 | GGAGGCGATCACACCGCAGACCCTGATCAACATCCGTCCAGTCGTGGCGG |
| M95.txt | SEQ ID NO 19 | GGAGGCGATCACACCGCAGACCCTGATCAACATCCGTCCAGTCGTGGCGG |
| M96.txt | SEQ ID NO 20 | GGAGGCGATCACACCGCAGACCCTGATCAACATCCGTCCAGTCGTGGCGG |
| M100.txt | SEQ ID NO 21 | GGAGGCGATCACACCGCAGACCCTGATCAACATCCGTCCAGTCGTGGCGG |
| M101.txt | SEQ ID NO 22 | GGAGGCGATCACACCGCAGACCCTGATCAACATCCGTCCAGTCGTGGCGG |
| M102.txt | SEQ ID NO 23 | GGAGGCGATCACACCGCAGACCCTGATCAACATCCGTCCAGTCGTGGCGG |
| M104.txt | SEQ ID NO 24 | CCCAGGACGTGGAGGCGATCACACCGCAGACCCTGATCAACATCCGTCCAGTCGTGGCGG |
| M105.txt | SEQ ID NO 25 | GGAGGCGATCACACCGCAGACCCTGATCAACATCCGTCCAGTCGTGGCGG |

TABLE 1-continued

| | | |
|---|---|---|
| M106.txt | SEQ ID NO 26 | GGAGGCGATCACACCGCAGACCCTGATCAACATCCGTCCCGTCGTGGCGG |
| MY111.txt | SEQ ID NO 27 | GGAGGCGATCACACCGCAGACCCTGATCAACATCCGTCCAGTCGTGGCGG |
| M76.txt | SEQ ID NO 28 | CCCAGGACGTGGAGGCGATCACACCGCAGACGTTGATCAACATCCGGCCGGTGGTCGCCG |
| MY451.txt | SEQ ID NO 29 | GGAGGCGATCACACCGCAGACGTTGATCAACATCCGGCCGGTGGTCGCCG |
| ATCC2-chelnew.txt | SEQ ID NO 30 | CGCAGACCCTGATCAACATCCGTCCCGTCGTGGCGG |
| M10.txt | SEQ ID NO 31 | TCCGTCCCGTCGTGGCGG |
| M11-662.txt | SEQ ID NO 32 | TGATCAACATCCGTCCCGTCGTGGCGG |
| M12.txt | SEQ ID NO 33 | TCCGTCCCGTCGTGGCGG |
| M13_2_662.txt | SEQ ID NO 34 | TGATCAACATCCGTCCCGTCGTGGCGG |
| M14.txt | SEQ ID NO 35 | CCCAGGACGTGGAGGCGATCACACCGCAGACCCTGATCAACATCCGTCCCGTCGTGGCGG |
| M15.txt | SEQ ID NO 36 | TCCGTCCCGTCGTGGCGG |
| M16.txt | SEQ ID NO 37 | TCCGTCCCGTCGTGGCGG |
| M17_2_662.txt | SEQ ID NO 38 | GCAGACCCTGATCAACATCCGTCCCGTCGTGGCGG |
| M50.txt | SEQ ID NO 39 | TCCGTCCCGTCGTGGCGG |
| M51.txt | SEQ ID NO 40 | TCCGTCCCGTCGTGGCGG |
| M115.txt | SEQ ID NO 41 | TCCGTCCCGTCGTGGCGG |
| M116.txt | SEQ ID NO 42 | TCCGTCCCGTCGTGGCGG |
| M119.txt | SEQ ID NO 43 | TCCGTCCCGTCGTGGCGG |
| MY109.txt | SEQ ID NO 44 | TCCGTCCCGTCGTGGCGG |
| MY200.txt | SEQ ID NO 45 | TCCGTCCCGTCGTGGCGG |
| MY207.txt | SEQ ID NO 46 | TCCGTCCCGTCGTGGCGG |
| MY209.txt | SEQ ID NO 47 | TCCGTCCCGTCGTGGCGG |
| M122.txt | SEQ ID NO 48 | GGAGGCGATCACACCGCAGACCCTGATCAACATCCGTCCCGTCGTGGCGG |
| M123.txt | SEQ ID NO 49 | GGAGGCGATCACACCGCAGACCCTGATCAACATCCGTCCCGTCGTGGCGG |
| M124.txt | SEQ ID NO 50 | GGAGGCGATCACACCGCAGACCCTGATCAACATCCGTCCCGTCGTGGCGG |
| Atcc3-for.txt | SEQ ID NO 51 | CCCAGGACGTGGAGGCGATCACACCGCAGACCCTGATCAACATCCGTCCCGTCGTGGCGG |
| M53.txt | SEQ ID NO 52 | CCCAGGACGTGGAGGCGATCACACCGCAGACCCTGATCAACATCCGTCCCGTCGTGGCGG |
| M54.txt | SEQ ID NO 53 | TCCGTCCCGTCGTGGCGG |
| M55.txt | SEQ ID NO 54 | CCCAGGACGTGGAGGCGATCACACCGCAGACCCTGATCAACATCCGTCCCGTCGTGGCGG |
| M56.txt | SEQ ID NO 55 | CCCAGGACGTGGAGGCGATCACACCGCAGACCCTGATCAACATCCGTCCCGTCGTGGCGG |
| M74(Mav12).txt | SEQ ID NO 56 | TCCGTCCCGTCGTGGCGG |
| M77.txt | SEQ ID NO 57 | CCCAGGACGTGGAGGCGATCACACCGCAGACCCTGATCAACATCCGCCCCGTCGTGGCGG |
| M118.txt | SEQ ID NO 58 | GGAGGCGATCACACCGCAGACCCTGATCAACATCCGTCCCGTCGTGGCGG |
| MY221.txt | SEQ ID NO 59 | GGAGGCGATCACACCGCAGACCCTGATCAACATCCGTCCCGTCGTGGCGG |
| MY223.txt | SEQ ID NO 60 | GGAGGCGATCACACCGCAGACCCTGATCAACATCCGCCCCGTCGTGGCGG |
| MY225.txt | SEQ ID NO 61 | GGAGGCGATCACACCGCAGACCCTGATCAACATCCGTCCCGTCGTGGCGG |
| My341.txt | SEQ ID NO 62 | GGAGGCGATCACACCGCAGACCCTGATCAACATCCGTCCCGTCGTGGCGG |
| My715.txt | SEQ ID NO 63 | GGAGGCGATCACACCGCAGACCCTGATCAACATCCGTCCCGTCGTGGCGG |
| MY470.txt | SEQ ID NO 64 | TCCGTCCGGTCGTTGCCG |
| Atcc4-go.txt | SEQ ID NO 65 | CCCAGGACGTGGAGGCGATCACACCGCAGACCCTGATCAACATCCGGCCGGTCGTCGCCG |
| ATCC4-0-Gord.txt | SEQ ID NO 66 | CCCAGGACGTGGAGGCGATCACACCGCAGACCCTGATCAACATCCGGCCGGTCGTCGCCG |
| M78(lz).txt | SEQ ID NO 67 | CCCAGGACGTGGAGGCGATCACACCGCAGACCCTGATCAACATCCGGCCGGTCGTCGCCG |
| M79(jd).txt | SEQ ID NO 68 | CCCAGGACGTGGAGGCGATCACACCGCAGACCCTGATCAACATCCGGCCGGTCGTGGCCG |
| M80(lg).txt | SEQ ID NO 69 | CCCAGGACGTGGAGGCGATCACACCGCAGACCCTGATCAACATCCGGCCGGTCGTCGCCG |
| M81(ll).txt | SEQ ID NO 70 | CCCAGGACGTGGAGGCGATCACACCGCAGACCCTGATCAACATCCGGCCGGTCGTCGCTG |
| M82(rm).txt | SEQ ID NO 71 | CCCAGGACGTGGAGGCGATCACACCGCAGACCCTGATCAACATCCGGCCGGTCGTCGCCG |
| M83(mb).txt | SEQ ID NO 72 | CCCAGGACGTGGAGGCGATCACACCGCAGACCCTGATCAACATCCGGCCGGTCGTCGCCG |
| M84(ow).txt | SEQ ID NO 73 | CCCAGGACGTGGAGGCGATCACACCGCAGACCCTGATCAACATCCGGCCGGTCGTCGCCG |
| M85(lb).txt | SEQ ID NO 74 | CCCAGGACGTGGAGGCGATCACACCGCAGACCCTGATCAACATCCGGCCGGTCGTCGCCG |
| M86(rb).txt | SEQ ID NO 75 | CCCAGGACGTGGAGGCGATCACACCGCAGACCCTGATCAACATCCGGCCGGTCGTCGCCG |
| M87(wn).txt | SEQ ID NO 76 | CCCAGGACGTGGAGGCGATCACACCGCAGACCCTGATCAACATCCGGCCGGTCGTCGCCG |
| M90(gordDB).txt | SEQ ID NO 77 | CCCAGGACGTGGAGGCGATCACACCGCAGACCCTGATCAACATCCGGCCGGTCGTCGCCG |
| m126.txt | SEQ ID NO 78 | CCCAGGACGTGGAGGCGATCACACCGCAGACCCTGATCAACATCCGGCCGGTCGTCGCCG |
| M128.txt | SEQ ID NO 79 | CCCAGGACGTGGAGGCGATCACACCGCAGACCCTGATCAACATCCGGCCGGTCGTCGCCG |
| My103.txt | SEQ ID NO 80 | GGAGGCGATCACACCGCAGACCCTGATCAACATCCGGCCGGTCGTCGCCG |
| MY475.txt | SEQ ID NO 81 | GGAGGCGATCACACCGCAGACCCTGATCAACATCCGGCCGGTCGTCGCCG |
| MY476.txt | SEQ ID NO 82 | GGAGGCGATCACACCGCAGACCCTGATCAACATCCGGCCGGTCGTCGCCG |
| MY830.txt | SEQ ID NO 83 | GGAGGCGATCACACCGCAGACCCTGATCAACATCCGGCCCGTCGTCGCCG |
| Atcc5-int.txt | SEQ ID NO 84 | CCCAGGACGTGGAGGCGATCACACCGCAGACCCTGATCAACATCCGGCCGGTCGTCGCCG |
| ATCC5-0int.txt | SEQ ID NO 85 | CCCAGGACGTGGAGGCGATCACACCGCAGACCCTGATCAACATCCGGCCGGTCGTCGCCG |
| M18.txt | SEQ ID NO 86 | CCCAGGACGTGGAGGCGATCACACCGCAGACCCTGATCAACATCCGGCCGGTCGTCGCCG |
| M19.txt | SEQ ID NO 87 | CCCAGGACGTGGAGGCGATCACACCGCAGACCCTGATCAACATCCGGCCGGTCGTCGCCG |
| M20.txt | SEQ ID NO 88 | CCCAGGACGTGGAGGCGATCACACCGCAGACCCTGATCAACATCCGGCCGGTCGTCGCCG |
| M21.txt | SEQ ID NO 89 | CCCAGGACGTGGAGGCGATCACACCGCAGACCCTGATCAACATCCGGCCGGTCGTCGCCG |
| M22.txt | SEQ ID NO 90 | CCCAGGACGTGGAGGCGATCACACCGCAGACCCTGATCAACATCCGGCCGGTCGTCGCCG |
| M23.txt | SEQ ID NO 91 | CCCAGGACGTGGAGGCGATCACACCGCAGACCCTGATCAACATCCGGCCGGTCGTCGCCG |
| M24.txt | SEQ ID NO 92 | CCCAGGACGTGGAGGCGATCACACCGCAGACCCTGATCAACATCCGGCCGGTCGTCGCCG |
| M25.txt | SEQ ID NO 93 | CCCAGGACGTGGAGGCGATCACACCGCAGACCCTGATCAACATCCGGCCGGTCGTCGCCG |
| M26.txt | SEQ ID NO 94 | CCCAGGACGTGGAGGCGATCACACCGCAGACCCTGATCAACATCCGGCCGGTCGTCGCCG |
| M27.txt | SEQ ID NO 95 | CCCAGGACGTGGAGGCGATCACACCGCAGACCCTGATCAACATCCGGCCGGTCGTCGCCG |
| M28.txt | SEQ ID NO 96 | CCCAGGACGTGGAGGCGATCACACCGCAGACCCTGATCAACATCCGGCCGGTCGTCGCCG |
| M107.txt | SEQ ID NO 97 | GGAGGCGATCACACCGCAGACCCTGATCAACATCCGGCCGGTCGTCGCCG |
| MY107.txt | SEQ ID NO 98 | GGAGGCGATCACACCGCAGACCCTGATCAACATCCGGCCGGTCGTCGCCG |
| MY112.txt | SEQ ID NO 99 | GGAGGCGATCACACCGCAGACCCTGATCAACATCCGGCCGGTCGTCGCCG |
| MY312.txt | SEQ ID NO 100 | GGAGGCGATCACACCGCAGACCCTGATCAACATCCGGCCGGTCGTCGCCG |
| Atcc6-kan.txt | SEQ ID NO 101 | CCCAGGACGTGGAGGCGATCACACCGCAGACACTGATCAACATCCGCCCGGTGGTCGCCG |
| ATCC6-0Kan.txt | SEQ ID NO 102 | CCCAGGACGTGGAGGCGATCACACCGCAGACACTGATCAACATCCGCCCGGTGGTCGCCG |
| M1.txt | SEQ ID NO 103 | CCCAGGACGTGGAGGCGATCACACCGCAGACACTGATCAACATCCGCCCGGTGGTCGCCG |
| M2.txt | SEQ ID NO 104 | CCCAGGACGTGGAGGCGATCACACCGCAGACACTGATCAACATCCGCCCGGTGGTCGCCG |
| M3.txt | SEQ ID NO 105 | CCCAGGACGTGGAGGCGATCACACCGCAGACACTGATCAACATCCGCCCGGTGGTCGCCG |
| M4.txt | SEQ ID NO 106 | CCCAGGACGTGGAGGCGATCACACCGCAGACACTGATCAACATCCGCCCGGTGGTCGCCG |
| M6.txt | SEQ ID NO 107 | CCCAGGACGTGGAGGCGATCACACCGCAGACACTGATCAACATCCGCCCGGTGGTCGCCG |
| M7.txt | SEQ ID NO 108 | CCCAGGACGTGGAGGCGATCACACCGCAGACACTGATCAACATCCGCCCGGTGGTCGCCG |
| M9.txt | SEQ ID NO 109 | TCCGCCCGGTGGTCGCCG |
| M57.txt | SEQ ID NO 110 | CCCAGGACGTGGAGGCGATCACACCGCAGACACTGATCAACATCCGCCCGGTGGTCGCCG |
| M58.txt | SEQ ID NO 111 | CCCAGGACGTGGAGGCGATCACACCGCAGACACTGATCAACATCCGCCCGGTGGTCGCCG |
| M59.txt | SEQ ID NO 112 | CCCAGGACGTGGAGGCGATCACACCGCAGACACTGATCAACATCCGCCCGGTGGTCGCCG |

TABLE 1-continued

| | | |
|---|---|---|
| M60 . txt | SEQ ID NO 113 | CCCAGGACGTGGAGGCGATCACACCGCAGACACTGATCAACATCCGCCCGGTGGTCGCCG |
| M61 . txt | SEQ ID NO 114 | CCCAGGACGTGGAGGCGATCACACCGCAGACACTGATCAACATCCGCCCGGTGGTCGCCG |
| M62 . txt | SEQ ID NO 115 | CCCAGGACGTGGAGGCGATCACACCGCAGACACTGATCAACATCCGCCCGGTGGTCGCCG |
| MY106 . txt | SEQ ID NO 116 | GGAGGCGATCACACCGCAGACACTGATCAACATCCGCCCGGTGGTCGCCG |
| MY216 . txt | SEQ ID NO 117 | GGAGGCGATCACACCGCAGACACTGATCAACATCCGCCCGGTGGTCGCCG |
| MY218 . txt | SEQ ID NO 118 | GGAGGCGATCACACCGCAGACACTGATCAACATCCGCCCGGTGGTCGCCG |
| MY226 . txt | SEQ ID NO 119 | GGAGGCGATCACACCGCAGACACTGATCAACATCCGCCCGGTGGTCGCCG |
| M109 . txt | SEQ ID NO 120 | GGAGGCGATCACACCGCAGACGCTGATCAACATCCGGCCGGTGGTCGCCG |
| M111 . txt | SEQ ID NO 121 | GGAGGCGATCACACCGCAGACGCTGATCAACATCCGGCCGGTGGTCGCCG |
| M112 . txt | SEQ ID NO 122 | GGAGGCGATCACACCGCAGACGCTGATCAACATCCGGCCGGTGGTCGCCG |
| M113 . txt | SEQ ID NO 123 | GGAGGCGATCACACCGCAGACGCTGATCAACATCCGGCCGGTGGTCGCCG |
| M114 . txt | SEQ ID NO 124 | GGAGGCGATCACACCGCAGACGCTGATCAACATCCGGCCGGTGGTCGCCG |
| MY325 . txt | SEQ ID NO 125 | GGAGGCGATCACACCGCAGACGCTGATCAACATCCGGCCGGTGGTCGCCG |
| MY718 . txt | SEQ ID NO 126 | GGAGGCGATCACACCGCAGACGCTGATCAACATCCGGCCGGTGGTCGCCG |
| MY214 . txt | SEQ ID NO 127 | GGAGGCGATCACACCGCAGACGTTGATCAACATCCGTCCGGTCGTTGCCG |
| MY224 . txt | SEQ ID NO 128 | GGAGGCGATCACACCGCAGACGTTGATCAACATCCGTCCGGTCGTTGCCG |
| My244 . txt | SEQ ID NO 129 | GGAGGCGATCACACCGCAGACGCTGATCAACATCCGTCCGGTCGTTGCCG |
| My339 . txt | SEQ ID NO 130 | GGAGGCGATCACACCGCAGACGCTGATCAACATCCGTCCGGTCGTTGCCG |
| My343 . txt | SEQ ID NO 131 | GGAGGCGATCACACCGCAGACGCTGATCAACATCCGTCCGGTCGTTGCCG |
| MY458 . txt | SEQ ID NO 132 | TCCGTCCCGTCGTGGCGG |
| MY809 . txt | SEQ ID NO 133 | TCCGTCCCGTCGTGGCGG |
| MY817 . txt | SEQ ID NO 134 | TCCGTCCCGTCGTGGCGG |
| MY821 . txt | SEQ ID NO 135 | TCCGTCCNGTCGTGGCGG |
| MY824 . txt | SEQ ID NO 136 | TCCGTCCCGTCGTGGCGG |
| MY102 . txt | SEQ ID NO 137 | GGAGGCGATCACACCGCAGACCCTGATCAACATCCGCCCGGTGGTCGCCG |
| My105 . txt | SEQ ID NO 138 | GGAGGCGATCACACCGCAGACCCTGATCAACATCCGCCCGGTGGTCGCCG |
| MY251 . txt | SEQ ID NO 139 | GGAGGCGATCACACCGCAGACCCTGATCAACATCCGTCCGGTGGTCGCCG |
| My256 . txt | SEQ ID NO 140 | GGAGGCGATCACACCGCAGACCCTGATCAACATCCGTCCGGTGGTCGCCG |

| | | |
|---|---|---|
| M60 . txt | SEQ ID NO 113 | CCCAGGACGTGGAGGCGATCACACCGCAGACACTGATCAACATCCGCCCGGTGGTCGCCG |
| M61 . txt | SEQ ID NO 114 | CCCAGGACGTGGAGGCGATCACACCGCAGACACTGATCAACATCCGCCCGGTGGTCGCCG |
| M62 . txt | SEQ ID NO 115 | CCCAGGACGTGGAGGCGATCACACCGCAGACACTGATCAACATCCGCCCGGTGGTCGCCG |
| MY106 . txt | SEQ ID NO 116 | GGAGGCGATCACACCGCAGACACTGATCAACATCCGCCCGGTGGTCGCCG |
| MY216 . txt | SEQ ID NO 117 | GGAGGCGATCACACCGCAGACACTGATCAACATCCGCCCGGTGGTCGCCG |
| MY218 . txt | SEQ ID NO 118 | GGAGGCGATCACACCGCAGACACTGATCAACATCCGCCCGGTGGTCGCCG |
| MY226 . txt | SEQ ID NO 119 | GGAGGCGATCACACCGCAGACACTGATCAACATCCGCCCGGTGGTCGCCG |
| M109 . txt | SEQ ID NO 120 | GGAGGCGATCACACCGCAGACGCTGATCAACATCCGGCCGGTGGTCGCCG |
| M111 . txt | SEQ ID NO 121 | GGAGGCGATCACACCGCAGACGCTGATCAACATCCGGCCGGTGGTCGCCG |
| M112 . txt | SEQ ID NO 122 | GGAGGCGATCACACCGCAGACGCTGATCAACATCCGGCCGGTGGTCGCCG |
| M113 . txt | SEQ ID NO 123 | GGAGGCGATCACACCGCAGACGCTGATCAACATCCGGCCGGTGGTCGCCG |
| M114 . txt | SEQ ID NO 124 | GGAGGCGATCACACCGCAGACGCTGATCAACATCCGGCCGGTGGTCGCCG |
| MY325 . txt | SEQ ID NO 125 | GGAGGCGATCACACCGCAGACGCTGATCAACATCCGGCCGGTGGTCGCCG |
| MY718 . txt | SEQ ID NO 126 | GGAGGCGATCACACCGCAGACGCTGATCAACATCCGGCCGGTGGTCGCCG |
| MY214 . txt | SEQ ID NO 127 | GGAGGCGATCACACCGCAGACGTTGATCAACATCCGTCCGGTCGTTGCCG |
| MY224 . txt | SEQ ID NO 128 | GGAGGCGATCACACCGCAGACGTTGATCAACATCCGTCCGGTCGTTGCCG |
| My244 . txt | SEQ ID NO 129 | GGAGGCGATCACACCGCAGACGCTGATCAACATCCGTCCGGTCGTTGCCG |
| My339 . txt | SEQ ID NO 130 | GGAGGCGATCACACCGCAGACGCTGATCAACATCCGTCCGGTCGTTGCCG |
| My343 . txt | SEQ ID NO 131 | GGAGGCGATCACACCGCAGACGCTGATCAACATCCGTCCGGTCGTTGCCG |
| MY458 . txt | SEQ ID NO 132 | TCCGTCCCGTCGTGGCGG |
| MY809 . txt | SEQ ID NO 133 | TCCGTCCCGTCGTGGCGG |
| MY817 . txt | SEQ ID NO 134 | TCCGTCCCGTCGTGGCGG |
| MY821 . txt | SEQ ID NO 135 | TCCGTCCNGTCGTGGCGG |
| MY824 . txt | SEQ ID NO 136 | TCCGTCCCGTCGTGGCGG |
| MY102 . txt | SEQ ID NO 137 | GGAGGCGATCACACCGCAGACCCTGATCAACATCCGCCCGGTGGTCGCCG |
| My105 . txt | SEQ ID NO 138 | GGAGGCGATCACACCGCAGACCCTGATCAACATCCGCCCGGTGGTCGCCG |
| MY251 . txt | SEQ ID NO 139 | GGAGGCGATCACACCGCAGACCCTGATCAACATCCGTCCGGTGGTCGCCG |
| My256 . txt | SEQ ID NO 140 | GGAGGCGATCACACCGCAGACCCTGATCAACATCCGTCCGGTGGTCGCCG |

| | | |
|---|---|---|
| M38 . txt | SEQ ID NO 169 | CCCAGGACGTGGAGGCGATCACACCGCAGACCTTGATCAACATCCGCCCCGTGGTCGCCG |
| M39 . txt | SEQ ID NO 170 | CCCAGGACGTGGAGGCGATCACACCGCAGACCTTGATCAACATCCGCCCCGTGGTCGCCG |
| M40 . txt | SEQ ID NO 171 | CCCAGGACGTGGAGGCGATCACACCGCAGACCTTGATCAACATCCGCCCCGTGGTCGCCG |
| M41 . txt | SEQ ID NO 172 | CCCAGGACGTGGAGGCGATCACACCGCAGACCTTGATCAACATCCGCCCCGTGGTCGCCG |
| M42 . txt | SEQ ID NO 173 | CCCAGGACGTGGAGGCGATCACACCGCAGACCTTGATCAACATCCGCCCCGTGGTCGCCG |
| M43 . txt | SEQ ID NO 174 | CCCAGGACGTGGAGGCGATCACACCGCAGACCTTGATCAACATCCGCCCCGTGGTCGCCG |
| M44 . txt | SEQ ID NO 175 | CCCAGGACGTGGAGGCGATCACACCGCAGACCTTGATCAACATCCGCCCCGTGGTCGCCG |
| M45 . txt | SEQ ID NO 176 | CCCAGGACGTGGAGGCGATCACACCGCAGACCTTGATCAACATCCGCCCCGTGGTCGCCG |
| M46 . txt | SEQ ID NO 177 | CCCAGGACGTGGAGGCGATCACACCGCAGACCTTGATCAACATCCGCCCCGTGGTCGCCG |
| M47 . txt | SEQ ID NO 178 | CCCAGGACGTGGAGGCGATCACACCGCAGACCTTGATCAACATCCGCCCCGTGGTCGCCG |
| M68 (Mav6) . txt | SEQ ID NO 179 | CCCAGGACGTGGAGGCGATCACACCGCAGACCTTGATCAACATCCGCCCCGTGGTCGCCG |
| M89 . txt | SEQ ID NO 180 | CCCAGGACGTGGAGGCGATCACACCGCAGACCTTGATCAACATCCGCCCCGTGGTCGCCG |
| M66 (Mav4) . txt | SEQ ID NO 181 | CCCAGGACGTGGAGGCGATCACACCGCAGACGCTGATCAACATCCGTCCGGTCGTCGCCG |
| | | 10 20 30 40 50 60 |

TABLE 1-continued

BASE NOS 61–120

| | | |
|---|---|---|
| ATCC9-Mtb.txt | SEQ ID NO 1 | CGATCAAGGAGTTCTTCGGCACCAGCCAGCTGAGCCAATTCATGGACCAGAACAACCCGC |
| MY621.txt | SEQ ID NO 2 | CGATCAAGGAGTTCTTCGGAACCAGCCAGCTGTCGCAGTTCATGGACCAGAACAACCCGC |
| Atcc1-av.txt | SEQ ID NO 3 | CGATCAAGGAGTTCTTCGGCACCAGCCAGCTGTCCCAGTTCATGGACCAGAACAACCCGC |
| M29.txt | SEQ ID NO 4 | CGATCAAGGAGTTCTTCGGCACCAGCCAGCTGTCCCAGTTCATGGACCAGAACAACCCGC |
| M30.txt | SEQ ID NO 5 | CGATCAAGGAGTTCTTCGGCACCAGCCAGCTGTCCCAGTTCATGGACCAGAACAACCCGC |
| M31.txt | SEQ ID NO 6 | CGATCAAGGAGTTCTTCGGCACCAGCCAGCTGTCCCAGTTCATGGACCAGAACAACCCGC |
| M32.txt | SEQ ID NO 7 | CGATCAAGGAGTTCTTCGGCACCAGCCAGCTGTCCCAGTTCATGGACCAGAACAACCCGC |
| M33.txt | SEQ ID NO 8 | CGATCAAGGAGTTCTTCGGCACCAGCCAGCTGTCCCAGTTCATGGACCAGAACAACCCGC |
| M34.txt | SEQ ID NO 9 | CGATCAAGGAGTTCTTCGGCACCAGCCAGCTGTCCCAGTTCATGGACCAGAACAACCCGC |
| M48-new.txt | SEQ ID NO 10 | CGATCAAGGAGTTCTTCGGCACCAGCCAGCTGTCCCAGTTCATGGACCAGAACAACCCGC |
| M49.txt | SEQ ID NO 11 | CGATCAAGGAGTTCTTCGGCACCAGCCAGTTGTCCCAGTTCATGGACCAGAACAACCCGC |
| M64(Mav2).txt | SEQ ID NO 12 | CGATCAAGGAGTTCTTCGGCACCAGCCAGCTGTCCCAGTTCATGGACCAGAACAACCCGC |
| M65(Mav3).txt | SEQ ID NO 13 | CGATCAAGGAGTTCTTCGGCACCAGCCAGCTGTCCCAGTTCATGGACCAGAACAACCCGC |
| M67(Mav5).txt | SEQ ID NO 14 | CGATCAAGGAGTTCTTCGGCACCAGCCAGCTGTCCCAGTTCATGGACCAGAACAACCCGC |
| M69(Mav7).txt | SEQ ID NO 15 | CGATCAAGGAGTTCTTCGGCACCAGCCAGCTGTCCCAGTTCATGGACCAGAACAACCCGC |
| M71(Mav9).txt | SEQ ID NO 16 | CGATCAAGGAGTTCTTCGGCACCAGCCAGCTGTCCCAGTTCATGGACCAGAACAACCCGC |
| M91.txt | SEQ ID NO 17 | CGATCAAGGAGTTCTTCGGCACCAGCCAGCTGTCCCAGTTCATGGACCAGAACAACCCGC |
| M94.txt | SEQ ID NO 18 | CGATCAAGGAGTTCTTCGGCACCAGCCAGCTGTCCCAGTTCATGGACCAGAACAACCCGC |
| M95.txt | SEQ ID NO 19 | CGATCAAGGAGTTCTTCGGCACCAGCCAGCTGTCCCAGTTCATGGACCAGAACAACCCGC |
| M96.txt | SEQ ID NO 20 | CGATCAAGGAGTTCTTCGGCACCAGCCAGCTGTCCCAGTTCATGGACCAGAACAACCCGC |
| M100.txt | SEQ ID NO 21 | CGATCAAGGAGTTCTTCGGCACCAGCCAGCTGTCCCAGTTCATGGACCAGAACAACCCGC |
| M101.txt | SEQ ID NO 22 | CGATCAAGGAGTTCTTCGGCACCAGCCAGCTGTCCCAGTTCATGGACCAGAACAACCCGC |
| M102.txt | SEQ ID NO 23 | CGATCAAGGAGTTCTTCGGCACCAGCCAGCTGTCCCAGTTCATGGACCAGAACAACCCGC |
| M104.txt | SEQ ID NO 24 | CGATCAAGGAGTTCTTCGGCACCAGCCAGCTGTCCCAGTTCATGGACCAGAACAACCCGC |
| M105.txt | SEQ ID NO 25 | CGATCAAGGAGTTCTTCGGCACCAGCCAGCTGTCCCAGTTCATGGACCAGAACAACCCGC |
| M106.txt | SEQ ID NO 26 | CGATCAAGGAATTCTTCGGCACCAGCCAGCTGTCGCAGTTCATGGACCAGAACAACCCGC |
| MY111.txt | SEQ ID NO 27 | CGATCAAGGAGTTCTTCGGCACCAGCCAGCTGTCCCAGTTCATGGACCAGAACAACCCGC |
| M76.txt | SEQ ID NO 28 | CGATCAAGGAGTTCTTCGGCACCAGCCAGCTGAGCCAATTCATGGACCAGAACAACCCGC |
| | | |
| MY451.txt | SEQ ID NO 29 | CGATCAAGGAGTTCTTCGGCACCAGCCAGCTGAGCCAATTCATGGACCAGAACAACCCGC |
| ATCC2-chelnew.txt | SEQ ID NO 30 | CGATCAAGGAGTTCTTCGGAACCAGCCAGCTGTCGCGATTCATGGACCAGAACAACCCGC |
| M10.txt | SEQ ID NO 31 | CGATCAAGGAGTTCTTCGGAACCAGCCAGCTGTCGCGATTCATGGACCAGAACAACCCGC |
| M11-662.txt | SEQ ID NO 32 | CGATCAAGGAGTTCTTCGGAACCAGCCAGCTGTCGCGATTCATGGACCAGAACAACCCGC |
| M12.txt | SEQ ID NO 33 | CGATCAAGGAGTTCTTCGGAACCAGCCAGCTGTCGCGATTCATGGACCAGAACAACCCGC |
| M13_2_662.txt | SEQ ID NO 34 | CGATCAAGGAGTTCTTCGGAACCAGCCAGCTGTCGCGATTCATGGACCAGAACAACCCGC |
| M14.txt | SEQ ID NO 35 | CGATCAAGGAGTTCTTCGGAACCAGCCAGCTCTCGCGATTCATGGACCAGAACAACCCGC |
| M15.txt | SEQ ID NO 36 | CGATCAAGGAGTTCTTCGGAACCAGCCAGCTGTCGCGATTCATGGACCAGAACAACCCGC |
| M16.txt | SEQ ID NO 37 | CGATCAAGGAGTTCTTCGGAACCAGCCAGCTGTCGCGATTCATGGACCAGAACAACCCGC |
| M17_2_662.txt | SEQ ID NO 38 | CGATCAAGGAGTTCTTCGGAACCAGCCAGCTGTCGCGATTCATGGACCAGAACAACCCGC |
| M50.txt | SEQ ID NO 39 | CGATCAAGGAGTTCTTCGGAACCAGCCAGCTGTCGCGATTCATGGACCAGAACAACCCGC |
| M51.txt | SEQ ID NO 40 | CGATCAAGGAGTTCTTCGGAACCAGCCAGCTGTCGCGATTCATGGACCAGAACAACCCGC |
| M115.txt | SEQ ID NO 41 | CGATCAAGGAGTTCTTCGGAACCAGCCAGCTGTCGCGATTCATGGACCAGAACAACCCGC |
| M116.txt | SEQ ID NO 42 | CGATCAAGGAGTTCTTCGGAACCAGCCAGCTGTCGCGATTCATGGACCAGAACAACCCGC |
| M119.txt | SEQ ID NO 43 | CGATCAAGGAGTTCTTCGGAACCAGCCAGCTGTCGCGATTCATGGACCAGAACAACCCGC |
| MY109.txt | SEQ ID NO 44 | CGATCAAGGAGTTCTTCGGAACCAGCCAGCTGTCGCGATTCATGGACCAGAACAACCCGC |
| MY200.txt | SEQ ID NO 45 | CGATCAAGGAGTTCTTCGGAACCAGCCAGCTGTCGCGATTCATGGACCAGAACAACCCGC |
| MY207.txt | SEQ ID NO 46 | CGATCAAGGAGTTCTTCGGAACCAGCCAGCTGTCGCGATTCATGGACCAGAACAACCCGC |
| MY209.txt | SEQ ID NO 47 | CGATCAAGGAGTTCTTCGGAACCAGCCAGCTGTCGCGATTCATGGACCAGAACAACCCGC |
| M122.txt | SEQ ID NO 48 | CGATCAAGGAGTTCTTCGGCACCAGCCAGCTGTCGCGATTCATGGACCAGAACAACCCGC |
| M123.txt | SEQ ID NO 49 | CGATCAAGGAGTTCTTCGGCACCAGCCAGCTGTCGCGATTCATGGACCAGAACAACCCGC |
| M124.txt | SEQ ID NO 50 | CGATCAAGGAGTTCTTCGGCACCAGCCAGCTCTCGCGATTCATGGATCAGAACAACCCGC |
| Atcc3-for.txt | SEQ ID NO 51 | CGATCAAGGAGTTCTTCGGAACGTCGCAGCTGTCGCGATTCATGGATCAGAACAACCCGC |
| M53.txt | SEQ ID NO 52 | CGATCAAGGAATTCTTCGGCACCAGCCAGCTGTCGCGATTCATGGACCAGAACAACCCGC |
| M54.txt | SEQ ID NO 53 | CGATCAAGGAGTTCTTCGGTACCAGCCAGCTGTCGCGATTCATGGACCAGAACAACCCGC |
| M55.txt | SEQ ID NO 54 | CGATCAAGGAGTTCTTCGGAACGTCGCAGCTGTCGCGATTCATGGATCAGAACAACCCGC |
| M56.txt | SEQ ID NO 55 | CGATCAAGGAGTTCTTCGGCACCAGCCAGCTGTCGCGATTCATGGACCAGAACAACCCGC |
| M74(Mav12).txt | SEQ ID NO 56 | CGATCAAGGAGTTCTTCGGAACGTCGCAGCTGTCGCGATTCATGGATCAGAACAACCCGC |

TABLE 1-continued

| | | |
|---|---|---|
| M77.txt | SEQ ID NO 57 | CGATCAAGGAGTTCTTCGGCACCAGCCAGCTGTCGCAGTTCATGGACCAGAACAACCCGC |
| M118.txt | SEQ ID NO 58 | CGATCAAGGAGTTCTTCGGCACCAGCCAGCTGTCGCAGTTCATGGACCAGAACAACCCGC |
| MY221.txt | SEQ ID NO 59 | CGATCAAGGAGTTCTTCGGAACGTCGCAGCTGTCGCAGTTCATGGATCAGAACAACCCGC |
| MY223.txt | SEQ ID NO 60 | CGATCAAGGAGTTCTTCGGCACCAGCCAGCTGTCGCAGTTCATGGACCAGAACAACCCGC |
| MY225.txt | SEQ ID NO 61 | CGATCAAGGAGTTCTTCGGAACGTCGCAGCTGTCGCAGTTCATGGATCAGAACAACCCGC |
| My341.txt | SEQ ID NO 62 | CGATCAAGGAGTTCTTCGGAACGTCGCAGCTGTCGCAGTTCATGGATCAGAACAACCCGC |
| My715.txt | SEQ ID NO 63 | CGATCAAGGAGTTCTTCGGAACGTCGCAGCTGTCGCAGTTCATGGATCAGAACAACCCGC |
| MY470.txt | SEQ ID NO 64 | CGATCAAGGAGTTCTTCGGAACCAGCCAGCTGTCGCAGTTCATGGACCAGAACAACCCGC |
| Atcc4-go.txt | SEQ ID NO 65 | CGATCAAGGAGTTCTTCGGCACCAGCCAGCTCTCGCAGTTCATGGACCAGAACAACCCGC |
| ATCC4-0-Gord.txt | SEQ ID NO 66 | CGATCAAGGAGTTCTTCGGCACCAGCCAGCTCTCGCAGTTCATGGACCAGAACAACCCGC |
| M78(lz).txt | SEQ ID NO 67 | CGATCAAGGAGTTCTTCGGCACCAGCCAGCTCTCGCAGTTCATGGACCAGAACAACCCGC |
| M79(jd).txt | SEQ ID NO 68 | CGATCAAGGAGTTCTTCGGCACCAGCCAGCTGTCGCAGTTCATGGACCAGAACAACCCGC |
| M80(lg).txt | SEQ ID NO 69 | CGATCAAGGAGTTCTTCGGCACCAGCCAGCTCTCGCAGTTCATGGACCAGAACAACCCGC |
| M81(ll).txt | SEQ ID NO 70 | CGATCAAGGAGTTCTTCGGCACCAGCCAGCTCTCGCAGTTCATGGACCAGAACAACCCGC |
| M82(rm).txt | SEQ ID NO 71 | CGATCAAGGAGTTCTTCGGCACCAGCCAGCTCTCGCAGTTCATGGACCAGAACAACCCGC |
| M83(mb).txt | SEQ ID NO 72 | CGATCAAGGAGTTCTTCGGCACCAGCCAGCTCTCGCAGTTCATGGACCAGAACAACCCGC |
| M84(ow).txt | SEQ ID NO 73 | CGATCAAGGAGTTCTTCGGCACCAGCCAGCTCTCGCAGTTCATGGACCAGAACAACCCGC |
| M85(lb).txt | SEQ ID NO 74 | CGATCAAGGAGTTCTTCGGCACCAGCCAGCTCTCGCAGTTCATGGACCAGAACAACCCGC |
| M86(rb).txt | SEQ ID NO 75 | CGATCAAGGAGTTCTTCGGCACCAGCCAGCTCTCGCAGTTCATGGACCAGAACAACCCGC |
| M87(wn).txt | SEQ ID NO 76 | CGATCAAGGAGTTCTTCGGCACCAGCCAGCTCTCGCAGTTCATGGACCAGAACAACCCGC |
| M90(gordDB).txt | SEQ ID NO 77 | CGATCAAGGAGTTCTTCGGCACCAGCCAGCTGTCGCAGTTCATGGACCAGAACAACCCGC |
| m126.txt | SEQ ID NO 78 | CGATCAAGGAGTTCTTCGGCACCAGCCAGCTCTCGCAGTTCATGGACCAGAACAACCCGC |
| M128.txt | SEQ ID NO 79 | CGATCAAGGAGTTCTTCGGCACCAGCCAGCTCTCGCAGTTCATGGACCAGAACAACCCCC |
| My103.txt | SEQ ID NO 80 | CGATCAAGGAGTTCTTCGGCACCAGCCAGCTCTCGCAGTTCATGGACCAGAACAACCCGC |
| MY475.txt | SEQ ID NO 81 | CGATCAAGGAGTTCTTCGGCACCAGCCAGCTCTCGCAGTTCATGGACCAGAACAACCCGC |
| MY476.txt | SEQ ID NO 82 | CGATCAAGGAGTTCTTCGGCACCAGCCAGCTCTCGCAGTTCATGGACCAGAACAACCCGC |
| MY830.txt | SEQ ID NO 83 | CGATCAAGGAGTTCTTCGGCACCAGCCAGCTCTCGCAGTTCATGGACCAGAACAACCCGC |
| Atcc5-int.txt | SEQ ID NO 84 | CGATCAAGGAGTTCTTCGGCACCAGCCAGCTGAGCCAGTTCATGGACCAGAACAACCCGC |
| ATCC5-0int.txt | SEQ ID NO 85 | CGATCAAGGAGTTCTTCGGCACCAGCCAGCTGAGCCAGTTCATGGACCAGAACAACCCGC |
| M18.txt | SEQ ID NO 86 | CGATCAAGGAGTTCTTCGGCACCAGCCAGCTGAGCCAGTTCATGGACCAGAACAACCCGC |
| M19.txt | SEQ ID NO 87 | CGATCAAGGAGTTCTTCGGCACCAGCCAGCTGAGCCAGTTCATGGACCAGAACAACCCGC |
| M20.txt | SEQ ID NO 88 | CGATCAAGGAGTTCTTCGGCACCAGCCAGCTGAGCCAGTTCATGGACCAGAACAACCCGC |
| M21.txt | SEQ ID NO 89 | CGATCAAGGAGTTCTTCGGCACCAGCCAGCTGAGCCAGTTCATGGACCAGAACAACCCGC |
| M22.txt | SEQ ID NO 90 | CGATCAAGGAGTTCTTCGGCACCAGCCAGCTGAGCCAGTTCATGGACCAGAACAACCCGC |
| M23.txt | SEQ ID NO 91 | CGATCAAGGAGTTCTTCGGCACCAGCCAGCTGAGCCAGTTCATGGACCAGAACAACCCGC |
| M24.txt | SEQ ID NO 92 | CGATCAAGGAGTTCTTCGGCACCAGCCAGCTGAGCCAGTTCATGGACCAGAACAACCCGC |
| M25.txt | SEQ ID NO 93 | CGATCAAGGAGTTCTTCGGCACCAGCCAGCTGAGCCAGTTCATGGACCAGAACAACCCGC |
| M26.txt | SEQ ID NO 94 | CGATCAAGGAGTTCTTCGGCACCAGCCAGCTGAGCCAGTTCATGGACCAGAACAACCCGC |
| M27.txt | SEQ ID NO 95 | CGATCAAGGAGTTCTTCGGCACCAGCCAGCTGAGCCAGTTCATGGACCAGAACAACCCGC |
| M28.txt | SEQ ID NO 96 | CGATCAAGGAGTTCTTCGGCACCAGCCAGCTGAGCCAGTTCATGGACCAGAACAACCCGC |
| M107.txt | SEQ ID NO 97 | CGATCAAGGAGTTCTTCGGCACCAGCCAGCTGAGCCAGTTCATGGACCAGAACAACCCGC |
| MY107.txt | SEQ ID NO 98 | CGATCAAGGAGTTCTTCGGCACCAGCCAGCTGAGCCAGTTCATGGACCAGAACAACCCGC |
| MY112.txt | SEQ ID NO 99 | CGATCAAGGAGTTCTTCGGCACCAGCCAGCTGAGCCAGTTCATGGACCAGAACAACCCGC |
| MY312.txt | SEQ ID NO 100 | CGATCAAGGAGTTCTTCGGCACCAGCCAGCTGAGCCAGTTCATGGACCAGAACAACCCGC |
| Atcc6-kan.txt | SEQ ID NO 101 | CCATCAAGGAGTTCTTCGGCACCAGCCAGCTCTCCCAGTTCATGGACCAGAACAACCCGC |
| ATCC6-0Kan.txt | SEQ ID NO 102 | CCATCAAGGAGTTCTTCGGCACCAGCCAGCTCTCCCAGTTCATGGACCAGAACAACCCGC |
| M1.txt | SEQ ID NO 103 | CCATCAAGGAGTTCTTCGGCACCAGCCAGCTCTCCCAGTTCATGGACCAGAACAACCCGC |
| M2.txt | SEQ ID NO 104 | CCATCAAGGAGTTCTTCGGCACCAGCCAGCTCTCCCAGTTCATGGACCAGAACAACCCGC |
| M3.txt | SEQ ID NO 105 | CCATCAAGGAGTTCTTCGGCACCAGCCAGCTCTCCCAGTTCATGGACCAGAACAACCCGC |
| M4.txt | SEQ ID NO 106 | CCATCAAGGAGTTCTTCGGCACCAGCCAGCTGTCGCAGTTCATGGACCAGAACAACCCGT |
| M6.txt | SEQ ID NO 107 | CCATCAAGGAGTTCTTCGGCACCAGCCAGCTCTCCCAGTTCATGGACCAGAACAACCCGC |
| M7.txt | SEQ ID NO 108 | CCATCAAGGAGTTCTTCGGCACCAGCCAGCTCTCCCAGTTCATGGACCAGAACAACCCGC |
| M9.txt | SEQ ID NO 109 | CCATCAAGGAGTTCTTCGGCACCAGCCAGCTCTCCCAGTTCATGGACCAGAACAACCCGC |
| M57.txt | SEQ ID NO 110 | CCATCAAGGAGTTCTTCGGCACCAGCCAGCTCTCCCAGTTCATGGACCAGAACAACCCGC |
| M58.txt | SEQ ID NO 111 | CCATCAAGGAGTTCTTCGGCACCAGCCAGCTCTCCCAGTTCATGGACCAGAACAACCCGC |
| M59.txt | SEQ ID NO 112 | CCATCAAGGAGTTCTTCGGCACCAGCCAGCTCTCCCAGTTCATGGACCAGAACAACCCGC |
| M60.txt | SEQ ID NO 113 | CCATCAAGGAGTTCTTCGGCACCAGCCAGCTCTCCCAGTTCATGGACCAGAACAACCCGC |
| M61.txt | SEQ ID NO 114 | CCATCAAGGAGTTCTTCGGCACCAGCCAGCTCTCCCAGTTCATGGACCAGAACAACCCGC |
| M62.txt | SEQ ID NO 115 | CCATCAAGGAGTTCTTCGGCACCAGCCAGCTCTCCCAGTTCATGGACCAGAACAACCCGC |
| MY106.txt | SEQ ID NO 116 | CCATCAAGGAGTTCTTCGGCACCAGCCAGCTCTCCCAGTTCATGGACCAGAACAACCCGC |
| MY216.txt | SEQ ID NO 117 | CCATCAAGGAGTTCTTCGGCACCAGCCAGCTCTCCCAGTTCATGGACCAGAACAACCCGC |
| MY218.txt | SEQ ID NO 118 | CCATCAAGGAGTTCTTCGGCACCAGCCAGCTCTCCCAGTTCATGGACCAGAACAACCCGC |
| MY226.txt | SEQ ID NO 119 | CCATCAAGGAGTTCTTCGGCACCAGCCAGCTCTCCCAGTTCATGGACCAGAACAACCCGC |
| M109.txt | SEQ ID NO 120 | CGATCAAGGAGTTCTTCGGCACCAGCCAGCTGTCGCAGTTCATGGACCAGAACAACCCGC |
| M111.txt | SEQ ID NO 121 | CGATCAAGGAGTTCTTCGGCACCAGCCAGCTGTCGCAGTTCATGGACCAGAACAACCCGC |
| M112.txt | SEQ ID NO 122 | CGATCAAGGAGTTCTTCGGCACCAGCCAGCTGTCGCAGTTCATGGACCAGAACAACCCGC |
| M113.txt | SEQ ID NO 123 | CGATCAAGGAGTTCTTCGGCACCAGCCAGCTGTCGCAGTTCATGGACCAGAACAACCCGC |
| M114.txt | SEQ ID NO 124 | CGATCAAGGAGTTCTTCGGCACCAGCCAGCTGTCGCAGTTCATGGACCAGAACAACCCGC |
| MY325.txt | SEQ ID NO 125 | CGATCAAGGAGTTCTTCGGCACCAGCCAGCTGTCGCAGTTCATGGACCAGAACAACCCGC |
| MY718.txt | SEQ ID NO 126 | CGATCAAGGAGTTCTTCGGCACCAGCCAGCTGTCGCAGTTCATGGACCAGAACAACCCGC |
| MY214.txt | SEQ ID NO 127 | CGATCAAGGAGTTCTTCGGAACCAGCCAGCTGTCGCAGTTCATGGACCAGAACAACCCGC |
| MY224.txt | SEQ ID NO 128 | CGATCAAGGAGTTCTTCGGAACCAGCCAGCTGTCGCAGTTCATGGACCAGAACAACCCGC |
| My244.txt | SEQ ID NO 129 | CGATCAAGGAGTTCTTCGGAACCAGCCAGCTGTCGCAGTTCATGGACCAGAACAACCCGC |
| My339.txt | SEQ ID NO 130 | CGATCAAGGAGTTCTTCGGAACCAGCCAGCTGTCGCAGTTCATGGACCAGAACAACCCGC |
| My343.txt | SEQ ID NO 131 | CGATCAAGGAGTTCTTCGGAACCAGCCAGCTGTCGCAGTTCATGGACCAGAACAACCCGC |
| MY458.txt | SEQ ID NO 132 | CGATCAAGGAGTTCTTCGGTACGTCGCAGCTGTCGCAGTTCATGGACCAGAACAACCCGC |
| MY809.txt | SEQ ID NO 133 | CGATCAAGGAGTTCTTCGGCACGTCGCAGCTGTCGCAGTTCATGGACCAGAACAACCCGC |
| MY817.txt | SEQ ID NO 134 | CGATCAAGGAGTTCTTCGGCACGTCGCAGCTGTCGCAGTTCATGGACCAGAACAACCCGC |
| MY821.txt | SEQ ID NO 135 | CGATCAAGGAGTTCTTCGGCACGTCGCAGCTGTCGCAGTTCATGGACCAGAACAACCCGC |
| MY824.txt | SEQ ID NO 136 | CGATCAAGGAGTTCTTCGGCACGTSGCAGCTGTCGCAGTTCATGGACCAGAACAACCCGC |
| MY102.txt | SEQ ID NO 137 | CGATCAAGGAGTTCTTCGGCACCAGCCAGCTCTCCCAGTTCATGGACCAGAACAACCCGT |
| My105.txt | SEQ ID NO 138 | CGATCAAGGAGTTCTTCGGCACCAGCCAGCTCTCCCAGTTCATGGACCAGAACAACCCGT |
| MY251.txt | SEQ ID NO 139 | CGATCAAGGAGTTCTTCGGCACCAGCCAGCTCTCCCAGTTCATGGACCAGAACAACCCGT |
| My256.txt | SEQ ID NO 140 | CGATCAAGGAGTTCTTCGGCACCAGCCAGCTCTCCCAGTTCATGGACCAGAACAACCCGT |

TABLE 1-continued

| | | |
|---|---|---|
| My294.txt | SEQ ID NO 141 | CGATCAAGGAGTTCTTCGGCACCAGCCAGCTCTCCCAGTTCATGGACCAGAACAACCCGT |
| MY354.txt | SEQ ID NO 142 | CGATCAAGGAGTTCTTCGGCACCAGCCAGCTCTCCCAGTTCATGGACCAGAACAACCCGC |
| Atcc7-scr.txt | SEQ ID NO 143 | CGATCAAGGAGTTCTTCGGCACCAGCCAGCTCTCGCAGTTCATGGACCAGAACAACCCGC |
| ATCC7-0scr.txt | SEQ ID NO 144 | CGATCAAGGAGTTCTTCGGCACCAGCCAGCTCTCGCAGTTCATGGACCAGAACAACCCGC |
| MY121.txt | SEQ ID NO 145 | CGATCAAGGAGTTCTTCGGCACCAGCCAGCTCTCCCAGTTCATGGACCAGAACAACCCGC |
| MY249.txt | SEQ ID NO 146 | CGATCAAGGAGTTCTTCGGCACCAGCCAGCTCTCGCAGTTCATGGACCAGAACAACCCGC |
| MY372.txt | SEQ ID NO 147 | CGATCAAGGAGTTCTTCGGCACCAGCCAGCTCTCCCAGTTCATGGACCAGAACAACCCGC |
| MY378.txt | SEQ ID NO 148 | CGATCAAGGAGTTCTTCGGCACCAGCCAGCTCTCGCAGTTCATGGACCAGAACAACCCGC |
| MY484.txt | SEQ ID NO 149 | CGATCAAGGAGTTCTTCGGCACCAGCCAGCTGTCGCAGTTCATGGACCAGAACAACCCGC |
| My556.txt | SEQ ID NO 150 | CGATCAAGGAGTTCTTCGGCACCAGCCAGCTCTCGCAGTTCATGGACCAGAACAACCCGC |
| MY563.txt | SEQ ID NO 151 | CGATCAAGGAGTTCTTCGGCACCAGCCAGCTCTCGCAGTTCATGGACCAGAACAACCCGC |
| MY586.txt | SEQ ID NO 152 | CGATCAAGGAGTTCTTCGGCACCAGCCAGCTCTCGCAGTTCATGGACCAGAACAACCCGC |
| Atcc8-sma.txt | SEQ ID NO 153 | CGATCAAGGAGTTCTTCGGCACCAGCCAGCTGTCGCAGTTCATGGACCAGAACAACCCGC |
| M35.txt | SEQ ID NO 154 | CGATCAAGGAGTTCTTCGGAAACGTCGCAGCTGTCGCAGTTCATGGACCAGAACAACCCGC |
| M36.txt | SEQ ID NO 155 | CGATCAAGGAGTTCTTCGGCACCAGCCAGCTGTCGCAGTTCATGGACCAGAACAACCCGC |
| M37.txt | SEQ ID NO 156 | CGATCAAGGAGTTCTTCGGCACCAGCCAGCTGTCGCAGTTCATGGACCAGAACAACCCGC |
| m125.txt | SEQ ID NO 157 | CGATCAAGGAGTTCTTCGGCACCAGCCAGCTCTCGCAGTTCATGGACCAGAACAACCCGC |
| MY143.txt | SEQ ID NO 158 | CGATCAAGGAGTTCTTCGGCACCAGCCAGCTGTCGCAGTTCATGGACCAGAACAACCCGC |
| My104.txt | SEQ ID NO 159 | CGATCAAGGAGTTCTTCGGCACCAGCCAGCTCTCGCAGTTCATGGACCAGAACAACCCGC |
| MY196.txt | SEQ ID NO 160 | CGATCAAGGAGTTCTTCGGCACCAGCCAGCTCTCGCAGTTCATGGACCAGAACAACCCGC |
| MY357.txt | SEQ ID NO 161 | CGATCAAGGAGTTCTTCGGCACCAGCCAGCTCTCGCAGTTCATGGACCAGAACAACCCGC |
| My358.txt | SEQ ID NO 162 | CGATCAAGGAGTTCTTCGGCACCAGCCAGCTCTCGCAGTTCATGGACCAGAACAACCCGC |
| My480.txt | SEQ ID NO 163 | CGATCAAGGAGTTCTTCGGCACCAGCCAGCTCTCGCAGTTCATGGACCAGAACAACCCGC |
| MY212.txt | SEQ ID NO 164 | CGATTAAGGAGTTCTTCGGCACCAGCCAGCTCTCGCAGTTCATGGACCAGAACAACCCGC |
| MY491.txt | SEQ ID NO 165 | CGATCAAGGAGTTCTTCGGCACCAGCCAGCTCTCGCAGTTCATGGACCAGAACAACCCGC |
| MY497.txt | SEQ ID NO 166 | CGATCAAGGAGTTCTTCGGCACCAGCCAGCTCTCGCAGTTCATGGACCAGAACAACCCGC |
| MY816.txt | SEQ ID NO 167 | CGATCAAGGAGTTCTTCGGCACCAGCCAGCTGTCCCAGTTCATGGACCAGAACAACCCGC |
| Atcc10-xen.txt | SEQ ID NO 168 | CGATCAAGGAGTTCTTCGGCACCAGCCAGCTCTCGCAGTTCATGGATCAGAACAACCCGC |
| M38.txt | SEQ ID NO 169 | CGATCAAGGAGTTCTTCGGCACCAGCCAGCTCTCGCAGTTCATGGACTAGAACAACCCGC |
| M39.txt | SEQ ID NO 170 | CGATCAAGGAGTTCTTCGGCACCAGCCAGCTCTCGCAGTTCATGGACTAGAACAACCCGC |
| M40.txt | SEQ ID NO 171 | CGATCAAGGAGTTCTTCGGCACCAGCCAGCTCTCGCAGTTCATGGACTAGAACAACCCGC |
| M41.txt | SEQ ID NO 172 | CGATCAAGGAGTTCTTCGGCACCAGCCAGCTCTCGCAGTTCATGGACTAGAACAACCCGC |
| M42.txt | SEQ ID NO 173 | CGATCAAGGAGTTCTTCGGCACCAGCCAGCTCTCGCAGTTCATGGACTAGAACAACCCGC |
| M43.txt | SEQ ID NO 174 | CGATCAAGGAGTTCTTCGGCACCAGCCAGCTCTCGCAGTTCATGGACTAGAACAACCCGC |
| M44.txt | SEQ ID NO 175 | CGATCAAGGAGTTCTTCGGCACCAGCCAGCTCTCGCAGTTCATGGACTAGAACAACCCGC |
| M45.txt | SEQ ID NO 176 | CGATCAAGGAGTTCTTCGGCACCAGCCAGCTCTCGCAGTTCATGGACTAGAACAACCCGC |
| M46.txt | SEQ ID NO 177 | CGATCAAGGAGTTCTTCGGCACCAGCCAGCTCTCGCAGTTCATGGACTAGAACAACCCGC |
| M47.txt | SEQ ID NO 178 | CGATCAAGGAGTTCTTCGGCACCAGCCAGCTCTCGCAGTTCATGGACTAGAACAACCCGC |
| M68(Mav6).txt | SEQ ID NO 179 | CGATCAAGGAGTTCTTCGGCACCAGCCAGCTCTCGCAGTTCATGGACTAGAACAACCCGC |
| M89.txt | SEQ ID NO 180 | CGATCAAGGAGTTCTTCGGCACCAGCCAGCTCTCGCAGTTCATGGACTAGAACAACCCGC |
| M66(Mav4).txt | SEQ ID NO 181 | CGATCAAGGAGTTCTTCGGCACCAGCCAGCTGTCGCAGTTCATGGACCAGAACAACCCGC |
| | | 70 80 90 100 110 120 |

BASE NOS 121–180

| | | |
|---|---|---|
| ATCC9-Mtb.txt | SEQ ID NO 1 | TGTCGGGGTTGACCCACAAGCGCCGACTGTCGGCGCTGGGGCCCGGCGGTCTGTCACGTG |
| MY621.txt | SEQ ID NO 2 | TGTCGGGCCTGACCCACAAGCGTCGTCTGTCGGCGCTGGGCCCCGGTGGTCTGACCCGTG |
| Atcc1-av.txt | SEQ ID NO 3 | TGTCGGGGCTCACCCACAAGCGCCGCCTGTCGGCGCTGGGCCCGGGTGGTCTGTCCCGGG |
| M29.txt | SEQ ID NO 4 | TGTCGGGGCTCACCCACAAGCGCCGCCTGTCGGCGCTGGGCCCGGGTGGTCTGTCCCGGG |
| M30.txt | SEQ ID NO 5 | TGTCGGGGCTCACCCACAAGCGCCGCCTGTCGGCGCTGGGCCCGGGTGGTCTGTCCCGGG |
| M31.txt | SEQ ID NO 6 | TGTCGGGGCTCACCCACAAGCGCCGCCTGTCGGCGCTGGGCCCGGGTGGTCTGTCCCGGG |
| M32.txt | SEQ ID NO 7 | TGTCGGGGCTCACCCACAAGCGCCGCCTGTCGGCGCTGGGCCCGGGTGGTCTGTCCCGGG |
| M33.txt | SEQ ID NO 8 | TGTCGGGGCTCACCCACAAGCGCCGCCTGTCGGCGCTGGGCCCGGGTGGTCTGTCCCGGG |
| M34.txt | SEQ ID NO 9 | TGTCGGGGCTCACCCACAAGCGCCGCCTGTCGGCGCTGGGCCCGGGTGGTCTGTCCCGGG |
| M48-new.txt | SEQ ID NO 10 | TGTCGGGTCTGACCCACAAGCGCCGCCTGTCGGCGCTGGGCCCGGGTGGTCTGTCCCGGG |
| M49.txt | SEQ ID NO 11 | TGTCGGGGCTCACCCACAAGCGCCGCCTGTCGGCGCTGGGCCCGGGTGGTCTGTCCCGGG |
| M64(Mav2).txt | SEQ ID NO 12 | TGTCGGGGCTCACCCACAAGCGCCGCCTGTCGGCGCTGGGCCCGGGTGGTCTGTCCCGGG |
| M65(Mav3).txt | SEQ ID NO 13 | TGTCGGGGCTCACCCACAAGCGCCGCCTGTCGGCGCTGGGCCCGGGTGGTCTGTCCCGGG |
| M67(Mav5).txt | SEQ ID NO 14 | TGTCGGGGCTCACCCACAAGCGCCGCCTGTCGGCGCTGGGCCCGGGTGGTCTGTCCCGGG |
| M69(Mav7).txt | SEQ ID NO 15 | TGTCGGGGCTCACCCACAAGCGCCGCCTGTCGGCGCTGGGCCCGGGTGGTCTGTCCCGGG |
| M71(Mav9).txt | SEQ ID NO 16 | TGTCGGGGCTCACCCACAAGCGCCGCCTGTCGGCGCTGGGCCCGGGTGGTCTGTCCCGGG |
| M91.txt | SEQ ID NO 17 | TGTCGGGGCTCACCCACAAGCGCCGCCTGTCGGCGCTGGGCCCGGGTGGTCTGTCCCGGG |
| M94.txt | SEQ ID NO 18 | TGTCGGGGCTCACCCACAAGCGCCGCCTGTCGGCGCTGGGCCCGGGTGGTCTGTCCCGGG |
| M95.txt | SEQ ID NO 19 | TGTCGGGGCTCACCCACAAGCGCCGCCTGTCGGCGCTGGGCCCGGGTGGTCTGTCCCGGG |
| M96.txt | SEQ ID NO 20 | TGTCGGGGCTCACCCACAAGCGCCGCCTGTCGGCGCTGGGCCCGGGTGGTCTGTCCCGGG |
| M100.txt | SEQ ID NO 21 | TGTCGGGGCTCACCCACAAGCGCCGCCTGTCGGCGCTGGGCCCGGGTGGTCTGTCCCGGG |
| M101.txt | SEQ ID NO 22 | TGTCGGGGCTCACCCACAAGCGCCGCCTGTCGGCGCTGGGCCCGGGTGGTCTGTCCCGGG |
| M102.txt | SEQ ID NO 23 | TGTCGGGGCTCACCCACAAGCGCCGCCTGTCGGCGCTGGGCCCGGGTGGTCTGTCCCGGG |
| M104.txt | SEQ ID NO 24 | TGTCGGGGCTCACCCACAAGCGCCGCCTGTCGGCGCTGGGCCCGGGTGGTCTGTCCCGGG |
| M105.txt | SEQ ID NO 25 | TGTCGGGGCTCACCCACAAGCGCCGCCTGTCGGCGCTGGGCCCGGGTGGTCTGTCCCGGG |
| M106.txt | SEQ ID NO 26 | TGTCGGGTCTGACCCACAAGCGTCGTCTGTCGGCGCTGGGCCCCGGCGGTCTGTCCCGTG |
| MY111.txt | SEQ ID NO 27 | TGTCGGGGCTCACCCACAAGCGCCGCCTGTCGGCGCTGGGCCCGGGTGGTCTGTCCCGGG |
| M76.txt | SEQ ID NO 28 | TGTCGGGGTTGACCCACAAGCGCCGACTGTCGGCGCTGGGGCCCGGCGGTCTGTCACGTG |
| MY451.txt | SEQ ID NO 29 | TGTCGGGGTTGACCCACAAGCGCCGACTGTCGGCGCTGGGGCCCGGCGGTCTGTCACGTG |

TABLE 1-continued

| | | |
|---|---|---|
| ATCC2-chelnew.txt | SEQ ID NO 30 | TGTCGGGTCTGACCCACAAGCGTCGTCTGTCGGCGCTGGGCCCCGGTGGTCTGACTCGTG |
| M10.txt | SEQ ID NO 31 | TTTCGGGTCTGACCCACAAGCGTCGTCTGTCGGCTCTGGGCCCCGGTGGTCTGACCCGTG |
| M11-662.txt | SEQ ID NO 32 | TTTCGGGTCTGACCCACAAGCGTCGTCTGTCGGCTCTGGGCCCCGGTGGTCTGACCCGTG |
| M12.txt | SEQ ID NO 33 | TGTCGGGTCTGACCCACAAGCGTCGTCTTTCGGCGCTGGGCCCCGGTGGTCTGACCCGTG |
| M13_2_662.txt | SEQ ID NO 34 | TTTCGGGTCTGACCCACAAGCGTCGTCTGTCGGCTCTGGGCCCCGGTGGTCTGACCCGTG |
| M14.txt | SEQ ID NO 35 | TGTCGGGTCTGACCCACAAGCGTCGTCTGTCGGCGCTGGGCCCGGGTGGTCTGACCCGTG |
| M15.txt | SEQ ID NO 36 | TTTCGGGTCTGACCCACAAGCGTCGTCTGTCGGCTCTGGGCCCCGGTGGTCTGACCCGTG |
| M16.txt | SEQ ID NO 37 | TTTCGGGTCTGACCCACAAGCGTCGTCTGTCGGCTCTGGGCCCCGGTGGTCTGACCCGTG |
| M17_2_662.txt | SEQ ID NO 38 | TGTCGGGTCTGACCCACAAGCGTCGTCTTTCGGCGCTGGGCCCCGGTGGTCTGACCCGTG |
| M50.txt | SEQ ID NO 39 | TGTCGGGTCTGACCCACAAGCGTCGTCTGTCGGCGCTGGGCCCCGGTGGTCTGACCCGTG |
| M51.txt | SEQ ID NO 40 | TGTCGGGTCTGACCCACAAGCGTCGTCTTTCGGCGCTGGGCCCCGGTGGTCTGACCCGTG |
| M115.txt | SEQ ID NO 41 | TTTCGGGTCTGACCCACAAGCGTCGTCTGTCGGCTCTGGGCCCCGGTGGTCTGACCCGTG |
| M116.txt | SEQ ID NO 42 | TTTCGGGTCTGACCCACAAGCGTCGTCTGTCGGCTCTGGGCCCCGGTGGTCTGACCCGTG |
| M119.txt | SEQ ID NO 43 | TTTCGGGTCTGACCCACAAGCGTCGTCTGTCGGCTCTGGGCCCCGGTGGTCTGACCCGTG |
| MY109.txt | SEQ ID NO 44 | TTTCGGGTCTGACCCACAAGCGTCGTCTGTCGGCTCTGGGCCCCGGTGGTCTGACCCGTG |
| MY200.txt | SEQ ID NO 45 | TGTCGGGCCTGACCCACAAGCGTCGTCTGTCGGCGCTGGGCCCCGGTGGTCTGACCCGTG |
| MY207.txt | SEQ ID NO 46 | TGTCGGGCCTGACCCACAAGCGTCGTCTGTCGGCGCTGGGCCCCGGTGGTCTGACCCGTG |
| MY209.txt | SEQ ID NO 47 | TGTCGGGCCTGACCCACAAGCGTCGTCTGTCGGCGCTGGGCCCCGGTGGTCTGACCCGTG |
| M122.txt | SEQ ID NO 48 | TCTCGGGCCTGACCCACAAGCGCCGCCTGTCGGCGCTGGGCCCCGGCGGTCTGTCCCGTG |
| M123.txt | SEQ ID NO 49 | TCTCGGGCCTGACCCACAAGCGCCGCCTGTCGGCGCTGGGCCCCGGCGGTCTGTCCCGTG |
| M124.txt | SEQ ID NO 50 | TGTCGGGCCTGACCCACAAGCGCCGCCTGTCGGCGCTGGGCCCCGGTGGTCTGTCCCGTG |
| Atcc3-for.txt | SEQ ID NO 51 | TGTCGGGTCTGACCCACAAGCGTCGTCTGTCGGCGCTGGGCCCCGGCGGTCTGTCCCGTG |
| M53.txt | SEQ ID NO 52 | TGTCGGGTCTGACCCACAAGCGTCGTCTGTCGGCGCTGGGCCCCGGCGGTCTGTCCCGTG |
| M54.txt | SEQ ID NO 53 | TTTCGGGTCTGACCCACAAGCGTCGCCTGTCGGCGCTGGGCCCCGGCGGTCTGTCCCGTG |
| M55.txt | SEQ ID NO 54 | TGTCGGGTCTGACCCACAAGCGTCGTCTGTCGGCGCTGGGCCCCGGCGGTCTGTCCCGTG |
| M56.txt | SEQ ID NO 55 | TGTCGGGTCTGACCCACAAGCGTCGCCTGTCGGCGCTGGGCCCCGGCGGTCTGTCCCGTG |
| M74(Mav12).txt | SEQ ID NO 56 | TGTCGGGTCTGACCCACAAGCGTCGTCTGTCGGCGCTGGGCCCCGGCGGTCTGTCCCGTG |
| M77.txt | SEQ ID NO 57 | TGTCGGGTCTGACCCACAAGCGTCGTCTGTCGGCGCTGGGCCCCGGCGGTCTGTCCCGTG |
| M118.txt | SEQ ID NO 58 | TGTCGGGTCTGACCCACAAGCGTCGCCTGTCGGCGCTGGGCCCCGGCGGTCTGTCCCGTG |
| MY221.txt | SEQ ID NO 59 | TGTCGGGTCTGACCCACAAGCGTCGTCTGTCGGCGCTGGGCCCCGGCGGTCTGTCCCGTG |
| MY223.txt | SEQ ID NO 60 | TGTCGGGTCTGACCCACAAGCGTCGTCTGTCGGCGCTGGGCCCCGGCGGTCTGTCCCGTG |
| MY225.txt | SEQ ID NO 61 | TGTCGGGTCTGACCCACAAGCGTCGTCTGTCGGCGCTGGGCCCCGGCGGTCTGTCCCGTG |
| My341.txt | SEQ ID NO 62 | TGTCGGGTCTGACCCACAAGCGTCGTCTGTCGGCGCTGGGCCCCGGCGGTCTGTCCCGTG |
| My715.txt | SEQ ID NO 63 | TGTCGGGTCTGACCCACAAGCGTCGTCTGTCGGCGCTGGGCCCCGGCGGTCTGTCCCGTG |
| MY470.txt | SEQ ID NO 64 | TCTCCGGTCTCACCCACAAGCGCCGCCTCTCGGCGCTGGGGCCGGGCGGTCTGTCCCGTG |
| Atcc4-go.txt | SEQ ID NO 65 | TGTCGGGTCTGACCCACAAGCGTCGTCTGTCGGCGCTGGGGCCGGGTGGTCTGTCCCGTG |
| ATCC4-0-Gord.txt | SEQ ID NO 66 | TGTCGGGTCTGACCCACAAGCGTCGTCTGTCGGCGCTGGGGCCGGGTGGTCTGTCCCGTG |
| M78(lz).txt | SEQ ID NO 67 | TTTCGGGCCTCACCCACAAGCGTCGTCTGTCGGCGCTGGGGCCCGGCGGTCTGTCCCGTG |
| M79(jd).txt | SEQ ID NO 68 | TGTCGGGTCTGACCCACAAGCGTCGCCTGTCGGCGCTGGGGCCGGGTGGTCTGTCCCGTG |
| M80(lg).txt | SEQ ID NO 69 | TTTCGGGCCTCACCCACAAGCGTCGTCTGTCGGCGCTGGGGCCCGGCGGTCTGTCCCGTG |
| M81(ll).txt | SEQ ID NO 70 | TTTCGGGCCTCACCCACAAGCGTCGTCTGTCGGCGCTGGGGCCCGGCGGTCTGTCCCGTG |
| M82(rm).txt | SEQ ID NO 71 | TGTCGGGTCTGACCCACAAGCGTCGTCTGTCGGCGCTGGGGCCGGGTGGTCTGTCCCGTG |
| M83(mb).txt | SEQ ID NO 72 | TGTCGGGTCTGACCCACAAGCGTCGTCTGTCGGCGCTGGGGCCGGGTGGTCTGTCCCGTG |
| M84(ow).txt | SEQ ID NO 73 | TTTCGGGCCTCACCCACAAGCGTCGTCTGTCGGCGCTGGGGCCCGGCGGTCTGTCCCGTG |
| M85(lb).txt | SEQ ID NO 74 | TGTCGGGTCTGACCCACAAGCGTCGTCTGTCGGCGCTGGGGCCGGGTGGTCTGTCCCGTG |
| M86(rb).txt | SEQ ID NO 75 | TGTCGGGTCTGACCCACAAGCGTCGTCTCTCGGCGCTGGGGCCGGGTGGTCTGTCCCGTG |
| M87(wn).txt | SEQ ID NO 76 | TGTCGGGTCTGACCCACAAGCGTCGTCTGTCGGCGCTGGGGCCGGGTGGTCTGTCCCGTG |
| M90(gordDB).txt | SEQ ID NO 77 | TGTCGGGTCTGACTCACAAGCGTCGTCTGTCGGCGCTGGGGCCTGGCGGTCTGTCACGTG |
| m126.txt | SEQ ID NO 78 | TGTCGGGTCTGACCCACAAGCGTCGTCTGTCGGCGCTGGGGCCGGGTGGTCTGTCCCGTG |
| M128.txt | SEQ ID NO 79 | TGTCGGGTCTCACCCACAAGCGGCGTCTGTCGGCGCTCGGGCCGGGTGGTCTGTCGCGTG |
| My103.txt | SEQ ID NO 80 | TGTCGGGTCTGACCCACAAGCGTCGTCTGTCGGCGCTGGGGCCGGGTGGTCTGTCCCGTG |
| MY475.txt | SEQ ID NO 81 | TCTCGGGTCTGACCCACAAGCGTCGTCTGTCGGCGCTGGGTCCGGGTGGTCTGTCCCGTG |
| MY476.txt | SEQ ID NO 82 | TGTCGGGTCTGACCCACAAGCGTCGTCTGTCGGCGCTGGGGCCGGGTGGTCTGTCCCGTG |
| MY830.txt | SEQ ID NO 83 | TGTCCGGTTTGACGCACAAGAGGCGTCTGTCCGCGCTGGGGCCGGGTGGTCTGTCCCGTG |
| Atcc5-int.txt | SEQ ID NO 84 | TGTCCGGTCTGACCCACAAGCGCCGCCTCTCGGCGCTGGGCCCCGGCGGTCTGTCCCGTG |
| ATCC5-0int.txt | SEQ ID NO 85 | TGTCCGGTCTGACCCACAAGCGCCGCCTCTCGGCGCTGGGCCCCGGCGGTCTGTCCCGTG |
| M18.txt | SEQ ID NO 86 | TGTCCGGTCTGACCCACAAGCGCCGCCTCTCGGCGCTGGGCCCCGGCGGTCTGTCCCGTG |
| M19.txt | SEQ ID NO 87 | TGTCCGGTCTGACCCACAAGCGCCGCCTCTCGGCGCTGGGCCCCGGCGGTCTGTCCCGTG |
| M20.txt | SEQ ID NO 88 | TGTCCGGTCTGACCCACAAGCGCCGCCTCTCGGCGCTGGGCCCCGGCGGTCTGTCCCGTG |
| M21.txt | SEQ ID NO 89 | TGTCCGGTCTGACCCACAAGCGCCGCCTCTCGGCGCTGGGCCCCGGCGGTCTGTCCCGTG |
| M22.txt | SEQ ID NO 90 | TGTCCGGTCTGACCCACAAGCGCCGCCTCTCGGCGCTGGGCCCCGGCGGTCTGTCCCGTG |
| M23.txt | SEQ ID NO 91 | TGTCCGGTCTGACCCACAAGCGCCGCCTCTCGGCGCTGGGCCCCGGCGGTCTGTCCCGTG |
| M24.txt | SEQ ID NO 92 | TGTCCGGTCTGACCCACAAGCGCCGCCTCTCGGCGCTGGGCCCCGGCGGTCTGTCCCGTG |
| M25.txt | SEQ ID NO 93 | TGTCCGGTCTGACCCACAAGCGCCGCCTCTCGGCGCTGGGCCCCGGCGGTCTGTCCCGTG |
| M26.txt | SEQ ID NO 94 | TGTCCGGTCTGACCCACAAGCGCCGCCTCTCGGCGCTGGGCCCCGGCGGTCTGTCCCGTG |
| M27.txt | SEQ ID NO 95 | TGTCCGGTCTGACCCACAAGCGCCGCCTCTCGGCGCTGGGCCCCGGCGGTCTGTCCCGTG |
| M28.txt | SEQ ID NO 96 | TGTCCGGTCTGACCCACAAGCGCCGCCTCTCGGCGCTGGGCCCCGGCGGTCTGTCCCGTG |
| M107.txt | SEQ ID NO 97 | TGTCCGGTCTGACCCACAAGCGCCGCCTCTCGGCGCTGGGCCCCGGCGGTCTGTCCCGTG |
| MY107.txt | SEQ ID NO 98 | TGTCCGGTCTGACCCACAAGCGCCGCCTCTCGGCGCTGGGCCCCGGCGGTCTGTCCCGTG |
| MY112.txt | SEQ ID NO 99 | TGTCCGGTCTGACCCACAAGCGCCGCCTCTCGGCGCTGGGCCCCGGCGGTCTGTCCCGTG |
| MY312.txt | SEQ ID NO 100 | TGTCCGGTCTGACCCACAAGCGCCGCCTCTCGGCGCTGGGCCCCGGCGGTCTGTCCCGTG |
| Atcc6-kan.txt | SEQ ID NO 101 | TGTCGGGCCTCACCCACAAGCGCCGGCTTTCGGCGCTGGGGCCGGGCGGTCTGTCCCGGG |
| ATCC6-0Kan.txt | SEQ ID NO 102 | TGTCGGGCCTCACCCACAAGCGCCGGCTTTCGGCGCTGGGGCCGGGCGGTCTGTCCCGGG |
| M1.txt | SEQ ID NO 103 | TGTCGGGCCTCACCCACAAGCGCCGGCTTTCGGCGCTGGGGCCGGGCGGTCTGTCCCGGG |
| M2.txt | SEQ ID NO 104 | TGTCGGGCCTCACCCACAAGCGCCGGCTTTCGGCGCTGGGGCCGGGCGGTCTGTCCCGGG |
| M3.txt | SEQ ID NO 105 | TGTCGGGCCTCACCCACAAGCGCCGGCTTTCGGCGCTGGGGCCGGGCGGTCTGTCCCGGG |
| M4.txt | SEQ ID NO 106 | TGTCGGGCCTGACCCACAAGCGCCGGCTTTCGGCGCTGGGGCCGGGCGGTCTGTCCCGTG |
| M6.txt | SEQ ID NO 107 | TGTCGGGCCTCACCCACAAGCGCCGGCTTTCGGCGCTGGGGCCGGGCGGTCTGTCCCGGG |
| M7.txt | SEQ ID NO 108 | TGTCGGGCCTCACCCACAAGCGCCGGCTTTCGGCGCTGGGGCCGGGCGGTCTGTCCCGGG |
| M9.txt | SEQ ID NO 109 | TGTCGGGCCTCACCCACAAGCGCCGGCTTTCGGCGCTGGGGCCGGGCGGTCTGTCCCGGG |
| M57.txt | SEQ ID NO 110 | TGTCGGGCCTCACCCACAAGCGCCGGCTTTCGGCGCTGGGGCCGGGCGGTCTGTCCCGGG |
| M58.txt | SEQ ID NO 111 | TGTCGGGCCTCACCCACAAGCGCCGGCTTTCGGCGCTGGGGCCGGGCGGTCTGTCCCGGG |
| M59.txt | SEQ ID NO 112 | TGTCGGGCCTCACCCACAAGCGCCGGCTTTCGGCGCTGGGGCCGGGCGGTCTGTCCCGGG |

TABLE 1-continued

| | | |
|---|---|---|
| M60.txt | SEQ ID NO 113 | TGTCGGGCCTCACCCACAAGCGCCGGCTTTCGGCGCCGGGGCCGGGCGGTCTGTCCCGGG |
| M61.txt | SEQ ID NO 114 | TGTCGGGCCTCACCCACAAGCGCCGGCTTTCGGCGCTGGGGCCGGGCGGTCTGTCCCGGG |
| M62.txt | SEQ ID NO 115 | TGTCGGGCCTCACCCACAAGCGCCGGCTTTCGGCGCTGGGGCCGGGCGGTCTGTCCCGGG |
| MY106.txt | SEQ ID NO 116 | TGTCGGGCCTCACCCACAAGCGCCGGCTTTCGGCGCTGGGGCCGGGCGGTCTGTCCCGGG |
| MY216.txt | SEQ ID NO 117 | TGTCGGGCCTCACCCACAAGCGCCGGCTTTCGGCGCTGGGGCCGGGCGGTCTGTCCCGGG |
| MY218.txt | SEQ ID NO 118 | TGTCGGGCCTCACCCACAAGCGCCGGCTTTCGGCGCTGGGGCCGGGCGGTCTGTCCCGGG |
| MY226.txt | SEQ ID NO 119 | TGTCGGGCCTCACCCACAAGCGCCGGCTTTCGGCGCTGGGGCCGGGCGGTCTGTCCCGGG |
| M109.txt | SEQ ID NO 120 | TGTCGGGGCTGACCCACAAGCGCCGGCTGTCGGCGCTGGGCCCGGGTGGTCTGTCGCGTG |
| M111.txt | SEQ ID NO 121 | TGTCGGGGCTGACCCACAAGCGCCGGCTGTCGGCGCTGGGCCCGGGTGGTCTGTCGCGTG |
| M112.txt | SEQ ID NO 122 | TGTCGGGGCTGACCCACAAGCGCCGGCTGTCGGCGCTGGGCCCGGGTGGTCTGTCGCGTG |
| M113.txt | SEQ ID NO 123 | TGTCGGGGCTGACCCACAAGCGCCGGCTGTCGGCGCTGGGCCCGGGTGGTCTGTCGCGTG |
| M114.txt | SEQ ID NO 124 | TGTCGGGGCTGACCCACAAGCGCCGGCTGTCGGCGCTGGGCCCGGGTGGTCTGTCGCGTG |
| MY325.txt | SEQ ID NO 125 | TGTCGGGGCTGACCCACAAGCGCCGGCTGTCGGCGCTGGGCCCGGGTGGTCTGTCGCGTG |
| MY718.txt | SEQ ID NO 126 | TGTCGGGGCTGACCCACAAGCGCCGGCTGTCGGCGCTGGGCCCGGGTGGTCTGTCGCGTG |
| MY214.txt | SEQ ID NO 127 | TCTCCGGTCTCACCCACAAGCGCCGCCTCTCGGCGCTGGGGCCGGGCGGTCTGTCCCGTG |
| MY224.txt | SEQ ID NO 128 | TCTCCGGTCTCACCCACAAGCGCCGCCTCTCGGCGCTGGGGCCGGGCGGTCTGTCCCGTG |
| My244.txt | SEQ ID NO 129 | TCTCCGGTCTCACCCACAAGCGCCGCCTCTCGGCGCTGGGGCCGGGCGGTCTGTCCCGTG |
| My339.txt | SEQ ID NO 130 | TCTCCGGTCTCACCCACAAGCGCCGCCTCTCGGCGCTGGGGCCGGGCGGTCTGTCCCGTG |
| My343.txt | SEQ ID NO 131 | TCTCCGGTCTCACCCACAAGCGCCGTCTCTCGGCGCTGGGGCCGGGCGGTCTGTCCCGTG |
| MY458.txt | SEQ ID NO 132 | TGTCGGGTCTGACCCACAAGCGTCGTCTGTCGGCGCTGGGCCCCGGTGGTCTGTCCCGTG |
| MY809.txt | SEQ ID NO 133 | TGTCGGGTCTGACCCACAAGCGTCGTCTGTCGGCGCTGGGCCCCGGTGGTCTGTCCCGTG |
| MY817.txt | SEQ ID NO 134 | TGTCGGGTCTGACCCACAAGCGTCGTCTGTCGGCGCTGGGCCCCGGTGGTCTGTCCCGTG |
| MY821.txt | SEQ ID NO 135 | TGTCGGGTCTGACCCACAAGCGTCGTCTGTCGGCGCTGGGCCCCGGTGGTCTGTCCCGTG |
| MY824.txt | SEQ ID NO 136 | TGTCGGGTCTGACCCACAAGCGTCGTCTGTCGGCGCTGGGCCCCGGTGGTCTGTCCCGTG |
| MY102.txt | SEQ ID NO 137 | TGTCGGGTCTGACCCACAAGCGCCGCCTGTCGGCGCTGGGACCGGGCGGTCTGTCGCGTG |
| My105.txt | SEQ ID NO 138 | TGTCGGGTCTGACCCACAAGCGCCGCCTGTCGGCGCTGGGACCGGGCGGTCTGTCGCGTG |
| MY251.txt | SEQ ID NO 139 | TGTCGGGTCTGACCCACAAGCGCCGCCTGTCGGCGCTGGGACCGGGCGGTCTGTCGCGTG |
| My256.txt | SEQ ID NO 140 | TGTCGGGTCTGACCCACAAGCGCCGCCTGTCGGCGCTGGGACCGGGCGGTCTGTCGCGTG |
| My294.txt | SEQ ID NO 141 | TGTCGGGTCTGACCCACAAGCGCCGCCTGTCGGCGCTGGGACCGGGCGGTCTGTCGCGTG |
| MY354.txt | SEQ ID NO 142 | TGTCGGGTCTGACCCACAAGCGCCGGCTGTCGGCGCTGGGGCCCGGTGGTCTGTCCCGTG |
| Atcc7-scr.txt | SEQ ID NO 143 | TGTCGGGCCTGACCCACAAGCGCCGCCTGTCGGCGCTGGGCCCGGGTGGTCTGTCCCGCG |
| ATCC7-0scr.txt | SEQ ID NO 144 | TGTCGGGCCTGACCCACAAGCGCCGCCTGTCGGCGCTGGGCCCGGGTGGTCTGTCCCGCG |
| MY121.txt | SEQ ID NO 145 | TGTCGGGTCTGACCCACAAGCGCCGCCTGTCGGCGCTGGGCCCGGGCGGTCTGTCCCGTG |
| MY249.txt | SEQ ID NO 146 | TGTCGGGCCTGACCCACAAGCGCCGCCTGTCGGCGCTGGGCCCGGGTGGTCTGTCCCGCG |
| MY372.txt | SEQ ID NO 147 | TGTCGGGTCTGACGCACAAGCGCCGCCTGTCGGCGCTGGGCCCCGGCGGTCTGTCCCGTG |
| MY378.txt | SEQ ID NO 148 | TGTCGGGCCTGACCCACAAGCGCCGCCTGTCGGCGCTGGGCCCGGGTGGTCTGTCCCGCG |
| MY484.txt | SEQ ID NO 149 | TGTCGGGTCTGACCCACAAGCGCCGCCTCTCGGCGCTGGGACCCGGTGGTCTGTCCCGTG |
| My556.txt | SEQ ID NO 150 | TGTCGGGTCTTACCCACAAGCGCCGCCTGTCGGCGCTGGGGCCGGGCGGTCTGTCCCGTG |
| MY563.txt | SEQ ID NO 151 | TGTCGGGTCTTACCCACAAGCGCCGCCTGTCGGCGCTGGGGCCGGGCGGTCTGTCCCGTG |
| MY586.txt | SEQ ID NO 152 | TGTCGGGTCTCACCCACAAGCGCCGCCTGTCGGCGCTGGGGCCGGGCGGTCTGTCCCGTG |
| Atcc8-sme.txt | SEQ ID NO 153 | TGTCGGGTCTGACCCACAAGCGTCGTCTTTCGGCGCTGGGCCCCGGCGGTCTGTCCCGTG |
| M35.txt | SEQ ID NO 154 | TGTCCGGTCTGACCCACAAGCGCCGCCTGTCGGCGCTGGGCCCGGGTGGTCTGTCCCGTG |
| M36.txt | SEQ ID NO 155 | TGTCGGGTCTGACCCACAAGCGTCGTCTGTCGGCGCTGGGCCCGGGCGGTCTGTCCCGTG |
| M37.txt | SEQ ID NO 156 | TGTCGGGTCTGACCCACAAGCGTCGTCTTTCGGCGCTGGGCCCCGGCGGTCTGTCCCGTG |
| m125.txt | SEQ ID NO 157 | TCTCCGGTCTGACGCACAAGCGGCGTCTGTCCGCTTTGGGGCCGGGCGGTCTGTCCCGTG |
| MY143.txt | SEQ ID NO 158 | TGTCGGGTCTGACCCACAAGCGTCGTCTTTCGGCGCTGGGCCCCGGCGGTCTGTCCCGTG |
| My104.txt | SEQ ID NO 159 | TCTCCGGTCTGACGCACAAGCGGCGTCTGTCCGCTTTGGGGCCGGGCGGTCTGTCCCGTG |
| My196.txt | SEQ ID NO 160 | TCTCCGGTCTGACGCACAAGCGGCGTCTGTCCGCTTTGGGGCCGGGCGGTCTGTCCCGTG |
| MY357.txt | SEQ ID NO 161 | TCTCCGGTCTGACGCACAAGCGGCGTCTGTCCGCTCTGGGGCCGGGCGGTCTGTCCCGTG |
| My358.txt | SEQ ID NO 162 | TCTCCGGTCTGACGCACAAGCGGCGTCTGTCCGCTCTGGGGCCGGGCGGTCTGTCCCGTG |
| My480.txt | SEQ ID NO 163 | TCTCCGGTCTGACGCACAAGCGGCGTCTGTCCGCTTTGGGGCCGGGCGGTCTGTCCCGTG |
| MY212.txt | SEQ ID NO 164 | TGTCGGGTCTGACCCACAAGCGCCGGCTGTCGGCGCTGGG-CCGGGTGGTCTGTCCCGTG |
| MY491.txt | SEQ ID NO 165 | TGTCGGGTCTGACCCACAAGCGCCGGCTGTCGGCGCTGGG-CCGGGTGGTCTGTCCCGTG |
| MY497.txt | SEQ ID NO 166 | TGTCGGGTCTGACCCACAAGCGCCGGCTGTCGGCGCTGGG-CCGGGTGGTCTGTCCCGTG |
| MY816.txt | SEQ ID NO 167 | TGTCCGGGCTCACCCACAAGCGCCGCCTNTCGGCGCTGGGGCCGGGCGGTCTGTCGCGTG |
| Atcc10-kan.txt | SEQ ID NO 168 | TGTCGGGGCTCACCCACAAGCGGCGGCTCTCGGCGCTTGG-CCGGGCGGTCTGTCGCGCG |
| M38.txt | SEQ ID NO 169 | TGTCGGGGCTCACCCACAAGCGGCGGCTCTCGGCGCTTGGTCCGGGCGGTCTGTCGCGCG |
| M39.txt | SEQ ID NO 169 | TGTCGGGGCTCACCCACAAGCGGCGGCTCTCGGCGCTTGGTCCGGGCGGTCTGTCGCGCG |
| M40.txt | SEQ ID NO 169 | TGTCGGGGCTCACCCACAAGCGGCGGCTCTCGGCGCTTGGTCCGGGCGGTCTGTCGCGCG |
| M41.txt | SEQ ID NO 169 | TGTCGGGGCTCACCCACAAGCGGCGGCTCTCGGCGCTTGGTCCGGGCGGTCTGTCGCGCG |
| M42.txt | SEQ ID NO 169 | TGTCGGGGCTCACCCACAAGCGGCGGCTCTCGGCGCTTGGTCCGGGCGGTCTGTCGCGCG |
| M43.txt | SEQ ID NO 169 | TGTCGGGGCTCACCCACAAGCGGCGGCTCTCGGCGCTTGGTCCGGGCGGTCTGTCGCGCG |
| M44.txt | SEQ ID NO 169 | TGTCGGGGCTCACCCACAAGCGGCGGCTCTCGGCGCTTGGTCCGGGCGGTCTGTCGCGCG |
| M45.txt | SEQ ID NO 169 | TGTCGGGGCTCACCCACAAGCGGCGGCTCTCGGCGCTTGGTCCGGGCGGTCTGTCGCGCG |
| M46.txt | SEQ ID NO 169 | TGTCGGGGCTCACCCACAAGCGGCGGCTCTCGGCGCTTGGTCCGGGCGGTCTGTCGCGCG |
| M47.txt | SEQ ID NO 169 | TGTCGGGGCTCACCCACAAGCGGCGGCTCTCGGCGCTTGGTCCGGGCGGTCTGTCGCGCG |
| M68(Mav6).txt | SEQ ID NO 169 | TGTCGGGGCTCACCCACAAGCGGCGGCTCTCGGCGCTTGGTCCGGGCGGTCTGTCGCGCG |
| M89.txt | SEQ ID NO 169 | TGTCGGGGCTCACCCACAAGCGGCGGCTCTCGGCGCTTGGTCCGGGCGGTCTGTCGCGCG |
| M66(Mav4).txt | SEQ ID NO 169 | TGTCGGGCCTGACCCACAAGCGCCGGCTGTCGGCGCTGGGCCCGGGCGGTCTGTCCCGTG |
| | | 130 140 150 160 170 180 |

TABLE 1-continued

BASE NOS 181–240

| | | |
|---|---|---|
| ATCC9-Mtb.txt | SEQ ID NO 1 | AGCGTGCCGGGCTGGAGGTCCGCGACGTGCACCCGTCGCACTACGGCCGGATGTGCCCGA |
| MY621.txt | SEQ ID NO 2 | AGCGCGCCGGCCTCGAGGTCCGCGACGTGCACCCCTCGCACTACGGCCGCATGTGCCCGA |
| Atcc1-av.txt | SEQ ID NO 3 | AGCGGGCCGGGCTGGAGGTCCGCGACGTGCACCCGTCCCACTACGGCCGGATGTGCCCGA |
| M29.txt | SEQ ID NO 4 | AGCGGGCCGGGCTGGAGGTCCGCGACGTGCACCCGTCCCACTACGGCCGGATGTGCCCGA |
| M30.txt | SEQ ID NO 5 | AGCGGGCCGGGCTGGAGGTCCGCGACGTGCACCCGTCCCACTACGGCCGGATGTGCCCGA |
| M31.txt | SEQ ID NO 6 | AGCGGGCCGGGCTGGAGGTCCGCGACGTGCACCCGTCCCACTACGGCCGGATGTGCCCGA |
| M32.txt | SEQ ID NO 7 | AGCGGGCCGGGCTGGAGGTCCGCGACGTGCACCCGTCCCACTACGGCCGGATGTGCCCGA |
| M33.txt | SEQ ID NO 8 | AGCGGGCCGGGCTGGAGGTCCGCGACGTGCACCCGTCCCACTACGGCCGGATGTGCCCGA |
| M34.txt | SEQ ID NO 9 | AGCGGGCCGGGCTGGAGGTCCGCGACGTGCACCCGTCCCACTACGGCCGGATGTGCCCGA |
| M48-new.txt | SEQ ID NO 10 | AGCGGGCCGGCCTGGAGGTCCGTGACGTGCACCCGTCSCACTACGGCCGGATGTGCCCGA |
| M49.txt | SEQ ID NO 11 | AGCGGGCCGGGCTGGAGGTCCGCGACGTGCACCCGTCCCACTACGGCCGGATGTGCCCGA |
| M64(Mav2).txt | SEQ ID NO 12 | AGCGGGCCGGGCTGGAGGTCCGCGACGTGCACCCGTCCCACTACGGCCGGATGTGCCCGA |
| M65(Mav3).txt | SEQ ID NO 13 | AGCGGGCCGGGCTGGAGGTCCGCGACGTGCACCCGTCCCACTACGGCCGGATGTGCCCGA |
| M67(Mav5).txt | SEQ ID NO 14 | AGCGGGCCGGGCTGGAGGTCCGCGACGTGCACCCGTCCCACTACGGCCGGATGTGCCCGA |
| M69(Mav7).txt | SEQ ID NO 15 | AGCGGGCCGGGCTGGAGGTCCGCGACGTGCACCCGTCCCACTACGGCCGGATGTGCCCGA |
| M71(Mav9).txt | SEQ ID NO 16 | AGCGGGCCGGGCTGGAGGTCCGCGACGTGCACCCGTCCCACTACGGCCGGATGTGCCCGA |
| M91.txt | SEQ ID NO 17 | AGCGGGCCGGGCTGGAGGTCCGCGACGTGCACCCGTCCCACTACGGCCGGATGTGCCCGA |
| M94.txt | SEQ ID NO 18 | AGCGGGCCGGGCTGGAGGTCCGCGACGTGCACCCGTCCCACTACGGCCGGATGTGCCCGA |
| M95.txt | SEQ ID NO 19 | AGCGGGCCGGGCTGGAGGTCCGCGACGTGCACCCGTCCCACTACGGCCGGATGTGCCCGA |
| M96.txt | SEQ ID NO 20 | AGCGGGCCGGGCTGGAGGTCCGCGACGTGCACCCGTCCCACTACGGCCGGATGTGCCCGA |
| M100.txt | SEQ ID NO 21 | AGCGGGCCGGGCTGGAGGTCCGCGACGTGCACCCGTCCCACTACGGCCGGATGTGCCCGA |
| M101.txt | SEQ ID NO 22 | AGCGGGCCGGGCTGGAGGTCCGCGACGTGCACCCGTCCCACTACGGCCGGATGTGCCCGA |
| M102.txt | SEQ ID NO 23 | AGCGGGCCGGGCTGGAGGTCCGCGACGTGCACCCGTCCCACTACGGCCGGATGTGCCCGA |
| M104.txt | SEQ ID NO 24 | AGCGGGCCGGGCTGGAGGTCCGCGACGTGCACCCGTCCCACTACGGCCGGATGTGCCCGA |
| M105.txt | SEQ ID NO 25 | AGCGGGCCGGGCTGGAGGTCCGCGACGTGCACCCGTCCCACTACGGCCGGATGTGCCCGA |
| M106.txt | SEQ ID NO 26 | AGCGCGCCGGCCTTGAGGTCCGCGACGTGCACTCCAGCCACTACGGCCGCATGTGCCCGA |
| MY111.txt | SEQ ID NO 27 | AGCGGGCCGGGCTGGAGGTCCGCGACGTGCACCCGTCCCACTACGGCCGGATGTGCCCGA |
| M76.txt | SEQ ID NO 28 | AGCGTGCCGGGCTGGAGGTCCGCGACGTGCACCCGTCGCACTACGGCCGGATGTGCCCGA |
| MY451.txt | SEQ ID NO 29 | AGCGTGCCGGGCTGGAGGTCCGCGACGTGCACCCGTCGCACTACGGCCGGATGTGCCCGA |
| | | |
| ATCC2-chelnew.txt | SEQ ID NO 30 | ACCGCGCCGGCCTTGAGGTCCGCGACGTGCACCCCTCGCACTACGGCCGCATGTGCCCGA |
| M10.txt | SEQ ID NO 31 | ACCGCGCTGGCCTTGAGGTCCGCGACGTGCACCCCTCGCACTACGGCCGCATGTGCCCGA |
| M11-662.txt | SEQ ID NO 32 | ACCGCGCTGGCCTTGAGGTCCGCGACGTGCACCCCTCGCACTACGGCCGCATGTGCCCGA |
| M12.txt | SEQ ID NO 33 | ACCGCGCCGGCCTTGAGGTCCGCGACGTGCACCCCTCGCACTACGGCCGCATGTGCCCGA |
| M13_2_662.txt | SEQ ID NO 34 | ACCGCGCTGGCCTTGAGGTCCGCGACGTGCACCCCTCGCACTACGGCCGCATGTGCCCGA |
| M14.txt | SEQ ID NO 35 | ACCGCGCCGGCCTTGAGGTCCGTGACGTGCACCCCTCGCACTATGGCCGCATGTGCCCGA |
| M15.txt | SEQ ID NO 36 | ACCGCGCTGGCCTTGAGGTCCGCGACGTGCACCCCTCGCACTACGGCCGCATGTGCCCGA |
| M16.txt | SEQ ID NO 37 | ACCGCGCTGGCCTTGAGGTCCGCGACGTGCACCCCTCGCACTACGGCCGCATGTGCCCGA |
| M17_2_662.txt | SEQ ID NO 38 | ACCGCGCCGGCCTTGAGGTCCGCGACGTGCACCCCTCGCACTACGGCCGCATGTGCCCGA |
| M50.txt | SEQ ID NO 39 | ACCGCGCCGGCCTTGAGGTCCGTGACGTGCACCCCTCGCACTACGGCCGCATGTGCCCGA |
| M51.txt | SEQ ID NO 40 | ACCGCGCCGGCCTTGAGGTCCGCGACGTGCACCCCTCGCACTACGGCCGCATGTGCCCGA |
| M115.txt | SEQ ID NO 41 | ACCGCGCTGGCCTTGAGGTCCGCGACGTGCACCCCTCGCACTACGGCCGCATGTGCCCGA |
| M116.txt | SEQ ID NO 42 | ACCGCGCTGGCCTTGAGGTCCGCGACGTGCACCCCTCGCACTACGGCCGCATGTGCCCGA |
| M119.txt | SEQ ID NO 43 | ACCGCGCTGGCCTTGAGGTCCGCGACGTGCACCCCTCGCACTACGGCCGCATGTGCCCGA |
| MY109.txt | SEQ ID NO 44 | ACCGCGCTGGCCTTGAGGTCCGCGACGTGCACCCCTCGCACTACGGCCGCATGTGCCCGA |
| MY200.txt | SEQ ID NO 45 | ACCGCGCCGGCCTCGAGGTCCGCGACGTGCACCCCTCGCACTACGGCCGCATGTGCCCGA |
| MY207.txt | SEQ ID NO 46 | ACCGCGCCGGCCTCGAGGTCCGCGACGTGCACCCCTCGCACTACGGCCGCATGTGCCCGA |
| MY209.txt | SEQ ID NO 47 | ACCGCGCCGGCCTCGAGGTCCGCGACGTGCACCCCTCGCACTACGGCCGCATGTGCCCGA |
| M122.txt | SEQ ID NO 48 | AGCGCGCCGGCCTCGAGGTCCGCGACGTGCACGCATCGCACTACGGCCGCATGTGCCCGA |
| M123.txt | SEQ ID NO 49 | AGCGCGCCGGCCTCGAGGTCCGCGACGTGCACGCGTCGCACTACGGCCGCATGTGCCCGA |
| M124.txt | SEQ ID NO 50 | AGCGTGCCGGCCTCGAGGTCCGCGACGTGCACTCCAGCCACTACGGCCGCATGTGCCCGA |
| Atcc3-for.txt | SEQ ID NO 51 | AGCGCGCCGGCCTTGAGGTCCGCGACGTCCACTCGTCGCACTACGGCCGCATGTGCCCGA |
| M53.txt | SEQ ID NO 52 | AGCGCGCCGGCCTTGAGGTCCGCGACGTGCACTCCAGCCACTACGGCCGCATGTGCCCGA |
| M54.txt | SEQ ID NO 53 | AGCGTGCCGGCCTTGAGGTCCGCGACGTGCACGCCAGCCACTACGGCCGCATGTGCCCGA |
| M55.txt | SEQ ID NO 54 | AGCGCGCCGGCCTTGAGGTCCGCGACGTCCACTCGTCGCACTACGGCCGCATGTGTCCGA |
| M56.txt | SEQ ID NO 55 | AGCGTGCCGGCCTTGAGGTCCGCGACGTGCACTCCAGCCACTACGGCCGCATGTGCCCGA |
| M74(Mav12).txt | SEQ ID NO 56 | AGCGCGCCGGCCTTGAGGTCCGCGACGTCCACTCGTCGCACTACGGCCGCATGTGTCCGA |

TABLE 1-continued

| | | |
|---|---|---|
| M77.txt | SEQ ID NO 57 | AGCGCGCCGGCCTTGAGGTCCGCGACGTGCACTCCAGCCACTACGGCCGCATGTGCCCGA |
| M118.txt | SEQ ID NO 58 | AGCGTGCCGGCCTTGAGGTCCGCGACGTGCACTCCAGCCACTACGGCCGCATGTGCCCGA |
| MY221.txt | SEQ ID NO 59 | AGCGCGCCGGCCTTGAGGTCCGCGACGTCCACTCGTCGCACTACGGCCGCATGTGCCCGA |
| MY223.txt | SEQ ID NO 60 | AGCGCGCCGGCCTTGAGGTCCGCGACGTGCACTCCAGCCACTACGGCCGCATGTGCCCGA |
| MY225.txt | SEQ ID NO 61 | AGCGCGCCGGCCTTGAGGTCCGCGACGTCCACTCGTCGCACTACGGCCGCATGTGCCCGA |
| My341.txt | SEQ ID NO 62 | AGCGCGCCGGCCTTGAGGTCCGCGACGTCCACTCGTCGCACTACGGCCGCATGTGCCCGA |
| My715.txt | SEQ ID NO 63 | AGCGCGCCGGCCTTGAGGTCCGCGACGTCCACTCGTCGCACTACGGCCGCATGTGTCCGA |
| MY470.txt | SEQ ID NO 64 | AGCGCGCCGGTCTGGAAGTTCGTGACGTGCACCCGTCGCACTACGGCCGGATGTGCCCGA |
| Atcc4-go.txt | SEQ ID NO 65 | AGCGTGCGGGTCTGGAAGTACGTGACGTGCACCCGTCGCACTACGGCCGCATGTGCCCGA |
| ATCC4-0-Gord.txt | SEQ ID NO 66 | AGCGTGCGGTGCTGGAAGTACGTGACGTGCACCCGTCGCACTACGGCCGCATGTGCCCGA |
| M78(lz).txt | SEQ ID NO 67 | AGCGGGCCGGCCTGGAGGTCCGTGACGTCCACCCGTCGCACTACGGCCGCATGTGCCCGA |
| M79(jd).txt | SEQ ID NO 68 | AGCGTGCCGGCCTGGAGGTCCGTGACGTCCACCCGTCGCACTACGGCCGCATGTGCCCGA |
| M80(lg).txt | SEQ ID NO 69 | AGCGGGCCGGCCTGGAGGTCCGTGACGTCCACCCGTCGCACTACGGCCGCATGTGCCCGA |
| M81(ll).txt | SEQ ID NO 70 | AGCGGGCCGGCCTGGAGGTCCGTGACGTCCACCCGTCGCACTACGGCCGCATGTGCCCGA |
| M82(rm).txt | SEQ ID NO 71 | AGCGTGCGGGTCTGGAAGTACGTGACGTGCACCCGTCGCACTACGGCCGCATGTGCCCGA |
| M83(mb).txt | SEQ ID NO 72 | AGCGTGCGGGTCTGGAAGTACGTGACGTGCACCCGTCGCACTACGGCCGCATGTGCCCGA |
| M84(ow).txt | SEQ ID NO 73 | AGCGGGCCGGCCTGGAGGTCCGTGACGTCCACCCGTCGCACTACGGCCGCATGTGCCCGA |
| M85(lb).txt | SEQ ID NO 74 | AGCGTGCGGGTCTGGAAGTACGTGACGTGCACCCGTCGCACTACGGCCGCATGTGCCCGA |
| M86(rb).txt | SEQ ID NO 75 | AGCGCGCCGGTCTGGAGGTCCGTGACGTCCACCCGTCGCACTACGGCCGCATGTGCCCGA |
| M87(wn).txt | SEQ ID NO 76 | AGCGTGCGGGTCTGGAAGTACGTGACGTGCACCCGTCGCACTACGGCCGCATGTGCCCGA |
| M90(gordDB).txt | SEQ ID NO 77 | AGCGCGCCGGCCTGGAAGTCCGTGACGTCCACCCGTCGCACTACGGCCGGATGTGCCCGA |
| m126.txt | SEQ ID NO 78 | AGCGTGCGGGTCTGGAAGTACGTGACGTGCACCCGTCGCACTACGGCCGCATGTGCCCGA |
| M128.txt | SEQ ID NO 79 | AGCGTGCGGGTCTGGAAGTCCGTGACGTCCACCCGTCGCACTACGGCCGCATGTGCCCGA |
| My103.txt | SEQ ID NO 80 | AGCGTGCGGGTCTGGAAGTACGTGACGTGCACCCGTCGCACTACGGCCGCATGTGCCCGA |
| MY475.txt | SEQ ID NO 81 | AGCGCGCCGGTCTGGAGGTCCGTGACGTCCACCCGTCGCACTACGGCCGCATGTGCCCGA |
| MY476.txt | SEQ ID NO 82 | AGCGTGCGGGTCTGGAAGTACGTGACGTGCACCCGTCGCACTACGGCCGCATGTGCCCGA |
| MY830.txt | SEQ ID NO 83 | AGCGGGCCGGCCTGGAGGTCCGTGACGTGCACCCGTCGCACTACGGCCGGATGTGCCCGA |
| Atcc5-int.txt | SEQ ID NO 84 | AGCGCGCCGGCCTGGAGGTCCGTGACGTCCACCCCTCGCACTACGGCCGGATGTGCCCGA |
| ATCC5-0int.txt | SEQ ID NO 85 | AGCGCGCCGGCCTGGAGGTCCGTGACGTCCACCCCTCGCACTACGGCCGGATGTGCCCGA |
| M18.txt | SEQ ID NO 86 | AGCGCGCCGGCCTGGAGGTCCGTGACGTCCACCCCTCGCACTACGGCCGGATGTGCCCGA |
| M19.txt | SEQ ID NO 87 | AGCGCGCCGGCCTGGAGGTCCGTGACGTCCACCCCTCGCACTACGGCCGGATGTGCCCGA |
| M20.txt | SEQ ID NO 88 | AGCGCGCCGGCCTGGAGGTCCGTGACGTCCACCCCTCGCACTACGGCCGGATGTGCCCGA |
| M21.txt | SEQ ID NO 89 | AGCGCGCCGGCCTGGAGGTCCGTGACGTCCACCCCTCGCACTACGGCCGGATGTGCCCGA |
| M22.txt | SEQ ID NO 90 | AGCGCGCCGGCCTGGAGGTCCGTGACGTCCACCCCTCGCACTACGGCCGGATGTGCCCGA |
| M23.txt | SEQ ID NO 91 | AGCGCGCCGGCCTGGAGGTCCGTGACGTCCACCCCTCGCACTACGGCCGGATGTGCCCGA |
| M24.txt | SEQ ID NO 92 | AGCGCGCCGGCCTGGAGGTCCGTGACGTCCACCCCTCGCACTACGGCCGGATGTGCCCGA |
| M25.txt | SEQ ID NO 93 | AGCGCGCCGGCCTGGAGGTCCGTGACGTCCACCCCTCGCACTACGGCCGGATGTGCCCGA |
| M26.txt | SEQ ID NO 94 | AGCGCGCCGGCCTGGAGGTCCGTGACGTCCACCCCTCGCACTACGGCCGGATGTGCCCGA |
| M27.txt | SEQ ID NO 95 | AGCGCGCCGGCCTGGAGGTCCGTGACGTCCACCCCTCGCACTACGGCCGGATGTGCCCGA |
| M28.txt | SEQ ID NO 96 | AGCGCGCCGGCCTGGAGGTCCGTGACGTCCACCCCTCGCACTACGGCCGGATGTGCCCGA |
| M107.txt | SEQ ID NO 97 | AGCGCGCCGGCCTGGAGGTCCGTGACGTCCACCCCTCGCACTACGGCCGGATGTGCCCGA |
| MY107.txt | SEQ ID NO 98 | AGCGCGCCGGCCTGGAGGTCCGTGACGTCCACCCCTCGCACTACGGCCGGATGTGCCCGA |
| MY112.txt | SEQ ID NO 99 | AGCGCGCCGGCCTGGAGGTCCGTGACGTCCACCCCTCGCACTACGGCCGGATGTGCCCGA |
| MY312.txt | SEQ ID NO 100 | AGCGCGCCGGCCTGGAGGTCCGTGACGTCCACCCCTCGCACTACGGCCGGATGTGCCCGA |
| Atcc6-kan.txt | SEQ ID NO 101 | AGCGTGCCGGGCTGGAAGTGCGTGACGTGCACCCGTCGCACTACGGCCGCATGTGCCCGA |
| ATCC6-0Kan.txt | SEQ ID NO 102 | AGCGTGCCGGGCTGGAAGTTCGTGACGTGCACCCGTCGCACTACGGCCGCATGTGCCCGA |
| M1.txt | SEQ ID NO 103 | AGCGTGCCGGGCTGGAAGTGCGTGACGTGCACCCGTCGCACTACGGCCGCATGTGCCCGA |
| M2.txt | SEQ ID NO 104 | AGCGTGCCGGGCTGGAAGTGCGTGACGTGCACCCGTCGCACTACGGCCGCATGTGCCCGA |
| M3.txt | SEQ ID NO 105 | AGCGTGCCGGGCTGGAAGTGCGTGACGTGCACCCGTCGCACTACGGCCGCATGTGCCCGA |
| M4.txt | SEQ ID NO 106 | AGCGTGCCGGCCTGGAAGTGCGTGACGTGCACCCTTCGCACTACGGCCGGATGTGCCCGA |
| M6.txt | SEQ ID NO 107 | AGCGTGCCGGGCTGGAAGTGCGTGACGTGCACCCGTCGCACTACGGCCGCATGTGCCCGA |
| M7.txt | SEQ ID NO 108 | AGCGTGCCGGGCTGGAAGTGCGTGACGTGCACCCGTCGCACTACGGCCGCATGTGCCCGA |
| M9.txt | SEQ ID NO 109 | AGCGTGCCGGGCTGGAAGTGCGTGACGTGCACCCGTCGCACTACGGCCGCATGTGCCCGA |
| M57.txt | SEQ ID NO 110 | AGCGTGCCGGGCTGGAAGTGCGTGACGTGCACCCGTCGCACTACGGCCGCATGTGCCCGA |
| M58.txt | SEQ ID NO 111 | AGCGTGCCGGGCTGGAAGTGCGTGACGTGCACCCGTCGCACTACGGCCGCATGTGCCCGA |
| M59.txt | SEQ ID NO 112 | AGCGTGCCGGGCTGGAAGTGCGTGACGTGCACCCGTCGCACTACGGCCGCATGTGCCCGA |
| M60.txt | SEQ ID NO 113 | AGCGTGCCGGGCTGGAAGTGCGTGACGTGCACCCGTCGCACTACGGCCGCATGTGCCCGA |
| M61.txt | SEQ ID NO 114 | AGCGTGCCGGGCTGGAAGTGCGTGACGTGCACCCGTCGCACTACGGCCGCATGTGCCCGA |
| M62.txt | SEQ ID NO 115 | AGCGTGCCGGGCTGGAAGTGCGTGACGTGCACCCGTCGCACTACGGCCGCATGTGCCCGA |
| MY106.txt | SEQ ID NO 116 | AGCGTGCCGGGCTGGAAGTGCGTGACGTGCACCCGTCGCACTACGGCCGCATGTGCCCGA |
| MY216.txt | SEQ ID NO 117 | AGCGTGCCGGGCTGGAAGTGCGTGACGTGCACCCGTCGCACTACGGCCGCATGTGCCCGA |
| MY218.txt | SEQ ID NO 118 | AGCGTGCCGGGCTGGAAGTGCGTGACGTGCACCCGTCGCACTACGGCCGCATGTGCCCGA |
| MY226.txt | SEQ ID NO 119 | AGCGTGCCGGGCTGGAAGTGCGTGACGTGCACCCGTCGCACTACGGCCGCATGTGCCCGA |
| M109.txt | SEQ ID NO 120 | AGCGTGCCGGCTTGGAGGTCCGTGACGTGCACCCGTCGCACTACGGCCGGATGTGCCCGA |
| M111.txt | SEQ ID NO 121 | AGCGTGCCGGCTTGGAGGTCCGTGACGTGCACCCGTCGCACTACGGCCGGATGTGCCCGA |
| M112.txt | SEQ ID NO 122 | AGCGTGCCGGCTTGGAGGTCCGTGACGTGCACCCGTCGCACTACGGCCGGATGTGCCCGA |
| M113.txt | SEQ ID NO 123 | AGCGTGCCGGCTTGGAGGTCCGTGACGTGCACCCGTCGCACTACGGCCGGATGTGCCCGA |
| M114.txt | SEQ ID NO 124 | AGCGTGCCGGCTTGGAGGTCCGTGACGTGCACCCGTCGCACTACGGCCGGATGTGCCCGA |
| MY325.txt | SEQ ID NO 125 | AGCGTGCCGGCTTGGAGGTCCGTGACGTGCACCCGTCGCACTACGGCCGGATGTGCCCGA |
| MY718.txt | SEQ ID NO 126 | AGCGTGCCGGCTTGGAAGTTCGTGACGTGCACCCGTCGCACTACGGCCGGATGTGCCCGA |
| MY214.txt | SEQ ID NO 127 | AGCGCGCCGGTCTGGAAGTTCGTGACGTGCACCCGTCGCACTACGGCCGGATGTGCCCGA |
| MY224.txt | SEQ ID NO 128 | AGCGCGCCGGTCTGGAAGTTCGTGACGTGCACCCGTCGCACTACGGCCGGATGTGCCCGA |
| My244.txt | SEQ ID NO 129 | AGCGCGCCGGTCTGGAAGTTCGTGACGTGCACCCGTCGCACTACGGCCGGATGTGCCCGA |
| My339.txt | SEQ ID NO 130 | AGCGCGCCGGTCTGGAAGTGCGTGACGTGCACCCGTCGCACTACGGCCGGATGTGCCCGA |
| My343.txt | SEQ ID NO 131 | AGCGCGCCGGTCTGGAAGTGCGTGACGTGCACCCGTCGCACTACGGCCGGATGTGCCCGA |
| MY458.txt | SEQ ID NO 132 | AGCGCGCCGGCCTCGAGGTCCGCGACGTCCACTCGTCGCACTACGGCCGCATGTGCCCGA |
| MY809.txt | SEQ ID NO 133 | AGCGCGCCGGCCTCGAGGTCCGCGACGTCCACTCGTCGCACTACGGCCGCATGTGCCCGA |
| MY817.txt | SEQ ID NO 134 | AGCGCGCCGGCCTCGAGGTCCGCGACGTCCACTCGTCGCACTACGGCCGCATGTGCCCGA |
| MY821.txt | SEQ ID NO 135 | AGCGCGCCGGCCTCGAGGTCCGCGACGTCCACTCGTCGCACTACGGCCGCATGTGCCCGA |
| MY824.txt | SEQ ID NO 136 | AGCGCGCCGGCCTCGAGGTYCGCGACGTCCACTCGTCGCACTACGGCCGCATGTGCCCGA |
| MY102.txt | SEQ ID NO 137 | AGCGGGCCGGCCTGGAAGTTCGTGACGTGCACCCGTCCCACTACGGCCGGATGTGTCCGA |
| My105.txt | SEQ ID NO 138 | AGCGGGCCGGCCTGGAAGTTCGTGACGTGCACCCGTCCCACTACGGCCGGATGTGTCCGA |
| MY251.txt | SEQ ID NO 139 | AGCGGGCCGGCCTGGAAGTTCGTGACGTGCACCCGTCCCACTACGGCCGGATGTGTCCGA |
| MY256.txt | SEQ ID NO 140 | AGCGGGCCGGCCTGGAAGTTCGTGACGTGCACCCGTCCCACTACGGCCGGATGTGTCCGA |

TABLE 1-continued

| | | |
|---|---|---|
| My294.txt | SEQ ID NO 141 | AGCGGGCCGGCCTGGAAGTTCGTGACGTGCACCCGTCCCACTACGGCCGGATGTGTCCGA |
| MY354.txt | SEQ ID NO 142 | AGCGCGCCGGCCTGGAAGTTCGTGACGTGCACCCGAGCCACTACGGCCGGATGTGTCCGA |
| Atcc7-scr.txt | SEQ ID NO 143 | AGCGGGCCGGGCTGGAGGTCCGGGACGTGCACCCGTCGCACTACGGCCGGATGTGCCCGA |
| ATCC7-0scr.txt | SEQ ID NO 144 | AGCGGGCCGGGCTGGAGGTCCGGGACGTGCACCCGTCGCACTACGGCCGGATGTGCCCGA |
| MY121.txt | SEQ ID NO 145 | AGCGGGCCGGCCTCGAGGTGCGCGACGTGCACCCGTCGCACTACGGCCGGATGTGCCCGA |
| MY249.txt | SEQ ID NO 146 | AGCGGGCCGGGCTGGAGGTCCGGGACGTGCACCCGTCGCACTACGGCCGGATGTGCCCGA |
| MY372.txt | SEQ ID NO 147 | AGCGGGCCGGGCTGGAGGTCCGCGACGTGCACCCGTCGCACTACGGCCGGATGTGCCCGA |
| MY378.txt | SEQ ID NO 148 | AGCGGGCCGGGCTGGAGGTCCGGGACGTGCACCCGTCGCACTACGGCCGGATGTGCCCGA |
| MY484.txt | SEQ ID NO 149 | AGCGTGCGGGCCTCGAGGTCCGTGACGTACACCCGTCGCACTACGGCCGGATGTGTCCGA |
| My556.txt | SEQ ID NO 150 | AGCGGGCGGGCCTCGAGGTCCGCGATGTGCACCCGTCGCACTACGGCCGGATGTGTCCGA |
| MY563.txt | SEQ ID NO 151 | AGCGGGCGGGCCTCGAGGTCCGCGATGTGCACCCGTCGCACTACGGCCGGATGTGTCCGA |
| MY586.txt | SEQ ID NO 152 | AGCGGGCTGGCCTCGAGGTCCGAGACGTGCACCCGTCGCACTACGGCCGGATGTGTCCGA |
| Atcc8-sme.txt | SEQ ID NO 153 | AGCGGGCCGGCCTCGAGGTCCGCGACGTGCACCCCAGCCACTACGGCCGCATGTGCCCGA |
| M35.txt | SEQ ID NO 154 | AGCGCGCCGGCCTGGAGGTCCGCGACGTGCACTCCAGCCACTACGGCCGGATGTGCCCGA |
| M36.txt | SEQ ID NO 155 | AGCGCGCCGGCCTGGAGGTCCGCGACGTGCACTCCAGCCACTACGGCCGGATGTGCCCGA |
| M37.txt | SEQ ID NO 156 | AGCGCGCCGGCCTCGAGGTCCGCGACGTGCACCCCAGCCACTACGGCCGCATGTGCCCGA |
| m125.txt | SEQ ID NO 157 | AGCGCGCCGGGCTGGAGGTCCGTGACGTGCACCCGTCGCACTACGGCCGGATGTGCCCGA |
| MY143.txt | SEQ ID NO 158 | AGCGGGCCGGCCTCGAGGTCCGCGACGTGCACCCCAGCCACTACGGCCGCATGTGCCCGA |
| My104.txt | SEQ ID NO 159 | AGCGCGCCGGGCTGGAGGTCCGTGACGTGCACCCGTCGCACTACGGCCGGATGTGCCCGA |
| MY196.txt | SEQ ID NO 160 | AGCGGGCCGGGCTGGAGGTCCGTGACGTGCACCCGTCGCACTACGGCCGGATGTGCCCGA |
| MY357.txt | SEQ ID NO 161 | AGCGGGCCGGGCTGGAGGTCCGTGACGTGCACCCGTCGCACTACGGCCGGATGTGCCCGA |
| My358.txt | SEQ ID NO 162 | AGCGGGCCGGGCTGGAGGTCCGTGACGTGCACCCGTCGCACTACGGCCGGATGTGCCCGA |
| My480.txt | SEQ ID NO 163 | AGCGGGCCGGGCTGGAGGTCCGTGACGTGCACCCGTCGCACTACGGCCGGATGTGCCCGA |
| MY212.txt | SEQ ID NO 164 | AACGGGCCGGGCTTGAGGTCCGTGACGTGCACCCGTCCCACTACGGCCGGATGTGTCCGA |
| MY491.txt | SEQ ID NO 165 | AGCGGGCCGGGCTTGAGGTCCGTGACGTGCACCCGTCCCACTACGGCCGGATGTGTCCGA |
| MY497.txt | SEQ ID NO 166 | AGCGGGCCGGGCTTGAGGTCCGTGACGTGCACCCGTCCCACTACGGCCGGATGTGTCCGA |
| MY816.txt | SEQ ID NO 167 | AGCGCGCGGGCCTCGAGGTTCGTGACGTGCACCCGTCGCACTACGGCCGGATGTGCCCGA |
| ATCC10-xen.txt | SEQ ID NO 168 | AGCGGGCCGGGCTGGAGGTCCGTGACGTGCACTCGAGCCACTACGGCCGGATGTGCCCGA |
| | | |
| M38.txt | SEQ ID NO 169 | AGCGGGCCGGGCTGGAGGTCCGTGACGTGCACTCGAGCCACTACGGCCGGATGTGCCCGA |
| M39.txt | SEQ ID NO 170 | AGCGGGCCGGGCTGGAGGTCCGTGACGTGCACTCGAGCCACTACGGCCGGATGTGCCCGA |
| M40.txt | SEQ ID NO 171 | AGCGGGCCGGGCTGGAGGTCCGTGACGTGCACTCGAGCCACTACGGCCGGATGTGCCCGA |
| M41.txt | SEQ ID NO 172 | AGCGGGCCGGGCTGGAGGTCCGTGACGTGCACTCGAGCCACTACGGCCGGATGTGCCCGA |
| M42.txt | SEQ ID NO 173 | AGCGGGCCGGGCTGGAGGTCCGTGACGTGCACTCGAGCCACTACGGCCGGATGTGCCCGA |
| M43.txt | SEQ ID NO 174 | AGCGGGCCGGGCTGGAGGTCCGTGACGTGCACTCGAGCCACTACGGCCGGATGTGCCCGA |
| M44.txt | SEQ ID NO 175 | AGCGGGCCGGGCTGGAGGTCCGTGACGTGCACTCGAGCCACTACGGCCGGATGTGCCCGA |
| M45.txt | SEQ ID NO 176 | AGCGGGCCGGGCTGGAGGTCCGTGACGTGCACTCGAGCCACTACGGCCGGATGTGCCCGA |
| M46.txt | SEQ ID NO 177 | AGCGGGCCGGGCTGGAGGTCCGTGACGTGCACTCGAGCCACTACGGCCGGATGTGCCCGA |
| M47.txt | SEQ ID NO 178 | AGCGGGCCGGGCTGGAGGTCCGTGACGTGCACTCGAGCCACTACGGCCGGATGTGCCCGA |
| M68(Mav6).txt | SEQ ID NO 179 | AGCGGGCCGGGCTGGAGGTCCGTGACGTGCACTCGAGCCACTACGGCCGGATGTGCCCGA |
| M89.txt | SEQ ID NO 180 | AGCGGGCCGGGCTGGAGGTCCGTGACGTGCACTCGAGCCACTACGGCCGGATGTGCCCGA |
| M66(Mav4).txt | SEQ ID NO 181 | AGCGCGCCGGCCTCGAGGTCCGCGACGTGCACCCGTCGCACTACGGCCGCATGTGCCCGA |
| | | 190 200 210 220 230 240 |

BASE NOS 241–300

| | | |
|---|---|---|
| ATCC9-Mtb.txt | SEQ ID NO 1 | TCGAAACCCCTGAGGGGCCCAACATCGGTCTGATCGGCTCGCTGTCGGTGTACGCGCGGG |
| MY621.txt | SEQ ID NO 2 | TCGAGACCCCGGAAGGCCCGAACATCGGCCTGATCGGCTCGCTGTCGGTGTACGCGCGGG |
| Atcc1-av.txt | SEQ ID NO 3 | TCGAGACCCCGGAAGGTCCCAACATCGGCCTGATCGGCTCGCTGTCGGTGTACGCGCGGG |
| M29.txt | SEQ ID NO 4 | TCGAGACCCCGGAAGGTCCCAACATCGGCCTGATCGGCTCGCTGTCGGTGTATGCGCGGG |
| M30.txt | SEQ ID NO 5 | TCGAGACCCCGGAAGGTCCCAACATCGGCCTGATCGGCTCGCTGTCGGTGTATGCGCGGG |
| M31.txt | SEQ ID NO 6 | TCGAGACCCCGGAAGGTCCCAACATCGGCCTGATCGGCTCGCTGTCGGTGTATGCGCGGG |
| M32.txt | SEQ ID NO 7 | TCGAGACCCCGGAAGGTCCCAACATCGGCCTGATCGGCTCGCTGTCGGTGTATGCGCGGG |
| M33.txt | SEQ ID NO 8 | TCGAGACCCCGGAAGGTCCCAACATCGGCCTGATCGGCTCGCTGTCGGTGTATGCGCGGG |
| M34.txt | SEQ ID NO 9 | TCGAGACCCCGGAAGGTCCCAACATCGGCCTGATCGGCTCGCTGTCGGTGTATGCGCGGG |
| M48-new.txt | SEQ ID NO 10 | TCGAGACCCCGGAAGGTCCCAACATCGGCCTGATCGGCTCGCTGTCGGTGTAYGCGCGGG |
| M49.txt | SEQ ID NO 11 | TCGAGACCCCGGAAGGTCCCAACATCGGCCTGATCGGCTCGCTGTCGGTGTACGCGCGGG |
| M64(Mav2).txt | SEQ ID NO 12 | TCGAGACCCCGGAAGGTCCCAACATCGGCCTGATCGGCTCGCTGTCGGTGTATGCGCGGG |
| M65(Mav3).txt | SEQ ID NO 13 | TCGAGACCCCGGAAGGTCCCAACATCGGCCTGATCGGCTCGCTGTCGGTGTATGCGCGGG |
| M67(Mav5).txt | SEQ ID NO 14 | TCGAGACCCCGGAAGGTCCCAACATCGGCCTGATCGGCTCGCTGTCGGTGTATGCGCGGG |
| M69(Mav7).txt | SEQ ID NO 15 | TCGAGACCCCGGAAGGTCCCAACATCGGCCTGATCGGCTCGCTGTCGGTGTATGCGCGGG |
| M71(Mav9).txt | SEQ ID NO 16 | TCGAGACCCCGGAAGGTCCCAACATCGGCCTGATCGGCTCGCTGTCGGTGTATGCGCGGG |
| M91.txt | SEQ ID NO 17 | TCGAGACCCCGGAAGGTCCCAACATCGGCCTGATCGGCTCGCTGTCGGTGTATGCGCGGG |
| M94.txt | SEQ ID NO 18 | TCGAGACCCCGGAAGGTCCCAACATCGGCCTGATCGGCTCGCTGTCGGTGTATGCGCGGG |
| M95.txt | SEQ ID NO 19 | TCGAGACCCCGGAAGGTCCCAACATCGGCCTGATCGGCTCGCTGTCGGTGTATGCGCGGG |
| M96.txt | SEQ ID NO 20 | TCGAGACCCCGGAAGGTCCCAACATCGGCCTGATCGGCTCGCTGTCGGTGTATGCGCGGG |
| M100.txt | SEQ ID NO 21 | TCGAGACCCCGGAAGGTCCCAACATCGGCCTGATCGGCTCGCTGTCGGTGTATGCGCGGG |
| M101.txt | SEQ ID NO 22 | TCGAGACCCCGGAAGGTCCCAACATCGGCCTGATCGGCTCGCTGTCGGTGTATGCGCGGG |
| M102.txt | SEQ ID NO 23 | TCGAGACCCCGGAAGGTCCCAACATCGGCCTGATCGGCTCGCTGTCGGTGTATGCGCGGG |
| M104.txt | SEQ ID NO 24 | TCGAGACCCCGGAAGGTCCCAACATCGGCCTGATCGGCTCGCTGTCGGTGTATGCGCGGG |
| M105.txt | SEQ ID NO 25 | TCGAGACCCCGGAAGGTCCCAACATCGGCCTGATCGGCTCGCTGTCGGTGTATGCGCGGG |
| M106.txt | SEQ ID NO 26 | TCGAGACCCCTGAAGGTCCGAACATCGGCCTGATCGGCTCGCTGTCGGTGTACGCCCGGG |
| MY111.txt | SEQ ID NO 27 | TCGAGACCCCGGAAGGTCCCAACATCGGCCTGATCGGCTCGCTGTCGGTGTATGCGCGGG |
| M76.txt | SEQ ID NO 28 | TCGAAACCCCTGAAGGGCCCAACATCGGCCTGATCGGCTCGCTGTCGGTGTACGCGCGGG |

TABLE 1-continued

| | | |
|---|---|---|
| MY451.txt | SEQ ID NO 29 | TCGAAACCCCTGAGGGGCCCAACATCGGTCTGATCGGCTCGCTGTCGGTGTACGCGCGGG |
| ATCC2-chelnew.txt | SEQ ID NO 30 | TCGAGACCCCGGAAGGCCCGAACATCGGTCTGATCGGTTCGCTGTCGGTGTACGCGCGGG |
| M10.txt | SEQ ID NO 31 | TCGAGACCCCGGAAGGCCCGAACATCGGCCTGATCGGTTCGCTTTCGGTGTACGCGCGGG |
| M11-662.txt | SEQ ID NO 32 | TCGAGACCCCGGAAGGCCCGAACATCGGCCTGATCGGTTCGCTTTCGGTGTACGCGCGGG |
| M12.txt | SEQ ID NO 33 | TCGAGACCCCGGAAGGCCCGAACATCGGCCTGATCGGTTCGCTGTCGGTGTACGCGCGGG |
| M13_2_662.txt | SEQ ID NO 34 | TCGAGACCCCGGAAGGCCCGAACATCGGCCTGATCGGTTCGCTTTCGGTGTACGCGCGGG |
| M14.txt | SEQ ID NO 35 | TCGAGACCCCGGAAGGCCCGAACATCGGCCTGATCGGCTCGCTGTCGGTGTACGCGCGCG |
| M15.txt | SEQ ID NO 36 | TCGAGACCCCGGAAGGCCCGAACATCGGCCTGATCGGTTCGCTTTCGGTGTACGCGCGGG |
| M16.txt | SEQ ID NO 37 | TCGAGACCCCGGAAGGCCCGAACATCGGCCTGATCGGTTCGCTTTCGGTGTACGCGCGGG |
| M17_2_662.txt | SEQ ID NO 38 | TCGAGACCCCGGAAGGCCCGAACATCGGCCTGATCGGTTCGCTGTCGGTGTACGCGCGGG |
| M50.txt | SEQ ID NO 39 | TCGAGACCCCGGAAGGCCCGAACATCGGCCTGATCGGTTCGCTGTCGGTGTACGCGCGGG |
| M51.txt | SEQ ID NO 40 | TCGAGACCCCGGAAGGCCCGAACATCGGCCTGATCGGTTCGCTGTCGGTGTACGCGCGGG |
| M115.txt | SEQ ID NO 41 | TCGAGACCCCGGAAGGCCCGAACATCGGCCTGATCGGTTCGCTTTCGGTGTACGCGCGGG |
| M116.txt | SEQ ID NO 42 | TCGAGACCCCGGAAGGCCCGAACATCGGCCTGATCGGTTCGCTTTCGGTGTACGCGCGGG |
| M119.txt | SEQ ID NO 43 | TCGAGACCCCGGAAGGCCCGAACATCGGCCTGATCGGTTCGCTTTCGGTGTACGCGCGGG |
| MY109.txt | SEQ ID NO 44 | TCGAGACCCCGGAAGGCCCGAACATCGGCCTGATCGGTTCGCTTTCGGTGTACGCGCGGG |
| MY200.txt | SEQ ID NO 45 | TCGAGACCCCGGAAGGCCCGAACATCGGCCTGATCGGCTCGCTGTCGGTGTACGCGCGCG |
| MY207.txt | SEQ ID NO 46 | TCGAGACCCCGGAAGGCCCGAACATCGGCCTGATCGGCTCGCTGTCGGTGTACGCGCGCG |
| MY209.txt | SEQ ID NO 47 | TCGAGACCCCGGAAGGCCCGAACATCGGCCTGATCGGCTCGCTGTCGGTGTACGCGCGGG |
| M122.txt | SEQ ID NO 48 | TCGAGACCCCGGAGGGTCCGAACATCGGCCTGATCGGCTCGCTGTCGGTGTACGCGCGGG |
| M123.txt | SEQ ID NO 49 | TCGAGACCCCGGAGGGTCCGAACATCGGCCTGATCGGCTCGCTGTCGGTGTACGCGCGGG |
| M124.txt | SEQ ID NO 50 | TCGAGACCCCGGAAGGCCCGAACATCGGCCTGATCGGCTCGCTGTCGGTGTACGCGCGGG |
| Atcc3-for.txt | SEQ ID NO 51 | TCGAGACCCCTGAGGGTCCGAACATCGGTCTGATCGGTTCGCTTTCGGTGTACGCGCGGG |
| M53.txt | SEQ ID NO 52 | TCGAGACCCCTGAGGGTCCGAACATCGGTCTGATCGGCTCGCTGTCGGTGTACGCCCGGG |
| M54.txt | SEQ ID NO 53 | TCGAGACCCCTGAGGGTCCGAACATCGGTCTGATCGGCTCGCTGTCGGTGTACGCCCGGG |
| M55.txt | SEQ ID NO 54 | TCGAGACCCCTGAGGGTCCGAACATCGGTCTGATCGGTTCGCTTTCGGTGTACGCGCGGG |
| M56.txt | SEQ ID NO 55 | TCGAGACCCCTGAGGGTCCGAACATCGGTCTGATCGGTTCGCTGTCGGTGTACGCCCGGG |
| M74(Mav12).txt | SEQ ID NO 56 | TCGAGACCCCTGAGGGTCCGAACATCGGTCTGATCGGTTCGCTTTCGGTGTACGCGCGGG |
| M77.txt | SEQ ID NO 57 | TCGAGACCCCTGAGGGTCCGAACATCGGTCTGATCGGCTCGCTGTCGGTGTACGCCCGGG |
| M118.txt | SEQ ID NO 58 | TCGAGACCCCTGAGGGTCCGAACATCGGTCTGATCGGTTCGCTGTCGGTGTACGCCCGGG |
| MY221.txt | SEQ ID NO 59 | TCGAGACCCCTGAGGGTCCGAACATCGGTCTGATCGGTTCGCTTTCGGTGTACGCGCGGG |
| MY223.txt | SEQ ID NO 60 | TCGAGACCCCTGAGGGTCCGAACATCGGTCTGATCGGCTCGCTGTCGGTGTACGCCCGGG |
| MY225.txt | SEQ ID NO 61 | TCGAGACCCCTGAGGGTCCGAACATCGGTCTGATCGGTTCGCTTTCGGTGTACGCGCGGG |
| My341.txt | SEQ ID NO 62 | TCGAGACCCCTGAGGGTCCGAACATCGGTCTGATCGGTTCGCTTTCGGTGTACGCGCGGG |
| My715.txt | SEQ ID NO 63 | TCGAGACCCCTGAGGGTCCGAACATCGGCCTGATCGGTTCGCTTTCGGTGTACGCGCGGG |
| MY470.txt | SEQ ID NO 64 | TCGAGACGCCGGAAGGGCCGAACATCGGCCTGATCGGTTCACTGTCGGTGTACGCCCGGG |
| Atcc4-go.txt | SEQ ID NO 65 | TCGAGACGCCGGAAGGCCCCAACATCGGCCTGATCGGTTCGCTGTCGGTGTACGCGCGGG |
| ATCC4-0-Gord.txt | SEQ ID NO 66 | TCGAGACGCCGGAAGGCCCGAACATCGGCCTGATCGGTTCGCTGTCGGTGTACGCGCGGG |
| M78(lz).txt | SEQ ID NO 67 | TCGAGACTCCGGAAGGCCCCAACATCGGCCTGATCGGCTCACTGTCGGTGTACGCGCGGG |
| M79(jd).txt | SEQ ID NO 68 | TCGAGACCCCGGAAGGCCCGAACATCGGCCTGATCGGCTCGCTGTCGGTGTACGCGCGGG |
| M80(lg).txt | SEQ ID NO 69 | TCGAGACTCCGGAAGGCCCGAACATCGGCCTGATCGGCTCACTGTCGGTGTACGCGCGGG |
| M81(ll).txt | SEQ ID NO 70 | TCGAGACTCCGGAAGGCCCGAACATCGGCCTGATCGGCTCGCTGTCGGTGTACGCGCGGG |
| M82(rm).txt | SEQ ID NO 71 | TCGAGACGCCGGAAGGCCCGAACATCGGCCTGATCGGTTCGCTGTCGGTGTACGCGCGGG |
| M83(mb).txt | SEQ ID NO 72 | TCGAGACGCCGGAAGGCCCGAACATCGGCCTGATCGGTTCGCTGTCGGTGTACGCGCGGG |
| M84(ow).txt | SEQ ID NO 73 | TCGAGACTCCGGAAGGCCCGAACATCGGCCTGATCGGCTCGCTGTCGGTGTACGCGCGGG |
| M85(lb).txt | SEQ ID NO 74 | TCGAGACGCCGGAAGGCCCGAACATCGGCCTGATCGGTTCGCTGTCGGTGTACGCGCGGG |
| M86(rb).txt | SEQ ID NO 75 | TCGAGACCCCGGAAGGTCCGAACATCGGCCTGATCGGCTCGCTGTCGGTGTACGCGCGGG |
| M87(wn).txt | SEQ ID NO 76 | TCGAGACGCCGGAAGGCCCGAACATCGGCCTGATCGGTTCGCTGTCGGTGTACGCGCGGG |
| M90(gordDB).txt | SEQ ID NO 77 | TCGAGACCCCGGAAGGCCCGAACATCGGCCTGATCGGCTCGCTGTCGGTGTACGCGCGGG |
| m126.txt | SEQ ID NO 78 | TCGAGACGCCGGAAGGCCCGAACATCGGCCTGATCGGTTCGCTGTCGGTGTACGCGCGGG |
| M128.txt | SEQ ID NO 79 | TCGAGACCCCGGAAGGTCCGAACATCGGCCTGATCGGCTCGCTGTCGGTGTACGCGCGGG |
| My103.txt | SEQ ID NO 80 | TCGAGACGCCGGAAGGCCCGAACATCGGCCTGATCGGTTCGCTGTCGGTGTACGCGCGGG |
| MY475.txt | SEQ ID NO 81 | TCGAGACCCCGGAAGGTCCGAACATCGGCCTGATCGGCTCGCTGTCGGTGTACGCGCGGG |
| MY476.txt | SEQ ID NO 82 | TCGAGACGCCGGAAGGCCCGAACATCGGCCTGATCGGTTCGCTGTCGGTGTACGCGCGGG |
| MY830.txt | SEQ ID NO 83 | TCGAGACCCCGGAAGGTCCGAACATCGGTCTGATCGGGTCGCTGTCGGTGTACGCGCGGG |
| Atcc5-int.txt | SEQ ID NO 84 | TCGAGACCCCGGAGGGTCCCAACATCGGTCTGATCGGCTCGCTGTCGGTGTACGCGCGGG |
| ATCC5-0int.txt | SEQ ID NO 85 | TCGAGACCCCGGAGGGTCCCAACATCGGTCTGATCGGCTCGCTGTCGGTGTACGCGCGGG |
| M18.txt | SEQ ID NO 86 | TCGAGACCCCGGAGGGTCCCAACATCGGTCTGATCGGCTCGCTGTCGGTGTACGCGCGGG |
| M19.txt | SEQ ID NO 87 | TCGAGACCCCGGAGGGTCCCAACATCGGTCTGATCGGCTCGCTGTCGGTGTACGCGCGGG |
| M20.txt | SEQ ID NO 88 | TCGAGACCCCGGAGGGTCCCAACATCGGTCTGATCGGCTCGCTGTCGGTGTACGCGCGGG |
| M21.txt | SEQ ID NO 89 | TCGAGACCCCGGAGGGTCCCAACATCGGTCTGATCGGCTCGCTGTCGGTGTACGCGCGGG |
| M22.txt | SEQ ID NO 90 | TCGAGACCCCGGAGGGTCCCAACATCGGTCTGATCGGCTCGCTGTCGGTGTACGCGCGGG |
| M23.txt | SEQ ID NO 91 | TCGAGACCCCGGAGGGTCCCAACATCGGTCTGATCGGCTCGCTGTCGGTGTACGCGCGGG |
| M24.txt | SEQ ID NO 92 | TCGAGACCCCGGAGGGTCCCAACATCGGTCTGATCGGCTCGCTGTCGGTGTACGCGCGGG |
| M25.txt | SEQ ID NO 93 | TCGAGACCCCGGAGGGTCCCAACATCGGTCTGATCGGCTCGCTGTCGGTGTACGCGCGGG |
| M26.txt | SEQ ID NO 94 | TCGAGACCCCGGAGGGTCCCAACATCGGTCTGATCGGCTCGCTGTCGGTGTACGCGCGGG |
| M27.txt | SEQ ID NO 95 | TCGAGACCCCGGAGGGTCCCAACATCGGTCTGATCGGCTCGCTGTCGGTGTACGCGCGGG |
| M28.txt | SEQ ID NO 96 | TCGAGACCCCGGAGGGTCCCAACATCGGTCTGATCGGCTCGCTGTCGGTGTACGCGCGGG |
| M107.txt | SEQ ID NO 97 | TCGAGACCCCGGAGGGTCCCAACATCGGTCTGATCGGCTCGCTGTCGGTGTACGCGCGGG |
| MY107.txt | SEQ ID NO 98 | TCGAGACCCCGGAGGGTCCCAACATCGGTCTGATCGGCTCGCTGTCGGTGTACGCGCGGG |
| MY112.txt | SEQ ID NO 99 | TCGAGACCCCGGAGGGTCCCAACATCGGTCTGATCGGCTCGCTGTCGGTGTACGCGCGGG |
| MY312.txt | SEQ ID NO 100 | TCGAGACCCCGGAGGGTCCCAACATCGGTCTGATCGGCTCGCTGTCGGTGTACGCGCGGG |
| Atcc6-kan.txt | SEQ ID NO 101 | TCGAGACCCCGGAGGGTCCCAACATCGGTCTGATCGGCTCGCTGTCGGTGTACGCGCGGG |
| ATCC6-0Kan.txt | SEQ ID NO 102 | TCGAGACCCCGGAGGGTCCCAACATCGGCCTGATCGGCTCGCTGTCGGTGTACGCACGGG |
| M1.txt | SEQ ID NO 103 | TCGAGACCCCGGAGGGTCCCAACATCGGCCTGATCGGCTCGCTGTCGGTGTACGCACGGG |
| M2.txt | SEQ ID NO 104 | TCGAGACCCCGGAGGGTCCCAACATCGGCCTGATCGGCTCGCTGTCGGTGTACGCACGGG |
| M3.txt | SEQ ID NO 105 | TCGAGACCCCGGAGGGTCCCAACATCGGCCTGATCGGCTCGCTGTCGGTGTACGCACGGG |
| M4.txt | SEQ ID NO 106 | TCGAGACCCCGGAGGGTCCCAACATCGGCCTGATCGGATCGCTGTCGGTGTACGCGCGGG |
| M6.txt | SEQ ID NO 107 | TCGAGACCCCGGAGGGTCCCAACATCGGCCTGATCGGCTCGCTGTCGGTGTACGCACGGG |
| M7.txt | SEQ ID NO 108 | TCGAGACCCCGGAGGGTCCCAACATCGGCCTGATCGGCTCGCTGTCGGTGTACGCACGGG |
| M9.txt | SEQ ID NO 109 | TCGAGACCCCGGAGGGTCCCAACATCGGCCTGATCGGCTCGCTGTCGGTGTACGCACGGG |
| M57.txt | SEQ ID NO 110 | TCGAGACCCCGGAGGGTCCCAACATCGGCCTGATCGGCTCGCTGTCGGTGTACGCACGGG |
| M58.txt | SEQ ID NO 111 | TCGAGACCCCGGAGGGTCCCAACATCGGCCTGATCGGCTCGCTGTCGGTGTACGCACGGG |
| M59(Mav4).txt | SEQ ID NO 112 | TCGAGACCCCGGAGGGTCCCAACATCGGCCTGATCGGCTCGCTGTCGGTGTACGCACGGG |

TABLE 1-continued

| | | |
|---|---|---|
| M60.txt | SEQ ID NO 113 | TCGAGACCCCGGAGGGTCCCAACATCGGCCTGATCGGCTCGCTGTCGGTGTACGCACGGG |
| M61.txt | SEQ ID NO 114 | TCGAGACCCCGGAGGGTCCCAACATCGGCCTGATCGGCTCGCTGTCGGTGTACGCACGGG |
| M62.txt | SEQ ID NO 115 | TCGAGACCCCGGAGGGTCCCAACATCGGCCTGATCGGCTCGCTGTCGGTGTACGCACGGG |
| MY106.txt | SEQ ID NO 116 | TCGAGACCCCGGAGGGTCCCAACATCGGCCTGATCGGCTCGCTGTCGGTGTACGCACGGG |
| MY216.txt | SEQ ID NO 117 | TCGAGACCCCGGAGGGTCCCAACATCGGCCTGATCGGCTCGCTGTCGGTGTACGCACGGG |
| MY218.txt | SEQ ID NO 118 | TCGAGACCCCGGAGGGTCCCAACATCGGCCTGATCGGCTCGCTGTCGGTGTACGCACGGG |
| MY226.txt | SEQ ID NO 119 | TCGAGACCCCGGAGGGTCCCAACATCGGCCTGATCGGCTCGCTGTCGGTGTACGCACGGG |
| M109.txt | SEQ ID NO 120 | TCGAGACCCCGGAGGGTCCGAACATCGGCCTGATCGGTTCGCTGTCGGTGTACGCGCGGG |
| M111.txt | SEQ ID NO 121 | TCGAGACCCCGGAGGGTCCGAACATCGGCCTGATCGGTTCGCTGTCGGTGTACGCGCGGG |
| M112.txt | SEQ ID NO 122 | TCGAGACCCCGGAGGGTCCGAACATCGGCCTGATCGGTTCGCTGTCGGTGTACGCGCGGG |
| M113.txt | SEQ ID NO 123 | TCGAGACCCCGGAGGGTCCGAACATCGGCCTGATCGGTTCGCTGTCGGTGTACGCGCGGG |
| M114.txt | SEQ ID NO 124 | TCGAGACCCCGGAGGGTCCGAACATCGGCCTGATCGGTTCGCTGTCGGTGTACGCGCGGG |
| MY325.txt | SEQ ID NO 125 | TCGAGACCCCGGAGGGTCCGAACATCGGCCTGATCGGTTCGCTGTCGGTGTACGCGCGGG |
| MY718.txt | SEQ ID NO 126 | TCGAGACCCCGGAGGGTCCGAACATCGGCCTGATCGGTTCGCTGTCGGTGTACGCGCGGG |
| MY214.txt | SEQ ID NO 127 | TCGAGACGCCGGAAGGGCCGAACATCGGTCTGATCGGTTCACTGTCGGTGTACGCCCGGG |
| MY224.txt | SEQ ID NO 128 | TCGAGACGCCGGAAGGGCCGAACATCGGTCTGATCGGTTCACTGTCGGTGTACGCCCGGG |
| My244.txt | SEQ ID NO 129 | TCGAGACGCCGGAAGGGCCGAACATCGGTCTGATCGGTTCACTGTCGGTGTACGCCCGGG |
| My339.txt | SEQ ID NO 130 | TCGAGACGCCGGAAGGGCCGAACATCGGTCTGATCGGTTCACTGTCGGTGTACGCCCGGG |
| My343.txt | SEQ ID NO 131 | TCGAGACGCCGGAAGGGCCGAACATCGGTCTGATCGGTTCACTGTCGGTGTACGCCCGGG |
| MY458.txt | SEQ ID NO 132 | TCGAGACCCCTGAAGGCCCGAACATCGGTCTGATCGGCTCGCTGTCGGTGTACGCGCGGG |
| MY809.txt | SEQ ID NO 133 | TCGAGACCCCGGAAGGCCCGAACATCGGTCTGATCGGCTCGCTGTCGGTGTACGCACGGG |
| MY817.txt | SEQ ID NO 134 | TCGAGACCCCGGAAGGCCCGAACATCGGTCTGATCGGCTCGCTGTCGGTGTACGCACGGG |
| MY821.txt | SEQ ID NO 135 | TCGAGACCCCGGAAGGCCCGAACATCGGTCTGATCGGCTCRCTGTCGGTGTACGCACGGG |
| MY824.txt | SEQ ID NO 136 | TCGAGACCCCGGAAGGCCCGAACATCGGTCTGATCGGCTCRCTGTCGGTGTACGCACGGG |
| MY102.txt | SEQ ID NO 137 | TCGAGACCCCGGAAGGCCCGAACATCGGTCTGATCGGGTCGCTGTCGGTGTACGCGCGGG |
| My105.txt | SEQ ID NO 138 | TCGAGACCCCGGAAGGCCCGAACATCGGTCTGATCGGGTCGCTGTCGGTGTACGCGCGGG |
| MY251.txt | SEQ ID NO 139 | TCGAGACCCCGGAAGGCCCGAACATCGGTCTGATCGGGTCGCTGTCGGTGTACGCGCGGG |
| My256.txt | SEQ ID NO 140 | TCGAGACCCCGGAAGGCCCGAACATCGGTCTGATCGGGTCGCTGTCGGTGTACGCGCGGG |
| My294.txt | SEQ ID NO 141 | TCGAGACCCCGGAAGGCCCGAACATCGGTCTGATCGGGTCGCTGTCGGTGTACGCGCGGG |
| MY354.txt | SEQ ID NO 142 | TCGAGACCCCGGAAGGCCCGAACATCGGTCTGATCGGGTCGCTGTCGGTGTACGCGCGGG |
| Atcc7-scr.txt | SEQ ID NO 143 | TCGAGACCCCGGAGGGTCCCAACATCGGTCTGATCGGCTCGCTGTCGGTGTACGCGCGGG |
| ATCC7-0scr.txt | SEQ ID NO 144 | TCGAGACCCCGGAGGGTCCCAACATCGGTCTGATCGGCTCGCTGTCGGTGTACGCGCGGG |
| MY121.txt | SEQ ID NO 145 | TCGAGACCCCGGAGGGTCCCAACATCGGCCTGATCGGCTCGCTGTCGGTGTACGCGCGGG |
| MY249.txt | SEQ ID NO 146 | TCGAGACCCCGGAGGGTCCCAACATCGGTCTGATCGGCTCGCTGTCGGTGTACGCGCGGG |
| MY372.txt | SEQ ID NO 147 | TCGAGACCCCGGAGGGGCCGAACATCGGTCTGATCGGCTCGCTGTCGGTGTACGCCCGGG |
| MY378.txt | SEQ ID NO 148 | TCGAGACCCCGGAGGGTCCCAACATCGGTCTGATCGGCTCGCTGTCGGTGTACGCGCGGG |
| MY484.txt | SEQ ID NO 149 | TCGAAACCCCGGAGGGGCCGAACATCGGTCTGATCGGGTCGCTGTCGGTGTACGCCCGGG |
| My556.txt | SEQ ID NO 150 | TCGAGACCCCCGAGGGTCCGAACATCGGTCTGATCGGGTCGCTATCGGTGTACGCGCGGG |
| MY563.txt | SEQ ID NO 151 | TCGAGACCCCCGAGGGTCCGAACATCGGTCTGATCGGGTCGCTATCGGTGTACGCGCGGG |
| MY586.txt | SEQ ID NO 152 | TCGAGACCCCCGAGGGTCCGAACATCGGTCTGATCGGGTCGCTGTCGGTGTACGCGCGGG |
| Atcc8-sme.txt | SEQ ID NO 153 | TCGAGACCCCTGAGGGTCCCAACATCGGTCTGATCGGTTCGCTGTCGGTGTACGCCCGCG |
| M35.txt | SEQ ID NO 154 | TCGAGACCCCGGAAGGCCCGAACATCGGCCTGATCGGTTCGCTGTCGGTGTACGCGCGGG |
| M36.txt | SEQ ID NO 155 | TCGAGACCCCGGAAGGCCCGAACATCGGCCTGATCGGTTCGCTGTCGGTGTACGCGCGGG |
| M37.txt | SEQ ID NO 156 | TCGAGACCCCTGAGGGTCCCAACATCGGTCTGATCGGTTCGCTGTCGGTGTACGCCGCCG |
| m125.txt | SEQ ID NO 157 | TCGAGACCCCGGAGGGTCCGAATATCGGTCTGATCGGGTCGCTGTCGGTGTACGCACGGG |
| MY143.txt | SEQ ID NO 158 | TCGAGACCCCTGAGGGTCCCAACATCGGTCTGATCGGTTCGCTGTCGGTGTACGCCCGCG |
| My104.txt | SEQ ID NO 159 | TCGAGACCCCGGAGGGTCCGAATATCGGTCTGATCGGGTCGCTGTCGGTGTACGCACGGG |
| MY196.txt | SEQ ID NO 160 | TCGAGACCCCGGAGGGTCCGAATATTGGTCTGATCGGGTCGCTGTCGGTGTACGCACGGG |
| MY357.txt | SEQ ID NO 161 | TCGAGACCCCGGAGGGTCCGAATATCGGTCTGATCGGGTCGCTGTCGGTGTACGCACGGG |
| My358.txt | SEQ ID NO 162 | TCGAGACCCCGGAGGGTCCGAATATCGGTCTGATCGGGTCGCTGTCGGTGTACGCACGGG |
| My480.txt | SEQ ID NO 163 | TCGAGACCCCGGAGGGTCCGAATATCGGTCTGATCGGGTCGCTGTCGGTGTACGCACGGG |
| MY212.txt | SEQ ID NO 164 | TCGAGACCCCGGAGGGTCCGAACATCGGTCTGATCGGCTCGCTGGCGACTTACGCGCGGG |
| MY491.txt | SEQ ID NO 165 | TCGAGACCCCGGAGGGTCCGAACATCGGTCTGATCGGCTCGCTGGCGACTTACGCGCGGG |
| MY497.txt | SEQ ID NO 166 | TCGAGACCCCGGAGGGTCCGAACATCGGTCTGATCGGCTCRCTGGCGACCTACGCGCGGG |
| MY816.txt | SEQ ID NO 167 | TCGAGACCCCCGAGGGTCCGAACATCGGTCTGATCGGTTCRCTGTCGGTGTACGCGCGGG |
| Atcc10-xen.txt | SEQ ID NO 168 | TCGAAACCCCGGAGGGCCCGAACATCGGTTTGATCGGCTCGCTGTCGGTGTACGCGCGGG |
| M38.txt | SEQ ID NO 169 | TCGAAACCCCGGAGGGCCCGAACATCGGTTTGATCGGCTCGCTGTCGGTGTACGCGCGGG |
| M39.txt | SEQ ID NO 170 | TCGAAACCCCGGAGGGCCCGAACATCGGTTTGATCGGCTCGCTGTCGGTGTACGCGCGGG |
| M40.txt | SEQ ID NO 171 | TCGAAACCCCGGAGGGCCCGAACATCGGTTTGATCGGCTCGCTGTCGGTGTACGCGCGGG |
| M41.txt | SEQ ID NO 172 | TCGAAACCCCGGAGGGCCCGAACATCGGTTTGATCGGCTCGCTGTCGGTGTACGCGCGGG |
| M42.txt | SEQ ID NO 173 | TCGAAACCCCGGAGGGCCCGAACATCGGTTTGATCGGCTCGCTGTCGGTGTACGCGCGGG |
| M43.txt | SEQ ID NO 174 | TCGAAACCCCGGAGGGCCCGAACATCGGTTTGATCGGCTCGCTGTCGGTGTACGCGCGGG |
| M44.txt | SEQ ID NO 175 | TCGAAACCCCGGAGGGCCCGAACATCGGTTTGATCGGCTCGCTGTCGGTGTACGCGCGGG |
| M45.txt | SEQ ID NO 176 | TCGAAACCCCGGAGGGCCCGAACATCGGTTTGATCGGCTCGCTGTCGGTGTACGCGCGGG |
| M46.txt | SEQ ID NO 177 | TCGAAACCCCGGAGGGCCCGAACATCGGTTTGATCGGCTCGCTGTCGGTGTACGCGCGGG |
| M47.txt | SEQ ID NO 178 | TCGAAACCCCGGAGGGCCCGAACATCGGTTTGATCGGCTCGCTGTCGGTGTACGCGCGGG |
| M68(Mav6).txt | SEQ ID NO 179 | TCGAAACCCCGGAGGGCCCGAACATCGGTTTGATCGGCTCGCTGTCGGTGTACGCGCGGG |
| M89.txt | SEQ ID NO 180 | TCGAAACCCCGGAGGGCCCGAACATCGGTTTGATCGGCTCGCTGTCGGTGTACGCGCGGG |
| M66(Mav4).txt | SEQ ID NO 181 | TCGAGACCCCGGAGGGTCCGAACATCGGTCTGATCGGCTCGCTGTCGGTGTACGCGAGGG |
| | | 250 260 270 280 290 300 |

TABLE 1-continued

BASE NOS 301–360

| | | |
|---|---|---|
| ATCC9-Mtb.txt | SEQ ID NO 1 | TCAACCCGTTCGGGTTCATCGAAACGCCGTACCGCAAGGTGGTCGACGGCGTGGTTAGCG |
| MY621.txt | SEQ ID NO 2 | TCAACCCGTTCGGTTTCATCGAGACGCCTTACCGGAAGGTCTCGGACGGAGTTGTCACCG |
| Atcc1-av.txt | SEQ ID NO 3 | TCAACCCGTTCGGGTTCATCGAGACGCCGTACCGCAAGGTGGTCGACGGCGTGGTCACCG |
| M29.txt | SEQ ID NO 4 | TCAACCCGTTCGGGTTCATCGAGACGCCGTACCGCAAGGTGGTCGACGGCGTGGTCACCG |
| M30.txt | SEQ ID NO 5 | TCAACCCGTTCGGGTTCATCGAGACGCCGTACCGCAAGGTGGTCGACGGCGTGGTCACCG |
| M31.txt | SEQ ID NO 6 | TCAACCCGTTCGGGTTCATCGAGACGCCGTACCGCAAGGTGGTCGACGGCGTGGTCACCG |
| M32.txt | SEQ ID NO 7 | TCAACCCGTTCGGGTTCATCGAGACGCCGTACCGCAAGGTGGTCGACGGCGTGGTCACCG |
| M33.txt | SEQ ID NO 8 | TCAACCCGTTCGGGTTCATCGAGACGCCGTACCGCAAGGTGGTCGACGGCGTGGTCACCG |
| M34.txt | SEQ ID NO 9 | TCAACCCGTTCGGGTTCATCGAGACGCCGTACCGCAAGGTGGTCGACGGCGTGGTCACCG |
| M48-new.txt | SEQ ID NO 10 | TSAACCCGTTCGGGTTCATCGAGACCCCGTACCGCAAGGTGGTCGACGGTGTGGTCACCG |
| M49.txt | SEQ ID NO 11 | TGAACCCGTTCGGCTTCATCGAGACGCCGTACCGCAAGGTGGTCGACGGCGTGGTCACCG |
| M64(Mav2).txt | SEQ ID NO 12 | TCAACCCGTTCGGGTTCATCGAGACGCCGTACCGCAAGGTGGTCGACGGCGTGGTCACCG |
| M65(Mav3).txt | SEQ ID NO 13 | TCAACCCGTTCGGGTTCATCGAGACGCCGTACCGCAAGGTGGTCGACGGCGTGGTCACCG |
| M67(Mav5).txt | SEQ ID NO 14 | TCAACCCGTTCGGGTTCATCGAGACGCCGTACCGCAAGGTGGTCGACGGCGTGGTCACCG |
| M69(Mav7).txt | SEQ ID NO 15 | TCAACCCGTTCGGGTTCATCGAGACGCCGTACCGCAAGGTGGTCGACGGCGTGGTCACCG |
| M71(Mav9).txt | SEQ ID NO 16 | TCAACCCGTTCGGGTTCATCGAGACGCCGTACCGCAAGGTGGTCGACGGCGTGGTCACCG |
| M91.txt | SEQ ID NO 17 | TCAACCCGTTCGGGTTCATCGAGACGCCGTACCGCAAGGTGGTCGACGGCGTGGTCACCG |
| M94.txt | SEQ ID NO 18 | TCAACCCGTTCGGGTTCATCGAGACGCCGTACCGCAAGGTGGTCGACGGCGTGGTCACCG |
| M95.txt | SEQ ID NO 19 | TCAACCCGTTCGGGTTCATCGAGACGCCGTACCGCAAGGTGGTCGACGGCGTGGTCACCG |
| M96.txt | SEQ ID NO 20 | TCAACCCGTTCGGGTTCATCGAGACGCCGTACCGCAAGGTGGTCGACGGCGTGGTCACCG |
| M100.txt | SEQ ID NO 21 | TCAACCCGTTCGGGTTCATCGAGACGCCGTACCGCAAGGTGGTCGACGGCGTGGTCACCG |
| M101.txt | SEQ ID NO 22 | TCAACCCGTTCGGGTTCATCGAGACGCCGTACCGCAAGGTGGTCGACGGCGTGGTCACCG |
| M102.txt | SEQ ID NO 23 | TCAACCCGTTCGGGTTCATCGAGACGCCGTACCGCAAGGTGGTCGACGGCGTGGTCACCG |
| M104.txt | SEQ ID NO 24 | TCAACCCGTTCGGGTTCATCGAGACGCCGTACCGCAAGGTGGTCGACGGCGTGGTCACCG |
| M105.txt | SEQ ID NO 25 | TCAACCCGTTCGGGTTCATCGAGACGCCGTACCGCAAGGTGGTCGACGGCGTGGTCACCG |
| M106.txt | SEQ ID NO 26 | TCAACCCGTTCGGCTTCATCGAGACCCCGTACCGCAAGGTCGTCGACGGTGTGGTCACCG |
| MY111.txt | SEQ ID NO 27 | TCAACCCGTTCGGGTTCATCGAGACGCCGTACCGCAAGGTGGTCGACGGCGTGGTCACCG |
| M76.txt | SEQ ID NO 28 | TCAACCCGTTCGGGTTCATCGAAACGCCGTACCGCAAGGTGGTCGACGGCGTGGTTAGCG |
| | | |
| MY451.txt | SEQ ID NO 29 | TCAACCCGTTCGGGTTCATCGAAACGCCGTACCGCAAGGTGGTCGACGGCGTGGTTAGCG |
| ATCC2-chelnew.txt | SEQ ID NO 30 | TCAACCCGTTCGGCTTCATCGAGACGCCGTACCGCAAGGTGTCCGAGGGTGTCGTCACCG |
| M10.txt | SEQ ID NO 31 | TCAACCCGTTCGGCTTCATCGAGACGCCGTACCGCAAGGTGTCCGAGGGTGTCGTCACCG |
| M11-662.txt | SEQ ID NO 32 | TCAACCCGTTCGGCTTCATCGAGACGCCGTACCGCAAGGTGTCCGAGGGTGTCGTCACCG |
| M12.txt | SEQ ID NO 33 | TCAACCCGTTCGGCTTCATCGAGACGCCGTACCGCAAGGTGTCCGAGGGTGTCGTCACCG |
| M13_2_662.txt | SEQ ID NO 34 | TCAACCCGTTCGGCTTCATCGAGACGCCGTACCGCAAGGTGTCCGAGGGTGTCGTCACCG |
| M14.txt | SEQ ID NO 35 | TTAACCCGTTCGGCTTCATCGAGACGCCGTACCGCAAGGTGGTCGAGGGTGTCGTCACCG |
| M15.txt | SEQ ID NO 36 | TCAACCCGTTCGGCTTCATCGAGACGCCGTACCGCAAGGTGTCCGAGGGTGTCGTCACCG |
| M16.txt | SEQ ID NO 37 | TCAACCCGTTCGGCTTCATCGAGACGCCGTACCGCAAGGTGTCCGAGGGTGTCGTCACCG |
| M17_2_662.txt | SEQ ID NO 38 | TCAACCCGTTCGGCTTCATCGAGACGCCGTACCGCAAGGTGTCCGAGGGTGTCGTCACCG |
| M50.txt | SEQ ID NO 39 | TCAACCCGTTCGGCTTCATCGAGACGCCGTACCGCAAGGTGTCCGAGGGTGTCGTCACCG |
| M51.txt | SEQ ID NO 40 | TCAACCCGTTCGGCTTCATCGAGACGCCGTACCGCAAGGTGTCCGAGGGTGTCGTCACCG |
| M115.txt | SEQ ID NO 41 | TCAACCCGTTCGGCTTCATCGAGACGCCGTACCGCAAGGTGTCCGAGGGTGTCGTCACCG |
| M116.txt | SEQ ID NO 42 | TCAACCCGTTCGGCTTCATCGAGACGCCGTACCGCAAGGTGTCCGAGGGTGTCGTCACCG |
| M119.txt | SEQ ID NO 43 | TCAACCCGTTCGGCTTCATCGAGACGCCGTACCGCAAGGTGTCCGAGGGTGTCGTCACCG |
| MY109.txt | SEQ ID NO 44 | TCAACCCGTTCGGCTTCATCGAGACGCCGTACCGCAAGGTGTCCGAGGGTGTCGTCACCG |
| MY200.txt | SEQ ID NO 45 | TCAACCCGTTCGGTTTCATCGAGACGCCTTACCGGAAGGTCTCGGACGGAGTTGTCACCG |
| MY207.txt | SEQ ID NO 46 | TCAACCCGTTCGGTTTCATCGAGACGCCTTACCGGAAGGTCTCGGACGGAGTTGTCACCG |
| MY209.txt | SEQ ID NO 47 | TCAACCCGTTCGGTTTCATCGAGACGCCTTACCGGAAGGTCTCGGACGGAGTTGTCACCG |
| M122.txt | SEQ ID NO 48 | TCAACCCGTTCGGCTTCATCGAGACGCCGTACCGCAAGGTCAAGGACGGTGTTGTCACCG |
| M123.txt | SEQ ID NO 49 | TCAACCCGTTCGGCTTCATCGAGACGCCGTACCGCAAGGTCAAGGACGGTGTTGTCACCG |
| M124.txt | SEQ ID NO 50 | TCAACCCGTTCGGCTTCATCGAGACCCCGTACCGCAAGGTCGTCGACGGCGTCGTCAGCG |
| Atcc3-for.txt | SEQ ID NO 51 | TCAACCCGTTCGGTTTCATCGAGACCCCGTACCGCAAGGTCGTCGACGGTGTGGTCACCG |
| M53.txt | SEQ ID NO 52 | TCAACCCGTTCGGCTTCATCGAGACCCCGTACCGCAAGGTCGTCGACGGTGTGGTCACCG |
| M54.txt | SEQ ID NO 53 | TCAACCCGTTCGGCTTCATCGAGACGCCGTACCGCAAGGTCGTCGACGGTGTGGTCACCG |
| M55.txt | SEQ ID NO 54 | TCAACCCGTTCGGTTTCATCGAGACCCCGTACCGCAAGGTCGTCGACGGTGTGGTCACCG |
| M56.txt | SEQ ID NO 55 | TCAACCCGTTCGGCTTCATCGAGACGCCGTACCGCAAGGTCGTCGACGGTGTGGTCTCCG |
| M57(Mav12).txt | SEQ ID NO 56 | TCAACCCGTTCGGTTTCATCGAGACCCCGTACCGCAAGGTCGTCGACGGTGTGGTCACCG |

TABLE 1-continued

| | | |
|---|---|---|
| M77.txt | SEQ ID NO 57 | TCAACCCGTTCGGCTTCATCGAGACGCCTTACCGCAAGGTTGTCGACGGTGTGGTCAGCG |
| M118.txt | SEQ ID NO 58 | TCAACCCGTTCGGCTTCATCGAGACGCCGTACCGCAAGGTCGTCGACGGTGTGGTCTCCG |
| MY221.txt | SEQ ID NO 59 | TCAACCCGTTCGGTTTCATCGAGACCCCGTACCGCAAGGTCGTCGACGGTGTGGTCACCG |
| MY223.txt | SEQ ID NO 60 | TCAACCCGTTCGGCTTCATCGAGACGCCTTACCGCAAGGTTGTCGACGGTGTGGTCAGCG |
| MY225.txt | SEQ ID NO 61 | TCAACCCGTTCGGTTTCATCGAGACCCCGTACCGCAAGGTCGTCGACGGTGTGGTCACCG |
| My341.txt | SEQ ID NO 62 | TCAACCCGTTCGGTTTCATCGAGACCCCGTACCGCAAGGTCGTCGACGGTGTGGTCACCG |
| My715.txt | SEQ ID NO 63 | TCAACCCGTTCGGTTTCATCGAGACCCCGTACCGCAAGGTCGTCGACGGTGTGGTCACCG |
| MY470.txt | SEQ ID NO 64 | TCAACCCGTTCGGGTTCATCGAGACGCCCTACCGCAAGGTGGTCGACGGGGTCGTTTCCG |
| Atcc4-go.txt | SEQ ID NO 65 | TCAACCCGTTCGGCTTCATCGAGACGCCTTATCGGAAGGTGGTGGATGGAGTCGTTTCTG |
| ATCC4-0-Gord.txt | SEQ ID NO 66 | TCAACCCGTTCGGCTTCATCGAGACGCCTTATCGGAAGGTGGTGGATGGAGTCGTTTCTG |
| M78(lz).txt | SEQ ID NO 67 | TGAACCCGTTCGGCTTCATCGAGACGCCGTATAGACGAGTGGTGAGCGGAGTTGTCACGG |
| M79(jd).txt | SEQ ID NO 68 | TCAACCCGTTCGGGTTCATCGAGACGCCGTACCGCAAGGTGGTGGAAGGTGTCGTCTCCG |
| M80(lg).txt | SEQ ID NO 69 | TGAACCCGTTCGGCTTCATCGAGACGCCGTATAGACGAGTGGTGAGCGGAGTTGTCACGG |
| M81(ll).txt | SEQ ID NO 70 | TGAACCCGTTCGGCTTCATCGAGACGCCGTACCGCGAGGTGGTCGACGGTGTGGTGACGG |
| M82(rm).txt | SEQ ID NO 71 | TCAACCCGTTCGGCTTCATCGAGACGCCTTATCGGAAGGTGGTGGATGGAGTCGTTTCTG |
| M83(mb).txt | SEQ ID NO 72 | TCAACCCGTTCGGCTTCATCGAGACGCCTTATCGGAAGGTGGTGGATGGAGTCGTTTCTG |
| M84(ow).txt | SEQ ID NO 73 | TGAACCCGTTCGGCTTCATCGAGACGCCGTACCGCGAGGTGGTCGACGGTGTGGTGACGG |
| M85(lb).txt | SEQ ID NO 74 | TCAACCCGTTCGGCTTCATCGAGACGCCTTATCGGAAGGTGGTGGATGGAGTCGTTTCTG |
| M86(rb).txt | SEQ ID NO 75 | TCAACCCGTTCGGCTTCATCGAGACGCCGTACCGGGAGGTTGTGGACGGGGTCGTCACAG |
| M87(wn).txt | SEQ ID NO 76 | TCAACCCGTTCGGCTTCATCGAGACGCCTTATCGGAAGGTGGTGGATGGAGTCGTTTCTG |
| M90(gordDB).txt | SEQ ID NO 77 | TCAACCCGTTCGGCTTCATCGAGACGCCTTATCGGAAGGTGGTCGACGGTGTGGTCTCCG |
| m126.txt | SEQ ID NO 78 | TCAACCCGTTCGGCTTCATCGAGACGCCTTATCGGAAGGTGGTGGATGGAGTCGTTTCTG |
| M128.txt | SEQ ID NO 79 | TCAACCCGTTCGGCTTCATCGAGACGCCTTATAGACGCGTCGTCAGCGGAGTTGTCACGG |
| My103.txt | SEQ ID NO 80 | TCAACCCGTTCGGCTTCATCGAGACGCCTTATCGGAAGGTGGTGGATGGAGTCGTTTCTG |
| MY475.txt | SEQ ID NO 81 | TCAACCCGTTCGGCTTCATCGAGACGCCGTACCGGGAGGTTGTGGACGGGGTCGTTACAG |
| MY476.txt | SEQ ID NO 82 | TCAACCCGTTCGGCTTCATCGAGACGCCTTATCGGAAGGTGGTGGATGGAGTCGTTTCTG |
| MY830.txt | SEQ ID NO 83 | TCAACCCGTTCGGGTTCATCGAGACGCCCTATCGGAAGGTGGTGGACGGGGTCGTCTCGG |
| Atcc5-int.txt | SEQ ID NO 84 | TGAACCCGTTCGGGTTCATCGAGACCCCGTACCGCAAGGTGGTCGACGGTGTGGTCACCG |
| ATCC5-0int.txt | SEQ ID NO 85 | TGAACCCGTTCGGGTTCATCGAGACCCCGTACCGCAAGGTGGTCGACGGTGTGGTCACCG |
| M18.txt | SEQ ID NO 86 | TGAACCCGTTCGGGTTCATCGAGACCCCGTACCGCAAGGTGGTCGACGGTGTGGTCACCG |
| M19.txt | SEQ ID NO 87 | TGAACCCGTTCGGGTTCATCGAGACCCCGTACCGCAAGGTGGTCGACGGTGTGGTCACCG |
| M20.txt | SEQ ID NO 88 | TGAACCCGTTCGGGTTCATCGAGACCCCGTACCGCAAGGTGGTCGACGGTGTGGTCACCG |
| M21.txt | SEQ ID NO 89 | TGAACCCCTTCGGGTTCATCGAGACCCCGTACCGCAAGGTGGTCGACGGTGTGGTCACCG |
| M22.txt | SEQ ID NO 90 | TGAACCCGTTCGGGTTCATCGAGACCCCGTACCGCAAGGTGGTCGACGGTGTGGTCACCG |
| M23.txt | SEQ ID NO 91 | TGAACCCCTTCGGGTTCATCGAGACCCCGTACCGCAAGGTGGTCGACGGTGTGGTCACCG |
| M24.txt | SEQ ID NO 92 | TGAACCCGTTCGGGTTCATCGAGACCCCGTACCGCAAGGTGGTCGACGGTGTGGTCACCG |
| M25.txt | SEQ ID NO 93 | TGAACCCGTTCGGGTTCATCGAGACCCCGTACCGCAAGGTGGTCGACGGTGTGGTCACCG |
| M26.txt | SEQ ID NO 94 | TGAACCCGTTCGGGTTCATCGAGACCCCGTACCGCAAGGTGGTCGACGGTGTGGTCACCG |
| M27.txt | SEQ ID NO 95 | TGAACCCGTTCGGGTTCATCGAGACCCCGTACCGCAAGGTGGTCGACGGTGTGGTCACCG |
| M28.txt | SEQ ID NO 96 | TGAACCCGTTCGGGTTCATCGAGACCCCGTACCGCAAGGTGGTCGACGGTGTGGTCACCG |
| M107.txt | SEQ ID NO 97 | TGAACCCCTTCGGGTTCATCGAGACCCCGTACCGCAAGGTGGTCGACGGTGTGGTCACCG |
| My107.txt | SEQ ID NO 98 | TGAACCCCTTCGGGTTCATCGAGACCCCGTACCGCAAGGTGGTCGACGGTGTGGTCACCG |
| My112.txt | SEQ ID NO 99 | TGAACCCGTTCGGGTTCATCGAGACCCCGTACCGCAAGGTGGTCGACGGTGTGGTCACCG |
| My312.txt | SEQ ID NO 100 | TGAACCCGTTCGGGTTCATCGAGACCCCGTACCGCAAGGTGGTCGACGGTGTGGTCACCG |
| Atcc6-kan.txt | SEQ ID NO 101 | TCAACCCGTTCGGCTTCATCGAGACGCCGTACCGCAAGGTGATCGACGGTCTCGTTACTG |
| ATCC6-0Kan.txt | SEQ ID NO 102 | TCAACCCGTTCGGCTTCATCGAGACGCCGTACCGCAAGGTGATCGACGGTCTCGTTACTG |
| M1.txt | SEQ ID NO 103 | TCAACCCGTTCGGCTTCATCGAGACGCCGTACCGCAAGGTGATCGACGGTCTCGTTACTG |
| M2.txt | SEQ ID NO 104 | TCAACCCGTTCGGCTTCATCGAGACGCCGTACCGCAAGGTGATCGACGGTCTCGTTACTG |
| M3.txt | SEQ ID NO 105 | TCAACCCGTTCGGCTTCATCGAGACGCCGTACCGCAAGGTGATCGACGGTCTCGTTACTG |
| M4.txt | SEQ ID NO 106 | TCAACCCGTTCGGCTTCATCGAGACGCCGTACCGGAAGGTGATCGACGGGCTGGTCACCG |
| M6.txt | SEQ ID NO 107 | TCAACCCGTTCGGCTTCATCGAGACGCCGTACCGCAAGGTGATCGACGGTCTCGTTACTG |
| M7.txt | SEQ ID NO 108 | TCAACCCGTTCGGCTTCATCGAGACGCCGTACCGCAAGGTGATCGACGGTCTCGTTACTG |
| M9.txt | SEQ ID NO 109 | TCAACCCGTTCGGCTTCATCGAGACGCCGTACCGCAAGGTGATCGACGGTCTCGTTACTG |
| M57.txt | SEQ ID NO 110 | TCAACCCGTTCGGCTTCATCGAGACGCCGTACCGCAAGGTGATCGACGGTCTCGTTACTG |
| M58.txt | SEQ ID NO 111 | TCAACCCGTTCGGCTTCATCGAGACGCCGTACCGCAAGGTGATCGACGGTCTCGTTACTG |
| M59.txt | SEQ ID NO 112 | TCAACCCGTTCGGCTTCATCGAGACGCCGTACCGCAAGGTGATCGACGGTCTCGTTACTG |
| M60.txt | SEQ ID NO 113 | TCAACCCGTTCGGCTTCATCGAGACGCCGTACCGCAAGGTGATCGACGGTCTCGTTACTG |
| M61.txt | SEQ ID NO 114 | TCAACCCGTTCGGCTTCATCGAGACGCCGTACCGCAAGGTGATCGACGGTCTCGTTACTG |
| M62.txt | SEQ ID NO 115 | TCAACCCGTTCGGCTTCATCGAGACGCCGTACCGCAAGGTGATCGACGGTCTCGTTACTG |
| MY106.txt | SEQ ID NO 116 | TCAACCCGTTCGGCTTCATCGAGACGCCGTACCGCAAGGTGATCGACGGTCTCGTTACTG |
| MY216.txt | SEQ ID NO 117 | TCAACCCGTTCGGCTTCATCGAGACGCCGTACCGCAAGGTGATCGACGGTCTCGTTACTG |
| MY218.txt | SEQ ID NO 118 | TCAACCCGTTCGGCTTCATCGAGACGCCGTACCGCAAGGTGATCGACGGTCTCGTTACTG |
| MY226.txt | SEQ ID NO 119 | TCAACCCGTTCGGCTTCATCGAGACGCCGTACCGCAAGGTGATCGACGGTCTCGTTACTG |
| M109.txt | SEQ ID NO 120 | TCAATCCGTTCGGGTTCATCGAGACGCCTTATCGGAAGGTTGTGGACGGTGTCGTTACTG |
| M111.txt | SEQ ID NO 121 | TCAATCCGTTCGGGTTCATCGAGACGCCTTATCGGAAGGTTGTGGACGGTGTCGTTACTG |
| M112.txt | SEQ ID NO 122 | TCAATCCGTTCGGGTTCATCGAGACGCCTTATCGGAAGGTTGTGGACGGTGTCGTTACTG |
| M113.txt | SEQ ID NO 123 | TCAATCCGTTCGGGTTCATCGAGACGCCTTATCGGAAGGTTGTGGACGGTGTCGTTACTG |
| M114.txt | SEQ ID NO 124 | TCAATCCGTTCGGGTTCATCGAGACGCCTTATCGGAAGGTTGTGGACGGTGTCGTTACTG |
| MY325.txt | SEQ ID NO 125 | TCAATCCGTTCGGGTTCATCGAGACGCCTTATCGGAAGGTTGTGGACGGTGTCGTTACTG |
| MY718.txt | SEQ ID NO 126 | TCAATCCGTTCGGGTTCATCGAGACGCCTTATCGGAAGGTTGTGGACGGTGTCGTTACTG |
| MY214.txt | SEQ ID NO 127 | TCAACCCGTTCGGGTTCATCGAGACGCCCTACCGCAAGGTGGTCGACGGGGTCGTTTCCG |
| MY224.txt | SEQ ID NO 128 | TCAACCCGTTCGGGTTCATCGAGACGCCCTACCGCAAGGTGGTCGACGGGGTCGTTTCCG |
| My244.txt | SEQ ID NO 129 | TCAACCCGTTCGGGTTCATCGAGACGCCCTACCGCAAGGTGGTCGACGGGGTCGTTTCCG |
| My339.txt | SEQ ID NO 130 | TCAACCCGTTCGGGTTCATCGAGACGCCCTACCGCAAGGTGGTCGACGGGGTCGTTTCCG |
| My343.txt | SEQ ID NO 131 | TCAACCCGTTCGGGTTCATCGAGACGCCCTACCGCAAGGTGGTCGACGGGGTCGTTTCCG |
| MY458.txt | SEQ ID NO 132 | TGAACCCGTTCGGCTTCATCGAGACCCCGTACCGCAAGGTCGTCGACGGCATCGTCACCG |
| MY809.txt | SEQ ID NO 133 | TCAACCCGTTCGGCTTCATCGAGACCCCGTACCGCAAGGTCGTCGACGGCATCGTCACCG |
| MY817.txt | SEQ ID NO 134 | TCAACCCGTTCGGCTTCATCGAGACCCCGTACCGCAAGGTCGTCGACGGCATCGTCACCG |
| MY821.txt | SEQ ID NO 135 | TCAACCCGTTCGGCTTCATCGAGACCCCGTACCGCAAGGTCGTCGACGGCATCGTCACCG |
| MY824.txt | SEQ ID NO 136 | TCAACCCGTTCGGCTTCATCGAGACCCCGTACCGCAAGGTCGTCGACGGCATCGTCACCG |
| MY102.txt | SEQ ID NO 137 | TCAACCCGTTCGGTTTCATCGAGACGCCCTACCGCAAGGTCGTGGACGGGGTCGTCACCG |
| My105.txt | SEQ ID NO 138 | TCAACCCGTTCGGTTTCATCGAGACGCCCTACCGCAAGGTCGTGGACGGGGTCGTCACCG |
| MY251.txt | SEQ ID NO 139 | TCAACCCGTTCGGTTTCATCGAGACGCCCTACCGCAAGGTCGTGGACGGGGTCGTCACCG |
| My256.txt | SEQ ID NO 140 | TCAACCCGTTCGGTTTCATCGAGACGCCCTACCGCAAGGTCGTGGACGGGGTCGTCACCG |

TABLE 1-continued

| | | |
|---|---|---|
| My294.txt | SEQ ID NO 141 | TCAACCCGTTCGGTTTCATCGAGACGCCCTACCGCAAGGTCGTGGACGGGGTCGTCACCG |
| MY354.txt | SEQ ID NO 142 | TGAACCCGTTCGGCTTCATCGAGACGCCCTACCGCAAGGTGGTCGACGGTGTCGTCAGCG |
| Atcc7-scr.txt | SEQ ID NO 143 | TCAACCCGTTCGGCTTCATCGAGACGCCGTACCGCAAGGTGGTCGACGGTGTGGTCACCG |
| ATCC7-0scr.txt | SEQ ID NO 144 | TCAACACGTTCGGCTTCATCGAGACGCCGTACCGCAAGGTGGTCGACGGTGTGGTCACCG |
| MY121.txt | SEQ ID NO 145 | TCAACCCGTTCGGGTTCATCGAGACGCCGTACCGCAAGGTCGTCGACGGTGTGGTCACCG |
| MY249.txt | SEQ ID NO 146 | TCAACCCGTTCGGCTTCATCGAGACGCCGTACCGCAAGGTGGTCGACGGTGTGGTCACCG |
| MY372.txt | SEQ ID NO 147 | TCAACCCGTTCGGCTTCATCGAGACCCCGTACCGCAAGGTGGTCGACGGTGTGGTCACCG |
| MY378.txt | SEQ ID NO 148 | TCAATCCGTTCGGCTTCATCGAGACGCCGTATCGCAAGGTGGTCGACGGTGTGGTCACCG |
| MY484.txt | SEQ ID NO 149 | TCAATCCGTTCGGGTTCATCGAGACGCCGTATCGCAAGGTTGTCGACGGTGTGGTCACCG |
| My556.txt | SEQ ID NO 150 | TCAATCCGTTCGGGTTCATCGAGACGCCGTACCGCAAGGTTGTCGACGGTGTGGTCACCG |
| MY563.txt | SEQ ID NO 151 | TCAATCCGTTCGGGTTCATCGAGACGCCGTACCGCAAGGTTGTCGACGGTGTGGTCACCG |
| MY586.txt | SEQ ID NO 152 | TCAATCCGTTCGGGTTCATCGAGACGCCGTACCGCAAGGTTGTCGACGGTGTGGTTACCG |
| Atcc8-sme.txt | SEQ ID NO 153 | TGAATCCGTTCGGCTTCATCGAGACGCCGTACCGCAAGGTCGAGAACGGTGTGGTCACCG |
| M35.txt | SEQ ID NO 154 | TCAATCCGTTCGGGTTCATCGAGACCCCGTACCGCAAGGTGATCGACGGCCAGGTCAGCG |
| M36.txt | SEQ ID NO 155 | TGAACCCGTTCGGTTTCATCGAGACCCCGTACCGCAAGGTCGTCGACGGTGTCATCACCG |
| M37.txt | SEQ ID NO 156 | TGAACCCGTTCGGCTTCATCGAGACGCCTTACCGCAAGGTCGAGAACGGTGTGGTCACCG |
| m125.txt | SEQ ID NO 157 | TCAACCCGTTCGGGTTCATCGAGACGCCGTATAGACGCGTCGTCAGCGGAGTTGTCACGG |
| MY143.txt | SEQ ID NO 158 | TGAACCCGTTCGGCTTCATCGAGACGCCGTACCGCAAGGTCGAGAACGGTGTGGTCACCG |
| My104.txt | SEQ ID NO 159 | TCAACCCGTTCGGGTTCATCGAGACGCCGTATAGACGCGTCGTCAGCGGAGTTGTCACGG |
| MY196.txt | SEQ ID NO 160 | TGAACCCGTTCGGGTTCATCGAGACGCCGTATAGACGCGTCGTCAGCGGAGTTGTCACGG |
| MY357.txt | SEQ ID NO 161 | TCAACCCGTTCGGGTTCATCGAGACGCCGTATAGACGCGTCGTCAGCGGAGTTGTCACGG |
| My358.txt | SEQ ID NO 162 | TCAACCCGTTCGGGTTCATCGAGACGCCGTATAGACGCGTCGTCAGCGGAGTTGTCACGG |
| My480.txt | SEQ ID NO 163 | TCAACCCGTTCGGGTTCATCGAGACGCCGTATAGACGCGTCGTCAGCGGAGTTGTCACGG |
| MY212.txt | SEQ ID NO 164 | TCAACCCGTTCGGGTTCATCGAAACCCCGTACCGCAAGGTCAACGACGGTGTGGTCAGCG |
| MY491.txt | SEQ ID NO 165 | TCAACCCGTTCGGGTTCATCGAAACCCCGTACCGCAAGGTCAACGACGGTGTGGTCAGCG |
| MY497.txt | SEQ ID NO 166 | TCAACCCGTTCGGGTTCATCGAAACCCCGTACCGCAAGGTCAACGACGGTGTGGTCAGCG |
| MY816.txt | SEQ ID NO 167 | TCAACCCGTTCGGGTTCATCGAGACGCCGTACCGCAAGGTGGTCGACGGTGTGGTCACCG |
| Atcc10-xen.txt | SEQ ID NO 168 | TCAACCCGTACGGGTTCATTGAGACGCCTTACCGCAAGGTGGTCAACGGCGTGGTCACCG |
| M38.txt | SEQ ID NO 169 | TCAACCCGTACGGGTTCATTGAGACGCCTTACCGCAAGGTGGTCAACGGCGTGGTCACCG |
| M39.txt | SEQ ID NO 170 | TCAACCCGTACGGGTTCATTGAGACGCCTTACCGCAAGGTGGTCAACGGCGTGGTCACCG |
| M40.txt | SEQ ID NO 171 | TCAACCCGTACGGGTTCATTGAGACGCCTTACCGCAAGGTGGTCAACGGCGTGGTCACCG |
| M41.txt | SEQ ID NO 172 | TCAACCCGTACGGGTTCATTGAGACGCCTTACCGCAAGGTGGTCAACGGCGTGGTCACCG |
| M42.txt | SEQ ID NO 173 | TCAACCCGTACGGGTTCATTGAGACGCCTTACCGCAAGGTGGTCAACGGCGTGGTCACCG |
| M43.txt | SEQ ID NO 174 | TCAACCCGTACGGGTTCATTGAGACGCCTTACCGCAAGGTGGTCAACGGCGTGGTCACCG |
| M44.txt | SEQ ID NO 175 | TCAACCCGTACGGGTTCATTGAGACGCCTTACCGCAAGGTGGTCAACGGCGTGGTCACCG |
| M45.txt | SEQ ID NO 176 | TCAACCCGTACGGGTTCATTGAGACGCCTTACCGCAAGGTGGTCAACGGCGTGGTCACCG |
| M46.txt | SEQ ID NO 177 | TCAACCCGTACGGGTTCATTGAGACGCCTTACCGCAAGGTGGTCAACGGCGTGGTCACCG |
| M47.txt | SEQ ID NO 178 | TCAACCCGTACGGGTTCATTGAGACGCCTTACCGCAAGGTGGTCAACGGCGTGGTCACCG |
| M68(Mav6).txt | SEQ ID NO 179 | TCAACCCGTACGGGTTCATTGAGACGCCTTACCGCAAGGTGGTCAACGGCGTGGTCACCG |
| M89.txt | SEQ ID NO 180 | TCAACCCGTACGGGTTCATTGAGACGCCTTACCGCAAGGTGGTCAACGGCGTGGTCACCG |
| M66(Mav4).txt | SEQ ID NO 181 | TCAACCCGTTCGGCTTCATCGAGACGCCGTACCGCAAGGTGGTCGACGG GTGGTCAGCG |
| | | 310 320 330 340 350 360 |

BASE NOS 361–420

| | | |
|---|---|---|
| ATCC9-Mtb.txt | SEQ ID NO 1 | ACGAGATCGTGTACCTGACCGCCGACGAGGAGGACCGCCACGTGGTGGCACAGGCCAATT |
| MY621.txt | SEQ ID NO 2 | ACGACATCCACTACCTGACGGCCGACGAAGAGGACCGCCACGTGGTGGCGCAGGCCAACT |
| Atcc1-av.txt | SEQ ID NO 3 | ACGAGATCCACTACCTGACCGCCGACGAGGAGGACCGCCACGTGGTGGCGCAGGCCAACT |
| M29.txt | SEQ ID NO 4 | ACGAGATCCACTACCTGACCGCCGACGAGGAGGACCGCCACGTGGTGGCGCAGGCCAACT |
| M30.txt | SEQ ID NO 5 | ACGAGATCCACTACCTGACCGCCGACGAGGAGGACCGCCACGTGGTGGCGCAGGCCAACT |
| M31.txt | SEQ ID NO 6 | ACGAGATCCACTACCTGACCGCCGACGAGGAGGACCGCCACGTGGTGGCGCAGGCCAACT |
| M32.txt | SEQ ID NO 7 | ACGAGATCCACTACCTGACCGCCGACGAGGAGGACCGCCACGTGGTGGCGCAGGCCAACT |
| M33.txt | SEQ ID NO 8 | ACGAGATCCACTACCTGACCGCCGACGAGGAGGACCGCCACGTGGTGGCGCAGGCCAACT |
| M34.txt | SEQ ID NO 9 | ACGAGATCCACTACCTGACCGCCGACGAGGAGGACCGCCACGTGGTGGCGCAGGCCAACT |
| M48-new.txt | SEQ ID NO 10 | ACGAGATCCACTACCTGACCGCCGACGAGGAGGACCGCCACGTGGTGGCGCAGGCCAACT |
| M49.txt | SEQ ID NO 11 | ACGAGATCCACTACCTGACCGCCGACGAGGAGGACCGCCACGTGGTGGCGCAGGCCAACT |
| M64(Mav2).txt | SEQ ID NO 12 | ACGAGATCCACTACCTGACCGCCGACGAGGAGGACCGCCACGTGGTGGCGCAGGCCAACT |
| M65(Mav3).txt | SEQ ID NO 13 | ACGAGATCCACTACCTGACCGCCGACGAGGAGGACCGCCACGTGGTGGCGCAGGCCAACT |
| M67(Mav5).txt | SEQ ID NO 14 | ACGAGATCCACTACCTGACCGCCGACGAGGAGGACCGCCACGTGGTGGCGCAGGCCAACT |
| M69(Mav7).txt | SEQ ID NO 15 | ACGAGATCCACTACCTGACCGCCGACGAGGAGGACCGCCACGTGGTGGCGCAGGCCAACT |
| M71(Mav9).txt | SEQ ID NO 16 | ACGAGATCCACTACCTGACCGCCGACGAGGAGGACCGCCACGTGGTGGCGCAGGCCAACT |
| M91.txt | SEQ ID NO 17 | ACGAGATCCACTACCTGACCGCCGACGAGGAGGACCGCCACGTGGTGGCGCAGGCCAACT |
| M94.txt | SEQ ID NO 18 | ACGAGATCCACTACCTGACCGCCGACGAGGAGGACCGCCACGTGGTGGCGCAGGCCAACT |
| M95.txt | SEQ ID NO 19 | ACGAGATCCACTACCTGACCGCCGACGAGGAGGACCGCCACGTGGTGGCGCAGGCCAACT |
| M96.txt | SEQ ID NO 20 | ACGAGATCCACTACCTGACCGCCGACGAGGAGGACCGCCACGTGGTGGCGCAGGCCAACT |
| M100.txt | SEQ ID NO 21 | ACGAGATCCACTACCTGACCGCCGACGAGGAGGACCGCCACGTGGTGGCGCAGGCCAACT |
| M101.txt | SEQ ID NO 22 | ACGAGATCCACTACCTGACCGCCGACGAGGAGGACCGCCACGTGGTGGCGCAGGCCAACT |
| M102.txt | SEQ ID NO 23 | ACGAGATCCACTACCTGACCGCCGACGAGGAGGACCGCCACGTGGTGGCGCAGGCCAACT |
| M104.txt | SEQ ID NO 24 | ACGAGATCCACTACCTGACCGCCGACGAGGAGGACCGCCACGTGGTGGCGCAGGCCAACT |
| M105.txt | SEQ ID NO 25 | ACGAGATCCACTACCTGACCGCCGACGAGGAGGACCGCCACGTGGTGGCGCAGGCCAACT |
| M106.txt | SEQ ID NO 26 | ACCAGATCGACTACCTGACCGCCGACGAGGAGGACCGCCACGTCGTGGCGCAGGCCAACT |
| MY111.txt | SEQ ID NO 27 | ACGAGATCCACTACCTGACCGCCGACGAGGAGGACCGCCACGTGGTGGCGCAGGCCAACT |
| M76.txt | SEQ ID NO 28 | ACGAGATCGTGTACCTGACCGCCGACGAGGAGGACCGCCACGTGGTGGCACAGGCCAATT |
| MY451.txt | SEQ ID NO 29 | ACGAGATCGTGTACCTGACCGCCGACGAGGAGGACCGCCACGTGGTGGCACAGGCCAATT |

TABLE 1-continued

| | | |
|---|---|---|
| ATCC2-chelnew.txt | SEQ ID NO 30 | ACGAGATCCACTACCTGACCGCCGACGAAGAGGACCGCCACGTGGTGGCGCAGGCCAACT |
| M10.txt | SEQ ID NO 31 | ACGAGATCCACTACCTGACCGCCGACGAAGAGGACCGCCACGTCGTGGCACAGGCCAACT |
| M11.txt | SEQ ID NO 32 | ACGAGATCCACTACCTGACCGCCGACGAAGAGGACCGCCACGTCGTGGCACAGGCCAACT |
| M12.txt | SEQ ID NO 33 | ACGAGATCCACTACCTGACCGCCGACGAAGAGGACCGCCACGTCGTGGCACAGGCCAACT |
| M13_2-662.txt | SEQ ID NO 34 | ACGAGATCCGCTACCTGACCGCCGACGAAGAGGACCGCCACGTCGTGGCACAGGCCAACT |
| M14.txt | SEQ ID NO 35 | ACGAGATCCACTACCTGACTGCCGACGAAGAGGACCGCCACGTGGTGGCGCAGGCCAACT |
| M15.txt | SEQ ID NO 36 | ACGAGATCCACTACCTGACCGCCGACGAAGAGGACCGCCACGTCGTGGCACAGGCCAACT |
| M16.txt | SEQ ID NO 37 | ACGAGATCCACTACCTGACCGCCGACGAAGAGGACCGCCACGTCGTGGCACAGGCCAACT |
| M17_2_662.txt | SEQ ID NO 38 | ACGAGATCCACTACCTGACCGCCGACGAAGAGGACCGCCACGTCGTGGCACAGGCCAACT |
| M50.txt | SEQ ID NO 39 | ACGACATCCACTACCTGACCGCCGACGAAGAGGACCGCCACGTCGTGGCACAGGCCAACT |
| M51.txt | SEQ ID NO 40 | ACGAGATCCACTACCTGACCGCCGACGAAGAGGACCGCCACGTGGTGGCGCAGGCCAACT |
| M115.txt | SEQ ID NO 41 | ACGAGATCCACTACCTGACCGCCGACGAAGAGGACCGCCACGTCGTGGCACAGGCCAACT |
| M116.txt | SEQ ID NO 42 | ACGAGATCCACTACCTGACCGCCGACGAAGAGGACCGCCACGTCGTGGCACAGGCCAACT |
| M119.txt | SEQ ID NO 43 | ACGAGATCCACTACCTGACCGCCGACGAAGAGGACCGCCACGTCGTGGCACAGGCCAACT |
| MY109.txt | SEQ ID NO 44 | ACGAGATCCACTACCTGACCGCCGACGAAGAGGACCGCCACGTCGTGGCACAGGCCAACT |
| MY200.txt | SEQ ID NO 45 | ACGAGATCCACTACCTGACGGCCGACGAAGAGGACCGCCACGTGGTGGCGCAGGCCAACT |
| MY207.txt | SEQ ID NO 46 | ACGAGATCCACTACCTGACGGCCGACGAAGAGGACCGCCACGTGGTGGCGCAGGCCAACT |
| MY209.txt | SEQ ID NO 47 | ACGACATCCACTACCTGACGGCCGACGAAGAGGACCGCCACGTGGTGGCGCAGGCCAACT |
| M122.txt | SEQ ID NO 48 | ATGACATCGAGTACCTGACCGCCGACGAGGAGGACCGCCACGTCGTGGCGCAGGCCAACT |
| M123.txt | SEQ ID NO 49 | ATGACATCGAGTACCTGACCGCCGACGAGGAGGACCGCCACGTCGTGGCGCAGGCCAACT |
| M126.txt | SEQ ID NO 50 | ACCAGATCGACTACCTGACCGCCGACGAGGAGGACCGCCACGTCGTGGCGCAGGCCAATT |
| Atcc3-for.txt | SEQ ID NO 51 | ACCAGATCGACTACCTGACCGCCGACGAGGAGGACCGCCACGTCGTGGCGCAGGCCAACT |
| M53.txt | SEQ ID NO 52 | ACCAGATCGACTACCTGACCGCCGACGAGGAGGACCGCCACGTCGTGGCGCAGGCCAACT |
| M54.txt | SEQ ID NO 53 | ACCAGATCGACTACCTGACCGCCGACGAGGAGGACNNTCACGTCGTGGCGCAGGCCAACT |
| M55.txt | SEQ ID NO 54 | ATCAGATCGACTACCTGACCGCCGACGAGGAGGACCGCCACGTCGTGGCGCAGGCCAACT |
| M56.txt | SEQ ID NO 55 | ACCAGATCGACTACCTGACCGCCGACGAGGAGGACCGCCACGTCGTGGCGCAGGCCAACT |
| M74(Mav12).txt | SEQ ID NO 56 | ATCAGATCKACTACCTGACCGCCGACGAGGAGGACCGCCACGTCGTGGCGCAGGCCAACT |
| M77.txt | SEQ ID NO 57 | ACCAGATCGACTACCTGACCGCCGACGAGGAGGACCGCCACGTCGTGGCGCAGGCCAACT |
| M118.txt | SEQ ID NO 58 | ACCAGATCGACTACCTGACCGCCGACGAGGAGGACCGCCACGTCGTGGCGCAGGCCAACT |
| MY221.txt | SEQ ID NO 59 | AYCAGATCGACTACCTGACCGCCGACGAGGAGGACCGCCACGTCGTGGCGCAGGCCAACT |
| MY223.txt | SEQ ID NO 60 | ACCAGATCGACTACCTGACCGCCGACGAGGAGGACCGCCACGTCGTGGCGCAGGCCAACT |
| MY225.txt | SEQ ID NO 61 | ATCAGATCGACTACCTGACCGCCGACGAGGAGGACCGCCACGTCGTGGCGCAGGCCAACT |
| My341.txt | SEQ ID NO 62 | ATCAGATCGACTACCTGACCGCCGACGAGGAGGACCGCCACGTCGTGGCGCAGGCCAACT |
| My715.txt | SEQ ID NO 63 | ATCAGATCGACTACCTGACCGCCGACGAGGAGGACCGCCACGTCGTGGCGCAGGCCAACT |
| MY470.txt | SEQ ID NO 64 | ACGAGATCCACTACCTGACCGCCGACGAGGAGGACCGCCACGTCGTGGCGCAGGCCAACT |
| Atcc4-go.txt | SEQ ID NO 65 | ACGAGATCCACTACCTCACCGCCGACGAGGAGGACCGCCACGTGGTGGCGCAGGCCAACT |
| ATCC4-0-Gord.txt | SEQ ID NO 66 | ACGAGATCCACTACCTAACCGCCGACGAGGAGGACCGCCACGTGGTGGCGCAGGCCAACT |
| M78(lz).txt | SEQ ID NO 67 | ATGAGATCCACTACCTCACCGCCGACGAGGAGGACCGCCACGTCGTGGCGCAGGCCAACT |
| M79(jd).txt | SEQ ID NO 68 | ACGAAATCCACTACCTGACCGCCGACGAGGAGGACCGCCACGTGGTGGCGCAGGCCAACT |
| M80(lg).txt | SEQ ID NO 69 | ATGAGATCCACTACCTCACCGCCGACGAGGAGGACCGCCACGTCGTGGCGCAGGCCAACT |
| M81(ll).txt | SEQ ID NO 70 | ACGAGATCCACTACCTCACCGCCGACGAGGAGGACCGCCACGTCGTGGCGCAGGCCAACT |
| M82(rm).txt | SEQ ID NO 71 | ACGAGATCCACTACCTCACCGCCGACGAGGAGGACCGCCACGTGGTGGCGCAGGCCAACT |
| M83(mb).txt | SEQ ID NO 72 | ACGAGATCCACTACCTCACCGCCGACGAGGAGGACCGCCACGTGGTGGCGCAGGCCAACT |
| M84(ow).txt | SEQ ID NO 73 | ACGAGATCCACTACCTCACCGCCGACGAGGAGGACCGCCACGTCGTGGCGCAGGCCAACT |
| M85(lb).txt | SEQ ID NO 74 | ACGAGATCCACTACCTCACCGCCGACGAGGAGGACCGCCACGTGGTGGCGCAGGCCAACT |
| M86(rb).txt | SEQ ID NO 75 | ACGAGATCCACTACCTGACCGCCGACGAGGAGGACCGCCACGTGGTGGCGCAGGCCAACT |
| M87(wn).txt | SEQ ID NO 76 | ACGAGATCCACTACCTCACCGCCGACGAGGAGGACCGCCACGTGGTGGCGCAGGCCAACT |
| M90(gordDB).txt | SEQ ID NO 77 | ATGAGATCCACTACCTGACCGCCGACGAAGGAGACCCCCACGTGGTGGCGCAGGCCAACT |
| m126.txt | SEQ ID NO 78 | ACGAGATCCACTACCTCACCGCCGACGAGGAGGACCGCCACGTGGTGGCGCAGGCCAACT |
| M128.txt | SEQ ID NO 79 | ATGAGATCCACTACCTGACCGCCGACGAGGAGGACCGCCACGTGGTGGCGCAGGCCAACT |
| My103.txt | SEQ ID NO 80 | ACGAGATCCACTACCTCACCGCCGACGAGGAGGACCGCCACGTGGTGGCGCAGGCCAACT |
| MY475.txt | SEQ ID NO 81 | ACGAGATCCACTACCTGACCGCCGACGAGGAGGACCGCCACGTGGTGGCGCAGGCCAACT |
| MY476.txt | SEQ ID NO 82 | ACGAGATCCACTACCTCACCGCCGACGAGGAGGACCGCCACGTGGTGGCGCAGGCCAACT |
| MY830.txt | SEQ ID NO 83 | ATGAGATCCACTACCTGACCGCCGACGAGGAGGACCGCCACGTCGTGGCGCAGGCCAACT |
| Atcc5-int.txt | SEQ ID NO 84 | ACGAGATCCACTACCTGACCGCCGACGAGGAGGACCGCCACGTCGTGGCGCAGGCCAACT |
| ATCC5-0int.txt | SEQ ID NO 85 | ACGAGATCCACTACCTGACCGCCGACGAGGAGGACCGCCACGTCGTGGCGCAGGCCAACT |
| M18.txt | SEQ ID NO 86 | ACGAGATCCACTACCTGACCGCCGACGAGGAGGACCGCCACGTCGTGGCGCAGGCCAACT |
| M19.txt | SEQ ID NO 87 | ACGAGATCCACTACCTGACCGCCGACGAGGAGGACCGCCACGTCGTGGCGCAGGCCAACT |
| M20.txt | SEQ ID NO 88 | ACGAGATCCACTACCTGACCGCCGACGAGGAGGACCGCCACGTCGTGGCGCAGGCCAACT |
| M21.txt | SEQ ID NO 89 | ACGAGATCCACTACCTGACCGCCGACGAGGAGGACCGCCACGTCGTGGCGCAGGCCAACT |
| M22.txt | SEQ ID NO 90 | ACGAGATCCACTACCTGACCGCCGACGAGGAGGACCGCCACGTCGTGGCGCAGGCCAACT |
| M23.txt | SEQ ID NO 91 | ACGAGATCCACTACCTGACCGCCGACGAGGAGGACCGCCACGTCGTGGCGCAGGCCAACT |
| M24.txt | SEQ ID NO 92 | ACGAGATCCACTACCTGACCGCCGACGAGGAGGACCGCCACGTCGTGGCGCAGGCCAACT |
| M25.txt | SEQ ID NO 93 | ACGAGATCCACTACCTGACCGCCGACGAGGAGGACCGCCACGTCGTGGCGCAGGCCAACT |
| M26.txt | SEQ ID NO 94 | ACGAGATCCACTACCTGACCGCCGACGAGGAGGACCGCCACGTCGTGGCGCAGGCCAACT |
| M27.txt | SEQ ID NO 95 | ACGAGATCCACTACCTGACCGCCGACGAGGAGGACCGCCACGTCGTGGCGCAGGCCAACT |
| M28.txt | SEQ ID NO 96 | ACGA ATCCACTACCTGACCGCCGACGAGGAGGACCGCCACGTCGTGGCGCAGGCCAACT |
| M107.txt | SEQ ID NO 97 | ACGAGATCCACTACCTGACCGCCGACGAGGAGGACCGCCACGTCGTGGCGCAGGCCAACT |
| MY107.txt | SEQ ID NO 98 | ACGAGATCCACTACCTGACCGCCGACGAGGAGGACCGCCACGTCGTGGCGCAGGCCAACT |
| MY112.txt | SEQ ID NO 99 | ACGAGATCCACTACCTGACCGCCGACGAGGAGGACCGCCACGTCGTGGCGCAGGCCAACT |
| MY312.txt | SEQ ID NO 100 | ACGAGATCCACTACCTGACCGCCGACGAGGAGGACCGCCACGTCGTGGCGCAGGCCAACT |
| Atcc6-kan.txt | SEQ ID NO 101 | ATGAGATCCACTACTTGACGGCCGACGAGGAGGACCGCCACGTCGTGGCACAGGCCAACT |
| ATCC6-0Kan.txt | SEQ ID NO 102 | ATGAGATCCACTACTTGACGGCCGACGAGGAGGACCGCCACGTCGTGGCACAGGCCAACT |
| M1.txt | SEQ ID NO 103 | ATGAGATCCACTACTTGACGGCCGACGAGGAGGACCGCCACGTCGTGGCACAGGCCAACT |
| M2.txt | SEQ ID NO 104 | ATGAGATCCACTACTTGACGGCCGACGAGGAGGACCGCCACGTCGTGGCACAGGCCAACT |
| M3.txt | SEQ ID NO 105 | ATGAGATCCACTACTTGACGGCCGACGAGGAGGACCGCCACGTCGTGGCACAGGCCAACT |
| M4.txt | SEQ ID NO 106 | ATGAGATCCACTACCTGACGGCCGACGAAGAGGACCGCCACGTCGTGGCACAGGCCAACT |
| M6.txt | SEQ ID NO 107 | ATGAGATCCACTACTTGACGGCCGACGAGGAGGACCGCCACGTCGTGGCACAGGCCAACT |
| M7.txt | SEQ ID NO 108 | ATGAGATCCACTACTTGACGGCCGACGAGGAGGACCGCCACGTCGTGGCACAGGCCAACT |
| M9.txt | SEQ ID NO 109 | ATGAGATCCACTACTTGACGGCCGACGAGGAGGACCGCCACGTCGTGGCACAGGCCAACT |
| M57.txt | SEQ ID NO 110 | ATGAGATCCACTACTTGACGGCCGACGAGGAGGACCGCCACGTCGTGGCACAGGCCAACT |
| M58.txt | SEQ ID NO 111 | ATGAGATCCACTACTTGACGGCCGACGAGGAGGACCGCCACGTCGTGGCACAGGCCAACT |
| M59.txt | SEQ ID NO 112 | ATGAGATCCACTACTTGACGGCCGACGAGGAGGACCGCCACGTCGTGGCACAGGCCAACT |

TABLE 1-continued

| | | |
|---|---|---|
| M60.txt | SEQ ID NO 113 | ATGAGATCCACTACTTGACGGCCGACGAGGAGGACCGCCACGTCGTGGCACAGGCCAACT |
| M61.txt | SEQ ID NO 114 | ATGAGATCCACTACTTGACGGCCGACGAGGAGGACCGCCACGTCGTGGCACAGGCCAACT |
| M62.txt | SEQ ID NO 115 | ATGAGATCCACTACTTGACGGCCGACGAGGAGGACCGCCACGTCGTGGCACAGGCCAACT |
| MY106.txt | SEQ ID NO 116 | ATGAGATCCACTACTTGACGGCCGACGAGGAGGACCGCCACGTCGTGGCACAGGCCAACT |
| MY216.txt | SEQ ID NO 117 | ATGAGATCCACTACTTGACGGCCGACGAGGAGGACCGCCACGTCGTGGCACAGGCCAACT |
| MY218.txt | SEQ ID NO 118 | ATGAGATCCACTACTTGACGGCCGACGAGGAGGACCGCCACGTCGTGGCACAGGCCAACT |
| MY226.txt | SEQ ID NO 119 | ATGAGATCCACTACTTGACGGCCGACGAGGAGGACCGCCACGTCGTGGCACAGGCCAACT |
| M109.txt | SEQ ID NO 120 | ACGAGATCGTCTACCTGACCGCCGACGAGGAGGACCGCCACGTCGTGGCGCAGGCCAACT |
| M111.txt | SEQ ID NO 121 | ACGAGATCGTCTACCTGACCGCCGACGAGGAGGACCGCCACGTCGTGGCGCAGGCCAACT |
| M112.txt | SEQ ID NO 122 | ACGAGATCGTCTACCTGACCGCCGACGAGGAGGACCGCCACGTCGTGGCGCAGGCCAACT |
| M113.txt | SEQ ID NO 123 | ACGAGATCGTCTACCTGACCGCCGACGAGGAGGACCGCCACGTCGTGGCGCAGGCCAACT |
| M114.txt | SEQ ID NO 124 | ACGAGATCGTCTACCTGACCGCCGACGAGGAGGACCGCCACGTCGTGGCGCAGGCCAACT |
| MY325.txt | SEQ ID NO 125 | ACGAGATCGTCTACCTGACCGCCGACGAGGAGGACCGCCACGTCGTGGCGCAGGCCAACT |
| MY718.txt | SEQ ID NO 126 | ACGAGATCGTCTACCTGACCGCCGACGAGGAGGACCGCCACGTCGTGGCGCAGGCCAACT |
| MY214.txt | SEQ ID NO 127 | ACGAGATCCACTACCTGACCGCCGACGAGGAGGACCGCCACGTCGTGGCGCAGGCCAACT |
| MY224.txt | SEQ ID NO 128 | ACGAGATCCACTACCTGACCGCCGACGAGGAGGACCGCCACGTCGTGGCGCAGGCCAACT |
| My244.txt | SEQ ID NO 129 | ACGAGATCCACTACCTGACCGCCGACGAGGAGGACCGCCACGTCGTGGCGCAGGCCAACT |
| My339.txt | SEQ ID NO 130 | ACGAGATCCACTACCTGACCGCCGACGAGGAGGACCGCCACGTCGTGGCGCAGGCCAACT |
| My343.txt | SEQ ID NO 131 | ACGAGATCCACTACCTGACCGCCGACGAGGAGGACCGCCACGTCGTGGCGCAGGCCAACT |
| MY458.txt | SEQ ID NO 132 | ATCAGATCGACTACCTGACCGCCGACGAGGAGGACCGCCACGTCGTGGCGCAGGCCAACT |
| MY809.txt | SEQ ID NO 133 | ATCAGATCGACTACCTGACCGCCGACGAGGAGGACCGCCACGTCGTGGCGCAGGCCAACT |
| MY817.txt | SEQ ID NO 134 | ATCAGATCGACTACCTGACCGCCGACGAGGAGGACCGCCACGTCGTGGCGCAGGCCAACT |
| MY821.txt | SEQ ID NO 135 | ATCAGATCGACTACCTGACCGCCGACGAGGAGGACCGCCACGTCGTGGCGCAGGCCAACT |
| MY824.txt | SEQ ID NO 136 | ATCAGATCGACTACCTGACCGCCGACGAGGAGGACCGCCACGTCGTGGCGCAGGCCAACT |
| MY102.txt | SEQ ID NO 137 | ACGAGATCCACTACCTGACCGCCGACGAGGAGGACCGCCACGTCGTGGCGCAGGCCAACT |
| My105.txt | SEQ ID NO 138 | ACGAGATCCACTACCTGACCGCCGACGAGGAGGACCGCCACGTCGTGGCGCAGGCCAACT |
| MY251.txt | SEQ ID NO 139 | ACGAGATCCACTACCTGACCGCCGACGAGGAGGACCGCCACGTTGTGGCGCAGGCCAACT |
| My256.txt | SEQ ID NO 140 | ACGAGATCCACTACCTGACCGCCGACGAGGAGGACCGCCACGTTGTGGCGCAGGCCAACT |
| My294.txt | SEQ ID NO 141 | ACGAGATCCACTACCTGACCGCCGACGAGGAGGACCGCCACGTCGTGGCGCAGGCCAACT |
| MY354.txt | SEQ ID NO 142 | ACGAGATCCACTACCTGACCGCCGACGAGGAGGACCGCCACGTCGTGGCGCAGGCCAACT |
| Atcc7-scr.txt | SEQ ID NO 143 | ACGAGATCCACTACCTGACCGCCGACGAGGAGGACCGTCACGTCGTGGCGCAGGCCAACT |
| ATCC7-Oscr.txt | SEQ ID NO 144 | ACGAGATCCACTACCTGACGGCCGACGAGGAGGACCGTCACGTCGTGGCGCAGGCCAACT |
| MY121.txt | SEQ ID NO 145 | ACGAGATCCACTACCTGACGGCCGACGAGGAGGACCGCCACGTCGTGGCGCAGGCCAACT |
| MY249.txt | SEQ ID NO 146 | ACGAGATCCACTACCTGACGGCCGACGAGGAGGACCGTCACGTCGTGGCGCAGGCCAACT |
| MY372.txt | SEQ ID NO 147 | ACGAGATTCACTACCTGACGGCCGACGAGGAGGACCGCCACGTGGTGGCGCAGGCCAACT |
| MY378.txt | SEQ ID NO 148 | ACGAGATCCACTACCTGACGGCCGACGAGGAGGACCGTCACGTCGTGGCGCAGGCCAACT |
| MY484.txt | SEQ ID NO 149 | ACGAGATCGAGTACCTGACGGCCGACGAGGAGGACCGCCACGTCGTGGCGCAGGCCAACT |
| My556.txt | SEQ ID NO 150 | ACGAGATCGAGTACCTGACGGCCGACGAGGAGGACCGCCACGTCGTGGCGCAGGCCAACT |
| MY563.txt | SEQ ID NO 151 | ACGAGATCGAGTACCTGACCGCCGACGAGGAGGACCGCCACGTCGTGGCGCAGGCCAACT |
| MY586.txt | SEQ ID NO 152 | ACGAGATCGAGTACCTGACCGCCGACGAGGAGGACCGCCACGTGGTGGCGCAGGCCAACT |
| Atcc8-sme.txt | SEQ ID NO 153 | ACCAGATCGACTACCTGACCGCCGACGAGGAGGACCGCCACGTCGTGGCGCAGGCCAACT |
| M35.txt | SEQ ID NO 154 | ATCAGATCGACTACCTCACCGCCGACGAGGAGGACCGCCACATCGTGGCGCAGGCCAACT |
| M36.txt | SEQ ID NO 155 | ACCAGATCGACTACCTGACCGCCGACGAGGAGGACCGCCACGTCGTGGCGCAGGCCAACT |
| M37.txt | SEQ ID NO 156 | ACCAGATCGACTACCTGACCGCCGACGAGGAGGACCGCCACGTCGTGGCGCAGGCCAACT |
| m.125.txt | SEQ ID NO 157 | ATGAGATCCACTACCTGACCGCCGACGAGGAGGACCGCCACGTCGTGGCGCAGGCCAACT |
| MY143.txt | SEQ ID NO 158 | ACCAGATCGACTACCTGACCGCCGACGAGGAGGACCGCCACGTCGTGGCGCAGGCCAACT |
| My104.txt | SEQ ID NO 159 | ATGAGATCCACTACCTGACCGCCGACGAGGAGGACCGCCACGTCGTGGCGCAGGCCAACT |
| MY196.txt | SEQ ID NO 160 | ATGAGATCCACTACCTGACCGCCGACGAGGAGGACCGCCACGTCGTGGCGCAGGCCAACT |
| MY357.txt | SEQ ID NO 161 | ATGAGATCCACTACCTGACCGCCGACGAGGAGGACCGCCACGTCGTGGCGCAGGCCAACT |
| My358.txt | SEQ ID NO 162 | ATGAGATCCACTACCTGACCGCCGACGAGGAGGACCGCCACGTCGTGGCGCAGGCCAACT |
| My480.txt | SEQ ID NO 163 | ATGAGATCCACTACCTGACCGCCGACGAGGAGGACCGCCACGTCGTGGCGCAGGCCAACT |
| MY212.txt | SEQ ID NO 164 | ATGAGATCGTCTACCTGACCGCCGACGAGGAGGACCGCCACGTCGTGGCGCAGGCCAACT |
| MY491.txt | SEQ ID NO 165 | ATGAGATCGTCTACCTGACCGCCGACGAGGAGGACCGCCACGTCGTGGCGCAGGCCAACT |
| MY497.txt | SEQ ID NO 166 | ATGAGATCGTCTACCTGACCGCCGACGAGGAGGACCGCCACGTCGTGGCGCAGGCCAACT |
| MY816.txt | SEQ ID NO 167 | AMCARATCGACTACCTGACCGCCGACGAGGAGGACCGCCACGTCGTGGCGCAGGCCAACT |
| Atcc10-xep.txt | SEQ ID NO 168 | ACGAGATCGTGTACCTGACCGCCGACGAGGAGGACCGCCATGTGGTGGCGCAGGCCAACT |
| M38.txt | SEQ ID NO 169 | ACGAGATCGTGTACCTGACCGCCGACGAGGAGGACCGCCATGTGGTGGCGCAGGCCAACT |
| M39.txt | SEQ ID NO 170 | ACGAGATCGTGTACCTGACCGCCGACGAGGAGGACCGCCATGTGGTGGCGCAGGCCAACT |
| M40.txt | SEQ ID NO 171 | ACGAGATCGTGTACCTGACCGCCGACGAGGAGGACCGCCATGTGGTGGCGCAGGCCAACT |
| M41.txt | SEQ ID NO 172 | ACGAGATCGTGTACCTGACCGCCGACGAGGAGGACCGCCATGTGGTGGCGCAGGCCAACT |
| M42.txt | SEQ ID NO 173 | ACGAGATCGTGTACCTGACCGCCGACGAGGAGGACCGCCATGTGGTGGCGCAGGCCAACT |
| M43.txt | SEQ ID NO 174 | ACGAGATCGTGTACCTGACCGCCGACGAGGAGGACCGCCATGTGGTGGCGCAGGCCAACT |
| M44.txt | SEQ ID NO 175 | ACGAGATCGTGTACCTGACCGCCGACGAGGAGGACCGCCATGTGGTGGCGCAGGCCAACT |
| M45.txt | SEQ ID NO 176 | ACGAGATCGTGTACCTGACCGCCGACGAGGAGGACCGCCATGTGGTGGCGCAGGCCAACT |
| M46.txt | SEQ ID NO 177 | ACGAGATCGTGTACCTGACCGCCGACGAGGAGGACCGCCATGTGGTGGCGCAGGCCAACT |
| M47.txt | SEQ ID NO 178 | ACGAGATCGTGTACCTGACCGCCGACGAGGAGGACCGCCATGTGGTGGCGCAGGCCAACT |
| M68(Mav6).txt | SEQ ID NO 179 | ACGAGATCGTGTACCTGACCGCCGACGAGGAGGACCGCCATGTGGTGGCGCAGGCCAACT |
| M89.txt | SEQ ID NO 180 | ACGAGATCGTGTACCTGACCGCCGACGAGGAGGACCGCCATGTGGTGGCGCAGGCCAACT |
| M66(Mav4).txt | SEQ ID NO 181 | ACGAGATCGTGTACCTGACCGCCGACGAGGAGGACCGCCACGTGGTGGCGCAGGCCAACT |
| | | 370 380 390 400 410 420 |

TABLE 1-continued

BASE NOS 421–480

| | | | |
|---|---|---|---|
| ATCC9-Mtb.txt | SEQ ID NO 1 | CGCCGATC | GATGCGGACGGTCGCTTCGTCGAGCCGCGCGTGCTGGTCC |
| MY621.txt | SEQ ID NO 2 | CGCCCGTG | GACGCCAACGGCCGCTTCACCGAGGAGAAGATCCTGGTTC |
| Atcc1-av.txt | SEQ ID NO 3 | CGCCGATC | GACGGCAAGGGCCGGTTCGCCGAGGCCCGGGTGCTGGTCC |
| M29.txt | SEQ ID NO 4 | CGCCGATC | GACGACAAGGGCCGGTTCGCGGAGGCCCGGGTGCTGGTCC |
| M30.txt | SEQ ID NO 5 | CGCCGATC | GACGACAAGGGCCGGTTCGCGGAGGCCCGGGTGCTGGTCC |
| M31.txt | SEQ ID NO 6 | CGCCGATC | GACGACAAGGGCCGGTTCGCGGAGGCCCGGGTGCTGGTCC |
| M32.txt | SEQ ID NO 7 | CGCCGATC | GACGACAAGGGCCGGTTCGCGGAGGCCCGGGTGCTGGTCC |
| M33.txt | SEQ ID NO 8 | CGCCGATC | GACGACAAGGGCCGGTTCGCGGAGGCCCGGGTGCTGGTCC |
| M34.txt | SEQ ID NO 9 | CGCCGATC | GACGACAAGGGCCGGTTCGCGGAGGCCCGGGTGCTGGTCC |
| M48-new.txt | SEQ ID NO 10 | CGCCGATC | GACGACAAGGGCCGGTTCGAGGAGKCCCGGGTGCTGGTCC |
| M49.txt | SEQ ID NO 11 | CGCCGATC | GACGACAAGGGCCGGTTCGCCGAGGCCCGGGTGCTGGTCC |
| M64(Mav2).txt | SEQ ID NO 12 | CGCCGATC | GACGACAAGGGCCGGTTCGCGGAGGCCCGGGTGCTGGTCC |
| M65(Mav3).txt | SEQ ID NO 13 | CGCCGATC | GACGACAAGGGCCGGTTCGCGGAGGCCCGGGTGCTGGTCC |
| M67(Mav5).txt | SEQ ID NO 14 | CGCCGATC | GACGACAAGGGCCGGTTCGCGGAGGCCCGGGTGCTGGTCC |
| M69(Mav7).txt | SEQ ID NO 15 | CGCCGATC | GACGACAAGGGCCGGTTCGCGGAGGCCCGGGTGCTGGTCC |
| M71(Mav9).txt | SEQ ID NO 16 | CGCCGATC | GACGACAAGGGCCGGTTCGCGGAGGCCCGGGTGCTGGTCC |
| M91.txt | SEQ ID NO 17 | CGCCGATC | GACGACAAGGGCCGGTTCGCGGAGGCCCGGGTGCTGGTCC |
| M94.txt | SEQ ID NO 18 | CGCCGATC | GACGACAAGGGCCGGTTCGCGGAGGCCCGGGTGCTGGTCC |
| M95.txt | SEQ ID NO 19 | CGCCGATC | GACGACAAGGGCCGGTTCGCGGAGGCCCGGGTGCTGGTCC |
| M96.txt | SEQ ID NO 20 | CGCCGATC | GACGACAAGGGCCGGTTCGCGGAGGCCCGGGTGCTGGTCC |
| M100.txt | SEQ ID NO 21 | CGCCGATC | GACGACAAGGGCCGGTTCGCGGAGGCCCGGGTGCTGGTCC |
| M101.txt | SEQ ID NO 22 | CGCCGATC | GACGACAAGGGCCGGTTCGCGGAGGCCCGGGTGCTGGTCC |
| M102.txt | SEQ ID NO 23 | CGCCGATC | GACGACAAGGGCCGGTTCGCGGAGGCCCGGGTGCTGGTCC |
| M104.txt | SEQ ID NO 24 | CGCCGATC | GACGACAAGGGCCGGTTCGCGGAGGCCCGGGTGCTGGTCC |
| M105.txt | SEQ ID NO 25 | CGCCGATC | GACGACAAGGGCCGGTTCGCGGAGGCCCGGGTGCTGGTCC |
| M106.txt | SEQ ID NO 26 | CGCCGATC | GGCGCGGACGGCAGCTTCACCGAAGACCGCGTGATGGTCC |
| MY111.txt | SEQ ID NO 27 | CGCCGATC | GACGACAAGGGCCGGTTCGCGGAGGCCCGGGTGCTGGTCC |
| M76.txt | SEQ ID NO 28 | CGCCGATC | GATGCGGACGGTCGCTTCGTCGAGCCGCGCGTGCTGGTCC |
| MY451.txt | SEQ ID NO 29 | CGCCGATC | GATGCGGACGGTCGCTTCGTCGAGCCGCGCGTGCTGGTCC |
| ATCC2-chelnew.txt | SEQ ID NO 30 | CGCCTGTG | GATGCCGACGGCCGCTTCACCGAGGACAAGATCCTGGTCC |
| M10.txt | SEQ ID NO 31 | CGCCTGTG | GATGCCGACGGCCGCTTCACCGAGGACAAGATCCTGGTCC |
| M11-662.txt | SEQ ID NO 32 | CGCCTGTG | GATGCCGACGGCCGCTTCACCGAGGACAAGATCCTGGTCC |
| M12.txt | SEQ ID NO 33 | CGCCTGTG | GACGCCGACGGCCGCTTCACCGAGGACAAGATCCTGGTCC |
| M13_2_662.txt | SEQ ID NO 34 | CGCCTGTG | GACGCCGACGGCCGCTTCACCGAGGACAAGATCCTGGTCC |
| M14.txt | SEQ ID NO 35 | CGCCGACC | GACGAGAAGGGCCGCTTCACCGAGGAGCGCGTCCTGGTGC |
| M15.txt | SEQ ID NO 36 | CGCCTGTG | GACGCCGACGGCCGCTTCACCGAGGACAAGATCCTGGTCC |
| M16.txt | SEQ ID NO 37 | CGCCTGTG | GACGCCGACGGCCGCTTCACCGAGGACAAGATCCTGGTCC |
| M17_2_662.txt | SEQ ID NO 38 | CGCCTGTG | GACGCCGACGGCCGCTTCACCGAGGACAAGATCCTGGTCC |
| M50.txt | SEQ ID NO 39 | CGCCTGTG | GACGCCGACGGCCGTTTCACCGAGGACAAGATCCTGGTCC |
| M51.txt | SEQ ID NO 40 | CGCCTGTG | GATGCGGACGGCCGCTTCACCGAGGACAAGATCCTGGTCC |
| M115.txt | SEQ ID NO 41 | CGCCTGTG | GATGCCGACGGCCGCTTCACCGAGGACAAGATCCTGGTCC |
| M116.txt | SEQ ID NO 42 | CGCCTGTG | GATGCCGACGGCCGCTTCACCGAGGACAAGATCCTGGTCC |
| M119.txt | SEQ ID NO 43 | CGCCTGT | GATGCCGACGGCCGCTTCACCGAGGACAAGATCCTGGTCC |
| MY109.txt | SEQ ID NO 44 | CGCCTGTG | GATGCCGACGGCCGCTTCACCGAGGACAAGATCCTGGTCC |
| MY200.txt | SEQ ID NO 45 | CGCCCGTG | GACGCCAACGGCCGCTTCACCGAGGAGAAGATCCTGGTTC |
| MY207.txt | SEQ ID NO 46 | CGCCCGTG | GACGCCAACGGCCGCTTCACCGAGGAGAAGATCCTGGTTC |
| MY209.txt | SEQ ID NO 47 | CGCCCGTG | GACGCCAACGGCCGCTTCACCGAGGAGAAGATCCTGGTTC |
| M122.txt | SEQ ID NO 48 | CGCCGATC | GATGACAACGGCCGCTTCCTGGAGGAGCGCGTCCTGGTCC |
| M123.txt | SEQ ID NO 49 | CGCCGATC | GATGACAACGGCCGCTTCCTGGAGGAGCGCGTCCTGGTCC |
| M124.txt | SEQ ID NO 50 | CGCCGCTC | GACGGTGACGGTCGTTTCGAGGAGGAGCGCGTCCTGGTCC |
| Atcc3-for.txt | SEQ ID NO 51 | CGCCGATC | GACGCGGACGGCCGGTTCACCGAGGACCGCGTGATGGTTC |
| M53.txt | SEQ ID NO 52 | CGCCGATC | GGCGCGGACGGCAGCTTCACCGAAGACCGCGTGATGGTCC |
| M54.txt | SEQ ID NO 53 | CGCCGATC | GACGCCGACGGCCGCTTCACCGAAGACCGCGTCATGGTGC |
| M55.txt | SEQ ID NO 54 | CGCCGATC | GACCCGGACGGCCGGTTCACCGAGGACCGCGTGATGGTTC |
| M56.txt | SEQ ID NO 55 | CGCCGATC | GACGCGGACGGCAGCTTCACCGAGGATCGCGTGATGGTCC |
| M74(May12).txt | SEQ ID NO 56 | CGCCGATC | GACCCGGACGGCCGGTTCACCGAGGACCGCGTGATGGTTC |

TABLE 1-continued

| | | | |
|---|---|---|---|
| M77.txt | SEQ ID NO 57 | CGCCGATC | GACACCGACGGTCGCTTCACCGAGGACCGCGTGATGGTCC |
| M118.txt | SEQ ID NO 58 | CGCCGATC | GACGCGGACGGCAGCTTCACCGAGGATCGCGTGATGGTCC |
| MY221.txt | SEQ ID NO 59 | CGCCGATC | GACCCGGACGGCCGGTTCACCGAGGACCGCGTGATGGTTC |
| MY223.txt | SEQ ID NO 60 | CGCCGATC | GACACCGACGGTCGCTTCACCGAGGACCGCGTGATGGTCC |
| MY225.txt | SEQ ID NO 61 | CGCCGATC | GACCCGGACGGCCGGTTCACCGAGGACCGCGTGATGGTTC |
| My341.txt | SEQ ID NO 62 | CGCCGATC | GACCCGGACGGCCGGTTCACCGAGGACCGCGTGATGGTTC |
| My715.txt | SEQ ID NO 63 | CGCCGATC | GACCCGGACGGCCGGTTCACCGAGGACCGCGTGATGGTTC |
| MY470.txt | SEQ ID NO 64 | CGCCGATC | GACGCGCAGGGCCGCTTCGTCGAGCCGCGCGTGCTGGTCC |
| Atcc4-go.txt | SEQ ID NO 65 | CGCCGATC | GACGAGACCGGCCGGTTTGCTGAGCCGCGCGTTCTGGTCC |
| ATCC4-O-Gord.txt | SEQ ID NO 66 | CGCCGATC | GACGAGACCGGCCGGTTTGCTGAGCCGCGCGTTCTGGTCC |
| M78(lz).txt | SEQ ID NO 67 | CGCCGATC | GACGAGAACGGCCGGTTTGTCGAGCCGCGCGTTCTGGTCC |
| M79(jd).txt | SEQ ID NO 68 | CGCCGATC | GACGAGACCGGTCGGTTCGTCGAGCCACGCGTTCTGGTCC |
| M80(lg).txt | SEQ ID NO 69 | CGCCGATC | GACGAGAACGGCCGGTTCGTCGAGCCGCGCGTTCTGGTCC |
| M81(ll).txt | SEQ ID NO 70 | CGCCGATC | GACGAGAACGGCCGCTTCGTCGAGCCGCGCGTTCTGGTCC |
| M82(rm).txt | SEQ ID NO 71 | CGCCGATC | GACGAGACCGGCCGGTTTGCTGAGCCGCGCGTTCTGGTCC |
| M83(mb).txt | SEQ ID NO 72 | CGCCGATC | GACGAGACCGGCCGGTTTGCTGAGCCGCGCGTTCTGGTCC |
| M84(ow).txt | SEQ ID NO 73 | CGCCGATC | GACGAGAACGGCCGCTTCGTCGAGCCGCGCGTTCTGGTCC |
| M85(lb).txt | SEQ ID NO 74 | CGCCGATC | GACGAGACCGGCCGGTTTGCTGAGCCGCGCGTTCTGGTCC |
| M86(rb).txt | SEQ ID NO 75 | CGCCGATC | GACGAGAACGGCCGGTTTGTCGAGCCGCGCGTTCTGGTCC |
| M87(wn).txt | SEQ ID NO 76 | CGCCGATC | GACGAGACCGGCCGGTTTGCTGAGCCGCGCGTTCTGGTCC |
| M90(gordDB).txt | SEQ ID NO 77 | CGCCGATC | GACGAGACCGGCCGGTTTGCCGAGCCGCGCGTTCTGGTCC |
| m126.txt | SEQ ID NO 78 | CGCCGATC | GACGAGACCGGCCGGTTTGCTGAGCCGCGCGTTCTGGTCC |
| M128.txt | SEQ ID NO 79 | CGCCGGTG | GCCGGTGCTTCTCACTTTGCTGAGCCGCGCGTTCTGGTCC |
| My103.txt | SEQ ID NO 80 | CGCCGATC | GACGAGACCGGCCGGTTTGCTGAGCCGCGCGTTCTGGTCC |
| MY475.txt | SEQ ID NO 81 | CGCCGATC | GACGAGACCGGCCGGTTTGTCGAGCCGCGCGTTCTGGTCC |
| MY476.txt | SEQ ID NO 82 | CGCCGATC | GACGAGACCGGCCGGTTTGCTGAGCCGCGCGTTCTGGTCC |
| MY830.txt | SEQ ID NO 83 | CGCCGATC | GACGAGAACGGCCGCTTCGTCGAGCCGCGCGTTCTGGTCC |
| Atcc5-int.txt | SEQ ID NO 84 | CGCCGATC | GACGCCAAGGGCCGGTTCGAGGAGTCGCGTGTGCTGGTCC |
| ATCC5-Oint.txt | SEQ ID NO 85 | CGCCGATC | GACGCCAAGGGCCGGTTCGAGGAGTCGCGCGTGCTGGTCC |
| M18.txt | SEQ ID NO 86 | CGCCGATC | GACGCCAAGGGCCGGTTCGAGGAGTCGCGCGTGCTGGTCC |
| M19.txt | SEQ ID NO 87 | CGCCGATC | GACGCCAAGGGCCGGTTCGACGAGTCGCGCGTGCTGGTCC |
| M20.txt | SEQ ID NO 88 | CGCCGATC | GACGCCAAGGGCCGGTTCGACGAGTCGCGCGTGCTGGTCC |
| M21.txt | SEQ ID NO 89 | CGCCGATC | GACGCCAAGGGCCGGTTCGACGAGTCGCGCGTGCTGGTCC |
| M22.txt | SEQ ID NO 90 | CGCCGATC | GACGCCAAGGGCCGGTTCGACGAGTCGCGCGTGCTGGTCC |
| M23.txt | SEQ ID NO 91 | CGCCGATC | GACGCCAAGGGCCGGTTCGACGAGTCGCGCGTGCTGGTCC |
| M24.txt | SEQ ID NO 92 | CGCCGATC | GACGCCAAGGGCCGGTTCGACGAGTCGCGCGTGCTGGTCC |
| M25.txt | SEQ ID NO 93 | CGCCGATC | GACGCCAAGGGCCGGTTCGACGAGTCGCGCGTGCTGGTCC |
| M26.txt | SEQ ID NO 94 | CGCCGATC | GACGCCAAGGGCCGGTTCGACGAGTCGCGCGTGCTGGTCC |
| M27.txt | SEQ ID NO 95 | CGCCGATC | GACGCCAAGGGCCGGTTCGACGAGTCGCGCGTGCTGGTCC |
| M28.txt | SEQ ID NO 96 | CGCCGATC | GACGCCAAGGGCCGGTTCGACGAGTCGCGCGTGCTGGTCC |
| M107.txt | SEQ ID NO 97 | CGCCGATC | GACGCCAAGGGCCGGTTCGACGAGTCGCGCGTGCTGGTCC |
| MY107.txt | SEQ ID NO 98 | CGCCGATC | GACGCCAAGGGCCGGTTCGACGAGTCGCGCGTGCTGGTCC |
| MY112.txt | SEQ ID NO 99 | CGCCGATC | GACGCCAAGGGCCGGTTCGACGAGTCGCGCGTCCTGGTCC |
| MY312.txt | SEQ ID NO 100 | CGCCGATC | GACGCCAAGGGCCGGTTCGACGAGTCGCGCGTGCTGGTCC |
| Atcc6-kan.txt | SEQ ID NO 101 | CGCCGATC | GACGCTGAGGGCCGGTTCGTCGAGCCGCGCGTGCTGGTGC |
| ATCC6-OKan.txt | SEQ ID NO 102 | CGCCGATC | GACGCTGAGGGCCGGTTCGTCGAGCCGCGCGTGCTGGTGC |
| M1.txt | SEQ ID NO 103 | CGCCGATC | GACGCTGAGGGCCGGTTCGTCGAGCCGCGCGTGCTGGTGC |
| M2.txt | SEQ ID NO 104 | CGCCGATC | GACGCTGAGGGCCGGTTCGTCGAGCCGCGCGTGCTGGTGC |
| M3.txt | SEQ ID NO 105 | CGCCGATC | GACGCTGAGGGCCGGTTCGTCGAGCCGCGCGTGCTGGTGC |
| M4.txt | SEQ ID NO 106 | CGCCGATC | GACGCTGACGGCCGCTTTGTCGAGCCGCGCGTTCTGGTGC |
| M6.txt | SEQ ID NO 107 | CGCCGATC | GACGCTGAGGGCCGGTTCGTCGAGCCGCGCGTGCTGGTGC |
| M7.txt | SEQ ID NO 108 | CGCCGATC | GACGCTGAGGGCCGGTTCGTCGAGCCGCGCGTGCTGGTGC |
| M9.txt | SEQ ID NO 109 | CGCCGATC | GACGCTGAGGGCCGGTTCGTCGAGCCGCGCGTGCTGGTGC |
| M57.txt | SEQ ID NO 110 | CGCCGATC | GACGCTGAGGGCCGGTTCGTCGAGCCGCGCGTGCTGGTGC |
| M58.txt | SEQ ID NO 111 | CGCCGATC | GACGCTGAGGGCCGGTTCGTCGAGCCGCGCGTGCTGGTGC |
| M59.txt | SEQ ID NO 112 | CGCCGATC | GACGCTGAGGGCCGGTTCGTCGAGCCGCGCGTGCTGGTGC |
| M60.txt | SEQ ID NO 113 | CGCCGATC | GACGCTGAGGGCCGGTTCGTCGAGCCGCGCGTGCTGGTGC |
| M61.txt | SEQ ID NO 114 | CGCCGATC | GACGCTGAGGGCCGGTTCGTCGAGCCGCGCGTGCTGGTGC |
| M62.txt | SEQ ID NO 115 | CGCCGATC | GACGCTGAGGGCCGGTTCGTCGAGCCGCGCGTGCTGGTGC |
| MY106.txt | SEQ ID NO 116 | CGCCGATC | GACGCTGAGGGCCGGTTCGTCGAGCCGCGCGTGCTGGTGC |
| MY216.txt | SEQ ID NO 117 | CGCCGATC | GACGCTGAGGGCCGGTTCGTCGAGCCGCGCGTGCTGGTGC |
| MY218.txt | SEQ ID NO 118 | CGCCGATC | GACGCTGAGGGCCGGTTCGTCGAGCCGCGCGTGCTGGTGC |
| MY226.txt | SEQ ID NO 119 | CGCCGATC | GACGCTGAGGGCCGGTTCGTCGAGCCGCGCGTGCTGGTGC |
| M109.txt | SEQ ID NO 120 | CGCCGACCAGACCCAACGAG | GCCGGTGCCGACGTTTTCGAAGAGGGGCGTGTCCTGGTTC |
| M111.txt | SEQ ID NO 121 | CGCCGACCAGACCCAACGAG | GCCGGTGCCGACGTTTTCGAAGAGGGGCGTGTCCTGGTTC |
| M112.txt | SEQ ID NO 122 | CGCCGACCAGACCCAACGAG | GCCGGTGCCGACGTTTTCGAAGAGGGGCGTGTCCTGGTTC |
| M113.txt | SEQ ID NO 123 | CGCCGACCAGACCCAACGAG | GCCGGTGCCGACGTTTTCGAAGAGGGGCGTGTCCTGGTTC |
| M114.txt | SEQ ID NO 124 | CGCCGACCAGACCCAACGAG | GCCGGTGCCGACGTTTTCGAAGAGGGGCGTGTCCTGGTTC |
| M325.txt | SEQ ID NO 125 | CGCCGACCAGACCCAACGAG | GCCGGTGCCGACGTTTTCGAAGAGGGGCGTGTCCTGGTTC |
| MY718.txt | SEQ ID NO 126 | CGCCGACCAGACCCAACGAG | GCCGGTGCCGACGTTTTCGAAGAGGGGCGTGTCCTGGTTC |
| MY214.txt | SEQ ID NO 127 | CGCCGATC | GACGCGCAGGGCCGCTTCGTCGAGCCGCGCGTGCTGGTCC |
| MY224.txt | SEQ ID NO 128 | CGCCGATC | GACGCGCAGGGCCGCTTCGTCGAGCCGCGCGTGCTGGTCC |
| My244.txt | SEQ ID NO 129 | CGCCGATC | GACGCGCAGGGCCGCTTCGTCGAGCCGCGCGTGCTGGTCC |
| My339.txt | SEQ ID NO 130 | CGCCGATC | GACGCGCAGGGCCGCTTCGTCGAGCCGCGCGTGCTGGTCC |
| My343.txt | SEQ ID NO 131 | CGCCGATC | GACGCGCAGGGCCGCTTCGTCGAGCCGCGCGTGCTGGTCC |
| MY458.txt | SEQ ID NO 132 | CGCCGCTG | GACGCGAACGGCCACTTCACCGAGGAGAAGATCCTCGTCC |
| MY809.txt | SEQ ID NO 133 | CGCCGCTG | GACGCGAACGGCCACTTCACCGAGGAGAAGATCCTCGTCC |
| MY817.txt | SEQ ID NO 134 | CGCCGCTG | GACGCGAACGGCCACTTCACCGAGGAGAAGATCCTCGTCC |
| MY821.txt | SEQ ID NO 135 | CGCCGCTG | GACGCGAACGGCCACTTCACCGAGGAGAAGATCCTCGTCC |
| MY824.txt | SEQ ID NO 136 | CGCCGCTG | GACGCGAACGGCCACTTCACCGAGGAGAAGATCCTCGTCC |
| MY102.txt | SEQ ID NO 137 | CGCCGCTG | GAGGAGGACGGCCACTTCACCGAGGACCGGGTTCTGGTTC |
| My105.txt | SEQ ID NO 138 | CGCCGCTG | GAGGAGGACGGCCACTTCACCGAGGACCGGGTTCTGGTTC |
| MY251.txt | SEQ ID NO 139 | CGCCGCTG | GAGGAGGACGGCCACTTCACCGAGGACCGGGTTCTGGTTC |
| My256.txt | SEQ ID NO 140 | CGCCGCTG | GAGGAGGACGGCCACTTCACCGAGGACCGGGTTCTGGTTC |
| My294.txt | SEQ ID NO 141 | CGCCGCTG | GAGGAGGACGGCCACTTCACCGAGGACCGGGTTCTGGTTC |
| MY354.txt | SEQ ID NO 142 | CGCCGCTG | GAGGACGACGGCCGGTTCGCCGAGGAACGAGTTCTGGTGC |
| Atcc7-scr.txt | SEQ ID NO 143 | CGCCGATC | GACGCGAGCGGCCGGTTCGAGGAGTCGCGCGTCCTGGTCC |

TABLE 1-continued

| | | | |
|---|---|---|---|
| ATCC7-Oscr.txt | SEQ ID NO 144 | CGCCGATC | GACGCGAGCGGCCGGTTCGAGGAGTCGCGCGTCCTGGTCC |
| MY121.txt | SEQ ID NO 145 | CGCCGATC | GACGCGAGCGGCCGGTTCGAGGAGTCGCGCGTGCTGGTCC |
| MY249.txt | SEQ ID NO 146 | CGCCGATC | GACGCGAGCGGCCGGTTCGAGGAGTCGCGCGTCCTGGTCC |
| MY372.txt | SEQ ID NO 147 | CGCCGATC | GACGCGAACGGCCGGTTCGAGGAGTCGCGCGTCCTGGTCC |
| MY378.txt | SEQ ID NO 148 | CGCCGATC | GACGCGAGCGGCCGGTTCGAGGAGTCGCGCGTCCTGGTCC |
| MY484.txt | SEQ ID NO 149 | CGCCGATC | GACGCCGACGGCCGGTTCGAAGAGTCGCGTGTGCTGGTTC |
| My556.txt | SEQ ID NO 150 | CGCCGATC | GACCCCGACGGCCGCTTCGAAGAGTCGCGCGTGCTGGTTC |
| MY563.txt | SEQ ID NO 151 | CGCCGATC | GACCCCGACGGCCGCTTCGAAGAGTCGCGCGTGCTGGTTC |
| MY586.txt | SEQ ID NO 152 | CGCCGATC | GACGCCGACGGCCGCTTCGAAGAGTCGCGCGTACTGGTTC |
| Atcc8-sme.txt | SEQ ID NO 153 | CGCCGACC | GACGAGAACGGCCGCTTCACCGAGGACCGCGTCATGGTCC |
| M35.txt | SEQ ID NO 154 | CGCCGCTC | GACGACGAGGGCCGGTTCACCGAGGACAAGATCCTCGTCC |
| M36.txt | SEQ ID NO 155 | CGCCGATC | GACGACAACGGCCGGTTCACCGAGGACCGCGTGCTGGTGC |
| M37.txt | SEQ ID NO 156 | CGCCGACC | GACGAGAACGGCCGCTTCACCGAGGACCGCGTCATGGTCC |
| m125.txt | SEQ ID NO 157 | CGCCGATC | GACGCCGACGGACGGTTCGTCGAGGGACGCGTCCTGGTCC |
| MY143.txt | SEQ ID NO 158 | CGCCGACC | GACGAGAACGGCCGCTTCACCGAGGACCGCGTCATGGTCC |
| My104.txt | SEQ ID NO 159 | CGCCGATC | GACGCCGACGGACGGTTCGTCGAGGGACGTGTCCTGGTCC |
| MY196.txt | SEQ ID NO 160 | CGCCGATC | GACGCCGACGGACGGTTCGTCGAGGGACGTGTCCTGGTCC |
| MY357.txt | SEQ ID NO 161 | CGCCGATC | GACGCCGACGGACGGTTCGTCGAGGGACGCGTCCTGGTCC |
| My358.txt | SEQ ID NO 162 | CGCCGATC | GACGCCGACGGACGGTTCGTCGAGGGACGCGTCCTGGTCC |
| My480.txt | SEQ ID NO 163 | CGCCGATC | GAGGCCGACGGACGGTTCGTCGAGGGACGTGTCCTGGTCC |
| MY212.txt | SEQ ID NO 164 | CGCCGCTG | GAGGACGACAATCGCTTCACCGAGGACCGGGTTCTGGTGC |
| MY491.txt | SEQ ID NO 165 | CGCCGCTG | GAGGACGACAATCGCTTCACCGAGGACCGGGTTCTGGTGC |
| MY497.txt | SEQ ID NO 166 | CGCCGCTG | GACGACGACAGTCGCTTCGCCGAGGACCGAGTTCTGGTGC |
| MY816.txt | SEQ ID NO 167 | CGCCGATC | GACGCCGACGGCCGGTTCGCGGAGTCGCGTGTCCTGGTCC |
| Atcc10-xco.txt | SEQ ID NO 168 | CGCCGATC | GACGAGGATGGCCGCTTCACCGAGCCGCGGGTGCTGGTGC |
| M38.txt | SEQ ID NO 169 | CGCCGATC | GACGAGGATGGCCGCTTCACCGAGCCGCGGGTGCTGGTGC |
| M39.txt | SEQ ID NO 170 | CGCCGATC | GACGAGGATGGCCGCTTCACCGAGCCGCGGGTGCTGGTGC |
| M40.txt | SEQ ID NO 171 | CGCCGATC | GACGAGGATGGCCGCTTCACCGAGCCGCGGGTGCTGGTGC |
| M41.txt | SEQ ID NO 172 | CGCCGATC | GACGAGGATGGCCGCTTCACCGAGCCGCGGGTGCTGGTGC |
| M42.txt | SEQ ID NO 173 | CGCCGATC | GACGAGGATGGCCGCTTCACCGAGCCGCGGGTGCTGGTGC |
| M43.txt | SEQ ID NO 174 | CGCCGATC | GACGAGGATGGCCGCTTCACCGAGCCGCGGGTGCTGGTGC |
| M44.txt | SEQ ID NO 175 | CGCCGATC | GACGAGGATGGCCGCTTCACCGAGCCGCGGGTGCTGGTGC |
| M45.txt | SEQ ID NO 176 | CGCCGATC | GACGAGGATGGCCGCTTCACCGAGCCGCGGGTGCTGGTGC |
| M46.txt | SEQ ID NO 177 | CGCCGATC | GACGAGGATGGCCGCTTCACCGAGCCGCGGGTGCTGGTGC |
| M47.txt | SEQ ID NO 178 | CGCCGATC | GACGAGGATGGCCGCTTCACCGAGCCGCGGGTGCTGGTGC |
| M68 (Mav6) .txt | SEQ ID NO 179 | CGCCGATC | GACGAGGATGGCCGCTTCACCGAGCCGCGGGTGCTGGTGC |
| M89.txt | SEQ ID NO 180 | CGCCGATC | GACGAGGATGGCCGCTTCACCGAGCCGCGGGTGCTGGTGC |
| M66 (Mav4) .txt | SEQ ID NO 181 | CGCCGATC | GACGCCGACGGCCGGTTCGTCGAGGGCCGCGTCCTGGTCC |
| | | 430 | 440 450 460 470 480 |

BASE NOS 481–540

| | | |
|---|---|---|
| ATCC9-Mtb.txt | SEQ ID NO 1 | GCCGCAAGGCGGGCGAGGTGGAGTACGTGCCCTCGTCTGAGGTGGACTACATGGACGTCT |
| MY621.txt | SEQ ID NO 2 | GCCGCAAGGCCGGCGAGGTGGAGTTCGTGTCGGCGACCGAGGTCGACTACATGGATGTCT |
| Atcc1-av.TXT | SEQ ID NO 3 | GCCGCAAGGCGGGCGAGGTCGAGTACGTGCCCTCGTCCGAGGTGGACTACATGGACNTKT |
| M29.txt | SEQ ID NO 4 | GCCGCAAGGCGGGCGAGGTCGAGTACGTGCCCTCGTCCGAGGTGGACTACATGGACGTGT |
| M30.txt | SEQ ID NO 5 | GCCGCAAGGCGGGCGAGGTCGAGTACGTGCCCTCGTCCGAGGTGGACTACATGGACGTGT |
| M31.txt | SEQ ID NO 6 | GCCGCAAGGCGGGCGAGGTCGAGTACGTGCCCTCGTCCGAGGTGGACTACATGGACGTGT |
| M32.txt | SEQ ID NO 7 | GCCGCAAGGCGGGCGAGGTCGAGTACGTGCCCTCGTCCGAGGTGGACTACATGGACGTGT |
| M33.txt | SEQ ID NO 8 | GCCGCAAGGCGGGCGAGGTCGAGTACGTGCCCTCGTCCGAGGTGGACTACATGGACGTGT |
| M34.txt | SEQ ID NO 9 | GCCGCAAGGCGGGCGAGGTCGAGTACGTGCCCTCGTCCGAGGTGGACTACATGGACGTGT |
| M48-new.txt | SEQ ID NO 10 | GCCGCAAGGCGGGCGAGGTCGAGTACGTGCCCTCGTCCGAGGTGGACTACATGGACGTGT |
| M49.txt | SEQ ID NO 11 | GCCGCAAGGCGGGCGAGGTCGAGTACGTGCCCTCGTCCGAGGTGGACTACATGGACGTGT |
| M64(Mav2).txt | SEQ ID NO 12 | GCCGCAAGGCGGGCGAGGTCGAGTACGTGCCCTCGTCCGAGGTGGACTACATGGACGTGT |
| M65(Mav2).txt | SEQ ID NO 13 | GCCGCAAGGCGGGCGAGGTCGAGTACGTGCCCTCGTCCGAGGTGGACTACATGGACGTGT |
| M67(Mav5).txt | SEQ ID NO 14 | GCCGCAAGGCGGGCGAGGTCGAGTACGTGCCCTCGTCCGAGGTGGACTACATGGACGTGT |
| M69(Mav7).txt | SEQ ID NO 15 | GCCGCAAGGCGGGCGAGGTCGAGTACGTGCCCTCGTCCGAGGTGGACTACATGGACGTGT |
| M71(Mav9).txt | SEQ ID NO 16 | GCCGCAAGGCGGGCGAGGTCGAGTACGTGCCCTCGTCCGAGGTGGACTACATGGACGTGT |
| M91.txt | SEQ ID NO 17 | GCCGCAAGGCGGGCGAGGTCGAGTACGTGCCCTCGTCCGAGGTGGACTACATGGACGTGT |
| M94.txt | SEQ ID NO 18 | GCCGCAAGGCGGGCGAGGTCGAGTACGTGCCCTCGTCCGAGGTGGACTACATGGACGTGT |
| M95.txt | SEQ ID NO 19 | GCCGCAAGGCGGGCGAGGTCGAGTACGTGCCCTCGTCCGAGGTGGACTACATGGACGTGT |
| M96.txt | SEQ ID NO 20 | GCCGCAAGGCGGGCGAGGTCGAGTACGTGCCCTCGTCCGAGGTGGACTACATGGACGTGT |
| M100.txt | SEQ ID NO 21 | GCCGCAAGGCGGGCGAGGTCGAGTACGTGCCCTCGTCCGAGGTGGACTACATGGACGTGT |
| M101.txt | SEQ ID NO 22 | GCCGCAAGGCGGGCGAGGTCGAGTACGTGCCCTCGTCCGAGGTGGACTACATGGACGTGT |
| M102.txt | SEQ ID NO 23 | GCCGCAAGGCGGGCGAGGTCGAGTACGTGCCCTCGTCCGAGGTGGACTACATGGACGTGT |
| M104.txt | SEQ ID NO 24 | GCCGCAAGGCGGGCGAGGTCGAGTACGTGCCCTCGTCCGAGGTGGACTACATGGACGTGT |
| M105.txt | SEQ ID NO 25 | GCCGCAAGGCGGGCGAGGTCGAGTACGTGCCCTCGTCCGAGGTGGACTACATGGACGTGT |
| M106.txt | SEQ ID NO 26 | GCCGTAAGGCCGGCGAGGTCGAGAACGTGCCCCCGATCGACGTGGATTACATGGACGTGT |

TABLE 1-continued

| | | |
|---|---|---|
| MY111.txt | SEQ ID NO 27 | GCCGCAAGGCGGGCGAGGTCGAGTACGTGCCCTCGTCCGAGGTGGACTACATGGACGTGT |
| M76.txt | SEQ ID NO 28 | GCCGCAAGGCGGGCGAGGTGGAGTACGTGCCCTCGTCTGAGGTGGACTACATGGACGTCT |
| MY451.txt | SEQ ID NO 29 | GCCGCAAGGCGGGCGAGGTGGAGTACGTGCCCTCGTCTGAGGTGGACTACATGGACGTCT |
| ATCC2-chelnew.txt | SEQ ID NO 30 | GCCGTAAGGGTGGCGAGGTCGAGTTCGTCTCGGCGACCGAGGTGGACTACATGGACGTCT |
| M10.txt | SEQ ID NO 31 | GCCGTAAGGGTGGCGAGGTCGAGTTCGTCTCGGCGACCGAGGTGGACTACATGGACGTCT |
| M11.txt | SEQ ID NO 32 | GCCGTAAGGGTGGCGAGGTCGAGTTCGTCTCGGCGACCGAGGTGGACTACATGGACGTCT |
| M12.txt | SEQ ID NO 33 | GCCGTAAGGGTGGCGAGGTCGAGTTCGTCTCGGCGACCGAGGTGGACTACATGGACGTCT |
| M13_2_662.txt | SEQ ID NO 34 | GCCGTAAGGGTGGCGAGGTCGAGTTCGTCTCGGCGACCGAGGTGGACTACATGGACGTCT |
| M14.txt | SEQ ID NO 35 | GCCGTAAGGGTGGCGAGGTCGAGTTCGTGCCGTCGACCGGCGTCGACTACATGGACGTCT |
| M15.txt | SEQ ID NO 36 | GCCGTAAGGGTGGCGAGGTCGAGTTCGTCTCGGCGACCGAGGTGGACTACATGGACGTCT |
| M16.txt | SEQ ID NO 37 | GCCGTAAGGGTGGCGAGGTCGAGTTCGTCTCGGCGACCGAGGTGGACTACATGGACGTCT |
| M17_2_662.txt | SEQ ID NO 38 | GCCGTAAGGGTGGCGAGGTCGAGTTCGTCTCGGCGACCGAGGTGGACTACATGGACGTCT |
| M50.txt | SEQ ID NO 39 | GCCGTAAGGGTGGCGAGGTCGAGTTCGTCTCGGCGACCGAGGTGGACTACATGGACGTCT |
| M51.txt | SEQ ID NO 40 | GCCGTAAGGGTGGCGAGGTCGAGTTCGTCTCGGCGACCGAGGTGGACTACATGGACGTCT |
| M115.txt | SEQ ID NO 41 | GCCGTAAGGGTGGCGAGGTCGAGTTCGTCTCGGCGACCGAGGTGGACTACATGGACGTCT |
| M116.txt | SEQ ID NO 42 | GCCGTAAGGGTGGCGAGGTCGAGTTCGTCTCGGCGACCGAGGTGGACTACATGGACGTCT |
| M119.txt | SEQ ID NO 43 | GCCGTAAGGGTGGCGAGGTCGAGTTCGTCTCGGCGACCGAGGTGGACTACATGGACGTCT |
| MY109.txt | SEQ ID NO 44 | GCCGTAAGGGTGGCGAGGTCGAGTTCGTCTCGGCGACCGAGGTGGACTACATGGACGTCT |
| MY200.txt | SEQ ID NO 45 | GCCGCAAGGGCGGCGAGGTGGAGTTCGTGTCGGCGACCGAGGTCGACTACATGGATGTTT |
| MY207.txt | SEQ ID NO 46 | GCCGCAAGGGCGGCGAGGTGGAGTTCGTGTCGGCGACCGAGGTCGACTACATGGATGTTT |
| M122.txt | SEQ ID NO 47 | GCCGCAAGGGCGGCGAGGTGGAGTTCGTGTCGGCGACCGAGGTCGACTACATGGATGTCT |
| M123.txt | SEQ ID NO 48 | GCCGCAAGGGCGGCGAGGTCGAGCAGATCTCGTCGAGCGAGGTGGACTACATGGACGTCT |
| M124.txt | SEQ ID NO 49 | GCCGCAAGGGCGGCGAGGTCGAGCAGATCTCGTCGAGCGAGGTGGACTACATGGACGTCT |
| Atcc3-for.txt | SEQ ID NO 50 | GCCGTAAGGGCGGCGAGGTCGAGTTCGTCTCGGCGAGCGAGGTCGACTACATGGACGTCT |
| M53.txt | SEQ ID NO 51 | GTCGTAAGGGCGGCGAGGTCGAGAACGTGGCCCCGTCCGACGTCGACTACATGGACGTCT |
| M54.txt | SEQ ID NO 52 | GCCGTAAGGGCGGCGAGGTCGAGAACGTGGCCCCGATCGACGTGGATTACATGGACGTCT |
| M55.txt | SEQ ID NO 53 | GTCGTAAGGGCGGCGAGGTCGAGAACGTGGCCCCGTCCGACGTCGACTACATGGACGTCT |
| M56.txt | SEQ ID NO 54 | GTCGTAAGGGCGGCGAGGTCGAGAATGTGGCCCCGTCCGACGTCGACTACATGGACGTCT |
| M74(May12).txt | SEQ ID NO 55 | GGCGTAAGGGTGGCGAGGTCGAGAACGTGGCCCCGTCCGACGTCGACTACATGGACGTCT |
| | SEQ ID NO 56 | GTCGTAAGGGCGGCGAGGTCGAGAATGTGGCCCCGTCCGACGTCGACTACATGGACGTCT |

| | | |
|---|---|---|
| | SEQ ID NO 57 | GCCGTAAGGGTGGCGAGGTCGAGAACGTGGCCCCGTCCGACGTCGACTACATGGACGTCT |
| M77.txt | SEQ ID NO 56 | GCCGTAAGGGTGGCGAGGTCGAGAACGTGGCCCCGTCCGACGTCGACTACATGGACGTCT |
| M118.txt | SEQ ID NO 57 | GCCGTAAGGGCGGCGAGGTCGAGAACGTGGCCCCGTCCGACGTCGACTACATGGACGTCT |
| MY221.txt | SEQ ID NO 58 | GCCGTAAGGGTGGCGAGGTCGAGAACGTGGCCCCGTCCGACGTCGACTACATGGACGTCT |
| MY223.txt | SEQ ID NO 59 | GTCGTAAGGGCGGCGAGGTCGAGAACGTGGCCCCGTCCGACGTCGACTACATGGACGTCT |
| MY225.txt | SEQ ID NO 60 | GTCGTAAGGGCGGCGAGGTCGAGAACGTGGCCCCGTCCGACGTCGACTACATGGACGTCT |
| My341.txt | SEQ ID NO 61 | GTCGTAAGGGCGGCGAGGTCGAGAACGTGGCCCCGTCCGACGTCGACTACATGGACGTCT |
| My715.txt | SEQ ID NO 62 | GCCGGAAGGCGGGCGAGGTCGAGTACGTGCCCTCGTCAGAGGTGGACTACATGGACGTGT |
| MY470.txt | SEQ ID NO 63 | GCCGCAAGGCGGGCGAGGTGGAGTACGTGCCCTCGTCCGAGGTGGACTACATGGACGTCT |
| Atcc4-go.txt | SEQ ID NO 64 | GCCGCAAGGCGGGCGAGGTGGAGTACGTGCCCTCGTCCGAGGTGGACTACATGGACGTCT |
| ATCC-0-Gord.txt | SEQ ID NO 65 | GCCGCAAGGCGGGCGAGGTGGAGTACGTGCCCTCGTCCGAGGTCGACTACATGGACGTCT |
| M78 (lz) .txt | SEQ ID NO 66 | GCCGGAAGGCGGGCGAGGTCGAGTACGTGCCCTCGTCCGAGGTGGACTACATGGACGTCT |
| M79 (jd) .txt | SEQ ID NO 67 | GCCGCAAGGCGGGCGAGGTGGAGTACGTGCCCTCGTCCGAGGTCGACTACATGGACGTCT |
| M80 (lg) .txt | SEQ ID NO 68 | GCCGCAAGGCGGGCGAGGTGGAGTACGTGCCTTCGTCCGAGGTGGACTACATGGACGTCT |
| M81 (ll) .txt | SEQ ID NO 69 | GCCGCAAGGCGGGCGAGGTGGAGTACGTGCCCTCGTCCGAGGTGGACTACATGGACGTCT |
| M82 (rm) .txt | SEQ ID NO 70 | GCCGCAAGGCGGGCGAGGTGGAGTACGTGCCCTCGTCCGAGGTGGACTACATGGACGTCT |
| M83 (mb) .txt | SEQ ID NO 71 | GCCGCAAGGCGGGCGAGGTGGAGTACGTGCCCTCGTCCGAGGTGGACTACATGGACGTCT |
| M84 (ow) .txt | SEQ ID NO 72 | GCCGCAAGGCGGGCGAGGTGGAGTACGTGCCCTCGTCCGAGGTGGACTACATGGACGTCT |
| M85 (lb) .txt | SEQ ID NO 73 | GCCGCAAGGCGGGCGAGGTGGAGTACGTGCCCTCGTCCGAGGTGGACTACATGGACGTCT |
| M86 (rb).txt | SEQ ID NO 74 | GCCGCAAGGCGGGCGAGGTGGAGTACGTGCCCTCGTCCGAGGTGGACTACATGGACGTCT |
| M87 (wn) .txt | SEQ ID NO 75 | GCCGCAAGGCGGGCGAGGTCGAGTACGTGCCCTCGTCCGAGGTGGACTACATGGACGTCT |
| M90 (gordDB) .txt | SEQ ID NO 76 | GCCGCAAGGCGGGCGAGGTGGAGTACGTCCCCTCGTCCGAGGTGGACTACATGGACGTCT |
| m126.txt | SEQ ID NO 77 | GCCGCAAGGCGGGCGAGGTGGAGTACGTGCCGTCGTCCGAGGTGGACTACATGGACGTCT |
| M128.txt | SEQ ID NO 78 | GCCGCAAGGCGGGCGAGGTGGAGTACGTTCCCTCGTCCGAGGTGGACTACATGGACGTCT |
| My103.txt | SEQ ID NO 79 | GCCGCAAGGCGGGCGAGGTGGAGTACGTGCCTTCGTCCGAGGTGGACTACATGGACGTCT |
| MY475.txt | SEQ ID NO 80 | GCCGCAAGGCGGGCGAGGTGGAGTACGTGCCCTCGTCCGAGGTGGACTACATGGACGTCT |
| MY476.txt | SEQ ID NO 81 | GCCGCAAGGCGGGCGAGGTGGAGTACGTGCCCTCGTCCGAGGTGGACTACATGGACGTCT |
| MY830.txt | SEQ ID NO 82 | GCCGCAAGGCGGGCGAGGTGGAGTACGTGCCCTCGTCCGAGGTGGACTACATGGACGTCT |
| Atcc5-int.txt | SEQ ID NO 83 | GCCGGAAGGCGGGCGAGGTGGAGTACGTGCCGTCGTCCGAGGTGGACTACATGGACGTCT |

TABLE 1-continued

| | | |
|---|---|---|
| ATCC5-Oint.txt | SEQ ID NO 84 | GCCGGAAGGCGGGCGAGGTCGAGTACGTGCCCTCGTCCGAGGTGGACTACATGGACGTGT |
| M18.txt | SEQ ID NO 85 | GCCGGAAGGCGGGCGAGGTCGAGTACGTGCCCTCGTCCGAGGTGGACTACATGGACGTGT |
| M19.txt | SEQ ID NO 86 | GCCGGAAGGCGGGCGAGGTCGAGTACGTGCCCTCGTCCGAGGTGGACTACATGGACGTGT |
| M20.txt | SEQ ID NO 87 | GCCGGAAGGCGGGCGAGGTCGAGTACGTGCCCTCGTCCGAGGTGGACTACATGGACGTGT |
| M21.txt | SEQ ID NO 88 | GCCGGAAGGCGGGCGAGGTCGAGTACGTGCCCTCGTCCGAGGTGGACTACATGGACGTGT |
| M22.txt | SEQ ID NO 89 | GCCGGAAGGCGGGCGAGGTCGAGTACGTGCCCTCGTCCGAGGTGGACTACATGGACGTCT |
| M23.txt | SEQ ID NO 90 | GCCGGAAGGCGGGCGAGGTCGAGTACGTGCCCTCGTCCGAGGTGGACTACATGGACGTGT |
| M24.txt | SEQ ID NO 91 | GCCGGAAGGCGGGCGAGGTCGAGTACGTGCCCTCGTCCGAGGTGGACTACATGGACGTCT |
| M25.txt | SEQ ID NO 92 | GCCGGAAGGCGGGCGAGGTCGAGTACGTGCCCTCGTCCGAGGTGGACTACATGGACGTGT |
| M26.txt | SEQ ID NO 93 | GCCGGAAGGCGGGCGAGGTCGAGTACGTGCCCTCGTCCGAGGTGGACTACATGGACGTGT |
| M27.txt | SEQ ID NO 94 | GCCGGAAGGCGGGCGAGGTCGAGTACGTGCCCTCGTCCGAGGTGGACTACATGGACGTGT |
| M28.txt | SEQ ID NO 95 | GCCGGAAGGCGGGCGAGGTCGAGTACGTGCCCTCGTCCGAGGTGGACTACATGGACGTGT |
| M107.txt | SEQ ID NO 96 | GCCGGAAGGCGGGCGAGGTCGAGTACGTGCCCTCGTCCGAGGTGGACTACATGGACGTGT |
| MY107.txt | SEQ ID NO 97 | GCCGGAAGGCGGGCGAGGTCGAGTACGTGCCCTCGTCCGAGGTGGACTACATGGACGTCT |
| MY112.txt | SEQ ID NO 98 | GCCGGAAGGCGGGCGAGGTCGAGTACGTGCCCTCGTCCGAGGTGGACTACATGGACGTCT |
| MY312.txt | SEQ ID NO 99 | GCCGGAAGGCGGGCGAGGTCGAGTACGTGCCCTCGTCCGAGGTGGACTACATGGACGTGT |
| Atcc6-kan.txt | SEQ ID NO 100 | GCCGGAAGGCGGGCGAGGTCGAGTACGTGCCCTCGTCCGAGGTGGACTACATGGACGTGT |
| ATCC6-OKan.txt | SEQ ID NO 101 | GCCGCAAGGCCGGCGAGGTCGAGTACGTGGCCTCGTCCGAGGTGGACTACATGGACGTCT |
| M1.txt | SEQ ID NO 102 | GCCGCAAGGCCGGCGAGGTCGAGTACGTGGCCTCGTCCGAGGTGGACTACATGGACGTCT |
| M2.txt | SEQ ID NO 103 | GCCGCAAGGCCGGCGAGGTCGAGTACGTGGCCTCGTCCGAGGTGGACTACATGGACGTCT |
| M3.txt | SEQ ID NO 104 | GCCGCAAGGCCGGCGAGGTCGAGTACGTGGCCTCGTCCGAGGTGGACTACATGGACGTCT |
| M4.txt | SEQ ID NO 105 | GCCGCAAGGCCGGCGAGGTCGAGTACGTGGCCTCGTCCGAGGTGGACTACATGGACGTCT |
| M6.txt | SEQ ID NO 106 | GCCGCAAGGCGGGCGAGGTCGAATACGTCGCCTCCTCCGAGGTGGACTACATGGACGTCT |
| M7.txt | SEQ ID NO 107 | GCCGCAAGGCCGGCGAGGTCGAGTACGTGGCCTCGTCCGAGGTGGACTACATGGACGTCT |
| M9.txt | SEQ ID NO 108 | GCCGCAAGGCCGGCGAGGTCGAGTACGTGGCCTCGTCCGAGGTGGACTACATGGACGTCT |
| M57.txt | SEQ ID NO 109 | GCCGCAAGGCCGGCGAGGTCGAGTACGTGGCCTCGTCCGAGGTGGACTACATGGACGTCT |
| M58.txt | SEQ ID NO 110 | GCCGCAAGGCCGGCGAGGTCGAGTACGTGGCCTCGTCCGAGGTGGACTACATGGACGTCT |
| M59.txt | SEQ ID NO 111 | GCCGCAAGGCCGGCGAGGTCGAGTACGTGGCCTCGTCCGAGGTGGACTACATGGACGTCT |
| | SEQ ID NO 112 | GCCGCAAGGCCGGCGAGGTCGAGTACGTGGCCTCGTCCGAGGTGGACTACATGGACGTCT |

| | | |
|---|---|---|
| M60.txt | SEQ ID NO 113 | GCCGCAAGGCCGGCGAGGTCGAGTACGTGGCCTCGTCCGAGGTGGACTACATGGACGTCT |
| M61.txt | SEQ ID NO 114 | GCCGCAAGGCCGGCGAGGTCGAGTACGTGGCCTCGTCCGAGGTGGACTACATGGACGTCT |
| M62.txt | SEQ ID NO 115 | GCCGCAAGGCCGGCGAGGTCGAGTACGTGGCCTCGTCCGAGGTGGACTACATGGACGTCT |
| MY106.txt | SEQ ID NO 116 | GCCGCAAGGCCGGCGAGGTCGAGTACGTGGCCTCGTCCGAGGTGGACTACATGGACGTCT |
| MY216.txt | SEQ ID NO 117 | GCCGCAAGGCCGGCGAGGTCGAGTACGTGGCCTCGTCCGAGGTGGACTACATGGACGTCT |
| MY218.txt | SEQ ID NO 118 | GCCGCAAGGCCGGCGAGGTCGAGTACGTGGCCTCGTCCGAGGTGGACTACATGGACGTCT |
| MY226.txt | SEQ ID NO 119 | GCCGCAAGGCCGGCGAGGTCGAGTACGTGGCCTCGTCCGAGGTGGACTACATGGACGTCT |
| M109.txt | SEQ ID NO 120 | GCCGCAAGGCGGGCGAGGTCGAGTACGTGCCCAGCTCCGAGGTGGACTACATGGACGTCT |
| M111.txt | SEQ ID NO 121 | GCCGCAAGGCGGGCGAGGTGGAGTACGTGCCCAGCTCCGAGGTGGACTACATGGACGTCT |
| M112.txt | SEQ ID NO 122 | GCCGCAAGGCGGGCGAGGTGGAGTACGTGCCCAGCTCCGAGGTGGACTACATGGACGTCT |
| M113.txt | SEQ ID NO 123 | GCCGCAAGGCGGGCGAGGTGGAGTACGTGCCCAGCTCCGAGGTGGACTACATGGACGTCT |
| M114.txt | SEQ ID NO 124 | GCCGCAAGGCGGGCGAGGTGGAGTACGTGCCCAGCTCCGAGGTGGACTACATGGACGTCT |
| MY325.txt | SEQ ID NO 125 | GCCGCAAGGCGGGCGAGGTGGAGTACGTGCCCAGCTCCGAGGTGGACTACATGGACGTCT |
| MY718.txt | SEQ ID NO 126 | GCCGCAAGGCGGGCGAGGTGGAGTACGTGCCCAGCTCCGAGGTGGACTACATGGACGTCT |
| MY214.txt | SEQ ID NO 127 | GCCGGAAGGCGGGCGAGGTCGAGTACGTGCCCTCGTCAGAGGTGGACTACATGGACGTGT |
| MY224.txt | SEQ ID NO 128 | GCCGGAAGGCGGGCGAGGTCGAGTACGTGCCCTCGTCAGAGGTGGACTACATGGACGTGT |
| My244.txt | SEQ ID NO 129 | GCCGGAAGGCGGGCGAGGTCGAGTACGTGCCCTCGTCAGAGGTGGACTACATGGACGTGT |
| My339.txt | SEQ ID NO 130 | GCCGGAAGGCGGGCGAGGTCGAGTACGTGCCCTCGTCAGAGGTGGACTACATGGACGTGT |
| My343.txt | SEQ ID NO 131 | GCCGGAAGGCGGGCGAGGTCGAGTACGTGCCCTCGTCAGAGGTGGACTACATGGACGTGT |
| MY458.txt | SEQ ID NO 132 | GTCGTAAGGGCGGCGAGGTCGAGTTCGTCTCGGCGAACGACGTCGACTACATGGACGTCT |
| MY809.txt | SEQ ID NO 133 | GTCGTAAGGGCGGCGAGGTCGAGTTCGTCTCGGCGAACGACGTCGACTACATGGACGTCT |
| MY817.txt | SEQ ID NO 134 | GTCGTAAGGGCGGCGAGGTCGAGTTCGTCTCGGCGAACGACGTCGACTACATGGACGTCT |
| MY821.txt | SEQ ID NO 135 | GTCGTAAGGGCGGCGAGGTCGAGTTCGTCTCGGCGAACGACGTCGACTACATGGACGTCT |
| MY824.txt | SEQ ID NO 136 | GTCGTAAGGGCGGCGAGGTCGAGTTCGTCTCGGCGAACGACGTCGACTACATGGACGTCT |
| MY102.txt | SEQ ID NO 137 | GTCGTAAGGGTGGTGAGGTCGAGTACGTGTCTTCGGCCGAGGTCGACTACATGGACGTCT |
| My105.txt | SEQ ID NO 138 | GCCGTAAGGGTGGCGAGGTCGAGTACGTCTCTTCGGCCGAGGTCGACTACATGGACGTCT |
| MY251.txt | SEQ ID NO 139 | GTCGTAAGGGTGGTGAGGTCGAGTACGTCTCTTCGGCCGAGGTCGACTACATGGACGTCT |
| My256.txt | SEQ ID NO 140 | GTCGTAAGGGTGGTGAGGTCGAGTACGTCTCTTCGGCCGAGGTCGACTACATGGACGTCT |
| My294.txt | SEQ ID NO 141 | GTCGTAAGGGTGGTGAGGTCGAGTACGTGTCTTCGGCCGAGGTCGACTACATGGACGTCT |

| | | |
|---|---|---|
| MY354.txt | SEQ ID NO 142 | GCCGCAAGGGTGGCGAGGTCGAGTACGTGTCGTCGTCCGAGGTTGACTACATGGACGTCT |
| Atcc7-scr.txt | SEQ ID NO 143 | GCCGGAAGGCGGGCGAGGTCGAGTACGTGCCGTCGTCCGAGGTGGACTACATGGACGTGT |
| ATCC7-Oscr.txt | SEQ ID NO 144 | GCCGGAAGGCCGGCGAGGTCGAGTACGTGCCGTCGTCCGAGGTGGACTACATGGACGTGT |
| MY121.txt | SEQ ID NO 145 | GCCGGAAGGCGGGCGAGGTCGAGTACGTGCCGTCGTCCGAGGTGGACTACATGGACGTGT |
| MY249.txt | SEQ ID NO 146 | GCCGGAAGGCGGGCGAGGTCGAGTACGTGCCGTCGTCCGAGGTGGACTACATGGACGTGT |
| MY372.txt | SEQ ID NO 147 | GCCGGAAGGCGGGCGAGGTCGAGTACGTGCCGTCGTCCGAGGTGGACTACATGGACGTGT |
| MY378.txt | SEQ ID NO 148 | GCCGGAAGGCGGGCGAGGTCGAGTACGTGCCGTCGTCCGAGGTGGACTACATGGACGTGT |
| MY484.txt | SEQ ID NO 149 | GCCGCAAGGCGGGCGAGGTCGAGTACGTGCCGTCGTCCGAGGTGGACTACATGGACGTGT |
| My556.txt | SEQ ID NO 150 | GCCGTAAGGCGGGCGAGGTCGAATACGTGCCGTCGTCCGAGGTGGACTACATGGACGTGT |
| MY563.txt | SEQ ID NO 151 | GCCGTAAGGCGGGCGAGGTCGAATACGTGCCGTCGTCCGAGGTGGACTACATGGACGTGT |
| MY586.txt | SEQ ID NO 152 | GCCGTAAGGCGGGCGAGGTCGAGTACGTGCCGTCGTCCGAGGTGGACTACATGGACGTGT |
| Atcc8-sme.txt | SEQ ID NO 153 | GCGCGAAGGCGGGCGAGGTCGAGTTCGTCTCCGCGAACGAGGTGGACTACATGGACGTCT |
| M35.txt | SEQ ID NO 154 | GCCGTAAGGGCGGCGAGGTCGAGTTCGTCTCGGCGACCGAGGTGGACTACATGGACGTCT |
| M36.txt | SEQ ID NO 155 | GCCGCAAGGGCGGCGAGGTCGAGTTCGTCTCCGCGACCGAGGTGGACTACATGGACGTCT |
| M37.txt | SEQ ID NO 156 | GCGCGAAGGGCGGCGAGGTCGAGTTCGTCTCCGCGAACGAGGTGGACTACATGGACGTCT |
| m125.txt | SEQ ID NO 157 | GCCGCAAGGGCGGCGAGGTCGAGTACGTGCCCTCCTCCGAGGTGGACTACATGGACGTGT |
| MY143.txt | SEQ ID NO 158 | GCGCGAAGGCGGGCGAGGTCGAGTTCGTCTCCGCGAACGAGGTGGACTACATGGACGTCT |
| MY196.txt | SEQ ID NO 159 | GCCGCAAGGGCGGCGAGGTCGAGTACGTGCCCTCCTCCGAGGTGGACTACATGGACGTGT |
| MY397.txt | SEQ ID NO 160 | GCCGCAAGGCGGGCGAGGTCGAGTACGTGCCCTCCTCCGAGGTGGACTACATGGACGTGT |
| MY357.txt | SEQ ID NO 161 | GTCGCAAGGCGGGCGAGGTCGAGTACGTGCCCTCCTCCGAGGTGGACTACATGGACGTGT |
| My358.txt | SEQ ID NO 162 | GTCGCAAGGCGGGCGAGGTCGAGTACGTGCCCTCCTCCGAGGTGGACTACATGGACGTGT |
| My480.txt | SEQ ID NO 163 | GTCGCAAGGCGGGCGAGGTCGAGTACGTGCCCTCCTCCGAGGTGGACTACATGGACGTGT |
| MY212.txt | SEQ ID NO 164 | GTCGCAAGGGTGGCGAGGTCGAGTACGTGTCTTCGGCCGAGGTCGACTACATGGACGTCT |
| MY491.txt | SEQ ID NO 165 | GTCGCAAGGGTGGCGAGGTCGAGTACGTGTCTTCGGCCGAGGTCGACTACATGGACGTCT |
| MY497.txt | SEQ ID NO 166 | GTCGCAAGGGTGGTGAGGTCGAGTACGTGTCTTCGGCCGAGGTCGACTACATGGACGTCT |
| My816.txt | SEQ ID NO 167 | GCCGGAAGCCGGGCGAGGTCGAGTACGTGCCGTCGTCCGAGGTCGACTACATGGACGTGT |
| Atcc10-xco.txt | SEQ ID NO 168 | GTCGCAAGGGTGGTGAGGTCGAGTACGTGTCCTCCTCCGAGGTGGACTACATGGACGTCT |

TABLE 1-continued

| | | |
|---|---|---|
| M38.txt | SEQ ID NO 169 | GCCGCAAGGGTGGGGAGGTCGAGTACGTGTCCTCCTCCGAGGTGGACTACATGGACGTCT |
| M39.txt | SEQ ID NO 170 | GCCGCAAGGGTGGGGAGGTCGAGTACGTGTCCTCCTCCGAGGTGGACTACATGGACGTCT |
| M40.txt | SEQ ID NO 171 | GCCGCAAGGGTGGGGAGGTCGAGTACGTGTCCTCCTCCGAGGTGGACTACATGGACGTCT |
| M41.txt | SEQ ID NO 172 | GCCGCAAGGGTGGGGAGGTCGAGTACGTGTCCTCCTCCGAGGTGGACTACATGGACGTCT |
| M42.txt | SEQ ID NO 173 | GCCGCAAGGGTGGGGAGGTCGAGTACGTGTCCTCCTCCGAGGTGGACTACATGGACGTCT |
| M43.txt | SEQ ID NO 174 | GCCGCAAGGGTGGGGAGGTCGAGTACGTGTCCTCCTCCGAGGTGGACTACATGGACGTCT |
| M44.txt | SEQ ID NO 175 | GCCGCAAGGGTGGGGAGGTCGAGTACGTGTCCTCCTCCGAGGTGGACTACATGGACGTCT |
| M45.txt | SEQ ID NO 176 | GCCGCAAGGGTGGGGAGGTCGAGTACGTGTCCTCCTCCGAGGTGGACTACATGGACGTCT |
| M46.txt | SEQ ID NO 177 | GCCGCAAGGGTGGGGAGGTCGAGTACGTGTCCTCCTCCGAGGTGGACTACATGGACGTCT |
| M47.txt | SEQ ID NO 178 | GCCGCAAGGGTGGGGAGGTCGAGTACGTGTCCTCCTCCGAGGTGGACTACATGGACGTCT |
| M68(Mav6).txt | SEQ ID NO 179 | GCCGCAAGGGTGGGGAGGTCGAGTACGTGTCCTCCTCCGAGGTGGACTACATGGACGTCT |
| M89.txt | SEQ ID NO 180 | GCCGCAAGGGTGGGGAGGTCGAGTACGTGTCCTCCTCCGAGGTGGACTACATGGACGTCT |
| M66(Mav4).txt | SEQ ID NO 181 | GCCGCAAGGCGGGCGAGGTCGAGTACGTGCCCTCCTCCGAGGTGGACTACATGGACGTCT |
| | | 490 500 510 520 530 540 |

BASE NOS 541–600

| | | |
|---|---|---|
| ATCC9-Mtb.txt | SEQ ID NO 1 | CGCCCCGCCAGATGGTGTCGGTGGCCACCGCGATGATTCCCTTCCTGGAGCACGACGACG |
| MY621.txt | SEQ ID NO 2 | CGCCGCGCCAGATGGTGTCGGTCGCGACCGCCATGATCCCGTTCCTCGAGCACGACGACG |
| AtCC1-av.txt | SEQ ID NO 3 | CGCCGCGCCARATGGTGTCGGTGGCCACCGCGATGATCCCGTTCCTCGAGCACGACGACG |
| M29.txt | SEQ ID NO 4 | CGCCGCGCCAGATGGTGTCGGTGGCCACCGCGATGATCCCGTTCCTCGAGCACGACGACG |
| M30.txt | SEQ ID NO 5 | CGCCGCGCCAGATGGTGTCGGTGGCCACCGCGATGATCCCGTTCCTCGAGCACGACGACG |
| M31.txt | SEQ ID NO 6 | CGCCGCGCCAGATGGTGTCGGTGGCCACCGCGATGATCCCGTTCCTCGAGCACGACGACG |
| M32.txt | SEQ ID NO 7 | CGCCGCGCCAGATGGTGTCGGTGGCCACCGCGATGATCCCGTTCCTCGAGCACGACGACG |
| M33.txt | SEQ ID NO 8 | CGCCGCGCCAGATGGTGTCGGTGGCCACCGCGATGATCCCGTTCCTCGAGCACGACGACG |
| M34.txt | SEQ ID NO 9 | CGCCGCGCCAGATGGTGTCGGTGGCCACCGCGATGATCCCGTTCCTCGAGCACGACGACG |
| M48-new.txt | SEQ ID NO 10 | CGCCGCGCCAGATGGTGTCGGTGGCCACCGCGATGATCCCGTTCCTCGAGCACGACGACG |
| M49.txt | SEQ ID NO 11 | CGCCGCGCCAGATGGTGTCGGTGGCCACCGCGATGATCCCGTTCCTCGAGCACGACGACG |
| M64(Mav2).txt | SEQ ID NO 12 | CGCCGCGCCAGATGGTGTCGGTGGCCACCGCGATGATCCCGTTCCTCGAGCACGACGACG |
| M65(Mav3).txt | SEQ ID NO 13 | CGCCGCGCCAGATGGTGTCGGTGGCCACCGCGATGATCCCGTTCCTCGAGCACGACGACG |
| M67(Mav5).txt | SEQ ID NO 14 | CGCCGCGCCAGATGGTGTCGGTGGCCACCGCGATGATCCCGTTCCTCGAGCACGACGACG |
| M69(Mav7).txt | SEQ ID NO 15 | CGCCGCGCCAGATGGTGTCGGTGGCCACCGCGATGATCCCGTTCCTCGAGCACGACGACG |
| M71(Mav9).txt | SEQ ID NO 16 | CGCCGCGCCAGATGGTGTCGGTGGCCACCGCGATGATCCCGTTCCTCGAGCACGACGACG |
| M91.txt | SEQ ID NO 17 | CGCCGCGCCAGATGGTGTCGGTGGCCACCGCGATGATCCCGTTCCTCGAGCACGACGACG |
| M94.txt | SEQ ID NO 18 | CGCCGCGCCAGATGGTGTCGGTGGCCACCGCGATGATCCCGTTCCTCGAGCACGACGACG |
| M95.txt | SEQ ID NO 19 | CGCCGCGCCAGATGGTGTCGGTGGCCACCGCGATGATCCCGTTCCTCGAGCACGACGACG |
| M96.txt | SEQ ID NO 20 | CGCCGCGCCAGATGGTGTCGGTGGCCACCGCGATGATCCCGTTCCTCGAGCACGACGACG |
| M100.txt | SEQ ID NO 21 | CGCCGCGCCAGATGGTGTCGGTGGCCACCGCGATGATCCCGTTCCTCGAGCACGACGACG |
| M101.txt | SEQ ID NO 22 | CGCCGCGCCAGATGGTGTCGGTGGCCACCGCGATGATCCCGTTCCTCGAGCACGACGACG |
| M102.txt | SEQ ID NO 23 | CGCCGCGCCAGATGGTGTCGGTGGCCACCGCGATGATCCCGTTCCTCGAGCACGACGACG |
| M104.txt | SEQ ID NO 24 | CGCCGCGCCAGATGGTGTCGGTGGCCACCGCGATGATCCCGTTCCTCGAGCACGACGACG |
| M105.txt | SEQ ID NO 25 | CGCCGCGCCAGATGGTGTCGGTGGCCACCGCGATGATCCCGTTCCTCGAGCACGACGACG |
| M106.txt | SEQ ID NO 26 | CGCCGCGCCAGATGGTGTCGGTGGCCACCGCGATGATCCCGTTCCTCGAGCACGACGACG |
| MY111.txt | SEQ ID NO 27 | CGCCGCGCCAGATGGTGTCGGTCGCGACCGCGATGATCCCGTTCCTCGAGCACGACGACG |
| M76.txt | SEQ ID NO 28 | CGCCCCGCCAGATGGTGTCGGTGGCCACCGCGATGATTCCCTTCCTGGAGCACGACGACG |
| MY451.txt | SEQ ID NO 29 | CGCCCCGCCAGATGGTGTCGGTGGCCACCGCGATGATTCCCTTCCTGGAGCACGACGACG |
| ATCC2-chelnew.txt | SEQ ID NO 30 | CGCCGCGCCAGATGGTGTCGGTCGCGACCGCCATGATCCCGTTCCTCGAGCACGACGACG |

| | | |
|---|---|---|
| M10.txt | SEQ ID NO 31 | CGCCGCGCCAGATGGTGTCGGTCGCGACCGCCATGATCCCGTTCCTCGAGCACGACGACG |
| M11.txt | SEQ ID NO 32 | CGCCGCGCCAGATGGTGTCGGTCGCGACCGCCATGATCCCGTTCCTCGAGCACGACGACG |
| M12.txt | SEQ ID NO 33 | CGCCGCGCCAAATGGTGTCGGTCGCGACCGCCATGATCCCGTTCCTCGAGCACGACGACG |
| M13_2_662.txt | SEQ ID NO 34 | CGCCGCGCCAGATGGTGTCGGTCGCGACCGCCATGATCCCGTTCCTCGAGCACGACGACG |
| M14.txt | SEQ ID NO 35 | CGCCGCGCCAGATGGTGTCGGTCGCGACCGCGATGATCCCGTTCCTGGAGCACGACGACG |
| M15.txt | SEQ ID NO 36 | CGCCGCGCCAGATGGTGTCGGTCGCGACCGCCATGATCCCGTTCCTCGAGCACGACGACG |
| M16.txt | SEQ ID NO 37 | CGCCGCGCCAGATGGTGTCGGTCGCGACCGCCATGATCCCGTTCCTCGAGCACGACGACG |
| M17_2_662.txt | SEQ ID NO 38 | CGCCGCGCCAAATGGTGTCGGTCGCGACCGCCATGATCCCGTTCCTCGAGCACGACGACG |
| M50.txtM51.txt | SEQ ID NO 39 | CGCCGCGCCAGATGGTGTCGGTCGCGACCGCCATGATCCCGTTCCTCGAGCACGACGACG |
| M115.txt | SEQ ID NO 40 | CGCCGCGCCAGATGGTGTCGGTCGCGACCGCCATGATCCCGTTCCTCGAGCACGACGACG |
| M116.txt | SEQ ID NO 41 | CGCCGCGCCAGATGGTGTCGGTCGCGACCGCCATGATCCCGTTCCTCGAGCACGACGACG |
| M119.txt | SEQ ID NO 42 | CGCCGCGCCAGATGGTGTCGGTCGCGACCGCCATGATCCCGTTCCTCGAGCACGACGACG |
| MY109.txt | SEQ ID NO 43 | CGCCGCGCCAGATGGTGTCGGTCGCGACCGCCATGATCCCGTTCCTCGAGCACGACGACG |
| MY200.txt | SEQ ID NO 44 | CGCCGCGCCAGATGGTGTCGGTCGCGACCGCCATGATCCCGTTCCTCGAGCACGACGACG |
| MY207.txt | SEQ ID NO 45 | CGCCGCGCCAGATGGTGTCGGTCGCGACCGCCATGATCCCGTTCCTCGAGCACGACGACG |
| MY209.txt | SEQ ID NO 46 | CGCCGCGCCAGATGGTGTCGGTCGCGACCGCCATGATCCCGTTCCTCGAGCACGACGACG |
| M122.txt | SEQ ID NO 47 | CGCCGCGCCAGATGGTGTCGGTCGCGACCGCCATGATCCCGTTCCTCGAGCACGACGACG |
| M123.txt | SEQ ID NO 48 | CGCCGCGCCAGATGGTATCGGTCGCGACGGCCATGATCCCGTTCCTCGAGCACGACGACG |
| M124.txt | SEQ ID NO 49 | CGCCGCGCCAGATGGTATCGGTCGCGACGGCCATGATCCCGTTCCTCGAGCACGACGACG |
| Atcc3-for.txt | SEQ ID NO 50 | CGCCGCGCCAGATGGTGTCGGTCGCGACGGCGATGATCCCGTTCCTCGAGCACGACGACG |
| M53.txt | SEQ ID NO 51 | CGCCGCGCCAGATGGTGTCCGTCGCGACCGCGATGATCCCGTTCCTCGAGCACGACGACG |
| M54.txt | SEQ ID NO 52 | CGCCGCGCCAGATGGTGTCGGTCGCGACCGCGATGATCCCGTTCCTCGAGCACGACGACG |
| M55.txt | SEQ ID NO 53 | CGCCGCGCCAGATGGTGTCTGTCGCGACCGCGATGATCCCGTTCCTCGAGCACGACGACG |
| M56.txt | SEQ ID NO 54 | CGCCGCGCCAGATGGTGTCCGTCGCGACCGCGATGATCCCGTTCCTCGAGCACGACGACG |
| M74(May12).txt | SEQ ID NO 55 | CGCCGCGCCAGATGGTGTCTGTCGCGACCGCGATGATCCCGTTCCTCGAGCACGACGACG |
| | SEQ ID NO 56 | CGCCGCGCCAGATGGTGTCCGTCGCGACCGCGATGATCCCGTTCCTCGAGCACGACGACG |

TABLE 1-continued

| | | |
|---|---|---|
| M77.txt | SEQ ID NO 57 | CACCGCGCCAGATGGTGTCTGTCGCGACCGCGATGATCCCGTTCCTCGAGCACGACGACG |
| M118.txt | SEQ ID NO 58 | CGCCGCGCCAGATGGTGTCTGTCGCGACCGCGATGATCCCGTTCCTCGAGCACGACGACG |
| MY221.txt | SEQ ID NO 59 | CGCCGCGCCAGATGGTGTCCGTCGCGACCGCGATGATCCCGTTCCTCGAGCACGACGACG |
| MY223.txt | SEQ ID NO 60 | CACCGCGCCAGATGGTGTCTGTCGCGACCGCGATGATCCCGTTCCTCGAGCACGACGACG |
| MY225.txt | SEQ ID NO 61 | CGCCGCGCCAGATGGTGTCCGTCGCGACCGCGATGATCCCGTTCCTCGAGCACGACGACG |
| My341.txt | SEQ ID NO 62 | CGCCGCGCCAGATGGTGTCCGTCGCGACCGCGATGATCCCGTTCCTCGAGCACGACGACG |
| My715.txt | SEQ ID NO 63 | CGCCGCGCCAGATGGTGTCCGTCGCGACCGCGATGATCCCGTTCCTCGAGCACGACGACG |
| MY470.txt | SEQ ID NO 64 | CGCCGCGCCAGATGGTGTCGGTGGCCACCGCGATGATTCCGTTCCTCGAGCACGATGACG |
| Atcc4-go.txt | SEQ ID NO 65 | CGCCGCGCCAGATGGTGTCGGTGGCCACCGCGATGATTCCGTTCCTCGAACACGACGACG |
| ATCC4-O-Gord.txt | SEQ ID NO 66 | CGCCGCGCCAGATGGTGTCGGTGGCCACCGCGATGATTCCGTTCCTCGAACACGACGACG |
| M78(lz).txt | SEQ ID NO 67 | CGCCGCGCCAGATGGTGTCGGTGGCCACCGCCATGATTCCGTTCCTCGAGCACGACGACG |
| M79(jd).txt | SEQ ID NO 68 | CGCCGCGCCAGATGGTGTCGGTGGCCACCGCGATGATTCCGTTCCTCGAGCACGACGACG |
| M80(lg).txt | SEQ ID NO 69 | CGCCGCGCCAGATGGTGTCGGTGGCCACCGCCATGATTCCGTTCCTCGAGCACGACGACG |
| M81(ll).txt | SEQ ID NO 70 | CGCCGCGCCAGATGGTGTCGGTGGCCACCGCGATGATTCCGTTCCTCGAGCACGACGACG |
| M82(rm).txt | SEQ ID NO 71 | CGCCGCGCCAGATGGTGTCGGTGGCCACCGCGATGATTCCGTTCCTCGAACACGACGACG |
| M83(mb).txt | SEQ ID NO 72 | CGCCGCGCCAGATGGTGTCGGTGGCCACCGCGATGATTCCGTTCCTCGAACACGACGACG |
| M84(ow).txt | SEQ ID NO 73 | CGCCGCGCCAGATGGTGTCGGTGGCCACCGCGATGATTCCGTTCCTCGAACACGACGACG |
| M85(lb).txt | SEQ ID NO 74 | CGCCGCGCCAGATGGTGTCGGTGGCCACCGCGATGATTCCGTTCCTCGAACACGACGACG |
| M86(rb).txt | SEQ ID NO 75 | CGCCGCGCCAGATGGTGTCGGTGGCCACCGCGATGATCCCGTTCCTCGAGCACGACGACG |
| M87(wn).txt | SEQ ID NO 76 | CGCCGCGCCAGATGGTGTCGGTGGCCACCGCGATGATTCCGTTCCTCGAACACGACGACG |
| M90(gordDB).txt | SEQ ID NO 77 | CGCCGCGCCAGATGGTGTCGGTGGCCACCGCGATGATTCCGTTCCTCGAGCACGACGACG |
| m126.txt | SEQ ID NO 78 | CGCCGCGCCAGATGGTGTCGGTGGCCACCGCGATGATTCCGTTCCTCGAACACGACGACG |
| M128.txt | SEQ ID NO 79 | CGCCGCGCCAGATGGTGTCGGTGGCCACCGCGATGATTCCGTTCCTCGAGCACGACGACG |
| My103.txt | SEQ ID NO 80 | CGCCGCGCCAGATGGTGTCGGTGGCCACCGCGATGATTCCGTTCCTCGAACACGACGACG |
| MY475.txt | SEQ ID NO 81 | CGCCGCGCCAGATGGTGTCGGTGGCCACCGCGATGATCCCGTTCCTCGAGCACGACGACG |
| MY476.txt | SEQ ID NO 82 | CGCCGCGCCAGATGGTGTCGGTGGCCACCGCGATGATTCCGTTCCTCGAACACGACGACG |
| MY830.txt | SEQ ID NO 83 | CGCCGCGCCAGATGGTGTCGGTGGCCACGGCCATGATTCCGTTCCTCGAGCACGACGACG |
| Atcc5-int.txt | SEQ ID NO 84 | CACCGCGCCAGATGGTGTCGGTGGCCACCGCGATGATCCCGTTCCTCGAGCACGATGACG |
| ATCC5-Oint.txt | SEQ ID NO 85 | CACCGCGCCAGATGGTGTCGGTGGCCACCGCGATGATCCCGTTCCTCGAGCACGATGACG |
| M18.txt | SEQ ID NO 86 | CACCGCGCCAGATGGTGTCGGTGGCCACCGCGATGATCCCGTTCCTCGAGCACGATGACG |
| M19.txt | SEQ ID NO 87 | CGCCGCGCCAGATGGTGTCGGTGGCCACCGCGATGATCCCGTTCCTCGAGCACGATGACG |
| M20.txt | SEQ ID NO 88 | CGCCGCGCCAGATGGTGTCGGTGGCCACCGCGATGATCCCGTTCCTCGAGCACGATGACG |
| M21.txt | SEQ ID NO 89 | CGCCGCGCCAGATGGTGTCGGTGGCCACCGCGATGATCCCGTTCCTCGAGCACGATGACG |
| M22.txt | SEQ ID NO 90 | CGCCGCGCCAGATGGTGTCGGTGGCCACCGCGATGATCCCGTTCCTCGAGCACGATGACG |
| M23.txt | SEQ ID NO 91 | CGCCGCGCCAGATGGTGTCGGTGGCCACCGCGATGATCCCGTTCCTCGAGCACGATGACG |
| M24.txt | SEQ ID NO 92 | CGCCGCGCCAGATGGTGTCGGTGGCCACCGCGATGATCCCGTTCCTCGAGCACGATGACG |
| M25.txt | SEQ ID NO 93 | CACCGCGCCAGATGGTGTCGGTGGCCACCGCGATGATCCCGTTCCTCGAGCACGATGACG |
| M26.txt | SEQ ID NO 94 | CACCGCGCCAGATGGTGTCGGTGGCCACCGCGATGATCCCGTTCCTCGAGCACGATGACG |
| M27.txt | SEQ ID NO 95 | CACCGCGCCAGATGGTGTCGGTGGCCACCGCGATGATCCCGTTCCTCGAGCACGATGACG |
| M28.txt | SEQ ID NO 96 | CGCCGCGCCAGATGGTGTCGGTGGCCACCGCGATGATCCCGTTCCTCGAGCACGATGACG |
| M107.txt | SEQ ID NO 97 | CGCCGCGCCAGATGGTGTCGGTGGCCACCGCGATGATCCCGTTCCTCGAGCACGATGACG |
| MY107.txt | SEQ ID NO 98 | CGCCGCGCCAGATGGTGTCGGTGGCCACCGCGATGATCCCGTTCCTCGAGCACGATGACG |
| MY112).txt | SEQ ID NO 99 | CGCCGCGCCAGATGGTGTCGGTGGCCACCGCGATGATCCCGTTCCTCGAGCACGATGACG |
| MY312.txt | SEQ ID NO 100 | CGCCGCGCCAGATGGTGTCGGTGGCCACCGCGATGATCCCGTTCCTCGAGCACGATGACG |
| Atcc6-kan.txt | SEQ ID NO 101 | CGCCGCGCCAGATGGTGTCGGTGGCCACGGCCATGATTCCGTTCCTCGAGCACGACGACG |
| ATCC6-OKan.txt | SEQ ID NO 102 | CGCCGCGCCAGATGGTGTCGGTGGCCACGGCCATGATTCCGTTCCTCGAGCACGACGACG |
| M1.txt | SEQ ID NO 103 | CGCCGCGCCAGATGGTGTCGGTGGCCACGGCCATGATTCCGTTCCTCGAGCACGACGACG |
| M2.txt | SEQ ID NO 104 | CGCCGCGCCAGATGGTGTCGGTGGCCACGGCCATGATTCCGTTCCTCGAGCACGACGACG |
| M3.txt | SEQ ID NO 105 | CGCCGCGCCAGATGGTGTCGGTGGCCACGGCCATGATTCCGTTCCTCGAGCACGACGACG |
| M4.txt | SEQ ID NO 106 | CGCCGCGCCAAATGGTGTCGGTGGCCACCGCGATGATCCCGTTCCTCGAGCACGACGACG |
| M6.txt | SEQ ID NO 107 | CGCCGCGCCAGATGGTGTCGGTGGCCACGGCCATGATTCCGTTCCTCGAGCACGACGACG |
| M7.txt | SEQ ID NO 108 | CGCCACGCCAGATGGTGTCGGTGGCCACGGCCATGATTCCGTTCCTCGAGCACGACGACG |
| M9.txt | SEQ ID NO 109 | CGCCGCGCCAGATGGTGTCGGTGGCCACGGCCATGATTCCGTTCCTCGAGCACGACGACG |
| M57.txt | SEQ ID NO 110 | CGCCGCGCCAGATGGTGTCGGTGGCCACGGCCATGATTCCGTTCCTCGAGCACGACGACG |
| M58.txt | SEQ ID NO 111 | CGCCGCGCCAGATGGTGTCGGTGGCCACGGCCATGATTCCGTTCCTCGAGCACGACGACG |
| M59.txt | SEQ ID NO 112 | CGCCGCGCCAGATGGTGTCGGTGGCCACGGCCATGATTCCGTTCCTCGAGCACGACGACG |
| M60.txt | SEQ ID NO 113 | CGCCGCGCCAGATGGTGTCGGTGGCCACGGCCATGATTCCGTTCCTCGAGCACGACGACG |
| M61.txt | SEQ ID NO 114 | CGCCGCGCCAGATGGTGTCGGTGGCCACGGCCATGATTCCGTTCCTCGAGCACGACGACG |
| M62.txt | SEQ ID NO 115 | CGCCGCGCCAGATGGTGTCGGTGGCCACGGCCATGATTCCGTTCCTCGAGCACGACGACG |
| MY106.txt | SEQ ID NO 116 | CGCCGCGCCAGATGGTGTCGGTGGCCACGGCCATGATTCCGTTCCTCGAGCACGACGACG |
| MY216.txt | SEQ ID NO 117 | CGCCGCGCCAGATGGTGTCGGTGGCCACGGCCATGATTCCGTTCCTCGAGCACGACGACG |
| MY218.txt | SEQ ID NO 118 | CGCCGCGCCAGATGGTGTCGGTGGCCACGGCCATGATTCCGTTCCTCGAGCACGACGACG |
| MY226.txt | SEQ ID NO 119 | CGCCGCGCCAGATGGTGTCGGTGGCCACGGCCATGATTCCGTTCCTCGAGCACGACGACG |
| M109.txt | SEQ ID NO 120 | CGCCGCGGCAGATGGTGTCCGTGGCCACCGCCATGATTCCGTTCCTCGAGCACGACGACG |
| M111.txt | SEQ ID NO 121 | CGCCGCGGCAGATGGTGTCCGTGGCCACCGCCATGATTCCGTTCCTCGAGCACGACGACG |
| M112.txt | SEQ ID NO 122 | CGCCGCGGCAGATGGTGTCCGTGGCCACCGCCATGATTCCGTTCCTCGAGCACGACGACG |
| M113.txt | SEQ ID NO 123 | CGCCGCGGCAGATGGTGTCCGTGGCCACCGCCATGATTCCGTTCCTCGAGCACGACGACG |
| M114.txt | SEQ ID NO 124 | CGCCGCGGCAGATGGTGTCCGTGGCCACCGCCATGATTCCGTTCCTCGAGCACGACGACG |
| MY325.txt | SEQ ID NO 125 | CGCCGCGGCAGATGGTGTCCGTGGCCACCGCCATGATTCCGTTCCTCGAGCACGACGACG |
| MY718.txt | SEQ ID NO 126 | CGCCGCGGCAGATGGTGTCCGTGGCCACCGCCATGATTCCGTTCCTCGAGCACGACGACG |
| MY214.txt | SEQ ID NO 127 | CGCCGCGCCAGATGGTGTCGGTGGCCACCGCGATGATTCCGTTCCTCGAGCACGATGACG |
| MY224.txt | SEQ ID NO 128 | CGCCGCGCCAGATGGTGTCGGTGGCCACCGCGATGATTCCGTTCCTCGAGCACGATGACG |
| My244.txt | SEQ ID NO 129 | CGCCGCGCCAGATGGTGTCGGTGGCCACCGCGATGATTCCGTTCCTCGAGCACGATGACG |
| My339.txt | SEQ ID NO 130 | CGCCGCGCCAGATGGTGTCGGTGGCCACCGCGATGATTCCGTTCCTCGAGCACGATGACG |
| My343.txt | SEQ ID NO 131 | CGCCGCGCCAGATGGTGTCGGTGGCCACCGCGATGATTCCGTTCCTCGAGCACGATGACG |
| MY458.txt | SEQ ID NO 132 | CGCCGCGCCAGATGGTGTCGGTCGCGACCGCGATGATCCCGTTCCTGGAGCACGACGACG |
| MY809.txt | SEQ ID NO 133 | CGCCGCGCCAGATGGTGTCGGTCGCGACCGCGATGATCCCGTTCCTCGAGCACGACGACG |
| MY817.txt | SEQ ID NO 134 | CGCCGCGCCAGATGGTGTCGGTCGCGACCGCGATGATCCCGTTCCTCGAGCACGACGACG |
| MY821.txt | SEQ ID NO 135 | CGCCGCGCCAGATGGTGTCGGTCGCGACCGCGATGATCCCGTTCCTCGAGCACGACGACG |
| MY824.txt | SEQ ID NO 136 | CGCCGCGCCAGATGGTGTCGGTCGCGACCGCGATGATCCCGTTCCTCGAGCACGACGACG |
| MY102.txt | SEQ ID NO 137 | CACCGCGCCAGATGGTGTCGGTGGCCACGGCCATGATTCCGTTCCTCGAGCACGACGACG |
| My105.txt | SEQ ID NO 138 | CACCGCGCCAGATGGTGTCGGTGGCCACGGCCATGATCCCGTTCCTCGAGCACGACGACG |
| MY251.txt | SEQ ID NO 139 | CACCGCGCCAGATGGTGTCGGTGGCCACGGCCATGATTCCGTTCCTCGAGCACGACGACG |
| My256.txt | SEQ ID NO 140 | CACCGCGCCAGATGGTGTCGGTGGCCACGGCCATGATTCCGTTCCTCGAGCACGACGACG |
| My294.txt | SEQ ID NO 141 | CACCGCGCCAGATGGTGTCGGTGGCCACGGCCATGATTCCGTTCCTCGAGCACGACGACG |
| MY354.txt | SEQ ID NO 142 | CGCCGCGCCAGATGGTGTCGGTGGCCACGGCCATGATTCCGTTCCTCGAGCACGACGACG |

TABLE 1-continued

| | | |
|---|---|---|
| Atcc7-scr.txt | SEQ ID NO 143 | CGCCGCGCCAGATGGTGTCGGTGGCCACCGCCATGATCCCGTTCCTCGAGCACGACGACG |
| ATCC7-Oscr.txt | SEQ ID NO 144 | CGCCGCGCCAGATGGTGTCGGTGGCCACCGCCATGATCCCGTTCCTCGAGCACGACGACG |
| MY121.txt | SEQ ID NO 145 | CGCCGCGCCAGATGGTGTCGGTGGCCACCGCCATGATCCCGTTCCTCGAGCACGACGACG |
| MY249.txt | SEQ ID NO 146 | CGCCGCGCCAGATGGTGTCGGTGGCCACCGCCATGATCCCGTTCCTCGAGCACGACGACG |
| MY372.txt | SEQ ID NO 147 | CGCCGCGCCAGATGGTGTCGGTGGCCACCGCCATGATCCCGTTCCTCGAGCACGACGACG |
| MY378.txt | SEQ ID NO 148 | CGCCGCGCCAGATGGTGTCGGTGGCCACCGCCATGATCCCGTTCCTCGAGCACGACGACG |
| MY484.txt | SEQ ID NO 149 | CGCCGCGCCAGATGGTGTCGGTCGCGACGGCGATGATCCCGTTCCTCGAACACGACGACG |
| My556.txt | SEQ ID NO 150 | CGCCGCGCCAGATGGTGTCGGTGGCGACCGCGATGATCCCGTTCCTCGAACACGACGACG |
| MY563.txt | SEQ ID NO 151 | CGCCGCGCCAGATGGTGTCGGTGGCGACCGCGATGATCCCGTTCCTCGAGCACGACGACG |
| MY586.txt | SEQ ID NO 152 | CGCCGCGCCAGATGGTGTCGGTGGCTACCGCGATGATCCCGTTCCTCGAGCACGACGACG |
| Atcc8-sme.txt | SEQ ID NO 153 | CGCCGCGCCAGATGGTGTCGGTCGCGACGGCCATGATCCCGTTCCTCGAGCACGACGACG |
| M35.txt | SEQ ID NO 154 | CGCCGCGCCAGATGGTGTCGGTCGCGACGGCGATGATCCCGTTCCTCGAGCACGACGACG |
| M36.txt | SEQ ID NO 155 | CGCCGCGCCAGATGGTGTCGGTCGCTACGGCGATGATCCCGTTCCTCGAGCACGACGACG |
| M37.txt | SEQ ID NO 156 | CGCCGCGCCAGATGGTGTCGGTCGCCACGGCCATGATCCCGTTCCTCGAGCACGACGACG |
| m125.txt | SEQ ID NO 157 | CGCCGCGCCAGATGGTGTCGGTGGCCACCGCGATGATTCCGTTCCTCGAGCACGACGACG |
| MY143.txt | SEQ ID NO 158 | CGCCGCGCCAGATGGTGTCGGTCGCCACGGCCATGATCCCGTTCCTCGAGCACGACGACG |
| My104.txt | SEQ ID NO 159 | CGCCGCGCCAGATGGTGTCGGTGGCCACCGCGATGATTCCGTTCCTCGAGCACGACGACG |
| MY196.txt | SEQ ID NO 160 | CGCCGCGCCAGATGGTGTCGGTGGCCACCGCGATGATTCCGTTCCTCGAGCACGACGACG |
| MY357.txt | SEQ ID NO 161 | CGCCGCGCCAGATGGTGTCGGTGGCCACCGCGATGATTCCGTTCCTCGAGCACGACGACG |
| My358.txt | SEQ ID NO 162 | CGCCGCGCCAGATGGTGTCGGTCGCGACCGCGATGATTCCGTTCCTCGAGCACGACGACG |
| My480.txt | SEQ ID NO 163 | CGCCGCGCCAGATGGTGTCGGTCGCGACCGCGATGATTCCGTTCCTCGAGCACGACGACG |
| MY212.txt | SEQ ID NO 164 | CGCCGCGCCAGATGGTGTCGGTCGCGACGGCCATGATCCCGTTCCTGGAGCACGACGACG |
| MY491.txt | SEQ ID NO 165 | CGCCGCGCCAGATGGTGTCGGTCGCGACGGCCATGATCCCGTTCCTGGAGCACGACGACG |
| MY497.txt | SEQ ID NO 166 | CGCCGCGCCAGATGGTGTCGGTCGCGACGGCCATGATCCCGTTCCTGGAGCACGACGACG |
| MY816.txt | SEQ ID NO 167 | CGCCGCGCCAGATGGTGTCGGTGGCCACGGCCATGATCCCGTTCCTCGAGCACGACGACG |
| MY80-sme.txt | SEQ ID NO 168 | CGCCGCGCCAGATGGTGTCGGTGGCCACCGCGATGATCCCGTTCCTCGAGCACGACGACG |
| M38.txt | SEQ ID NO 169 | CGCCGCGCCAGATGGTGTCGGTGGCCACCGCGATGATCCCGTTCCTCGAGCACGACGACG |
| M39.txt | SEQ ID NO 170 | CGCCGCGCCAGATGGTGTCGGTGGCCACCGCGATGATCCCGTTCCTCGAGCACGACGACG |
| M40.txt | SEQ ID NO 171 | CGCCGCGCCAGATGGTGTCGGTGGCCACCGCGATGATCCCGTTCCTCGAGCACGACGACG |
| M41.txt | SEQ ID NO 172 | CGCCGCGCCAGATGGTGTCGGTGGCCACCGCGATGATCCCGTTCCTCGAGCACGACGACG |
| M42.txt | SEQ ID NO 173 | CGCCGCGCCAGATGGTGTCGGTGGCCACCGCGATGATCCCGTTCCTCGAGCACGACGACG |
| M43.txt | SEQ ID NO 174 | CGCCGCGCCAGATGGTGTCGGTGGCCACCGCGATGATCCCGTTCCTCGAGCACGACGACG |
| M44.txt | SEQ ID NO 175 | CGCCGCGCCAGATGGTGTCGGTGGCCACCGCGATGATCCCGTTCCTCGAGCACGACGACG |
| M45.txt | SEQ ID NO 176 | CGCCGCGCCAGATGGTGTCGGTGGCCACCGCGATGATCCCGTTCCTCGAGCACGACGACG |
| M46.txt | SEQ ID NO 177 | CGCCGCGCCAGATGGTGTCGGTGGCCACCGCGATGATCCCGTTCCTCGAGCACGACGACG |
| M47.txt | SEQ ID NO 178 | CGCCGCGCCAGATGGTGTCGGTGGCCACCGCGATGATCCCGTTCCTCGAGCACGACGACG |
| M68(Mav6).txt | SEQ ID NO 179 | CGCCGCGCCAGATGGTGTCGGTGGCCACCGCGATGATCCCGTTCCTCGAGCACGACGACG |
| M89.txt | SEQ ID NO 180 | CGCCGCGCCAGATGGTGTCGGTGGCCACCGCGATGATCCCGTTCCTCGAGCACGACGACG |
| M66(Mav4).txt | SEQ ID NO 181 | CGCCGCGCCAGATGGTGTCGGTGGCCACGGCCATGATCCCGTTCCTCGAGCACGACGACG |
| | | 550 560 570 580 590 600 |

BASE NOS 600–660

| | | |
|---|---|---|
| ATCC9-Mtb.txt | SEQ ID NO 1 | CCAACCGTGCCCTCATGGGGGCAAACATGCAGCGCCAGGCGGTGCCGCTGGTCCGTAGCG |
| MY621.txt | SEQ ID NO 2 | CCAACCGTGCCCTCATGGGTGCCAACATGCAGCGCCAGGCGGTTCCGCTGGTGCGTAGCG |
| Atcc1-av.txt | SEQ ID NO 3 | CCAACCGTGCCCTGATGGGCGCCAACATGCAKCGCCAGGCGGTTCCGCTGGTGCGCAGCG |
| M29.txt | SEQ ID NO 4 | CCAACCGTGCCCTGATGGGCGCCAACATGCAGCGCCAGGCGGTTCCGCTGGTGCGCAGCG |
| M30.txt | SEQ ID NO 5 | CCAACCGTGCCCTGATGGGCGCCAACATGCAGCGCCAGGCGGTTCCGCTGGTGCGCAGCG |
| M31.txt | SEQ ID NO 6 | CCAACCGTGCCCTGATGGGCGCCAACATGCAGCGCCAGGCGGTTCCGCTGGTGCGCAGCG |
| M32.txt | SEQ ID NO 7 | CCAACCGTGCCCTGATGGGCGCCAACATGCAGCGCCAGGCGGTTCCGCTGGTGCGCAGCG |
| M33.txt | SEQ ID NO 8 | CCAACCGTGCCCTGATGGGCGCCAACATGCAGCGCCAGGCGGTTCCGCTGGTGCGCAGCG |
| M34.txt | SEQ ID NO 9 | CCAACCGTGCCCTGATGGGCGCCAACATGCAGCGCCAGGCGGTTCCGCTGGTGCGCAGCG |
| M48-new.txt | SEQ ID NO 10 | CCAACCGTGCCCTGATGGGCGCCAACATGCAGCGCCAGGCGGTTCCGCTGGTGCGCAGCG |
| M49.txt | SEQ ID NO 11 | CCAACCGTGCCCTGATGGGCGCCAACATGCAGCGCCAGGCGGTTCCGCTGGTGCGCAGCG |
| M64(Mav2).txt | SEQ ID NO 12 | CCAACCGTGCCCTGATGGGCGCCAACATGCAGCGCCAGGCGGTTCCGCTGGTGCGCAGCG |
| M65(Mav3).txt | SEQ ID NO 13 | CCAACCGTGCCCTGATGGGCGCCAACATGCAGCGCCAGGCGGTTCCGCTGGTGCGCAGCG |
| M67(Mav5).txt | SEQ ID NO 14 | CCAACCGTGCCCTGATGGGCGCCAACATGCAGCGCCAGGCGGTTCCGCTGGTGCGCAGCG |
| M69(Mav7).txt | SEQ ID NO 15 | CCAACCGTGCCCTGATGGGCGCCAACATGCAGCGCCAGGCGGTTCCGCTGGTGCGCAGCG |
| M71(Mav9).txt | SEQ ID NO 16 | CCAACCGTGCCCTGATGGGCGCCAACATGCAGCGCCAGGCGGTTCCGCTGGTGCGCAGCG |
| M91.txt | SEQ ID NO 17 | CCAACCGTGCCCTGATGGGCGCCAACATGCAGCGCCAGGCGGTTCCGCTGGTGCGCAGCG |
| M94.txt | SEQ ID NO 18 | CCAACCGTGCCCTGATGGGCGCCAACATGCAGCGCCAGGCGGTTCCGCTGGTGCGCAGCG |
| M95.txt | SEQ ID NO 19 | CCAACCGTGCCCTGATGGGCGCCAACATGCAGCGCCAGGCGGTTCCGCTGGTGCGCAGCG |
| M96.txt | SEQ ID NO 20 | CCAACCGTGCCCTGATGGGCGCCAACATGCAGCGCCAGGCGGTTCCGCTGGTGCGCAGCG |
| M100.txt | SEQ ID NO 21 | CCAACCGTGCCCTGATGGGCGCCAACATGCAGCGCCAGGCGGTTCCGCTGGTGCGCAGCG |
| M101.txt | SEQ ID NO 22 | CCAACCGTGCCCTGATGGGCGCCAACATGCAGCGCCAGGCGGTTCCGCTGGTGCGCAGCG |
| M102.txt | SEQ ID NO 23 | CCAACCGTGCCCTGATGGGCGCCAACATGCAGCGCCAGGCGGTTCCGCTGGTGCGCAGCG |
| M104.txt | SEQ ID NO 24 | CCAACCGTGCCCTGATGGGCGCCAACATGCAGCGCCAGGCGGTTCCGCTGGTGCGCAGCG |
| M105.txt | SEQ ID NO 25 | CCAACCGTGCCCTGATGGGCGCCAACATGCAGCGCCAGGCGGTTCCGCTGGTGCGCAGCG |
| M106.txt | SEQ ID NO 26 | CCAACCGTGCCCTGATGGGTGCCAACATGCAGCGCCAGGCGGTTCCGCTGGTGCGTAGCG |
| MY111.txt | SEQ ID NO 27 | CCAACCGTGCCCTGATGGGCGCCAACATGCAGCGCCAGGCGGTTCCGCTGGTGCGCAGCG |

TABLE 1-continued

| | | |
|---|---|---|
| M76.txt | SEQ ID NO 28 | CCAACCGTGCCCTCATGGGGGCAAACATGCAGCGCCAGGCGGTGCCGCTGGTCCGTAGCG |
| MY451.txt | SEQ ID NO 29 | CCAACCGTGCCCTCATGGGGGCAAACATGCAGCGCCAGGCGGTGCCGCTGGTCCGTAGCG |
| ATCC2-chelnew.txt | SEQ ID NO 30 | CCAACCGTGCCCTCATGGGTGCCAACATGCAGCGCCAGGCGGTTCCGCTGGTGCGCAGCG |
| M10.txt | SEQ ID NO 31 | CCAACCGTGCCCTCATGGGTGCCAACATGCAGCGCCAGGCGGTTCCGCTGGTGCGCAGCG |
| M11-662.txt | SEQ ID NO 32 | CCAACCGTGCCCTCATGGGTGCCAACATGCAGCGCCAGGCGGTTCCGCTGGTGCGCAGCG |
| M12.txt | SEQ ID NO 33 | CCAACCGTGCCCTCATGGGTGCCAACATGCAGCGCCAGGCGGTTCCGCTGGTGCGCAGCG |
| M13_2_662.txt | SEQ ID NO 34 | CCAACCGTGCCCTCATGGGTGCCAACATGCAGCGCCAGGCGGTTCCGCTGGTGCGCAGCG |
| M14.txt | SEQ ID NO 35 | CCAACCGTGCCCTGATGGGTGCCAACATGCAGCGCCAGGCGGTTCCGCTGGTGCGTAGCG |
| M15.txt | SEQ ID NO 36 | CCAACCGTGCCCTCATGGGTGCCAACATGCAGCGCCAGGCGGTTCCGCTGGTGCGCAGCG |
| M16.txt | SEQ ID NO 37 | CCAACCGTGCCCTCATGGGTGCCAACATGCAGCGCCAGGCGGTTCCGCTGGTGCGCAGCG |
| M17_2_662.txt | SEQ ID NO 38 | CCAACCGTGCCCTCATGGGTGCCAACATGCAGCGCCAGGCGGTTCCGCTGGTGCGCAGCG |
| M50.txt | SEQ ID NO 39 | CCAACCGTGCCCTCATGGGTGCCAACATGCAGCGCCAGGCGGTTCCGCTGGTGCGCAGCG |
| M51.txt | SEQ ID NO 40 | CCAACCGTGCCCTCATGGGTGCCAACATGCAGCGCCAGGCGGTTCCGCTGGTGCGCAGCG |
| M115.txt | SEQ ID NO 41 | CCAACCGTGCCCTCATGGGTGCCAACATGCAGCGCCAGGCGGTTCCGCTGGTGCGCAGCG |
| M116.txt | SEQ ID NO 42 | CCAACCGTGCCCTCATGGGTGCCAACATGCAGCGCCAGGCGGTTCCGCTGGTGCGCAGCG |
| M119.txt | SEQ ID NO 43 | CCAACCGTGCCCTCATGGGTGCCAACATGCAGCGCCAGGCGGTTCCGCTGGTGCGCAGCG |
| MY109.txt | SEQ ID NO 44 | CCAACCGTGCCCTCATGGGTGCCAACATGCAGCGCCAGGCGGTTCCGCTGGTGCGCAGCG |
| MY200.txt | SEQ ID NO 45 | CCAACCGTGCCCTCATGGGTGCCAACATGCAGCGCCAGGCGGTTCCGCTGGTGCGTAGCG |
| MY207.txt | SEQ ID NO 46 | CCAACCGTGCCCTCATGGGTGCCAACATGCAGCGCCAGGCGGTTCCGCTGGTGCGTAGCG |
| MY209.txt | SEQ ID NO 47 | CCAACCGTGCCCTCATGGGTGCCAACATGCAGCGCCAGGCGGTTCCGCTGGTGCGTAGCG |
| M122.txt | SEQ ID NO 48 | CCAACCGCGCCCTGATGGGTGCCAACATGCAGCGCCAGGCGGTCCCGCTGGTGCGCAGCG |
| M123.txt | SEQ ID NO 49 | CCAACCGCGCCCTGATGGGTGCCAACATGCAGCGCCAGGCGGTCCCGCTGGTGCGCAGCG |
| M124.txt | SEQ ID NO 50 | CCAACCGCGCCCTGATGGGTGCCAACATGCAGCGCCAGGCGGTTCCGCTGGTCCGCAGCG |
| Atcc3-for.txt | SEQ ID NO 51 | CCAACCGCGCCCTGATGGGTGCCAACATGCAGCGCCAGGCGGTTCCGCTGGTGCGCAGCG |
| M53.txt | SEQ ID NO 52 | CCAACCGTGCCCTGATGGGTGCCAACATGCAGCGCCAGGCGGTTCCGCTGGTGCGTAGCG |
| M54.txt | SEQ ID NO 53 | CCAACCGCGCCCTGATGGGTGCCAACATGCAGCGCCAGGCGGTTCCACTGGTGCGCAGCG |
| M55.txt | SEQ ID NO 54 | CCAACCGCGCCCTGATGGGTGCCAACATGCAGCGCCAGGCGGTTCCGCTGGTGCGCAGCG |
| M56.txt | SEQ ID NO 55 | CCAACCGCGCCCTGATGGGTGCCAACATGCAGCGCCAGGCGGTTCCGCTGGTGCGCAGCG |
| M14(May 12).txt | SEQ ID NO 56 | CCAACCGCGCCCTGATGGGTGCCAACATGCAGCGCCAGGCGGTTCCGCTGGTGCGCAGCG |
| M77.txt | SEQ ID NO 57 | CCAACCGTGCCCTGATGGGTGCCAACATGCAGCGCCAGGCAGTTCCGCTGGTACGCAGCG |
| M118.txt | SEQ ID NO 58 | CCAACCGCGCCCTGATGGGTGCCAACATGCAGCGCCAGGCGGTTCCGCTGGTGCGCAGCG |
| MY221.txt | SEQ ID NO 59 | CCAACCGTGCCCTGATGGGTGCCAACATGCAGCGCCAGGCGGTTCCGCTGGTGCGCAGCG |
| MY223.txt | SEQ ID NO 60 | CCAACCGTGCCCTGATGGGTGCCAACATGCAGCGCCAGGCAGTTCCGCTGGTACGCAGCG |
| MY225.txt | SEQ ID NO 61 | CCAACCGCGCCCTGATGGGTGCCAACATGCAGCGCCAGGCGGTTCCGCTGGTGCGCAGCG |
| My341.txt | SEQ ID NO 62 | CCAACCGCGCCCTGATGGGTGCCAACATGCAGCGCCAGGCGGTTCCGCTGGTGCGCAGCG |
| My715.txt | SEQ ID NO 63 | CCAACCGCGCCCTGATGGGTGCCAACATGCAGCGCCAGGCGGTTCCGCTGGTGCGCAGCG |
| MY470.txt | SEQ ID NO 64 | CCAACCGCGCCTTGATGGGTGCCAACATGCAGCGSCAGGCGGTCCCGCTGGTGCGCAGCG |
| Atcc4-go.txt | SEQ ID NO 65 | CCAACCGTGCCCTGATGGGTGCCAACATGCAGCGCCAGGCGGTTCCGCTGGTGCGCAGCG |
| ATCC4-0-Gord.txt | SEQ ID NO 66 | CCAACCGTGCCCTGATGGGTGCCAACATGCAGCGCCAGGCGGTTCCGCTGGTGCGCAGCG |
| M78(lz).txt | SEQ ID NO 67 | CCAACCGTGCCCTGATGGGTGCCAACATGCAGCGCCAGGCGGTTCCGCTGGTCCGCAGCG |
| M79(jd).txt | SEQ ID NO 68 | CCAACCGCGCCCTGATGGGTGCCAACATGCAGCGCCAGGCGGTTCCGCTGGTGCGCAGCG |
| M80(lg).txt | SEQ ID NO 69 | CCAACCGTGCCCTGATGGGTGCCAACATGCAGCGCCAGGCGGTTCCGCTGGTGCGCAGCG |
| M81(ll).txt | SEQ ID NO 70 | CCAACCGTGCCCTGATGGGTGCCAACATGCAGCGCCAGGCGGTTCCGCTGGTCCGCAGCG |
| M82(rm).txt | SEQ ID NO 71 | CCAACCGTGCCCTGATGGGTGCCAACATGCAGCGCCAGGCGGTTCCGCTGGTGCGCAGCG |
| M83(mb).txt | SEQ ID NO 72 | CCAACCGTGCCCTGATGGGTGCCAACATGCAGCGCCAGGCGGTTCCGCTGGTGCGCAGCG |
| M84(ow).txt | SEQ ID NO 73 | CCAACCGTGCCCTGATGGGTGCCAACATGCAGCGCCAGGCGGTTCCGCTGGTCCGCAGCG |
| M85(lb).txt | SEQ ID NO 74 | CCAACCGTGCCCTGATGGGTGCCAACATGCAGCGCCAGGCGGTTCCGCTGGTGCGCAGCG |
| M86(rb).txt | SEQ ID NO 75 | CCAACCGTGCCCTGATGGGCGCCAACATGCAGCGCCAGGCGGTTCCGCTGGTGCGTAGCG |
| M87(wn).txt | SEQ ID NO 76 | CCAACCGTGCCCTGATGGGTGCCAACATGCAGCGCCAGGCGGTTCCGCTGGTGCGCAGCG |
| M90(gordDB).txt | SEQ ID NO 77 | CCAACCGTGCCCTGATGGGTGCCAACATGCAGCGCCAGGCGGTTCCGCTGGTGCGCAGCG |
| m126.txt | SEQ ID NO 78 | CCAACCGTGCCCTGATGGGTGCCAACATGCAGCGCCAGGCGGTTCCGCTGGTGCGCAGCG |
| M128.txt | SEQ ID NO 79 | CCAACCGTGCCCTGATGGGCGCCAACATGCAGCGCCAGGCGGTTCCGCTGGTGCGCAGCG |
| My103.txt | SEQ ID NO 80 | CCAACCGTGCCCTGATGGGTGCCAACATGCAGCGCCAGGCGGTTCCGCTGGTGCGCAGCG |
| MY475.txt | SEQ ID NO 81 | CCAACCGTGCCCTGATGGGCGCCAACATGCAGCGCCAGGCGGTTCCGCTGGTGCGCAGCG |
| MY476.txt | SEQ ID NO 82 | CCAACCGTGCCCTGATGGGTGCCAACATGCAGCGCCAGGCGGTTCCGCTGGTGCGCAGCG |
| MY830.txt | SEQ ID NO 83 | CCAACCGTGCCCTGATGGGCGCCAACATGCAGCGCCAGGCGGTTCCGCTGGTGCGTAGCG |
| Atcc5-int.txt | SEQ ID NO 84 | CCAACCGTGCCCTGATGGGCGCCAACATGCAGCGCCAGGCGGTTCCGCTGGTGCGCAGCG |
| ATCC5-0int.txt | SEQ ID NO 85 | CCAACCGTGCCCTGATGGGCGCCAACATGCAGCGCCAAGCGGTTCCGCTGGTGCGCAGCG |
| M18.txt | SEQ ID NO 86 | CCAACCGTGCCCTGATGGGCGCCAACATGCAGCGCCAGGCGGTTCCGCTGGTGCGCAGCG |
| M19.txt | SEQ ID NO 87 | CCAACCGTGCCCTGATGGGCGCCAACATGCAGCGCCAGGCGGTTCCGCTGGTGCGCAGCG |
| M20.txt | SEQ ID NO 88 | CCAACCGTGCCCTGATGGGCGCCAACATGCAGCGCCAGGCGGTTCCGCTGGTGCGCAGCG |
| M21.txt | SEQ ID NO 89 | CCAACCGTGCCCTGATGGGCGCCAACATGCAGCGCCAGGCGGTTCCGCTGGTGCGCAGCG |
| M22.txt | SEQ ID NO 90 | CCAACCGTGCCCTGATGGGCGCCAACATGCAGCGCCAGGCGGTTCCGCTGGTGCGCAGCG |
| M23.txt | SEQ ID NO 91 | CCAACCGTGCCCTGATGGGCGCCAACATGCAGCGCCAGGCGGTTCCGCTGGTGCGCAGCG |
| M24.txt | SEQ ID NO 92 | CCAACCGTGCCCTGATGGGCGCCAACATGCAGCGCCAGGCGGTTCCGCTGGTGCGCAGCG |
| M25.txt | SEQ ID NO 93 | CCAACCGTGCCCTGATGGGCGCCAACATGCAGCGCCAGGCGGTTCCGCTGGTGCGCAGCG |
| M26.txt | SEQ ID NO 94 | CCAACCGTGCCCTGATGGGCGCCAACATGCAGCGCCAGGCGGTTCCGCTGGTGCGCAGCG |
| M27.txt | SEQ ID NO 95 | CCAACCGTGCCCTGATGGGCGCCAACATGCAGCGCCAGGCGGTTCCGCTGGTGCGCAGCG |
| M28.txt | SEQ ID NO 96 | CCAACCGTGCCCTGATGGGCGCCAACATGCAGCGCCAGGCGGTTCCACTGGTGCGCAGCG |
| M107.txt | SEQ ID NO 97 | CCAACCGTGCCCTGATGGGCGCCAACATGCAGCGCCAGGCGGTTCCGCTGGTGCGCAGCG |
| MY107.txt | SEQ ID NO 98 | CCAACCGTGCCCTGATGGGCGCCAACATGCAGCGCCAGGCGGTTCCGCTGGTGCGCAGCG |
| MY112.txt | SEQ ID NO 99 | CCAACCGTGCCCTGATGGGCGCCAACATGCAGCGCCAGGCGGTTCCGCTGGTGCGCAGCG |
| MY312.txt | SEQ ID NO 100 | CCAACCGTGCCCTGATGGGCGCCAACATGCAGCGCCAGGCGGTTCCGCTGGTGCGCAGCG |
| Atcc6-kan.txt | SEQ ID NO 101 | CCAACCGGGCTCTGATGGGTGCCAACATGCAGCGCCAGGCGGTTCCGCTGGTGCGCAGCG |
| ATCC6-0Kan.txt | SEQ ID NO 102 | CCAACCGGGCTCTGATGGGTGCCAACATGCAGCGCCAGGCGGTTCCGCTGGTGCGCAGCG |
| M1.txt | SEQ ID NO 103 | CCAACCGGGCTCTGATGGGTGCCAACATGCAGCGCCAGGCGGTTCCGCTGGTGCGCAGCG |
| M2.txt | SEQ ID NO 104 | CCAACCGGGCTCTGATGGGTGCCAACATGCAGCGCCAGGCGGTTCCGCTGGTGCGCAGCG |
| M3.txt | SEQ ID NO 105 | CCAACCGGGCTCTGATGGGTGCCAACATGCAGCGCCAGGCGGTTCCGCTGGTGCGCAGCG |
| M4.txt | SEQ ID NO 106 | CCAACCGGGCACTGATGGGCGCCAACATGCAGCGTCAGGCGGTTCCGCTGGTACGCAGCG |
| M6.txt | SEQ ID NO 107 | CCAACCGGGCTCTGATGGGTGCCAACATGCAGCGCCAGGCGGTTCCGCTGGTGCGCAGCG |
| M7.txt | SEQ ID NO 108 | CCAACCGGGCTCTGATGGGTGCCAACATGCAGCGCCAGGCGGTTCCGCTGGTGCGCAGCG |
| M9.txt | SEQ ID NO 109 | CCAACCGGGCTCTGATGGGTGCCAACATGCAGCGCCAGGCGGTTCCGCTGGTGCGCAGCG |
| M57.txt | SEQ ID NO 110 | CCAACCGGGCTCTGATGGGTGCCAACATGCAGCGCCAGGCGGTTCCGCTGGTGCGCAGCG |
| M58.txt | SEQ ID NO 111 | CCAACCGGGCTCTGATGGGTGCCAACATGCAGCGCCAGGCGGTTCCGCTGGTGCGCAGCG |
| M59.txt | SEQ ID NO 112 | CCAACCGGGCTCTGATGGGTGCCAACATGCAGCGCCAGGCGGTTCCGCTGGTGCGCAGCG |

TABLE 1-continued

| | | |
|---|---|---|
| M60.txt | SEQ ID NO 113 | CCAACCGGGCTCTGATGGGTGCCAACATGCAGCGCCAGGCGGTTCCGCTGGTGCGCAGCG |
| M61.txt | SEQ ID NO 114 | CCAACCGGGCTCTGATGGGTGCCAACATGCAGCGCCAGGCGGTTCCGCTGGTGCGCAGCG |
| M62.txt | SEQ ID NO 115 | CCAACCGGGCTCTGATGGGTGCCAACATGCAGCGCCAGGCGGTTCCGCTGGTGCGCAGCG |
| MY106.txt | SEQ ID NO 116 | CCAACCGGGCTCTGATGGGTGCCAACATGCAGCGCCAGGCGGTTCCGCTGGTGCGCAGCG |
| MY216.txt | SEQ ID NO 117 | CCAACCGGGCTCTGATGGGTGCCAACATGCAGCGCCAGGCGGTTCCGCTGGTGCGCAGCG |
| MY218.txt | SEQ ID NO 118 | CCAACCGGGCTCTGATGGGTGCCAACATGCAGCGCCAGGCGGTTCCGCTGGTGCGCAGCG |
| MY226.txt | SEQ ID NO 119 | CCAACCGGGCTCTGATGGGTGCCAACATGCAGCGCCAGGCGGTTCCGCTGGTGCGCAGCG |
| M109.txt | SEQ ID NO 120 | CCAACCGTGCCCTGATGGGCGCCAACATGCAGCGCCAGGCGGTTCCGCTGGTGCGCAGCG |
| M111.txt | SEQ ID NO 121 | CCAACCGTGCCCTGATGGGCGCCAACATGCAGCGCCAGGCGGTTCCGCTGGTGCGCAGCG |
| M112.txt | SEQ ID NO 122 | CCAACCGTGCCCTGATGGGCGCCAACATGCAGCGCCAGGCGGTTCCGCTGGTGCGCAGCG |
| M113.txt | SEQ ID NO 123 | CCAACCGTGCCCTGATGGGCGCCAACATGCAGCGCCAGGCGGTTCCGCTGGTGCGCAGCG |
| M114.txt | SEQ ID NO 124 | CCAACCGTGCCCTGATGGGCGCCAACATGCAGCGCCAGGCGGTTCCGCTGGTGCGCAGCG |
| MY325.txt | SEQ ID NO 125 | CCAACCGTGCCCTGATGGGCGCCAACATGCAGCGCCAGGCGGTTCCGCTGGTGCGCAGCG |
| MY718.txt | SEQ ID NO 126 | CCAACCGTGCCCTGATGGGCGCCAACATGCAGCGCCAGGCGGTTCCGCTGGTGCGCAGCG |
| MY214.txt | SEQ ID NO 127 | CCAACCGCGCCCTGATGGGTGCCAACATGCAGCGCCAGGCGGTCCCGCTGGTGCGCAGCG |
| MY224.txt | SEQ ID NO 128 | CCAACCGCGCCCTGATGGGTGCCAACATGCAGCGCCAGGCGGTCCCGCTGGTGCGCAGCG |
| My244.txt | SEQ ID NO 129 | CCAACCGCGCCCTGATGGGTGCCAACATGCAGCGCCAGGCGGTCCCGCTGGTGCGCAGCG |
| My339.txt | SEQ ID NO 130 | CCAACCGCGCCCTGATGGGTGCCAACATGCAGCGCCAGGCGGTCCCGCTGGTGCGCAGCG |
| My343.txt | SEQ ID NO 131 | CCAACCGCGCCCTGATGGGTGCCAACATGCAGCGCCAGGCGGTCCCGCTGGTGCGCAGCG |
| MY458.txt | SEQ ID NO 132 | CCAACCGCGCCCTCATGGGTGCGAACATGCAGCGTCAGGCGGTTCCGCTGGTGCGCAGCG |
| MY809.txt | SEQ ID NO 133 | CCAACCGCGCCCTGATGGGTGCGAACATGCAGCGTCAGGCGGTTCCGCTGGTGCGCAGCG |
| MY817.txt | SEQ ID NO 134 | CCAACCGCGCCCTGATGGGTGCGAACATGCAGCGTCAGGCGGTTCCGCTGGTGCGCAGCG |
| MY821.txt | SEQ ID NO 135 | CCAACCGCGCCCTGATGGGTGCGAACATGCAGCGTCAGGCGGTTCCGCTGGTGCGCAGCG |
| MY824.txt | SEQ ID NO 136 | CCAACCGCGCCCTGATGGGTGCGAACATGCAGCGTCAGGCGGTTCCGCTGGTGCGCAGCG |
| MY102.txt | SEQ ID NO 137 | CCAACCGTGCCCTGATGGGCGCCAACATGCAGCGCCAGGCGGTTCCGCTGGTGCGCAGTG |
| My105.txt | SEQ ID NO 138 | CCAACCGTGCCCTGATGGGCGCCAACATGCAGCGCCAGGCGGTTCCGCTGGTGCGCAGTG |
| MY251.txt | SEQ ID NO 139 | CCAACCGTGCCCTGATGGGCGCCAACATGCAGCGCCAGGCGGTTCCGCTGGTGCGCAGTG |
| My256.txt | SEQ ID NO 140 | CCAACCGTGCCCTGATGGGCGCCAACATGCAGCGCCAGGCGGTTCCGCTGGTGCGCAGTG |
| My294.txt | SEQ ID NO 141 | CCAACCGTGCCCTGATGGGCGCCAACATGCAGCGCCAGGCGGTTCCGCTGGTGCGCAGTG |
| MY354.txt | SEQ ID NO 142 | CCAACCGTGCCCTGATGGGCGCCAACATGCAGCGTCAGGCGGTTCCGCTGGTGCGCAGCG |
| Atcc7-scr.txt | SEQ ID NO 143 | CCAACCGTGCCCTGATGGGCGCCAACATGCAGCGCCAGGCGGTTCCGCTGGTGCGCAGCG |
| ATCC7-Oscr.txt | SEQ ID NO 144 | CCAACCGTGCCCTGATGGGCGCCAACATGCAGCGCCAGGCGGTTCCGCTGGTGCGCAGCG |
| MY121.txt | SEQ ID NO 145 | CCAACCGTGCCCTGATGGGCGCCAACATGCAGCGCCAGGCGGTCCCGCTGGTGCGCAGCG |
| MY249.txt | SEQ ID NO 146 | CCAACCGTGCCCTGATGGGCGCCAACATGCAGCGCCAGGCGGTTCCGCTGGTGCGCAGCG |
| MY372.txt | SEQ ID NO 147 | CCAACCGTGCCCTGATGGGCGCCAACATGCAGCGTCAGGCGGTTCCGCTGGTGCGCAGCG |
| MY378.txt | SEQ ID NO 148 | CCAACCGTGCCCTGATGGGCGCCAACATGCAGCGCCAGGCGGTTCCGCTGGTGCGCAGCG |
| MY484.txt | SEQ ID NO 149 | CCAACCGCGCCCTGATGGGTGCCAACATGCAGCGCCAGGCGGTTCCGCTGGTGCGCAGCG |
| My556.txt | SEQ ID NO 150 | CCAACCGTGCCCTGATGGGTGCCAACATGCAGCGCCAGGCGGTTCCGCTGGTACGCAGCG |
| MY563.txt | SEQ ID NO 151 | CCAACCGTGCCCTGATGGGTGCCAACATGCAGCGCCAGGCGGTTCCGCTGGTACGCAGCG |
| MY586.txt | SEQ ID NO 152 | CCAACCGTGCCCTGATGGGTGCCAACATGCAGCGCCAGGCGGTTCCGCTGGTACGCAGCG |
| Atcc8-sme.txt | SEQ ID NO 153 | CCAACCGCGCCCTGATGGGTGCCAACATGCAGCGCCAGGCGGTTCCGCTGGTGCGCAGCG |
| M35.txt | SEQ ID NO 154 | CCAACCGTGCCCTGATGGGTGCCAACATGCAGCGCCAGGCGGTTCCGCTGGTCCGCAGCG |
| M36.txt | SEQ ID NO 155 | CCAACCGTGCCTTGATGGGTGCCAACATGCAGCGCCAGGCCGTTCCGCTGGTGCGCAGCG |
| M37.txt | SEQ ID NO 156 | CCAACCGCGCCCTGATGGGTGCCAACATGCAGCGCCAGGCGGTTCCGCTGGTGCGCAGCG |
| m125.txt | SEQ ID NO 157 | CCAACCGCGCCCTGATGGGTGCCAACATGCAGCGCCAGGCGGTTCCGCTGGTGCGCAGCG |
| MY143.txt | SEQ ID NO 158 | CCAACCGCGCCCTGATGGGTGCCAACATGCAGCGCCAGGCGGTTCCGCTGGTGCGCAGCG |
| My104.txt | SEQ ID NO 159 | CCAACCGCGCCCTGATGGGTGCCAACATGCAGCGCCAGGCGGTTCCGCTGGTGCGCAGCG |
| MY196.txt | SEQ ID NO 160 | CCAACCGCGCCCTGATGGGTGCCAACATGCAGCGCCAGGCGGTTCCGCTGGTGCGCAGCG |
| MY357.txt | SEQ ID NO 161 | CCAACCGCGCCCTGATGGGTGCCAACATGCAGCGCCAGGCGGTTCCGCTGGTGCGCAGCG |
| My358.txt | SEQ ID NO 162 | CCAACCGCGCCCTGATGGGTGCCAACATGCAGCGCCAGGCGGTTCCGCTGGTGCGCAGCG |
| My480.txt | SEQ ID NO 163 | CCAACCGCGCCCTGATGGGTGCCAACATGCAGCGCCAGGCGGTTCCGCTGGTGCGCAGCG |
| MY212.txt | SEQ ID NO 164 | CCAACCGGGCCCTGATGGGTGCCAACATGCAGCGTCAGGCGGTTCCCCTGGTGCGCAGCG |
| MY491.txt | SEQ ID NO 165 | CCAACCGGGCCCTGATGGGTGCCAACATGCAGCGTCAGGCGGTTCCCCTGGTGCGCAGCG |
| MY497.txt | SEQ ID NO 166 | CCAACCGTGCCCTGATGGGCGCCAACATGCAGCGTCAGGCGGTTCCCCTGGTGCGCAGCG |
| MY816.txt | SEQ ID NO 167 | CCAACCGTGCCCTGATGGGCGCCAACATGCAGCGCCAGGCGGTTCCGCTGGTGCGCAGCG |
| | SEQ ID NO 168 | CCAACCGCGCGTTGATGGGCGCGAACATGCAGCGCCAGGCCGTTCCGTTGGTGCGTAGCG |
| M38.txt | SEQ ID NO 169 | CCAACCGCGCGTTGATGGGCGCGAACATGCAGCGCCAGGCCGTTCCGTTGGTGCGTAGCG |
| M39.txt | SEQ ID NO 170 | CCAACCGCGCGTTGATGGGCGCGAACATGCAGCGCCAGGCCGTTCCGTTGGTGCGTAKCG |
| M40.txt | SEQ ID NO 171 | CCAACCGCGCGTTGATGGGCGCGAACATGCAGCGCCAGGCCGTTCCGTTGGTGCGTAGCG |
| M41.txt | SEQ ID NO 172 | CCAACCGCGCGTTGATGGGCGCGAACATGCAGCGCCAGGCCGTTCCGTTGGTGCGTAGCG |
| M42.txt | SEQ ID NO 173 | CCAACCGCGCGTTGATGGGCGCGAACATGCAGCGCCAGGCCGTTCCGTTGGTGCGTAGCG |
| M43.txt | SEQ ID NO 174 | CCAACCGCGCGTTGATGGGCGCGAACATGCAGCGCCAGGCCGTTCCGTTGGTGCGTAGCG |
| M44.txt | SEQ ID NO 175 | CCAACCGCGCGTTGATGGGCGCGAACATGCAGCGCCAGGCCGTTCCGTTGGTGCGTAGCG |
| M45.txt | SEQ ID NO 176 | CCAACCGCGCGTTGATGGGCGCGAACATGCAGCGCCAGGCCGTTCCGTTGGTGCGTAGCG |
| M46.txt | SEQ ID NO 177 | CCAACCGCGCGTTGATGGGCGCGAACATGCAGCGCCAGGCCGTTCCGTTGGTGCGTAGCG |
| M47.txt | SEQ ID NO 178 | CCAACCGCGCGTTGATGGGCGCGAACATGCAGCGCCAGGCCGTTCCGTTGGTGCGTAGCG |
| M68(Mav6).txt | SEQ ID NO 179 | CCAACCGCGCGTTGATGGGCGCGAACATGCAGCGCCAGGCCGTTCCGTTGGTGCGTAGCG |
| M89.txt | SEQ ID NO 180 | CCAACCGCGCGTTGATGGGCGCGAACATGCAGCGCCAGGCCGTTCCGTTGGTGCGTAGCG |
| M66(Mav4).txt | SEQ ID NO 181 | CCAACCGTGCCCTGATGGGCGCCAACATGCAGCGCCAGGCGGTTCCGCTGGTGCGCAGCG |
| | | 610 620 630 640 650 660 |

TABLE 1-continued

BASE NOS 660–720

| | | |
|---|---|---|
| ATCC9-Mtb.txt | SEQ ID NO 1 | AGGCCCCGCTGGTGGGCACCGGGATGGAGCTGCGCGCGGCGATCGACGCGGCGACGT |
| MY621.txt | SEQ ID NO 2 | AGGCTCCGCTGGTCGGTACC |
| Atcc1-av.txt | SEQ ID NO 3 | ANGCGCCGCTGGTGGGCACCGGCATGGAGCTGCGCGCGGCGATCGACGCGGCGACGT |
| M29.txt | SEQ ID NO 4 | AGGCGCCGCTGGTGGGCACCGGCATGGAGCTGCGCGCGGCGATCGACGCGGCGACGT |
| M30.txt | SEQ ID NO 5 | AGGCGCCGCTGGTGGGCACCGGCATGGAGCTGCGCGCGGCGATCGACGCGGCGACGT |
| M31.txt | SEQ ID NO 6 | AGGCGCCGCTGGTGGGCACCGGCATGGAGCTGCGCGCGGCGATCGACGCGGCGACGT |
| M32.txt | SEQ ID NO 7 | AGGCGCCGCTGGTGGGCACCGGCATGGAGCTGCGCGCGGCGATCGACGCGGCGACGT |
| M33.txt | SEQ ID NO 8 | AGGCGCCGCTGGTGGGCACCGGCATGGAGCTGCGCGCGGCGATCGACGCGGCGACGT |
| M34.txt | SEQ ID NO 9 | AGGCGCCGCTGGTGGGCACCGGCATGGAGCTGCGCGCGGCGATCGACGCGGCGACGT |
| M48-new.txt | SEQ ID NO 10 | AGGCGCCGCTGGTGGGCACCGGCATGGAGCTGCGCGCGGCGATCGACGCGGCGACGT |
| M49.txt | SEQ ID NO 11 | AGGCGCCGCTGGTGGGCACCGGCATGGAGCTGCGCGCGGCGATNGACGCGGCGACGT |
| M64(Mav2).txt | SEQ ID NO 12 | AGGCGCCGCTGGTGGGCACCGGCATGGAGCTGCGCGCGGCGATCGACGCGGCGACGT |
| M65(Mav3).txt | SEQ ID NO 13 | AGGCGCCGCTGGTGGGCACCGGCATGGAGCTGCGCGCGGCGATCGACGCGGCGACGT |
| M67(Mav5).txt | SEQ ID NO 14 | AGGCGCCGCTGGTGGGCACCGGCATGGAGCTGCGCGCGGCGATCGACGCGGCGACGT |
| M69(Mav7).txt | SEQ ID NO 15 | AGGCGCCGCTGGTGGGCACC |
| M71(Mav9).txt | SEQ ID NO 16 | AGGCGCCGCTGGTGGGCACCGGCATGGAGCTGCGCGCGGCGATCGACGCGGCGACGT |
| M91.txt | SEQ ID NO 17 | AAGCGCCGCTGGTGGGCACCGGCATGGAGCTGCGCGCGGCGATCGACGCGGCGACGT |
| M94.txt | SEQ ID NO 18 | AGGCGCCGCTGGTGGGCACCGGCATGGAGCTGCGCGCGGCGATCGACGC |
| M95.txt | SEQ ID NO 19 | AGGCGCCGCTGGTGGGCACCGGCATGGAGCTGCGCGCGGCGATCGACGC |
| M96.txt | SEQ ID NO 20 | AGGCGCCGCTGGTGGGCACCGGCATGGAGCTGCGCGCGGCGATCGACGC |
| M100.txt | SEQ ID NO 21 | AGGCGCCGCTGGTGGGCACCGGCATGGAGCTGCGCGCGGCGATCGACGC |
| M101.txt | SEQ ID NO 22 | AGGCGCCGCTGGTGGGCACCGGCATGGAGCTGCGCGCGGCGATCGACGC |
| M102.txt | SEQ ID NO 23 | AGGCGCCGCTGGTGGGCACCGGCATGGAGCTGCGCGCGGCGATCGACGC |
| M104.txt | SEQ ID NO 24 | AGGCGCCGCTGGTGGGCACCGGCATGGAGCTGCGCGCGGCGATCGACGCGGCGACGT |
| M105.txt | SEQ ID NO 25 | AGGCGCCGCTGGTGGGCACCGGCATGGAGCTGCGCGCGGCGATCGACGC |
| M106.txt | SEQ ID NO 26 | AGGCCCCGCTGGTCGGTACCGGTATGGAGTTGCGCGCGGCGATCGACGC |
| MY111.txt | SEQ ID NO 27 | AGGCGCCGCTGGTGGGCACCGGCATGGAGCTGCGCGCGGCGATCGACGC |
| M76.txt | SEQ ID NO 28 | AGGCCCCGCTGGTGGGCACCGGGATGGAGCTGCGCGCGGCGATCGACGCGGCGACGT |
| MY451.txt | SEQ ID NO 29 | AGGCCCCGCTGGTGGGCACCGGGATGGAGCTGCGCGCGGCGATCGACGC |
| ATCC2-chelnew.txt | SEQ ID NO 30 | AGGCCCCGCTGGTCGGTACCGGTATGGA |
| M10.txt | SEQ ID NO 31 | AGGCCCCGCTGGTCGGTACC |
| M11-662.txt | SEQ ID NO 32 | AGGCCCCGCTGGTCGGTACCGGTATGGAGCTG |
| M12.txt | SEQ ID NO 33 | AGGCCCCGCTGGTCGGTACC |
| M13_2_662.txt | SEQ ID NO 34 | AGGCCCCGCTGGTCGGTACCGGTATGGA |
| M14.txt | SEQ ID NO 35 | AGGCCCCGCTGGTCGGTACCGGTATGGAGCTGCGCGCGGCGATCGACGCGGCGACGT |
| M15.txt | SEQ ID NO 36 | AGGCCCCGCTGGTCGGTACC |
| M16.txt | SEQ ID NO 37 | AGGCCCCGCTGGTCGGTACC |
| M17_2_662.txt | SEQ ID NO 38 | AGGCCCCGCTGGTCGGTACCGGTATGGAG |
| M50.txt | SEQ ID NO 39 | AGGCCCCGCTGGTCGGTACC |
| M51.txt | SEQ ID NO 40 | AGGCCCCGCTGGTCGGTACC |
| M115.txt | SEQ ID NO 41 | AGGCCCCGCTGGTCGGTACC |
| M116.txt | SEQ ID NO 42 | AGGCCCCGCTGGTCGGTACC |
| M119.txt | SEQ ID NO 43 | AGGCCCCGCTGGTCGGTACC |
| MY109.txt | SEQ ID NO 44 | AGGCCCCGCTGGTCGGTACC |
| MY200.txt | SEQ ID NO 45 | AGGCTCCGCTGGTCGGTACC |
| MY207.txt | SEQ ID NO 46 | AGGCTCCGCTGGTCGGTACC |
| MY209.txt | SEQ ID NO 47 | AGGCTCCGCTGGTCGGTACC |
| M122.txt | SEQ ID NO 48 | AGGCCCCGCTGGTCGGCACCGGTATGGAGTTGCGCGCGGCGATCGACGC |
| M123.txt | SEQ ID NO 49 | AGGCCCCGCTGGTCGGCACCGGTATGGAGTTGCGCGCGGCGATCGACGC |
| M124.txt | SEQ ID NO 50 | AGGCGCCGTTGGTCGGTACCGGCATGGAACTGCGCGCGGCGATCGACGC |
| Atcc3-for.txt | SEQ ID NO 51 | AGGCCCCGCTGGTCGGTACCGGTATGGAGCTGCGCGCGGCGATCGACGCGGCGACGT |
| M53.txt | SEQ ID NO 52 | AGGCCCCGCTGGTCGGTACCGGTATGGAGTTGCGCGCGGCGATCGACGCGGCGACGT |
| M54.txt | SEQ ID NO 53 | AGGCCCCGCTGGTCGGTACC |
| M55.txt | SEQ ID NO 54 | AGGCCCCGCTGGTCGGTACCGGTATGGAGCTGCGCGCGGCGATCGACGCGGCGACGT |
| M56.txt | SEQ ID NO 55 | AGGCCCCGCTGGTCGGTACCGGTATGGAGTTGCGCGCGGCGATCGACGCGGCGACGT |
| M74(Mav12).txt | SEQ ID NO 56 | AGGCCCCGCTGGTCGGTACC |

TABLE 1-continued

| | | |
|---|---|---|
| M77.txt | SEQ ID NO 57 | AGGCCCCGCTGGTCGGTACCGGTATGGAGCTGCGCGCGGCGATCGACGCGGCGACGT |
| M118.txt | SEQ ID NO 58 | AGGCCCCGCTGGTCGGTACCGGCATGGAGTTGCGCGCGGCGATCGACGC |
| MY221.txt | SEQ ID NO 59 | AGGCCCCGCTGGTCGGTACCGGTATGGAGCTGCGCGCGGCGATCGACGC |
| MY223.txt | SEQ ID NO 60 | AGGCCCCGCTGGTCGGTACCGGTATGGAGCTGCGCGCGGCGATCGACGC |
| MY225.txt | SEQ ID NO 61 | AGGCCCCGCTGGTCGGTACCGGTATGGAGCTGCGCGCGGCGATCGACGC |
| My341.txt | SEQ ID NO 62 | AGGCCCCGCTGGTCGGTACCGGTATGGAGCTGCGCGCGGCGATCGACGC |
| My715.txt | SEQ ID NO 63 | AGGCCCCGCTGGTCGGTACCGGTATGGAGCTGCGCGCGGCGATCGACGC |
| MY470.txt | SEQ ID NO 64 | AGGCACCGCTGGTCGGTACC |
| Atcc4-go.txt | SEQ ID NO 65 | AGGCACCGCTGGTGGGCACCGGCATGGAGTTGCGCGCGGCGATCGACGCGGCGACGT |
| ATCC4-0-Gord.txt | SEQ ID NO 66 | AGGCACCGCTGGTGGGCACCGGCATGGAGTTGCGCGCGGCGATCGACGCGGCGACGT |
| M78(lz).txt | SEQ ID NO 67 | ARGCGCCGCTGGTGGGTACCGGCATGGAGTTGCGCGCGGCGATCGACGCGGCGACGT |
| M79(jd).txt | SEQ ID NO 68 | ARGCACCGCTGGTGGGCACCGGTATGGAATTGCGCGCGGCGATCGACGCGGCGACGT |
| M80(lg).txt | SEQ ID NO 69 | AGGCGCCGCTGGTGGGTACCGGCATGGAGTTGCGCGCGGCGATCGACGCGGCGACGT |
| M81(ll).txt | SEQ ID NO 70 | AGGCGCCGCTGGTGGGTACCGGCATGGAGTTGCGCGCGGCGATCGACGCGGCGACGT |
| M82(rm).txt | SEQ ID NO 71 | AGGCACCGCTGGTGGGCACCGGCATGGAGTTGCGCGCGGCGATCGACGCGGCGACGT |
| M83(mb).txt | SEQ ID NO 72 | AGGCACCGCTGGTGGGCACCGGCATGGAGTTGCGCGCGGCGATCGACGCGGCGACGT |
| M84(ow).txt | SEQ ID NO 73 | AGGCGCCGCTGGTGGGTACCGGCATGGAGTTGCGCGCGGCGNTCGACGCGGCGACGT |
| M85(lb).txt | SEQ ID NO 74 | AGGCACCGCTGGTGGGCACCGGCATGGAGTTGCGCGCGGCGATCGACGCGGCGACGT |
| M86(rb).txt | SEQ ID NO 75 | ARGCGCCGCTGGTGGGCACCGGCATGGAGCTGCGCGCGGCGATCGACGCGGCGACGT |
| M87(wn).txt | SEQ ID NO 76 | AGGCACCGCTGGTGGGCACCGGCATGGAGTTGCGCGCGGCGATCGACGCGGCGACGT |
| M90(gordDB).txt | SEQ ID NO 77 | AGGCACCGCTGGTGGGCACCGGTATGGAGTTGCGCGCGGCGATCGACGCGGCGACGT |
| m126.txt | SEQ ID NO 78 | AGGCACCGCTGGTGGGCACCGGCATGGAGTTGCGCGCGGNGATCGACGCGGCNACNN |
| M128.txt | SEQ ID NO 79 | AGGCGCCGCTGGTGGGCACCGGCATGGAGTTGCGCGCGGCGATCGACGCGGCGACGT |
| My103.txt | SEQ ID NO 80 | AGGCACCGCTGGTGGGCACCGGCATGGAGTTGCGCGCGGCGATCGACGC |
| MY475.txt | SEQ ID NO 81 | AGGCGCCGCTGGTGGGTACCGGCATGGAGCTGCGCGCGGCGATCGACGC |
| MY476.txt | SEQ ID NO 82 | AGGCACCGCTGGTGGGCACCGGCATGGAGTTGCGCGCGGCGATCGACGC |
| MY830.txt | SEQ ID NO 83 | AGGCGCCGTTGGTGGGCACCGGGATGGAGTTGCGCGCGGCGATCGACGC |
| Atcc5-int.txt | SEQ ID NO 84 | AGGCGCCGCTGGTGGGCACCGGCATGGAGCTGCGCGCGGCGATCGACGCGGCGACGT |
| ATCC5-0int.txt | SEQ ID NO 85 | AGGCGCCGCTGGTGGGCACCGGCATGGAGCTGCGCGCGGCGATCGACGCGGCGACGT |
| M18.txt | SEQ ID NO 86 | AGGCGCCGCTGGTGGGCACCGGCATGGAGCTGCGCGCGGCGATCGACGCGGCGACGT |
| M19.txt | SEQ ID NO 87 | AGGCGCCGCTGGTGGGCACCGGCATGGAGCTGCGCGCGGCGATCGACGCGGCGACGT |
| M20.txt | SEQ ID NO 88 | AGGCGCCGCTGGTGGGCACCGGCATGGAGCTGCGCGCGGCGATCGACGCGGCGACGT |
| M21.txt | SEQ ID NO 89 | AGGCGCCGCTGGTGGGCACCGGCATGGAGCTGCGCGCGGCGATCGACGCGGCGACGT |
| M22.txt | SEQ ID NO 90 | AGGCGCCGCTGGTGGGCACCGGCATGGAGCTGCGCGCGGCGATCGACGCGGCGACGT |
| M23.txt | SEQ ID NO 91 | AGGCGCCGCTGGTGGGCACCGGCATGGAGCTGCGCGCGGCGATCGACGCGGCGACGT |
| M24.txt | SEQ ID NO 92 | AGGCGCCGCTGGTGGGCACCGGCATGGAGCTGCGCGCGGCGATCGACGCGGCGACGT |
| M25.txt | SEQ ID NO 93 | AGGCGCCGCTGGTGGGCACCGGCATGGAGCTGCGCGCGGCGATCGACGCGGCGACGT |
| M26.txt | SEQ ID NO 94 | AGGCGCCGCTGGTGGGCACCGGCATGGAGCTGCGCGCGGCGATCGACGCGGCGACGT |
| M27.txt | SEQ ID NO 95 | AGGCGCCGCTGGTGGGCACCGGCATGGAGCTGCGCGCGGCGATCGACGCGGCGACGT |
| M28.txt | SEQ ID NO 96 | AGGCGCCGCTGGTGGGCACCGGCATGGAGCTGCGCGCGGCGATCGACGCGGCGACGT |
| M107.txt | SEQ ID NO 97 | AGGCGCCGCTGGTGGGCACCGGCATGGAGCTGCGCGCGGCGATCGACGC |
| MY107.txt | SEQ ID NO 98 | AGGCGCCGCTGGTGGGCACCGGCATGGAGCTGCGCGCGGCGATCGACGC |
| MY112.txt | SEQ ID NO 99 | AGGCGCCGCTGGTGGGCACCGGCATGGAGCTGCGCGCGGCGATCGACGC |
| MY312.txt | SEQ ID NO 100 | AGGCGCCGCTGGTGGGCACCGGCATGGAGCTGCGCGCGGCGATCGACGC |
| Atcc6-kan.txt | SEQ ID NO 101 | AGGCGCCGCTGGTGGGCACCGGCATGGAGTTGCGCGCGGCGATCGACGCGGCGACGT |
| ATCC6-0kan.txt | SEQ ID NO 102 | AGGCGCCGCTGGTGGGCACCGGCATGGAGTTGCGCGCGGCGATCGACGCGGCGACGT |
| M1.txt | SEQ ID NO 103 | AGGCGCCGCTGGTGGGCACCGGCATGGAGTTGCGCGCGGCGATCGACGCGGCGACGT |
| M2.txt | SEQ ID NO 104 | AGGCGCCGCTGGTGGGCACCGGCATGGAGTTGCGCGCGGCGATCGACGCGGCGACGT |
| M3.txt | SEQ ID NO 105 | AGGCGCCGCTGGTGGGCACCGGCATGGAGTTGCGCGCGGCGATCGACGCGGCGACGT |
| M4.txt | SEQ ID NO 106 | AGGCGCCGCTGGTGGGCACCGGCATGGAGTTGCGCGCGGCGATCGACGCGGCGACGT |
| M6.txt | SEQ ID NO 107 | AGGCGCCGCTGGTGGGCACCGGCATGGAGTTGCGCGCGGCGATCGACGCGGCGACGT |
| M7.txt | SEQ ID NO 108 | AGGCGCCGCTGGTGGGCACCGGCATGGAGTTGCGCGCGGCGATCGACGCGGCGACGT |
| M9.txt | SEQ ID NO 109 | AGGCGCCGCTGGTGGGCACC |
| M57.txt | SEQ ID NO 110 | AGGCGCCGCTGGTGGGCACCGGCATGGAGTTGCGCGCGGCGATCGACGCGGCGACGT |
| M58.txt | SEQ ID NO 111 | AGGCGCCGCTGGTGGGCACCGGCATGGAGTTGCGCGCGGCGATCGACGCGGCGACGT |
| M59.txt | SEQ ID NO 112 | AGGCGCCGCTGGTGGGCACCGGCATGGAGTTGCGCGCGGCGATCGACGCGGCGACGT |
| M60.txt | SEQ ID NO 113 | AGGCGCCGCTGGTGGGCACCGGCATGGAGTTGCGCGCGGCGATCGACGCGGCGACGT |
| M61.txt | SEQ ID NO 114 | AGGCGCCGCTGGTGGGCACCGGCATGGAGTTGCGCGCGGCGATCGACGCGGCGACGT |
| M62.txt | SEQ ID NO 115 | AGGCGCCGCTGGTGGGCACCGGCATGGAGTTGCGCGCGGCGATCGACGCGGCGACGT |
| MY106.txt | SEQ ID NO 116 | AGGCGCCGCTGGTGGGCACCGGCATGGAGTTGCGCGCGGCGATCGACGC |
| MY216.txt | SEQ ID NO 117 | AGGCGCCGCTGGTGGGCACCGGCATGGAGTTGCGCGCGGCGATCGACGC |
| MY218.txt | SEQ ID NO 118 | AGGCGCCGCTGGTGGGCACCGGCATGGAGTTGCGCGCGGCGATCGACGC |
| MY226.txt | SEQ ID NO 119 | AGGCGCCGCTGGTGGGCACCGGCATGGAGTTGCGCGCGGCGATCGACGC |
| M109.txt | SEQ ID NO 120 | AGGCGCCGCTGGTGGGCACCGGCATGGAGCTGCGCGCGGCGATCGACGC |
| M111.txt | SEQ ID NO 121 | AGGCGCCGCTGGTGGGCACCGGCATGGAGCTGCGCGCGGCGATCGACGC |
| M112.txt | SEQ ID NO 122 | AGGCGCCGCTGGTGGGCACCGGCATGGAGCTGCGCGCGGCGATCGACGC |
| M113.txt | SEQ ID NO 123 | AGGCGCCGCTGGTGGGCACCGGCATGGAGCTGCGCGCGGCGATCGACGC |
| M114.txt | SEQ ID NO 124 | AGGCGCCGCTGGTGGGCACCGGCATGGAGCTGCGCGCGGCGATCGACGC |
| MY325.txt | SEQ ID NO 125 | AGGCGCCGCTGGTGGGCACCGGCATGGAGCTGCGCGCGGCGATCGACGC |
| MY718.txt | SEQ ID NO 126 | AGGCGCCGCTGGTGGGCACCGGCATGGAGCTGCGCGCGGCGATCGACGC |
| MY214.txt | SEQ ID NO 127 | AGGCACCGCTGGTCGGTACCGGTATGGAGTTGCGCGCGGCGATCGACGC |
| MY224.txt | SEQ ID NO 128 | AGGCACCGCTGGTCGGTACCGGTATGGAGTTGCGCGCGGCGATCGACGC |
| My244.txt | SEQ ID NO 129 | AGGCACCGCTGGTCGGTACCGGTATGGAGTTGCGCGCGGCGATCGACGC |
| My339.txt | SEQ ID NO 130 | AGGCACCGCTGGTCGGTACCGGTATGGAGTTGCGCGCGGCGATCGACGC |
| My343.txt | SEQ ID NO 131 | AGGCACCGCTGGTCGGTACCGGTATGGAGTTGCGCGCGGCGATCGACGC |
| MY458.txt | SEQ ID NO 132 | AGGCCCCGCTGGTCGGTACC |
| MY809.txt | SEQ ID NO 133 | AGGCCCCGCTGGTCGGTACC |
| MY817.txt | SEQ ID NO 134 | AGGCCCCGCTGGTCGGTACC |
| MY821.txt | SEQ ID NO 135 | AGGCCCCGCTGGTCGGTACC |
| MY824.txt | SEQ ID NO 136 | AGGCCCCGCTGGTCGGTACC |
| MY102.txt | SEQ ID NO 137 | AGGCGCCGCTGGTGGGTACCGGCATGGAGCTGCGCGCGGCGATCGACGC |
| My105.txt | SEQ ID NO 138 | AGGCGCCGCTGGTGGGTACCGGCATGGAGCTGCGCGCGGCGATCGACGC |
| MY251.txt | SEQ ID NO 139 | AGGCGCCGCTGGTGGGTACCGGCATGGAGCTGCGCGCGGCGATCGACGC |
| My256.txt | SEQ ID NO 140 | AGGCGCCGCTGGTGGGTACTGGCATGGAGCTGCGCGCGGCGATCGACGC |
| My294.txt | SEQ ID NO 141 | AGGCGCCGCTGGTGGGTACCGGCATGGAGCTGCGCGCGGCGATCGACGC |

TABLE 1-continued

| | | |
|---|---|---|
| MY354.txt | SEQ ID NO 142 | AGGCGCCGCTGGTGGGCACCGGCATGGAGCTGCGCGCGGCGATCGACGC |
| Atcc7-scr.txt | SEQ ID NO 143 | AGGCGCCGCTGGTGGGCACCGGCATGGAGTTGCGCGCGGCGATCGACGCGGCGACGT |
| ATCC7-0scr.txt | SEQ ID NO 144 | AGGCGCCGCTGGTGGGCACCGGCATGGAGTTGCGCGCGGCGATCGACGCGGCGACGT |
| MY121.txt | SEQ ID NO 145 | AGGCGCCGCTGGTGGGCACCGGCATGGAGTTGCGCGCGGCGATCGACGC |
| MY249.txt | SEQ ID NO 146 | AGGCGCCGCTGGTGGGCACCGGCATGGAGTTGCGCGCGGCGATCGACGC |
| MY372.txt | SEQ ID NO 147 | AGGCGCCGCTGGTGGGCACCGGCATGGAGCTGCGCGCGGCGATCGACGC |
| MY378.txt | SEQ ID NO 148 | AGGCGCCGCTGGTGGGCACCGGCATGGAGTTGCGCGCGGCGATCGACGC |
| MY484.txt | SEQ ID NO 149 | AGGCACCGCTGGTGGGCACCGGGATGGAGTTGCGCGCGGCGATCGACGC |
| My556.txt | SEQ ID NO 150 | AGGCCCCGCTGGTCGGCACCGGGATGGAGCTGCGCGCGGCGATCGACGC |
| MY563.txt | SEQ ID NO 151 | AGGCCCCGCTGGTCGGCACCGGGATGGAGCTGCGCGCGGCGATCGACGC |
| MY586.txt | SEQ ID NO 152 | AGGCCCCGCTGGTCGGCACCGGGATGGAGCTGCGCGCGGCGATCGACGC |
| Atcc8-sme.txt | SEQ ID NO 153 | AGGCACCGCTGGTGGGTACCGGTATGGAACTGCGCGCGGCGATCGACGCGGCGACGT |
| M35.txt | SEQ ID NO 154 | AGGCCCCGCTGGTCGGCACC |
| M36.txt | SEQ ID NO 155 | AGGCCCCGCTGGTCGGCACCGGTATGGAGCTGCGCGCGGCGATCGACGCGGCGACGT |
| M37.txt | SEQ ID NO 156 | AGGCACCGCTGGTGGGTACCGGTATGGAACTGCGCGCGGCGATCGACGCGGCGACGT |
| m125.txt | SEQ ID NO 157 | AGGCACCGCTGGTGGGTACCGGTATGGAGTTGCGCGCGGNGATCGACGCGGNNACNN |
| MY143.txt | SEQ ID NO 158 | AGGCACCGCTGGTGGGTACCGGTATGGAACTGCGCGCGGCGATCGACGC |
| My104.txt | SEQ ID NO 159 | AGGCACCGCTGGTGGGTACCGGTATGGAGTTGCGCGCGGCGATCGACGC |
| MY196.txt | SEQ ID NO 160 | AGGCACCGCTGGTGGGTACCGGTATGGAGTTGCGCGCGGCGATCGACGC |
| MY357.txt | SEQ ID NO 161 | AGGCACCGCTGGTGGGTACCGGTATGGAGTTGCGCGCGGCGATCGACGC |
| My358.txt | SEQ ID NO 162 | AGGCACCGCTGGTGGGTACCGGTATGGAGTTGCGCGCGGCGATCGACGC |
| My480.txt | SEQ ID NO 163 | AGGCACCGCTGGTGGGTACCGGTATGGAGTTGCGCGCGGCGATCGACGC |
| MY212.txt | SEQ ID NO 164 | AGGCGCCGCTGGTGGGCACCGGCATGGAGCTGCGCGCGGCGATCGACGC |
| MY491.txt | SEQ ID NO 165 | AGGCGCCGCTGGTGGGCACCGGCATGGAGCTGCGCGCGGCGATCGACGC |
| MY497.txt | SEQ ID NO 166 | AGGCGCCGCTGGTGGGCACCGGCATGGAGCTGCGCGCGGCGATCGACGC |
| MY816.txt | SEQ ID NO 167 | AGGCGCCGCTGGTCGGTACCGGTATGGAGCTGCGCGCGGCGATCGACGC |
| | SEQ ID NO 168 | AGGCACCGCTGGTGGGCACCGGGATGGAATTGCGCGCGGCGATCGACGCGGCGACGT |
| M38.txt | SEQ ID NO 169 | AGGCACCGCTGGTGGGCACCGGGATGGAATTGCGCGCGGCGATCGACGCGGCGACGT |
| M39.txt | SEQ ID NO 170 | AGGCACCGCTGGTGGGCACCGGGATGGAATTGCGCGCGGCGATCGACGCGGCGACGT |
| M40.txt | SEQ ID NO 171 | AGGCACCGCTGGTGGGCACCGGGATGGAATTGCGCGCGGCGATCGACGCGGCGACGT |
| M41.txt | SEQ ID NO 172 | AGGCACCGCTGGTGGGCACCGGGATGGAATTGCGCGCGGCGATCGACGCGGCGACGT |
| M42.txt | SEQ ID NO 173 | AGGCACCGCTGGTGGGCACCGGGATGGAATTGCGCGCGGCGATCGACGCGGCGACGT |
| M43.txt | SEQ ID NO 174 | AGGCACCGCTGGTGGGCACCGGGATGGAATTGCGCGCGGCGATCGACGCGGCGACGT |
| M44.txt | SEQ ID NO 175 | AGGCACCGCTGGTGGGCACCGGGATGGAATTGCGCGCGGCGATCGACGCGGCGACGT |
| M45.txt | SEQ ID NO 176 | AGGCACCGCTGGTGGGCACCGGGATGGAATTGCGCGCGGCGATCGACGCGGCGACGT |
| M46.txt | SEQ ID NO 177 | AGGCACCGCTGGTGGGCACCGGGATGGAATTGCGCGCGGCGATCGACGCGGCGACGT |
| M47.txt | SEQ ID NO 178 | AGGCACCGCTGGTGGGCACCGGGATGGAATTGCGCGCGGCGATCGACGCGGCGACGT |
| M68(Mav6).txt | SEQ ID NO 179 | AGGCACCGCTGGTGGGCACCGGGATGGAATTGCGCGCGGCGATCGACGCGGCGACGT |
| M89.txt | SEQ ID NO 180 | AGGCACCGCTGGTGGGCACCGGGATGGAATTGCGCGCGGCGATCGACGCGGCGACGT |
| M66(Mav4).txt | SEQ ID NO 181 | AGGCGCCGCTGGTGGGCACCGGCATGGAGCTGCGCGCGGCGATCGACGCGGCGACGT |
| | | 670 680 690 700 710 720 |

TABLE 2

| Affy# | SAMPLE ID# | Alt. ID | SPECIES |
|---|---|---|---|
| MY621 | | ATCC | *M. abscessus* |
| ATCC1 | 25291 | ATCC-av | *M. avium* |
| M100 | 60300 | MAC | *M. avium* |
| M101 | 60112 | MAC | *M. avium* |
| M102 | 60268 | MAC | *M. avium* |
| M103 | 60270 | MAC | *M. avium* |
| M104 | 60272 | MAC | *M. avium* |
| M105 | 60293 | MAC | *M. avium* |
| M106 | 60313 | MAC | *M. avium* |
| M107 | 60345 | MAC | *M. avium* |
| M29 | 95-1764 | | *M. avium* |
| M30 | 95-1766 | | *M. avium* |
| M31 | 95-1768 | | *M. avium* |
| M32 | 95-1770 | | *M. avium* |
| M33 | 95-1775 | | *M. avium* |
| M34 | 95-1776 | | *M. avium* |
| M48 | 95-1765 | | *M. avium* |
| M49 | 95-1769 | | *M. avium* |
| M63 | MAC #1 | MAC | *M. avium* |
| M64 | MAC #2 | MAC | *M. avium* |
| M65 | MAC #3 | MAC | *M. avium* |
| M67 | MAC #5 | MAC | *M. avium* |
| M69 | MAC #7 | MAC | *M. avium* |
| M70 | MAC #8 | MAC | *M. avium* |
| M71 | MAC #9 | MAC | *M. avium* |
| M72 | MAC #10 | MAC | *M. avium* |
| M91 | FM | avium-intracell. FM(MAC) | *M. avium* |
| M92 | 60040 | MAC | *M. avium* |
| M93 | 60042 | MAC | *M. avium* |
| M94 | 60049 | MAC | *M. avium* |
| M95 | 60051 | MAC | *M. avium* |

TABLE 2-continued

| Affy# | SAMPLE ID# | Alt. ID | SPECIES |
|---|---|---|---|
| M96 | 60110 | MAC | *M. avium* |
| M97 | 60116 | MAC | *M. avium* |
| M98 | 60123 | MAC | *M. avium* |
| M99 | 60176 | MAC | *M. avium* |
| M76 | 92-773 | | *M. bovis* |
| MY451 | | | *M. bovis* |
| ATCC2 | 35752 | ATCC-chel(new) | *M. chelonae* |
| M10 | 95A9151 | | *M. chelonae* |
| M11 | 95A0477 | | *M. chelonae* |
| M115 | 60121 | | *M. chelonae* |
| M116 | 52942 | | *M. chelonae* |
| M117 | 43192 | | *M. chelonae* |
| M118 | 53180 | | *M. chelonae* |
| M119 | 53131 | | *M. chelonae* |
| M12 | 95A4883 | | *M. chelonae* |
| M120 | 52923 | | *M. chelonae* |
| M121 | 52919 | | *M. chelonae* |
| M13 | 95A2611 | | *M. chelonae* |
| M14 | 95A0779 | | *M. chelonae* |
| M15 | 95A8654 | | *M. chelonae* |
| M16 | 95A8882 | | *M. chelonae* |
| M17 | 95A8881 | | *M. chelonae* |
| M50 | 95A11814 | | *M. chelonae* |
| M51 | 95A1102 | | *M. chelonae* |
| M75 | #13 | MAC#13 | *M. chelonae* |
| MY109 | | | *M. chelonae* |
| MY200 | | | *M. chelonae* |
| MY207 | | | *M. chelonae* |
| MY209 | | | *M. chelonae* |
| M122 | 60025 | | *M. flavescens* |
| M123 | 60076 | | *M. flavescens* |
| M124 | 60252 | | *M. flavescens* |

TABLE 2-continued

| Affy# | SAMPLE ID# | Alt. ID | SPECIES |
|---|---|---|---|
| ATCC3 | 6841 | ATCC-for | *M. fortuitum* |
| M53 | 60305 | | *M. fortuitum* |
| M54 | 60344 | | *M. fortuitum* |
| M55 | 60435 | | *M. fortuitum* |
| M56 | 60447 | | *M. fortuitum* |
| M74 | #12 | MAC#12 | *M. fortuitum* |
| M88 | CH | fort. CH | *M. fortuitum* |
| MY221 | | | *M. fortuitum* |
| MY223 | | | *M. fortuitum* |
| MY225 | | | *M. fortuitum* |
| MY341 | | | *M. fortuitum* |
| MY715 | | | *M. fortuitum* |
| MY470 | | | *M. genevese* |
| ATCC4 | 14470 | ATCC-go | *M. gordonae* |
| ATCC4-0 | | gord. | *M. gordonae* |
| M125 | 60068 | | *M. gordonae* |
| M126 | 60182 | | *M. gordonae* |
| M127 | 60214 | | *M. gordonae* |
| M128 | 60283 | | *M. gordonae* |
| M78 | 92-942 | gord. LZ | *M. gordonae* |
| M79 | 93-692 | gord. JD | *M. gordonae* |
| M80 | 94-94 | gord. LG | *M. gordonae* |
| M81 | 93-1231 | gord. LL | *M. gordonae* |
| M82 | 93-463 | gord. RM | *M. gordonae* |
| M83 | 92-1219 | gord. MB | *M. gordonae* |
| M84 | 91-1131 | gord. OW | *M. gordonae* |
| M85 | 91-1478 | gord. LB | *M. gordonae* |
| M86 | 92-642 | gord. RB | *M. gordonae* |
| M87 | 93-1180 | gord. WN | *M. gordonae* |
| M90 | DB | gord. DB | *M. gordonae* |
| MY103 | | | *M. gordonae* |
| MY475 | | | *M. gordonae* |
| MY476 | | | *M. gordonae* |
| MY746 | | | *M. gordonae* |
| MY830 | | | *M. gordonae* |
| ATCC5 | | ATCC-int | *M. intracellulare* |
| ATCC5-0 | | intra | *M. intracellulare* |
| M16 | 95-1778 | | *M. intracellulare* |
| M19 | 95-1780 | | *M. intracellulare* |
| M20 | 95-1781 | | *M. intracellulare* |
| M21 | 95-1782 | | *M. intracellulare* |
| M22 | 95-1790 | | *M. intracellulare* |
| M23 | 95-1794 | | *M. intracellulare* |
| M24 | 95-1796 | | *M. intracellulare* |
| M25 | 95-1777 | | *M. intracellulare* |
| M26 | 95-1779 | | *M. intracellulare* |
| M27 | 95-1760 | | *M. intracellulare* |
| M28 | 95-1761 | | *M. intracellulare* |
| ATCC6 | 12478 | ATCC-kan | *M. kansasii* |
| ATCC6-0 | | kans. | *M. kansasii* |
| M1 | 95A5375 | | *M. kansasii* |
| M2 | 95A10299 | | *M. kansasii* |
| M3 | 95A0020 | | *M. kansasii* |
| M4 | 95A3977 | | *M. kansasii* |
| M5 | 95A4739 | | *M. kansasii* |
| M52 | 95A5381 | | *M. kansasii* |
| M57 | 60163 | | *M. kansasii* |
| M58 | 60180 | | *M. kansasii* |
| M59 | 60207 | | *M. kansasii* |
| M6 | 95A2695 | | *M. kansasii* |
| M60 | 60294 | | *M. kansasii* |
| M61 | 60308 | | *M. kansasii* |
| M62 | 60314 | | *M. kansasii* |
| M7 | 95A2694 | | *M. kansasii* |
| M73 | #11 | MAC#11 | *M. kansasii* |
| M8 | 94A9042 | | *M. kansasii* |
| M9 | 95A1275 | | *M. kansasii* |
| MY106 | | | *M. kansasii* |
| MY141 | | | *M. kansasii* |
| MY216 | | | *M. kansasii* |
| MY226 | | | *M. kansasii* |
| M108 | 60044 | | *M. maimoense* |
| M109 | 60149 | | *M. maimoense* |
| M110 | 60211 | | *M. maimoense* |
| M111 | 60202 | | *M. maimoense* |
| M112 | 60085 | | *M. maimoense* |
| M113 | 60047 | | *M. maimoense* |

TABLE 2-continued

| Affy# | SAMPLE ID# | Alt. ID | SPECIES |
|---|---|---|---|
| M114 | 60185 | | *M. maimoense* |
| MY325 | | ATCC | *M. maimoense* |
| MY718 | | maimo | *M. maimoense* |
| MY214 | | | *M. marinum* |
| MY224 | | | *M. marinum* |
| MY244 | | | *M. marinum* |
| MY339 | | | *M. marinum* |
| MY343 | | | *M. marinum* |
| MY458 | | ATCC | *M. mucogenicum* |
| MY809 | | | *M. mucogenicum* |
| MY817 | | | *M. mucogenicum* |
| MY821 | | | *M. mucogenicum* |
| MY824 | | | *M. mucogenicum* |
| MY102 | | | *M. nonchromagenicum* |
| MY105 | | | *M. nonchromagenicum* |
| MY251 | | | *M. nonchromagenicum* |
| MY256 | | | *M. nonchromagenicum* |
| MY294 | | | *M. nonchromagenicum* |
| ATCC7 | 19981 | ATCC-scr | *M. scrofulaceum* |
| ATCC7-0 | | scrof. | *M. scrofulaceum* |
| MY121 | | | *M. scrofulaceum* |
| MY249 | | | *M. scrofulaceum* |
| MY372 | | | *M. scrofulaceum* |
| MY378 | | | *M. scrofulaceum* |
| MY484 | | | *M. simiae* |
| MY555 | | | *M. simiae* |
| MY563 | | | *M. simiae* |
| MY586 | | | *M. simiae* |
| ATCC8 | 19420 | ATCC-sme | *M. smegmatis* |
| M35 | 95A1072 | | *M. smegmatis* |
| M36 | 95A8183 | | *M. smegmatis* |
| M37 | 95A4990 | | *M. smegmatis* |
| M77 | 92-144 | smeg. JL | *M. smegmatis* |
| MY143 | | ATCC | *M. smegmatis* |
| MY104 | | | *M. szulgai* |
| MY196 | | | *M. szulgai* |
| MY357 | | | *M. szulgai* |
| MY358 | | | *M. szulgai* |
| MY480 | | | *M. szulgai* |
| TB74 | C.17.96.5 | | M. tab M160 DR |
| MY387 | | | M. tb |
| MY418 | | | M. tb |
| MY437 | | | M. tb |
| MY462 | | | M. tb |
| TB59 | C.18.96.1 | | M. tb H37rv DR |
| TB67 | C.18.96.1 | | M. tb H37rv DR |
| TB73 | C.17.96.1 | | M. tb H37rv DR |
| TB60 | C.18.96.2 | | M. tb J35 DR |
| TB65 | C.22.96.9 | | M. tb M101 DR |
| TB62 | C.18.96.4 | | M. tb M104 DR |
| TB69 | C.18.96.3 | | M. tb M104 DR |
| TB72 | C.18.96.7 | | M. tb M104 DR |
| TB66 | C.22.96.10 | | M. tb M112 DR |
| TB63 | C.18.96.5 | | M. tb M140 DR |
| TB64 | C.18.96.6 | | M. tb M160 DR |
| TB70 | C.18.96.4 | | M. tb M160 DR |
| TB61 | C.18.96.3 | | M. tb M60 DR |
| TB68 | C.18.96.2 | | M. tb M60 DR |
| TB71 | C.18.96.6 | | M. tb M60 DR |
| MY212 | | | *M. terrae* |
| MY354 | | | *M. terrae* |
| MY491 | | | *M. terrae* |
| MY497 | | | *M. terrae* |
| MY816 | | | *M. triplex* |
| ATCC9 | 27294 | Mtb | *M. tuberculosis* |
| ATCC9-0 | | TB2020 | *M. tuberculosis* |
| N/A | 93-1071 | | *M. tuberculosis* |
| N/A | 93-336 | | *M. tuberculosis* |
| N/A | 92-852 | | *M. tuberculosis* |
| N/A | 92-1005 | | *M. tuberculosis* |
| N/A | 92-243 | | *M. tuberculosis* |
| N/A | 92-304 | | *M. tuberculosis* |
| N/A | 92-199 | | *M. tuberculosis* |
| N/A | 92-197 | | *M. tuberculosis* |
| N/A | 92-484 | | *M. tuberculosis* |
| N/A | 94-577 | | *M. tuberculosis* |
| TB1 | 936 | | *M. tuberculosis* |

TABLE 2-continued

| Affy# | SAMPLE ID# | Alt. ID | SPECIES |
|---|---|---|---|
| TB10 | 1122 | | *M. tuberculosis* |
| TB11 | 3407 | | *M. tuberculosis* |
| TB12 | 978 | | *M. tuberculosis* |
| TB13 | 3553 | | *M. tuberculosis* |
| TB14 | 3468 | | *M. tuberculosis* |
| TB15 | 2163 | | *M. tuberculosis* |
| TB16 | DW | DW | *M. tuberculosis* |
| TB17 | CB | CB | *M. tuberculosis* |
| TB18 | PB | PB | *M. tuberculosis* |
| TB19 | AA | AA | *M. tuberculosis* |
| TB2 | M0404A | | *M. tuberculosis* |
| TB20 | 3492 | | *M. tuberculosis* |
| TB21 | 1435 | | *M. tuberculosis* |
| TB22 | 896 | | *M. tuberculosis* |
| TB23 | 2268 | | *M. tuberculosis* |
| TB24 | 3455 | | *M. tuberculosis* |
| TB25 | 37 | | *M. tuberculosis* |
| TB26 | 173 | | *M. tuberculosis* |
| TB27 | 230 | | *M. tuberculosis* |
| TB28 | 2519 | | *M. tuberculosis* |
| TB29 | T29233 | | *M. tuberculosis* |
| TB3 | 1231 | | *M. tuberculosis* |
| TB30 | SP | SP | *M. tuberculosis* |
| TB31 | 3201 | | *M. tuberculosis* |
| TB32 | 3219 | | *M. tuberculosis* |
| TB33 | 80 | | *M. tuberculosis* |
| TB34 | 3442 | | *M. tuberculosis* |
| TB35 | 3502 | | *M. tuberculosis* |
| TB36 | 3759 | | *M. tuberculosis* |
| TB37 | 1295 | | *M. tuberculosis* |
| TB38 | 337 | | *M. tuberculosis* |
| TB39 | 394 | | *M. tuberculosis* |
| TB4 | 914 | | *M. tuberculosis* |
| TB40 | 499 | | *M. tuberculosis* |
| TB41 | 535 | | *M. tuberculosis* |
| TB42 | 607 | | *M. tuberculosis* |
| TB43 | 707 | | *M. tuberculosis* |
| TB44 | 692 | | *M. tuberculosis* |
| TB45 | 2408 | | *M. tuberculosis* |
| TB46 | 1069 | | *M. tuberculosis* |
| TB47 | M3262A | | *M. tuberculosis* |
| TB48 | 1338 | | *M. tuberculosis* |
| TB49 | 1368 | | *M. tuberculosis* |
| TB5 | 1145 | | *M. tuberculosis* |
| TB50 | 65 | | *M. tuberculosis* |
| TB51 | 727 | | *M. tuberculosis* |
| TB52 | 3455 | | *M. tuberculosis* |
| TB53 | 3506 | | *M. tuberculosis* |
| TB54 | 9600387 | | *M. tuberculosis* |

TABLE 2-continued

| Affy# | SAMPLE ID# | Alt. ID | SPECIES |
|---|---|---|---|
| TB55 | 9600173 | | *M. tuberculosis* |
| TB56 | 9503471 | | *M. tuberculosis* |
| TB57 | 9600309 | | *M. tuberculosis* |
| TB58 | 9600230 | | *M. tuberculosis* |
| TB6 | 1417 | | *M. tuberculosis* |
| TB7 | SM2341 | | *M. tuberculosis* |
| TB75 | 2098 | | *M. tuberculosis* |
| TB76 | 173/1 | | *M. tuberculosis* |
| TB77 | 1122/1 | | *M. tuberculosis* |
| TB78 | 1417/1 | | *M. tuberculosis* |
| TB8 | 1587 | | *M. tuberculosis* |
| TB9 | M7032A | | *M. tuberculosis* |
| ATCC10 | 19250 | ATCC-xen | *M. xenopi* |
| M129 | 60133 | | *M. xenopi* |
| M130 | 60200 | | *M. xenopi* |
| M131 | 60365 | | *M. xenopi* |
| M132 | 60387 | | *M. xenopi* |
| M38 | 95A5208 | | *M. xenopi* |
| M39 | 95A5399 | | *M. xenopi* |
| M40 | 95A3938 | | *M. xenopi* |
| M41 | 95A6762 | | *M. xenopi* |
| M42 | 95A0933 | | *M. xenopi* |
| M43 | 95A4320 | | *M. xenopi* |
| M44 | 95A3478 | | *M. xenopi* |
| M45 | 95A2997 | | *M. xenopi* |
| M46 | 95A8383 | | *M. xenopi* |
| M47 | 95A4319 | | *M. xenopi* |
| M68 | MAC #6 | MAC #6 | *M. xenopi* |
| M69 | SG | xen. SG | *M. xenopi* |
| MY219 | | | *M. xenopi* |
| MY250 | | | *M. xenopi* |
| MY252 | | | *M. xenopi* |
| MY254 | | | *M. xenopi* |
| MY255 | | | *M. xenopi* |
| MY107 | | | MAC |
| MY111 | | | MAC |
| MY112 | | | MAC |
| MY312 | | | MAC |
| M66 | MAC #4 | MAC #4 | unique |

What is claimed is:

1. An isolated rpoB nucleic acid fragment of a molecule consisting of a sequence selected from the group consisting of SEQ ID NOS: 2, 3, 4, 5, 6, 8, 9 and 10, wherein said fragment consists of at least about 100 contiguous bases of said sequence.

2. An isolated nucleic acid molecule consisting of a rpoB sequence selected from the group consisting of SEQ ID NOS: 2, 3, 4, 5, 6, 7, 8, 9 and 10.

3. An isolated probe which is the full complement of a rpoB sequence selected from the group consisting of SEQ ID NOS: 2, 3, 4, 5, 6, 7, 8, 9, and 10.

4. A method of classifying a mycobacteria, comprising providing a sample comprising a mycobacterial rpoB target nucleic acid from a mycobacteria;

determining the sequence of a segment of at least 50 contiguous bases from the target nucleic acid;

comparing the determined sequence to at least one sequence selected from the group consisting of SEQ ID NOS: 2, 3, 4, 5, 6, 7, 8, 9, and 10; and classifying the mycobacteria from the extent of similarity of the compared sequences.

5. The method of claim 4, wherein at least 100 contiguous bases are determined from the target nucleic acid.

6. The method of claim 4, wherein the determined sequence is compared with at least nine sequences selected from the group consisting SEQ ID NOS: 2, 3, 4, 5, 6, 7, 8, 9, and 10.

7. A method of classifying a mycobacteria, comprising providing a sample comprising a mycobacterial rpoB target nucleic acid;

determining the identity of one or more bases in the target sequence at one or more positions corresponding to one or more bases in a sequence selected from the group consisting of SEQ ID NOS: 2, 3, 4, 5, 6, 7, 8, 9, and 10, wherein the one or more bases of the sequence selected from the group consisting of SEQ ID NOS: 2, 3, 4, 5, 6, 7, 8, 9, and 10 differ from the corresponding one or more bases in SEQ ID NO: 1 when the sequences are maximally aligned, the identity of the one or more bases characterizing the species of mycobacteria that is present in the sample;

comparing the identified one or more bases in the target sequence to at least one sequence selected from the group consisting of SEQ ID NOS: 2, 3, 4, 5, 6, 7, 8, 9, and 10; and classifying the mycobacteria from the extent of similarity between the one or more bases identified in the target sequence and the corresponding one or more bases in the compared sequences.

8. The method of claim 7, wherein the identity of at least 10 bases in the target nucleic acid at positions corresponding to the one or more bases in the sequence selected from the group consisting of SEQ ID NOS: 2, 3, 4, 5, 6, 7, 8, 9, and 10 is determined.

9. The method of claim 8, wherein the identity of at least 20 bases in the target sequence at positions corresponding to the one or more bases in the sequence selected from the group consisting of SEQ ID NOS: 2, 3, 4, 5, 6, 7, 8, 9, and 10 is determined.

10. The method of claim 9, further comprising comparing the at least 20 determined bases with at least 20 bases occupying corresponding positions in each of at least nine sequences selected from the group consisting of SEQ ID NOS: 2, 3, 4, 5, 6, 7, 8, 9, and 10.

* * * * *

SEQUENCE LISTING

```
<160> NUMBER OF SEQ ID NOS: 181

<210> SEQ ID NO 1
<211> LENGTH: 705
<212> TYPE: DNA
<213> ORGANISM: Mycobacterium tuberculosis

<400> SEQUENCE: 1

cccaggacgt ggaggcgatc acaccgcaga cgttgatcaa catccggccg gtggtcgccg      60

cgatcaagga gttcttcggc accagccagc tgagccaatt catggaccag aacaacccgc     120

tgtcggggtt gacccacaag cgccgactgt cggcgctggg gcccggcggt ctgtcacgtg     180

agcgtgccgg gctggaggtc cgcgacgtgc acccgtcgca ctacggccgg atgtgcccga     240

tcgaaacccc tgaggggccc aacatcggtc tgatcggctc gctgtcggtg tacgcgcggg     300
```

-continued

```
tcaacccgtt cgggttcatc gaaacgccgt accgcaaggt ggtcgacggc gtggttagcg    360

acgagatcgt gtacctgacc gccgacgagg aggaccgcca cgtggtggca caggccaatt    420

cgccgatcga tgcggacggt cgcttcgtcg agccgcgcgt gctggtccgc cgcaaggcgg    480

gcgaggtgga gtacgtgccc tcgtctgagg tggactacat ggacgtctcg ccccgccaga    540

tggtgtcggt ggccaccgcg atgattccct tcctggagca cgacgacgcc aaccgtgccc    600

tcatgggggc aaacatgcag cgccaggcgg tgccgctggt ccgtagcgag gccccgctgg    660

tgggcaccgg gatggagctg cgcgcggcga tcgacgcggc gacgt                    705
```

<210> SEQ ID NO 2
<211> LENGTH: 626
<212> TYPE: DNA
<213> ORGANISM: Mycobacterium abscessus

<400> SEQUENCE: 2

```
tccgtcccgt cgtggcggcg atcaaggagt tcttcggaac cagccagctg tcgcagttca     60

tggaccagaa caacccgctg tcgggcctga cccacaagcg tcgtctgtcg gcgctgggcc    120

ccggtggtct gacccgtgac cgcgccggcc tcgaggtccg cgacgtgcac ccctcgcact    180

acggccgcat gtgcccgatc gagaccccgg aaggcccgaa catcggcctg atcggctcgc    240

tgtcggtgta cgcgcgggtc aacccgttcg gtttcatcga gacgccttac cggaaggtct    300

cggacggagt tgtcaccgac gacatccact acctgacggc cgacgaagag gaccgccacg    360

tggtggcgca ggccaactcg cccgtggacg ccaacggccg cttcaccgag gagaagatcc    420

tggttcgccg caagggcggc gaggtggagt tcgtgtcggc gaccgaggtc gactacatgg    480

atgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gtagcgaggc tccgctggtc ggtacc                                          626
```

<210> SEQ ID NO 3
<211> LENGTH: 705
<212> TYPE: DNA
<213> ORGANISM: Mycobacterium avium
<220> FEATURE:
<221> NAME/KEY: modified_base
<222> LOCATION: (525)...(525)
<223> OTHER INFORMATION: n = g,a,c or t
<220> FEATURE:
<221> NAME/KEY: modified_base
<222> LOCATION: (650)...(650)
<223> OTHER INFORMATION: n = g,a,c or t

<400> SEQUENCE: 3

```
cccaggacgt ggaggcgatc acaccgcaga ccctgatcaa catccgtccc gtcgtggcgg     60

cgatcaagga gttcttcggc accagccagc tgtcccagtt catggaccag aacaacccgc    120

tgtcggggct cacccacaag cgccgcctgt cggcgctggg cccgggtggt ctgtcccggg    180

agcgggccgg gctggaggtc cgcgacgtgc acccgtccca ctacggccgg atgtgcccga    240

tcgagacccc ggagggtccc aacatcggtc tgatcggctc gctgtcggtg tacgcgcggg    300

tcaacccgtt cgggttcatc gagacgccgt accgcaaggt ggtcgacggc gtggtcaccg    360

acgagatcca ctacctgacc gccgacgagg aggaccgcca cgtggtggcg caggccaact    420

cgccgatcga cggcaagggc cggttcgccg aggcccgggt gctggtccgc cgcaaggcgg    480

gcgaggtcga gtacgtgccc tcgtccgagg tggactacat ggacntktcs ccgcgccara    540

tggtgtcggt ggccaccgcg atgatcccgt tcctcgagca cgacgacgcc aaccgtgccc    600
```

-continued

```
tgatgggcgc caacatgcak cgccaggcgg ttccgctggt gcgcagcgan gcgccgctgg    660

tgggcaccgg catggagctg cgcgcggcga tcgacgcggc gacgt                    705


<210> SEQ ID NO 4
<211> LENGTH: 705
<212> TYPE: DNA
<213> ORGANISM: Mycobacterium avium

<400> SEQUENCE: 4

cccaggacgt ggaggcgatc acaccgcaga ccctgatcaa catccgtcca gtcgtggcgg     60

cgatcaagga gttcttcggc accagccagc tgtcccagtt catggaccag aacaacccgc    120

tgtcggggct cacccacaag cgccgcctgt cggcgctggg cccgggtggt ctgtcccggg    180

agcgggccgg gctggaggtc cgcgacgtgc acccgtccca ctacggccgg atgtgcccga    240

tcgagacccc ggagggtccc aacatcggtc tgatcggctc gctgtcggtg tatgcgcggg    300

tcaacccgtt cgggttcatc gagacgccgt accgcaaggt ggtcgacggc gtggtcaccg    360

acgagatcca ctacctgacc gccgacgagg aggaccgcca cgtggtggcg caggccaact    420

cgccgatcga cgacaagggc cggttcgcgg aggcccgggt gctggtccgc cgcaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705


<210> SEQ ID NO 5
<211> LENGTH: 705
<212> TYPE: DNA
<213> ORGANISM: Mycobacterium avium

<400> SEQUENCE: 5

cccaggacgt ggaggcgatc acaccgcaga ccctgatcaa catccgtcca gtcgtggcgg     60

cgatcaagga gttcttcggc accagccagc tgtcccagtt catggaccag aacaacccgc    120

tgtcggggct cacccacaag cgccgcctgt cggcgctggg cccgggtggt ctgtcccggg    180

agcgggccgg gctggaggtc cgcgacgtgc acccgtccca ctacggccgg atgtgcccga    240

tcgagacccc ggagggtccc aacatcggtc tgatcggctc gctgtcggtg tatgcgcggg    300

tcaacccgtt cgggttcatc gagacgccgt accgcaaggt ggtcgacggc gtggtcaccg    360

acgagatcca ctacctgacc gccgacgagg aggaccgcca cgtggtggcg caggccaact    420

cgccgatcga cgacaagggc cggttcgcgg aggcccgggt gctggtccgc cgcaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705


<210> SEQ ID NO 6
<211> LENGTH: 705
<212> TYPE: DNA
<213> ORGANISM: Mycobacterium avium

<400> SEQUENCE: 6

cccaggacgt ggaggcgatc acaccgcaga ccctgatcaa catccgtcca gtcgtggcgg     60
```

-continued

```
cgatcaagga gttcttcggc accagccagc tgtcccagtt catggaccag aacaacccgc    120
tgtcggggct cacccacaag cgccgcctgt cggcgctggg cccgggtggt ctgtcccggg    180
agcgggccgg gctggaggtc cgcgacgtgc acccgtccca ctacggccgg atgtgcccga    240
tcgagacccc ggagggtccc aacatcggtc tgatcggctc gctgtcggtg tatgcgcggg    300
tcaacccgtt cgggttcatc gagacgccgt accgcaaggt ggtcgacggc gtggtcaccg    360
acgagatcca ctacctgacc gccgacgagg aggaccgcca cgtggtggcg caggccaact    420
cgccgatcga cgacaagggc cggttcgcgg aggcccgggt gctggtccgc cgcaaggcgg    480
gcgaggtcga gtacgtgccc tcgtccgagg tggactacat ggacgtgtcg ccgcgccaga    540
tggtgtcggt ggccaccgcg atgatcccgt tcctcgagca cgacgacgcc aaccgtgccc    600
tgatgggcgc caacatgcag cgccaggcgg ttccgctggt gcgcagcgag gcgccgctgg    660
tgggcaccgg catggagctg cgcgcggcga tcgacgcggc gacgt                    705
```

<210> SEQ ID NO 7
<211> LENGTH: 705
<212> TYPE: DNA
<213> ORGANISM: Mycobacterium avium

<400> SEQUENCE: 7

```
cccaggacgt ggaggcgatc acaccgcaga ccctgatcaa catccgtcca gtcgtggcgg     60
cgatcaagga gttcttcggc accagccagc tgtcccagtt catggaccag aacaacccgc    120
tgtcggggct cacccacaag cgccgcctgt cggcgctggg cccgggtggt ctgtcccggg    180
agcgggccgg gctggaggtc cgcgacgtgc acccgtccca ctacggccgg atgtgcccga    240
tcgagacccc ggagggtccc aacatcggtc tgatcggctc gctgtcggtg tatgcgcggg    300
tcaacccgtt cgggttcatc gagacgccgt accgcaaggt ggtcgacggc gtggtcaccg    360
acgagatcca ctacctgacc gccgacgagg aggaccgcca cgtggtggcg caggccaact    420
cgccgatcga cgacaagggc cggttcgcgg aggcccgggt gctggtccgc cgcaaggcgg    480
gcgaggtcga gtacgtgccc tcgtccgagg tggactacat ggacgtgtcg ccgcgccaga    540
tggtgtcggt ggccaccgcg atgatcccgt tcctcgagca cgacgacgcc aaccgtgccc    600
tgatgggcgc caacatgcag cgccaggcgg ttccgctggt gcgcagcgag gcgccgctgg    660
tgggcaccgg catggagctg cgcgcggcga tcgacgcggc gacgt                    705
```

<210> SEQ ID NO 8
<211> LENGTH: 705
<212> TYPE: DNA
<213> ORGANISM: Mycobacterium avium

<400> SEQUENCE: 8

```
cccaggacgt ggaggcgatc acaccgcaga ccctgatcaa catccgtcca gtcgtggcgg     60
cgatcaagga gttcttcggc accagccagc tgtcccagtt catggaccag aacaacccgc    120
tgtcggggct cacccacaag cgccgcctgt cggcgctggg cccgggtggt ctgtcccggg    180
agcgggccgg gctggaggtc cgcgacgtgc acccgtccca ctacggccgg atgtgcccga    240
tcgagacccc ggagggtccc aacatcggtc tgatcggctc gctgtcggtg tatgcgcggg    300
tcaacccgtt cgggttcatc gagacgccgt accgcaaggt ggtcgacggc gtggtcaccg    360
acgagatcca ctacctgacc gccgacgagg aggaccgcca cgtggtggcg caggccaact    420
cgccgatcga cgacaagggc cggttcgcgg aggcccgggt gctggtccgc cgcaaggcgg    480
gcgaggtcga gtacgtgccc tcgtccgagg tggactacat ggacgtgtcg ccgcgccaga    540
```

-continued

```
tggtgtcggt ggccaccgcg atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705


<210> SEQ ID NO 9
<211> LENGTH: 705
<212> TYPE: DNA
<213> ORGANISM: Mycobacterium avium

<400> SEQUENCE: 9

cccaggacgt ggaggcgatc acaccgcaga ccctgatcaa catccgtcca gtcgtggcgg     60

cgatcaagga gttcttcggc accagccagc tgtcccagtt catggaccag aacaacccgc    120

tgtcggggct cacccacaag cgccgcctgt cggcgctggg cccgggtggt ctgtcccggg    180

agcgggccgg gctggaggtc cgcgacgtgc acccgtccca ctacggccgg atgtgcccga    240

tcgagacccc ggagggtccc aacatcggtc tgatcggctc gctgtcggtg tatgcgcggg    300

tcaacccgtt cgggttcatc gagacgccgt accgcaaggt ggtcgacggc gtggtcaccg    360

acgagatcca ctacctgacc gccgacgagg aggaccgcca cgtggtggcg caggccaact    420

cgccgatcga cgacaagggc cggttcgcgg aggcccgggt gctggtccgc cgcaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705


<210> SEQ ID NO 10
<211> LENGTH: 705
<212> TYPE: DNA
<213> ORGANISM: Mycobacterium avium

<400> SEQUENCE: 10

cccaggacgt ggaggcgatc acaccgcaga ccctgatcaa catccgtccr gtcgtggcgg     60

cgatcaagga gttcttcggc accagccagc tgtcccagtt catggaccag aacaacccgc    120

tgtcgggtct gacccacaag cgccgcctgt cggcgctggg cccgggtggt ctgtcccggg    180

agcgggccgg cctggaggtc cgtgacgtgc acccgtcsca ctacggccgg atgtgcccga    240

tcgagacccc ggagggtccc aacatcggtc tgatcggctc gctgtcggtg taygcgcggg    300

tsaacccgtt cgggttcatc gagaccccgt accgcaaggt ggtcgacggt gtggtcaccg    360

acgagatcca ctacctgacc gccgacgagg aggaccgcca cgtsgtggcg caggccaact    420

cgccgatcga cgacaagggc cggttcgagg agkcccgggt gctggtccgc cgsaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705


<210> SEQ ID NO 11
<211> LENGTH: 705
<212> TYPE: DNA
<213> ORGANISM: Mycobacterium avium
<220> FEATURE:
<221> NAME/KEY: modified_base
<222> LOCATION: (42)...(42)
```

-continued

<223> OTHER INFORMATION: n = g,a,c or t
<220> FEATURE:
<221> NAME/KEY: modified_base
<222> LOCATION: (692)...(692)
<223> OTHER INFORMATION: n = g,a,c or t

<400> SEQUENCE: 11
cccaggacgt ggaggcgatc acaccgcaga ccctgatcaa cntccgtccc gtcgtggcgg 60
cgatcaagga gttcttcggc accagccagt tgtcccagtt catggaccag aacaacccgc 120
tgtcggggct cacccacaag cgccgcctgt cggcgctggg cccgggtggt ctgtcccggg 180
agcgggccgg gctggaggtc cgcgacgtgc acccgtccca ctacggccgg atgtgcccga 240
tcgagacccc ggagggtccc aacatcggtc tgatcggctc gctgtcggtg tacgcgcggg 300
tgaacccgtt cggcttcatc gagacgccgt accgcaaggt ggtcgacggc gtggtcaccg 360
acgagatcca ctacctgacc gccgacgagg aggaccgcca cgtggtggcg caggccaact 420
cgccgatcga cgacaagggc cggttcgccg aggcccgggt gctggtccgc cgcaaggcgg 480
gcgaggtcga gtacgtgccc tcgtccgagg tggactacat ggacgtgtcg ccgcgccaga 540
tggtgtcggt ggccaccgcg atgatcccgt tcctcgagca cgacgacgcc aaccgtgccc 600
tgatgggcgc caacatgcag cgccaggcgg ttccgctggt gcgcagcgag gcgccgctgg 660
tgggcaccgg catggagctg cgcgcggcga tngacgcggc gacgt 705

<210> SEQ ID NO 12
<211> LENGTH: 705
<212> TYPE: DNA
<213> ORGANISM: Mycobacterium avium

<400> SEQUENCE: 12
cccaggacgt ggaggcgatc acaccgcaga ccctgatcaa catccgtcca gtcgtggcgg 60
cgatcaagga gttcttcggc accagccagc tgtcccagtt catggaccag aacaacccgc 120
tgtcggggct cacccacaag cgccgcctgt cggcgctggg cccgggtggt ctgtcccggg 180
agcgggccgg gctggaggtc cgcgacgtgc acccgtccca ctacggccgg atgtgcccga 240
tcgagacccc ggagggtccc aacatcggtc tgatcggctc gctgtcggtg tatgcgcggg 300
tcaacccgtt cgggttcatc gagacgccgt accgcaaggt ggtcgacggc gtggtcaccg 360
acgagatcca ctacctgacc gccgacgagg aggaccgcca cgtggtggcg caggccaact 420
cgccgatcga cgacaagggc cggttcgcgg aggcccgggt gctggtccgc cgcaaggcgg 480
gcgaggtcga gtacgtgccc tcgtccgagg tggactacat ggacgtgtcg ccgcgccaga 540
tggtgtcggt ggccaccgcg atgatcccgt tcctcgagca cgacgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 13
<211> LENGTH: 705
<212> TYPE: DNA
<213> ORGANISM: Mycobacterium avium

<400> SEQUENCE: 13
cccaggacgt ggaggcgatc acaccgcaga ccctgatcaa catccgtcca gtcgtggcgg 60
cgatcaagga gttcttcggc accagccagc tgtcccagtt catggaccag aacaacccgc 120
tgtcggggct cacccacaag cgccgcctgt cggcgctggg cccgggtggt ctgtcccggg 180
agcgggccgg gctggaggtc cgcgacgtgc acccgtccca ctacggccgg atgtgcccga 240

-continued

```
tcgagacccc ggagggtccc aacatcggtc tgatcggctc gctgtcggtg tatgcgcggg    300
tcaacccgtt cgggttcatc gagacgccgt accgcaaggt ggtcgacggc gtggtcaccg    360
acgagatcca ctacctgacc gccgacgagg aggaccgcca cgtggtggcg caggccaact    420
cgccgatcga cgacaagggc cggttcgcgg aggcccgggt gctggtccgc cgcaaggcgg    480
gcgaggtcga gtacgtgccc tcgtccgagg tggactacat ggacgtgtcg ccgcgccaga    540
tggtgtcggt ggccaccgcg atgatcccgt tcctcgagca cgacgacgcc aaccgtgccc    600
tgatgggcgc caacatgcag cgccaggcgg ttccgctggt gcgcagcgag gcgccgctgg    660
tgggcaccgg catggagctg cgcgcggcga tcgacgcggc gacgt                   705
```

<210> SEQ ID NO 14
<211> LENGTH: 705
<212> TYPE: DNA
<213> ORGANISM: Mycobacterium avium

<400> SEQUENCE: 14

```
cccaggacgt ggaggcgatc acaccgcaga ccctgatcaa catccgtcca gtcgtggcgg     60
cgatcaagga gttcttcggc accagccagc tgtcccagtt catggaccag aacaacccgc    120
tgtcggggct cacccacaag cgccgcctgt cggcgctggg cccgggtggt ctgtcccggg    180
agcgggccgg gctggaggtc cgcgacgtgc acccgtccca ctacggccgg atgtgcccga    240
tcgagacccc ggagggtccc aacatcggtc tgatcggctc gctgtcggtg tatgcgcggg    300
tcaacccgtt cgggttcatc gagacgccgt accgcaaggt ggtcgacggc gtggtcaccg    360
acgagatcca ctacctgacc gccgacgagg aggaccgcca cgtggtggcg caggccaact    420
cgccgatcga cgacaagggc cggttcgcgg aggcccgggt gctggtccgc cgcaaggcgg    480
gcgaggtcga gtacgtgccc tcgtccgagg tggactacat ggacgtgtcg ccgcgccaga    540
tggtgtcggt ggccaccgcg atgatcccgt tcctcgagca cgacgacgcc aaccgtgccc    600
tgatgggcgc caacatgcag cgccaggcgg ttccgctggt gcgcagcgag gcgccgctgg    660
tgggcaccgg catggagctg cgcgcggcga tcgacgcggc gacgt                   705
```

<210> SEQ ID NO 15
<211> LENGTH: 626
<212> TYPE: DNA
<213> ORGANISM: Mycobacterium avium

<400> SEQUENCE: 15

```
tccgtccagt cgtggcggcg atcaaggagt tcttcggcac cagccagctg tcccagttca     60
tggaccagaa caacccgctg tcggggctca cccacaagcg ccgcctgtcg gcgctgggcc    120
cgggtggtct gtcccgggag cgggccgggc tggaggtccg cgacgtgcac ccgtcccact    180
acggccggat gtgcccgatc gagaccccgg agggtcccaa catcggtctg atcggctcgc    240
tgtcggtgta tgcgcgggtc aacccgttcg ggttcatcga gacgccgtac cgcaaggtgg    300
tcgacggcgt ggtcaccgac gagatccact acctgaccgc cgacgaggag gaccgccacg    360
tggtggcgca ggccaactcg ccgatcgacg acaagggccg gttcgcggag gcccgggtgc    420
tggtccgccg caaggcgggc gaggtcgagt acgtgccctc gtccgaggtg gactacatgg    480
acgtgtcgcc gcgccagatg gtgtcggtgg ccaccgcgat gatcccgttc ctcgagcacg    540
acgacgccaa ccgtgccctg atgggcgcca acatgcagcg ccaggcggtt ccgctggtgc    600
gcagcgaggc gccgctggtg ggcacc                                         626
```

-continued

<210> SEQ ID NO 16
<211> LENGTH: 705
<212> TYPE: DNA
<213> ORGANISM: Mycobacterium avium

<400> SEQUENCE: 16
cccaggacgt ggaggcgatc acaccgcaga ccctgatcaa catccgtcca gtcgtggcgg 60
cgatcaagga gttcttcggc accagccagc tgtcccagtt catggaccag aacaacccgc 120
tgtcggggct cacccacaag cgccgcctgt cggcgctggg cccgggtggt ctgtcccggg 180
agcgggccgg gctggaggtc cgcgacgtgc acccgtccca ctacggccgg atgtgcccga 240
tcgagacccc ggagggtccc aacatcggtc tgatcggctc gctgtcggtg tatgcgcggg 300
tcaacccgtt cgggttcatc gagacgccgt accgcaaggt ggtcgacggc gtggtcaccg 360
acgagatcca ctacctgacc gccgacgagg aggaccgcca cgtggtggcg caggccaact 420
cgccgatcga cgacaagggc cggttcgcgg aggcccgggt gctggtccgc cgcaaggcgg 480
gcgaggtcga gtacgtgccc tcgtccgagg tggactacat ggacgtgtcg ccgcgccaga 540
tggtgtcggt ggccaccgcg atgatcccgt tcctcgagca cgacgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 17
<211> LENGTH: 705
<212> TYPE: DNA
<213> ORGANISM: Mycobacterium avium

<400> SEQUENCE: 17
cccaggacgt ggaggcgatc acaccgcaga ccctgatcaa catccgtcca gtcgtggcgg 60
cgatcaagga gttcttcggc accagccagc tgtcccagtt catggaccag aacaacccgc 120
tgtcggggct cacccacaag cgccgcctgt cggcgctggg cccgggtggt ctgtcccggg 180
agcgggccgg gctggaggtc cgcgacgtgc acccgtccca ctacggccgg atgtgcccga 240
tcgagacccc ggagggtccc aacatcggtc tgatcggctc gctgtcggtg tatgcgcggg 300
tcaacccgtt cgggttcatc gagacgccgt accgcaaggt ggtcgacggc gtggtcaccg 360
acgagatcca ctacctgacc gccgacgagg aggaccgcca cgtggtggcg caggccaact 420
cgccgatcga cgacaagggc cggttcgcgg aggcccgggt gctggtccgc cgcaaggcgg 480
gcgaggtcga gtacgtgccc tcgtccgagg tggactacat ggacgtgtcg ccgcgccaga 540
tggtgtcggt ggccaccgcg atgatcccgt tcctcgagca cgacgacgcc aaccgtgccc 600
tgatgggcgc caacatgcag cgccaggcgg ttccgctggt gcgcagcgaa gcgccgctgg 660
tgggcaccgg catggagctg cgcgcggcga tcgacgcggc gacgt 705

<210> SEQ ID NO 18
<211> LENGTH: 687
<212> TYPE: DNA
<213> ORGANISM: Mycobacterium avium

<400> SEQUENCE: 18
ggaggcgatc acaccgcaga ccctgatcaa catccgtcca gtcgtggcgg cgatcaagga 60
gttcttcggc accagccagc tgtcccagtt catggaccag aacaacccgc tgtcggggct 120
cacccacaag cgccgcctgt cggcgctggg cccgggtggt ctgtcccggg agcgggccgg 180
gctggaggtc cgcgacgtgc acccgtccca ctacggccgg atgtgcccga tcgagacccc 240

-continued

```
ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                         687
```

<210> SEQ ID NO 19
<211> LENGTH: 687
<212> TYPE: DNA
<213> ORGANISM: Mycobacterium avium

<400> SEQUENCE: 19

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180

gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                         687
```

<210> SEQ ID NO 20
<211> LENGTH: 687
<212> TYPE: DNA
<213> ORGANISM: Mycobacterium avium

<400> SEQUENCE: 20

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180

gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660
```

-continued

```
catggagctg cgcgcggcga tcgacgc                                         687
```

<210> SEQ ID NO 21
<211> LENGTH: 687
<212> TYPE: DNA
<213> ORGANISM: Mycobacterium avium

<400> SEQUENCE: 21

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180

gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                         687
```

<210> SEQ ID NO 22
<211> LENGTH: 687
<212> TYPE: DNA
<213> ORGANISM: Mycobacterium avium

<400> SEQUENCE: 22

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180

gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                         687
```

<210> SEQ ID NO 23
<211> LENGTH: 687
<212> TYPE: DNA
<213> ORGANISM: Mycobacterium avium

<400> SEQUENCE: 23

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180
```

-continued

```
gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                         687
```

<210> SEQ ID NO 24
<211> LENGTH: 705
<212> TYPE: DNA
<213> ORGANISM: Mycobacterium avium

<400> SEQUENCE: 24

```
cccaggacgt ggaggcgatc acaccgcaga ccctgatcaa catccgtcca gtcgtggcgg     60

cgatcaagga gttcttcggc accagccagc tgtcccagtt catggaccag aacaacccgc    120

tgtcggggct cacccacaag cgccgcctgt cggcgctggg cccgggtggt ctgtcccggg    180

agcgggccgg gctggaggtc cgcgacgtgc acccgtccca ctacggccgg atgtgcccga    240

tcgagacccc ggagggtccc aacatcggtc tgatcggctc gctgtcggtg tatgcgcggg    300

tcaacccgtt cgggttcatc gagacgccgt accgcaaggt ggtcgacggc gtggtcaccg    360

acgagatcca ctacctgacc gccgacgagg aggaccgcca cgtggtggcg caggccaact    420

cgccgatcga cgacaagggc cggttcgcgg aggcccgggt gctggtccgc cgcaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 25
<211> LENGTH: 687
<212> TYPE: DNA
<213> ORGANISM: Mycobacterium avium

<400> SEQUENCE: 25

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180

gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600
```

-continued

```
caacatgcag cgccaggcgg ttccgctggt gcgcagcgag gcgccgctgg tgggcaccgg    660

catggagctg cgcgcggcga tcgacgc                                        687
```

<210> SEQ ID NO 26
<211> LENGTH: 687
<212> TYPE: DNA
<213> ORGANISM: Mycobacterium avium

<400> SEQUENCE: 26

```
ggaggcgatc acaccgcaga ccctgatcaa catccgtccc gtcgtggcgg cgatcaagga     60

attcttcggc accagccagc tgtcgcagtt catggaccag aacaacccgc tgtcgggtct    120

gacccacaag cgtcgtctgt cggcgctggg ccccggcggt ctgtcccgtg agcgcgccgg    180

ccttgaggtc cgcgacgtgc actccagcca ctacggccgc atgtgcccga tcgagacccc    240

tgagggtccg aacatcggtc tgatcggctc gctgtcggtg tacgcccggg tcaacccgtt    300

cggcttcatc gagaccccgt accgcaaggt cgtcgacggt gtggtcaccg accagatcga    360

ctacctgacc gccgacgagg aggaccgcca cgtcgtggcg caggccaact cgccgatcgg    420

cgcggacggc agcttcaccg aagaccgcgt gatggtccgc cgtaagggcg gcgaggtcga    480

gaacgtggcc ccgatcgacg tggattacat ggacgtctcg ccgcgccaga tggtgtcggt    540

cgcgaccgcg atgatcccgt tcctcgagca cgacgacgcc aaccgtgccc tgatgggtgc    600

caacatgcag cgccaggcgg ttccgctggt gcgtagcgag gccccgctgg tcggtaccgg    660

tatggagttg cgcgcggcga tcgacgc                                        687
```

<210> SEQ ID NO 27
<211> LENGTH: 687
<212> TYPE: DNA
<213> ORGANISM: Mycobacterium avium complex (MAC)

<400> SEQUENCE: 27

```
ggaggcgatc acaccgcaga ccctgatcaa catccgtcca gtcgtggcgg cgatcaagga     60

gttcttcggc accagccagc tgtcccagtt catggaccag aacaacccgc tgtcggggct    120

cacccacaag cgccgcctgt cggcgctggg cccgggtggt ctgtcccggg agcgggccgg    180

gctggaggtc cgcgacgtgc acccgtccca ctacggccgg atgtgcccga tcgagacccc    240

ggagggtccc aacatcggtc tgatcggctc gctgtcggtg tatgcgcggg tcaacccgtt    300

cgggttcatc gagacgccgt accgcaaggt ggtcgacggc gtggtcaccg acgagatcca    360

ctacctgacc gccgacgagg aggaccgcca cgtggtggcg caggccaact cgccgatcga    420

cgacaagggc cggttcgcgg aggcccgggt gctggtccgc cgcaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                        687
```

<210> SEQ ID NO 28
<211> LENGTH: 705
<212> TYPE: DNA
<213> ORGANISM: Mycobacterium bovis

<400> SEQUENCE: 28

```
cccaggacgt ggaggcgatc acaccgcaga cgttgatcaa catccggccg gtggtcgccg     60

cgatcaagga gttcttcggc accagccagc tgagccaatt catggaccag aacaacccgc    120
```

-continued

```
tgtcggggtt gacccacaag cgccgactgt cggcgctggg gcccggcggt ctgtcacgtg    180

agcgtgccgg gctggaggtc cgcgacgtgc acccgtcgca ctacggccgg atgtgcccga    240

tcgaaacccc tgaggggccc aacatcggtc tgatcggctc gctgtcggtg tacgcgcggg    300

tcaacccgtt cgggttcatc gaaacgccgt accgcaaggt ggtcgacggc gtggttagcg    360

acgagatcgt gtacctgacc gccgacgagg aggaccgcca cgtggtggca caggccaatt    420

cgccgatcga tgcggacggt cgcttcgtcg agccgcgcgt gctggtccgc cgcaaggcgg    480

gcgaggtgga gtacgtgccc tcgtctgagg tggactacat ggacgtctcg ccccgccaga    540

tggtgtcggt ggccaccgcg atgattccct tcctggagca cgacgacgcc aaccgtgccc    600

tcatgggggc aaacatgcag cgccaggcgg tgccgctggt ccgtagcgag gccccgctgg    660

tgggcaccgg gatggagctg cgcgcggcga tcgacgcggc gacgt                    705
```

<210> SEQ ID NO 29
<211> LENGTH: 687
<212> TYPE: DNA
<213> ORGANISM: Mycobacterium bovis

<400> SEQUENCE: 29

```
ggaggcgatc acaccgcaga cgttgatcaa catccggccg gtggtcgccg cgatcaagga     60

gttcttcggc accagccagc tgagccaatt catggaccag aacaacccgc tgtcggggtt    120

gacccacaag cgccgactgt cggcgctggg gcccggcggt ctgtcacgtg agcgtgccgg    180

gctggaggtc cgcgacgtgc acccgtcgca ctacggccgg atgtgcccga tcgaaacccc    240

tgaggggccc aacatcggtc tgatcggctc gctgtcggtg tacgcgcggg tcaacccgtt    300

cgggttcatc gaaacgccgt accgcaaggt ggtcgacggc gtggttagcg acgagatcgt    360

gtacctgacc gccgacgagg aggaccgcca cgtggtggca caggccaatt cgccgatcga    420

tgcggacggt cgcttcgtcg agccgcgcgt gctggtccgc cgcaaggcgg gcgaggtgga    480

gtacgtgccc tcgtctgagg tggactacat ggacgtctcg ccccgccaga tggtgtcggt    540

ggccaccgcg atgattccct tcctggagca cgacgacgcc aaccgtgccc tcatgggggc    600

aaacatgcag cgccaggcgg tgccgctggt ccgtagcgag gccccgctgg tgggcaccgg    660

gatggagctg cgcgcggcga tcgacgc                                        687
```

<210> SEQ ID NO 30
<211> LENGTH: 652
<212> TYPE: DNA
<213> ORGANISM: Mycobacterium chelonae

<400> SEQUENCE: 30

```
cgcagaccct gatcaacatc cgtcccgtcg tggcggcgat caaggagttc ttcggaacca     60

gccagctgtc gcagttcatg gaccagaaca acccgctgtc gggtctgacc cacaagcgtc    120

gtctgtcggc gctgggcccc ggtggtctga ctcgtgaccg cgccggcctt gaggtccgcg    180

acgtgcaccc ctcgcactac ggccgcatgt gcccgatcga gaccccggaa ggcccgaaca    240

tcggtctgat cggttcgctg tcggtgtacg cgcgggtcaa cccgttcggc ttcatcgaga    300

cgccgtaccg caaggtgtcc gagggtgtcg tcaccgacga gatccactac ctgaccgccg    360

acgaagagga ccgccacgtg gtggcgcagg ccaactcgcc tgtggatgcc gacggccgct    420

tcaccgagga caagatcctg gtccgccgta agggtggcga ggtcgagttc gtctcggcga    480

ccgaggtgga ctacatggac gtctcgccgc gccagatggt gtcggtcgcg accgccatga    540
```

-continued

```
tcccgttcct cgagcacgac gacgccaacc gtgccctcat gggtgccaac atgcagcgcc    600

aggcggttcc gctggtgcgc agcgaggccc cgctggtcgg taccggtatg ga            652
```

<210> SEQ ID NO 31
<211> LENGTH: 626
<212> TYPE: DNA
<213> ORGANISM: Mycobacterium chelonae

<400> SEQUENCE: 31

```
tccgtcccgt cgtggcggcg atcaaggagt tcttcggaac cagccagctg tcgcagttca     60

tggaccagaa caacccgctt tcgggtctga cccacaagcg tcgtctgtcg gctctgggcc    120

ccggtggtct gacccgtgac cgcgctggcc ttgaggtccg cgacgtgcac ccctcgcact    180

acggccgcat gtgcccgatc gagaccccgg aaggcccgaa catcggcctg atcggttcgc    240

tttcggtgta cgcgcgggtc aacccgttcg gcttcatcga gacgccgtac cgcaaggtgt    300

ccgagggtgt cgtcaccgac gagatccact acctgaccgc cgacgaagag gaccgccacg    360

tcgtggcaca ggccaactcg cctgtggatg ccgacggccg cttcaccgag gacaagatcc    420

tggtccgccg taagggtggc gaggtcgagt tcgtctcggc gaccgaggtg gactacatgg    480

acgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gcagcgaggc cccgctggtc ggtacc                                         626
```

<210> SEQ ID NO 32
<211> LENGTH: 647
<212> TYPE: DNA
<213> ORGANISM: Mycobacterium chelonae

<400> SEQUENCE: 32

```
tgatcaacat ccgtcccgtc gtggcggcga tcaaggagtt cttcggaacc agccagctgt     60

cgcagttcat ggaccagaac aacccgcttt cgggtctgac ccacaagcgt cgtctgtcgg    120

ctctgggccc cggtggtctg acccgtgacc gcgctggcct tgaggtccgc gacgtgcacc    180

cctcgcacta cggccgcatg tgcccgatcg agaccccgga aggcccgaac atcggcctga    240

tcggttcgct ttcggtgtac gcgcgggtca acccgttcgg cttcatcgag acgccgtacc    300

gcaaggtgtc cgagggtgtc gtcaccgacg agatccacta cctgaccgcc gacgaagagg    360

accgccacgt cgtggcacag gccaactcgc ctgtggatgc cgacggccgc ttcaccgagg    420

acaagatcct ggtccgccgt aagggtggcg aggtcgagtt cgtctcggcg accgaggtgg    480

actacatgga cgtctcgccg cgccagatgg tgtcggtcgc gaccgccatg atcccgttcc    540

tcgagcacga cgacgccaac cgtgccctca tgggtgccaa catgcagcgc caggcggttc    600

cgctggtgcg cagcgaggcc ccgctggtcg gtaccggtat ggagctg                  647
```

<210> SEQ ID NO 33
<211> LENGTH: 626
<212> TYPE: DNA
<213> ORGANISM: Mycobacterium chelonae

<400> SEQUENCE: 33

```
tccgtcccgt cgtggcggcg atcaaggagt tcttcggaac cagccagctg tcgcagttca     60

tggaccagaa caacccgctg tcgggtctga cccacaagcg tcgtctttcg gcgctgggcc    120

ccggtggtct gacccgtgac cgcgccggcc ttgaggtccg cgacgtgcac ccctcgcact    180

acggccgcat gtgcccgatc gagaccccgg aaggcccgaa catcggcctg atcggttcgc    240
```

-continued tgtcggtgta cgcgcgggtc aacccgttcg gcttcatcga gacgccgtac cgcaaggtgt 300
ccgagggtgt cgtcaccgac gagatccact acctgaccgc cgacgaagag gaccgccacg 360
tcgtggcaca ggccaactcg cctgtggatg ccgacggccg cttcaccgag gacaagatcc 420
tggtccgccg taagggtggc gaggtcgagt tcgtctcggc gaccgaggtg gactacatgg 480
acgtctcgcc gcgccaaatg gtgtcggtcg cgaccgccat gatcccgttc ctcgagcacg 540
acgacgccaa ccgtgccctc atgggtgcca acatgcagcg ccaggcggtt ccgctggtgc 600
gcagcgaggc cccgctggtc ggtacc 626

<210> SEQ ID NO 34
<211> LENGTH: 643
<212> TYPE: DNA
<213> ORGANISM: Mycobacterium chelonae

<400> SEQUENCE: 34
tgatcaacat ccgtcccgtc gtggcggcga tcaaggagtt cttcggaacc agccagctgt 60
cgcagttcat ggaccagaac aacccgcttt cgggtctgac ccacaagcgt cgtctgtcgg 120
ctctgggccc cggtggtctg acccgtgacc gcgctggcct tgaggtccgc gacgtgcacc 180
cctcgcacta cggccgcatg tgcccgatcg agaccccgga aggcccgaac atcggcctga 240
tcggttcgct ttcggtgtac gcgcgggtca acccgttcgg cttcatcgag acgccgtacc 300
gcaaggtgtc cgagggtgtc gtcaccgacg agatccacta cctgaccgcc gacgaagagg 360
accgccacgt cgtggcacag gccaactcgc ctgtggatgc cgacggccgc ttcaccgagg 420
acaagatcct ggtccgccgt aagggtggcg aggtcgagtt cgtctcggcg accgaggtgg 480
actacatgga cgtctcgccg cgccagatgg tgtcggtcgc gaccgccatg atcccgttcc 540
tcgagcacga cgacgccaac cgtgccctca tgggtgccaa catgcagcgc caggcggttc 600
cgctggtgcg cagcgaggcc ccgctggtcg gtaccggtat gga 643

<210> SEQ ID NO 35
<211> LENGTH: 705
<212> TYPE: DNA
<213> ORGANISM: Mycobacterium chelonae

<400> SEQUENCE: 35
cccaggacgt ggaggcgatc acaccgcaga ccctgatcaa catccgtccc gtcgtggcgg 60
cgatcaagga gttcttcgga accagccagc tctcgcagtt catggaccag aacaacccgc 120
tgtcgggtct gacccacaag cgtcgtctgt cggcgctggg cccgggtggt ctgacccgtg 180
accgcgccgg ccttgaggtc cgtgacgtgc acccctcgca ctatggccgc atgtgcccga 240
tcgagacccc ggaaggcccg aacatcggcc tgatcggctc gctgtcggtg tacgcgcgcg 300
ttaacccgtt cggcttcatc gagacgccgt accgcaaggt ggtcgagggt gtcgtcaccg 360
acgagatccg ctacctgact gccgacgaag aggaccgcca cgtggtggcg caggccaact 420
cgccgaccga tgagaagggc cgcttcaccg aggagcgcgt cctggtgcgc cgtaagggtg 480
gcgaggtcga gttcgtgccg tcgacgggcg tcgactacat ggacgtctcg ccgcgccaga 540
tggtgtcggt cgcgaccgcg atgatcccgt tcctggagca cgacgacgcc aaccgtgccc 600
tgatgggtgc caacatgcag cgccaggcgg ttccgctggt gcgtagcgag gccccgctgg 660
tcggtaccgg tatggagctg cgcgcggcga tcgacgcggc gacgt 705

<210> SEQ ID NO 36

-continued

<211> LENGTH: 626
<212> TYPE: DNA
<213> ORGANISM: Mycobacterium chelonae

<400> SEQUENCE: 36
tccgtcccgt cgtggcggcg atcaaggagt tcttcggaac cagccagctg tcgcagttca 60
tggaccagaa caacccgctt tcgggtctga cccacaagcg tcgtctgtcg gctctgggcc 120
ccggtggtct gacccgtgac cgcgctggcc ttgaggtccg cgacgtgcac ccctcgcact 180
acggccgcat gtgcccgatc gagaccccgg aaggcccgaa catcggcctg atcggttcgc 240
tttcggtgta cgcgcgggtc aacccgttcg gcttcatcga gacgccgtac cgcaaggtgt 300
ccgagggtgt cgtcaccgac gagatccact acctgaccgc cgacgaagag gaccgccacg 360
tcgtggcaca ggccaactcg cctgtggatg ccgacggccg cttcaccgag gacaagatcc 420
tggtccgccg taagggtggc gaggtcgagt tcgtctcggc gaccgaggtg gactacatgg 480
acgtctcgcc gcgccagatg gtgtcggtcg cgaccgccat gatcccgttc ctcgagcacg 540
acgacgccaa ccgtgccctc atgggtgcca acatgcagcg ccaggcggtt ccgctggtgc 600
gcagcgaggc cccgctggtc ggtacc 626

<210> SEQ ID NO 37
<211> LENGTH: 626
<212> TYPE: DNA
<213> ORGANISM: Mycobacterium chelonae

<400> SEQUENCE: 37
tccgtcccgt cgtggcggcg atcaaggagt tcttcggaac cagccagctg tcgcagttca 60
tggaccagaa caacccgctt tcgggtctga cccacaagcg tcgtctgtcg gctctgggcc 120
ccggtggtct gacccgtgac cgcgctggcc ttgaggtccg cgacgtgcac ccctcgcact 180
acggccgcat gtgcccgatc gagaccccgg aaggcccgaa catcggcctg atcggttcgc 240
tttcggtgta cgcgcgggtc aacccgttcg gcttcatcga gacgccgtac cgcaaggtgt 300
ccgagggtgt cgtcaccgac gagatccact acctgaccgc cgacgaagag gaccgccacg 360
tcgtggcaca ggccaactcg cctgtggatg ccgacggccg cttcaccgag gacaagatcc 420
tggtccgccg taagggtggc gaggtcgagt tcgtctcggc gaccgaggtg gactacatgg 480
acgtctcgcc gcgccagatg gtgtcggtcg cgaccgccat gatcccgttc ctcgagcacg 540
acgacgccaa ccgtgccctc atgggtgcca acatgcagcg ccaggcggtt ccgctggtgc 600
gcagcgaggc cccgctggtc ggtacc 626

<210> SEQ ID NO 38
<211> LENGTH: 652
<212> TYPE: DNA
<213> ORGANISM: Mycobacterium chelonae

<400> SEQUENCE: 38
gcagaccctg atcaacatcc gtcccgtcgt ggcggcgatc aaggagttct tcggaaccag 60
ccagctgtcg cagttcatgg accagaacaa cccgctgtcg ggtctgaccc acaagcgtcg 120
tctttcggcg ctgggccccg gtggtctgac ccgtgaccgc gccggccttg aggtccgcga 180
cgtgcacccc tcgcactacg gccgcatgtg cccgatcgag accccggaag gcccgaacat 240
cggcctgatc ggttcgctgt cggtgtacgc gcgggtcaac ccgttcggct tcatcgagac 300
gccgtaccgc aaggtgtccg agggtgtcgt caccgacgag atccactacc tgaccgccga 360
cgaagaggac cgccacgtcg tggcacaggc caactcgcct gtggatgccg acggccgctt 420

-continued

```
caccgaggac aagatcctgg tccgccgtaa gggtggcgag gtcgagttcg tctcggcgac    480

cgaggtggac tacatggacg tctcgccgcg ccaaatggtg tcggtcgcga ccgccatgat    540

cccgttcctc gagcacgacg acgccaaccg tgccctcatg ggtgccaaca tgcagcgcca    600

ggcggttccg ctggtgcgca gcgaggcccc gctggtcggt accggtatgg ag            652
```

<210> SEQ ID NO 39
<211> LENGTH: 626
<212> TYPE: DNA
<213> ORGANISM: Mycobacterium chelonae

<400> SEQUENCE: 39

```
tccgtcccgt cgtggcggcg atcaaggagt tcttcggaac cagccagctg tcgcagttca     60

tggaccagaa caacccgctg tcgggtctga cccacaagcg tcgtctgtcg gcgctgggcc    120

ccggtggtct gacccgtgac cgcgccggcc ttgaggtccg cgacgtgcac ccctcgcact    180

acggccgcat gtgcccgatc gagaccccgg aaggcccgaa catcggcctg atcggttcgc    240

tgtcggtgta cgcgcgggtc aacccgttcg gcttcatcga gacgccgtac cgcaaggtgt    300

ccgagggtgt cgtcaccgac gacatccact acctgaccgc cgacgaagag gaccgccacg    360

tcgtggcaca ggccaactcg cctgtggacg ccgacggccg tttcaccgag gacaagatcc    420

tggtccgccg taagggtggc gaggtcgagt tcgtctcggc gaccgaggtg gactacatgg    480

acgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gcagcgaggc cccgctggtc ggtacc                                         626
```

<210> SEQ ID NO 40
<211> LENGTH: 626
<212> TYPE: DNA
<213> ORGANISM: Mycobacterium chelonae

<400> SEQUENCE: 40

```
tccgtcccgt cgtggcggcg atcaaggagt tcttcggaac cagccagctg tcgcagttca     60

tggaccagaa caacccgctg tcgggtctga cccacaagcg tcgtctttcg gcgctgggcc    120

ccggtggtct gacccgtgac cgcgccggcc ttgaggtccg cgacgtgcac ccctcgcact    180

acggccgcat gtgcccgatc gagaccccgg aaggcccgaa catcggactg atcggttcgc    240

tgtcggtgta cgcgcgggtc aacccgttcg gcttcatcga gacgccgtac cgcaaggtgt    300

ccgagggtgt cgtcaccgac gagatccact acctgaccgc cgacgaagag gaccgccacg    360

tggtggcgca ggccaactcg cctgtggatg cggacggccg cttcaccgag gacaagatcc    420

tggtccgccg taagggtggc gaggtcgagt tcgtctcggc gaccgaggtg gactacatgg    480

acgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gcagcgaggc cccgctggtc ggtacc                                         626
```

<210> SEQ ID NO 41
<211> LENGTH: 626
<212> TYPE: DNA
<213> ORGANISM: Mycobacterium chelonae

<400> SEQUENCE: 41

```
tccgtcccgt cgtggcggcg atcaaggagt tcttcggaac cagccagctg tcgcagttca     60
```

-continued

```
tggaccagaa caacccgctt tcgggtctga cccacaagcg tcgtctgtcg gctctgggcc    120

ccggtggtct gacccgtgac cgcgctggcc ttgaggtccg cgacgtgcac ccctcgcact    180

acggccgcat gtgcccgatc gagaccccgg aaggcccgaa catcggcctg atcggttcgc    240

tttcggtgta cgcgcgggtc aacccgttcg gcttcatcga gacgccgtac cgcaaggtgt    300

ccgagggtgt cgtcaccgac gagatccact acctgaccgc cgacgaagag gaccgccacg    360

tcgtggcaca ggccaactcg cctgtggatg ccgacggccg cttcaccgag gacaagatcc    420

tggtccgccg taagggtggc gaggtcgagt tcgtctcggc gaccgaggtg gactacatgg    480

acgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gcagcgaggc cccgctggtc ggtacc                                          626
```

<210> SEQ ID NO 42
<211> LENGTH: 626
<212> TYPE: DNA
<213> ORGANISM: Mycobacterium chelonae

<400> SEQUENCE: 42

```
tccgtcccgt cgtggcggcg atcaaggagt tcttcggaac cagccagctg tcgcagttca     60

tggaccagaa caacccgctt tcgggtctga cccacaagcg tcgtctgtcg gctctgggcc    120

ccggtggtct gacccgtgac cgcgctggcc ttgaggtccg cgacgtgcac ccctcgcact    180

acggccgcat gtgcccgatc gagaccccgg aaggcccgaa catcggcctg atcggttcgc    240

tttcggtgta cgcgcgggtc aacccgttcg gcttcatcga gacgccgtac cgcaaggtgt    300

ccgagggtgt cgtcaccgac gagatccact acctgaccgc cgacgaagag gaccgccacg    360

tcgtggcaca ggccaactcg cctgtggatg ccgacggccg cttcaccgag gacaagatcc    420

tggtccgccg taagggtggc gaggtcgagt tcgtctcggc gaccgaggtg gactacatgg    480

acgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gcagcgaggc cccgctggtc ggtacc                                          626
```

<210> SEQ ID NO 43
<211> LENGTH: 626
<212> TYPE: DNA
<213> ORGANISM: Mycobacterium chelonae

<400> SEQUENCE: 43

```
tccgtcccgt cgtggcggcg atcaaggagt tcttcggaac cagccagctg tcgcagttca     60

tggaccagaa caacccgctt tcgggtctga cccacaagcg tcgtctgtcg gctctgggcc    120

ccggtggtct gacccgtgac cgcgctggcc ttgaggtccg cgacgtgcac ccctcgcact    180

acggccgcat gtgcccgatc gagaccccgg aaggcccgaa catcggcctg atcggttcgc    240

tttcggtgta cgcgcgggtc aacccgttcg gcttcatcga gacgccgtac cgcaaggtgt    300

ccgagggtgt cgtcaccgac gagatccact acctgaccgc cgacgaagag gaccgccacg    360

tcgtggcaca ggccaactcg cctgtggatg ccgacggccg cttcaccgag gacaagatcc    420

tggtccgccg taagggtggc gaggtcgagt tcgtctcggc gaccgaggtg gactacatgg    480

acgtctcgcc gcgccagatg gtgtcggtcg cgaccgccat gatcccgttc ctcgagcacg    540

acgacgccaa ccgtgccctc atgggtgcca acatgcagcg ccaggcggtt ccgctggtgc    600

gcagcgaggc cccgctggtc ggtacc                                          626
```

-continued

<210> SEQ ID NO 44
<211> LENGTH: 626
<212> TYPE: DNA
<213> ORGANISM: Mycobacterium chelonae

<400> SEQUENCE: 44
tccgtcccgt cgtggcggcg atcaaggagt tcttcggaac cagccagctg tcgcagttca 60
tggaccagaa caacccgctt tcgggtctga cccacaagcg tcgtctgtcg gctctgggcc 120
ccggtggtct gacccgtgac cgcgctggcc ttgaggtccg cgacgtgcac ccctcgcact 180
acggccgcat gtgcccgatc gagaccccgg aaggcccgaa catcggcctg atcggttcgc 240
tttcggtgta cgcgcgggtc aacccgttcg gcttcatcga gacgccgtac cgcaaggtgt 300
ccgagggtgt cgtcaccgac gagatccact acctgaccgc cgacgaagag gaccgccacg 360
tcgtggcaca ggccaactcg cctgtggatg ccgacggccg cttcaccgag gacaagatcc 420
tggtccgccg taagggtggc gaggtcgagt tcgtctcggc gaccgaggtg gactacatgg 480
acgtctcgcc gcgccagatg gtgtcggtcg cgaccgccat gatcccgttc ctcgagcacg 540
acgacgccaa ccgtgccctc atgggtgcca acatgcagcg ccaggcggtt ccgctggtgc 600
gcagcgaggc cccgctggtc ggtacc 626

<210> SEQ ID NO 45
<211> LENGTH: 626
<212> TYPE: DNA
<213> ORGANISM: Mycobacterium chelonae

<400> SEQUENCE: 45
tccgtcccgt cgtggcggcg atcaaggagt tcttcggaac cagccagctg tcgcagttca 60
tggaccagaa caacccgctg tcgggcctga cccacaagcg tcgtctgtcg gcgctgggcc 120
ccggtggtct gacccgtgac cgcgccggcc tcgaggtccg cgacgtgcac ccctcgcact 180
acggccgcat gtgcccgatc gagaccccgg aaggcccgaa catcggcctg atcggctcgc 240
tgtcggtgta cgcgcgcgtc aacccgttcg gtttcatcga gacgccttac cggaaggtct 300
cggacggagt tgtcaccgac gagatccact acctgacggc cgacgaagag gaccgccacg 360
tggtggcgca ggccaactcg cccgtggacg ccaacggccg cttcaccgag gagaagatcc 420
tggttcgccg caagggcggc gaggtggagt tcgtgtcggc gaccgaggtc gactacatgg 480
atgtttcgcc gcgccagatg gtgtcggtcg cgaccgccat gatcccgttc ctcgagcacg 540
acgacgccaa ccgtgccctc atgggtgcca acatgcagcg ccaggcggtt ccgctggtgc 600
gtagcgaggc tccgctggtc ggtacc 626

<210> SEQ ID NO 46
<211> LENGTH: 626
<212> TYPE: DNA
<213> ORGANISM: Mycobacterium chelonae

<400> SEQUENCE: 46
tccgtcccgt cgtggcggcg atcaaggagt tcttcggaac cagccagctg tcgcagttca 60
tggaccagaa caacccgctg tcgggcctga cccacaagcg tcgtctgtcg gcgctgggcc 120
ccggtggtct gacccgtgac cgcgccggcc tcgaggtccg cgacgtgcac ccctcgcact 180
acggccgcat gtgcccgatc gagaccccgg aaggcccgaa catcggcctg atcggctcgc 240
tgtcggtgta cgcgcgcgtc aacccgttcg gtttcatcga gacgccttac cggaaggtct 300

-continued cggacggagt tgtcaccgac gagatccact acctgacggc cgacgaagag gaccgccacg 360
tggtggcgca ggccaactcg cccgtggacg ccaacggccg cttcaccgag gagaagatcc 420
tggttcgccg caagggcggc gaggtggagt tcgtgtcggc gaccgaggtc gactacatgg 480
atgtttcgcc gcgccagatg gtgtcggtcg cgaccgccat gatcccgttc ctcgagcacg 540
acgacgccaa ccgtgccctc atgggtgcca acatgcagcg ccaggcggtt ccgctggtgc 600
gtagcgaggc tccgctggtc ggtacc 626

<210> SEQ ID NO 47
<211> LENGTH: 626
<212> TYPE: DNA
<213> ORGANISM: Mycobacterium chelonae

<400> SEQUENCE: 47
tccgtcccgt cgtggcggcg atcaaggagt tcttcggaac cagccagctg tcgcagttca 60
tggaccagaa caacccgctg tcgggcctga cccacaagcg tcgtctgtcg gcgctgggcc 120
ccggtggtct gacccgtgac cgcgccggcc tcgaggtccg cgacgtgcac ccctcgcact 180
acggccgcat gtgcccgatc gagaccccgg aaggcccgaa catcggcctg atcggctcgc 240
tgtcggtgta cgcgcgggtc aacccgttcg gtttcatcga gacgccttac cggaaggtct 300
cggacggagt tgtcaccgac gacatccact acctgacggc cgacgaagag gaccgccacg 360
tggtggcgca ggccaactcg cccgtggacg ccaacggccg cttcaccgag gagaagatcc 420
tggttcgccg caagggcggc gaggtggagt tcgtgtcggc gaccgaggtc gactacatgg 480
atgtctcgcc gcgccagatg gtgtcggtcg cgaccgccat gatcccgttc ctcgagcacg 540
acgacgccaa ccgtgccctc atgggtgcca acatgcagcg ccaggcggtt ccgctggtgc 600
gtagcgaggc tccgctggtc ggtacc 626

<210> SEQ ID NO 48
<211> LENGTH: 687
<212> TYPE: DNA
<213> ORGANISM: Mycobacterium flavescens

<400> SEQUENCE: 48
ggaggcgatc acaccgcaga ccctgatcaa catccgtccc gtcgtggcgg cgatcaagga 60
gttcttcggc accagccagc tgtcgcagtt catggaccag aacaacccgc tctcgggcct 120
gacccacaag cgccgcctgt cggcgctggg ccccggcggt ctgtcccgtg agcgcgccgg 180
cctcgaggtc cgcgacgtgc acgcatcgca ctacggccgc atgtgcccga tcgagacccc 240
ggagggtccg aacatcggcc tgatcggctc gctgtcggtg tacgcgcggg tcaacccgtt 300
cggcttcatc gagacgccgt accgcaaggt caaggacggt gttgtcaccg atgacatcga 360
gtacctgacc gccgacgagg aggaccgcca cgtcgtggcg caggccaact cgccgatcga 420
tgacaacggc cgcttcctgg aggagcgcgt cctggtccgc cgcaagggcg gcgaggtcga 480
gcagatctcg tcgagcgagg tggactacat ggacgtctcg ccgcgccaga tggtatcggt 540
cgcgacggcc atgatcccgt tcctcgagca cgacgacgcc aaccgcgccc tgatgggtgc 600
caacatgcag cgccaggcgg tcccgctggt gcgcagcgag gccccgctgg tcggcaccgg 660
tatggagttg cgcgcggcga tcgacgc 687

<210> SEQ ID NO 49
<211> LENGTH: 687
<212> TYPE: DNA
<213> ORGANISM: Mycobacterium flavescens -continued

<400> SEQUENCE: 49
ggaggcgatc acaccgcaga ccctgatcaa catccgtccc gtcgtggcgg cgatcaagga 60
gttcttcggc accagccagc tgtcgcagtt catggaccag aacaacccgc tctcgggcct 120
gacccacaag cgccgcctgt cggcgctggg ccccggcggt ctgtcccgtg agcgcgccgg 180
cctcgaggtc cgcgacgtgc acgcgtcgca ctacggccgc atgtgcccga tcgagacccc 240
ggagggtccg aacatcggcc tgatcggctc gctgtcggtg tacgcgcggg tcaacccgtt 300
cggcttcatc gagacgccgt accgcaaggt caaggacggt gttgtcaccg atgacatcga 360
gtacctgacc gccgacgagg aggaccgcca cgtcgtggcg caggccaact cgccgatcga 420
tgacaacggc cgcttcctgg aggagcgcgt cctggtccgc cgcaagggcg gcgaggtcga 480
gcagatctcg tcgagcgagg tggactacat ggacgtctcg ccgcgccaga tggtatcggt 540
cgcgacggcc atgatcccgt tcctcgagca cgacgacgcc aaccgcgccc tgatgggtgc 600
caacatgcag cgccaggcgg tcccgctggt gcgcagcgag gccccgctgg tcggcaccgg 660
tatggagttg cgcgcggcga tcgacgc 687

<210> SEQ ID NO 50
<211> LENGTH: 687
<212> TYPE: DNA
<213> ORGANISM: Mycobacterium flavescens

<400> SEQUENCE: 50
ggaggcgatc acaccgcaga ccctgatcaa catccgtccc gtcgtggcgg cgatcaagga 60
gttcttcggc accagccagc tctcgcagtt catggatcag aacaacccgc tgtcgggcct 120
gacccacaag cgccgcctgt cggcgctggg ccccggtggt ctgtcccgtg agcgtgccgg 180
cctcgaggtc cgcgacgtgc actccagcca ctacggccgc atgtgcccga tcgagacccc 240
ggaaggcccg aacatcggcc tgatcggctc gctgtcggtg tacgcgcggg tcaacccgtt 300
cggcttcatc gagaccccgt accgcaaggt cgtcgacggc gtcgtcagcg accagatcga 360
ctacctgacc gccgacgagg aggaccgcca cgtcgtggcg caggccaatt cgccgctcga 420
cggtgacggt cgtttcgagg aggagcgcgt cctggtccgc cgtaagggcg gcgaggtcga 480
gttcgtctcg gcgagcgagg tcgactacat ggacgtctcg ccgcgccaga tggtgtcggt 540
cgcgacggcg atgatcccgt tcctcgagca cgacgacgcc aaccgcgccc tgatgggtgc 600
gaacatgcag cgccaggcgg ttccgctggt ccgcagcgag gcgccgttgg tcggtaccgg 660
catggaactg cgcgcggcga tcgacgc 687

<210> SEQ ID NO 51
<211> LENGTH: 705
<212> TYPE: DNA
<213> ORGANISM: Mycobacterium fortuitum

<400> SEQUENCE: 51
cccaggacgt ggaggcgatc acaccgcaga ccctgatcaa catccgtccc gtcgtggcgg 60
cgatcaagga gttcttcgga acgtcgcagc tgtcgcagtt catggatcag aacaacccgc 120
tgtcgggtct gacccacaag cgtcgtctgt cggcgctggg ccccggcggt ctgtcccgtg 180
agcgcgccgg ccttgaggtc cgcgacgtcc actcgtcgca ctacggccgc atgtgcccga 240
tcgagacccc tgagggtccg aacatcggtc tgatcggttc gctttcggtg tacgcgcggg 300
tcaacccgtt cggtttcatc gagaccccgt accgcaaggt cgtcgacggt gtggtcaccg 360

-continued

```
accagatcga ctacctgacc gccgacgagg aggaccgcca cgtcgtggcg caggccaact    420

cgccgatcga cccggacggc cggttcaccg aggaccgcgt gatggttcgt cgtaagggcg    480

gcgaggtcga gaacgtggcc ccgtccgacg tcgactacat ggacgtctcg ccgcgccaga    540

tggtgtccgt cgcgaccgcg atgatcccgt tcctcgagca cgacgacgcc aaccgcgccc    600

tgatgggtgc caacatgcag cgccaggcgg ttccgctggt gcgcagcgag gccccgctgg    660

tcggtaccgg tatggagctg cgcgcggcga tcgacgcggc gacgt                    705
```

<210> SEQ ID NO 52
<211> LENGTH: 705
<212> TYPE: DNA
<213> ORGANISM: Mycobacterium fortuitum

<400> SEQUENCE: 52

```
cccaggacgt ggaggcgatc acaccgcaga ccctgatcaa catccgtccc gtcgtggcgg     60

cgatcaagga attcttcggc accagccagc tgtcgcagtt catggaccag aacaacccgc    120

tgtcgggtct gacccacaag cgtcgtctgt cggcgctggg ccccggcggt ctgtcccgtg    180

agcgcgccgg ccttgaggtc cgcgacgtgc actccagcca ctacggccgc atgtgcccga    240

tcgagacccc tgagggtccg aacatcggtc tgatcggctc gctgtcggtg tacgcccggg    300

tcaacccgtt cggcttcatc gagaccccgt accgcaaggt cgtcgacggt gtggtcaccg    360

accagatcga ctacctgacc gccgacgagg aggaccgcca cgtcgtggcg caggccaact    420

cgccgatcgg cgcggacggc agcttcaccg aagaccgcgt gatggtccgc cgtaagggcg    480

gcgaggtcga gaacgtggcc ccgatcgacg tggattacat ggacgtctcg ccgcgccaga    540

tggtgtcggt cgcgaccgcg atgatcccgt tcctcgagca cgacgacgcc aaccgtgccc    600

tgatgggtgc caacatgcag cgccaggcgg ttccgctggt gcgtagcgag gccccgctgg    660

tcggtaccgg tatggagttg cgcgcggcga tcgacgcggc gacgt                    705
```

<210> SEQ ID NO 53
<211> LENGTH: 626
<212> TYPE: DNA
<213> ORGANISM: Mycobacterium fortuitum
<220> FEATURE:
<221> NAME/KEY: modified_base
<222> LOCATION: (340)...(340)
<223> OTHER INFORMATION: n = g,a,c or t
<220> FEATURE:
<221> NAME/KEY: modified_base
<222> LOCATION: (354)...(355)
<223> OTHER INFORMATION: n = g,a,c or t

<400> SEQUENCE: 53

```
tccgtcccgt cgtggcggcg atcaaggagt tcttcggtac cagccagctg tcgcagttca     60

tggaccagaa caacccgctt tcgggtctga cccacaagcg tcgcctgtcg gcgctgggcc    120

ccggcggtct gtcccgtgag cgtgccggcc ttgaggtccg cgacgtgcac gccagccact    180

acggccgcat gtgcccgatc gagacccctg agggtccgaa catcggtctg atcggctcgc    240

tgtcggtgta cgcccgggtc aacccgttcg gcttcatcga gacgccgtac cgcaaggtcg    300

tcgacggtgt ggtcaccgac cagatcgact acctgaccgn cgacgaggag gacnntcacg    360

tcgtggcgca ggccaactcg ccgatcgacg ccgacggccg cttcaccgaa gaccgcgtca    420

tggtgcgtcg taagggcggc gaggtcgaga acgtggcccc gtccgacgtc gactacatgg    480

acgtctcgcc gcgccagatg gtgtctgtcg cgaccgcgat gatcccgttc ctcgagcacg    540

acgacgccaa ccgcgccctg atgggtgcca acatgcagcg ccaggcggtt ccactggtgc    600
```

-continued gcagcgaggc cccgctggtc ggtacc 626

<210> SEQ ID NO 54
<211> LENGTH: 705
<212> TYPE: DNA
<213> ORGANISM: Mycobacterium fortuitum

<400> SEQUENCE: 54
cccaggacgt ggaggcgatc acaccgcaga ccctgatcaa catccgtccc gtcgtggcgg 60
cgatcaagga gttcttcgga acgtcgcagc tgtcgcagtt catggatcag aacaacccgc 120
tgtcgggtct gacccacaag cgtcgtctgt cggcgctggg ccccggcggt ctgtcccgtg 180
agcgcgccgg ccttgaggtc cgcgacgtcc actcgtcgca ctacggccgc atgtgtccga 240
tcgagacccc tgagggtccg aacatcggtc tgatcggttc gctttcggtg tacgcgcggg 300
tcaacccgtt cggtttcatc gagaccccgt accgcaaggt cgtcgacggt gtggtcaccg 360
atcagatcga ctacctgacc gccgacgagg aggaccgcca cgtcgtggcg caggccaact 420
cgccgatcga cccggacggc cggttcaccg aggaccgcgt gatggttcgt cgtaagggcg 480
gcgaggtcga gaatgtggcc ccgtccgacg tcgactacat ggacgtctcg ccgcgccaga 540
tggtgtccgt cgcgaccgcg atgatcccgt tcctcgagca cgacgacgcc aaccgcgccc 600
tgatgggtgc caacatgcag cgccaggcgg ttccgctggt gcgcagcgag gccccgctgg 660
tcggtaccgg tatggagctg cgcgcggcga tcgacgcggc gacgt 705

<210> SEQ ID NO 55
<211> LENGTH: 705
<212> TYPE: DNA
<213> ORGANISM: Mycobacterium fortuitum

<400> SEQUENCE: 55
cccaggacgt ggaggcgatc acaccgcaga ccctgatcaa catccgtccc gtcgtggcgg 60
cgatcaagga gttcttcggc accagccagc tgtcgcagtt catggaccag aacaacccgc 120
tgtcgggtct gacccacaag cgtcgcctgt cggcgctggg ccccggcggt ctgtcccgtg 180
agcgtgccgg ccttgaggtc cgcgacgtgc actccagcca ctacggccgc atgtgcccga 240
tcgagacccc tgagggtccg aacatcggtc tgatcggttc gctgtcggtg tacgcccggg 300
tcaacccgtt cggcttcatc gagacgccgt accgcaaggt cgtcgacggt gtggtctccg 360
accagatcga ctacctgacc gccgacgagg aggaccgcca cgtcgtggcg caggccaact 420
cgccgatcga cgcggacggc agcttcaccg aggatcgcgt gatggtccgg cgtaagggtg 480
gcgaggtcga gaacgtggcc ccgtccgacg tcgactacat ggacgtctcg ccgcgccaga 540
tggtgtctgt cgcgaccgcg atgatcccgt tcctcgagca cgacgacgcc aaccgcgccc 600
tgatgggtgc caacatgcag cgccaggcgg ttccgctggt gcgcagcgag gccccgctgg 660
tcggtaccgg catggagttg cgcgcggcga tcgacgcggc gacgt 705

<210> SEQ ID NO 56
<211> LENGTH: 626
<212> TYPE: DNA
<213> ORGANISM: Mycobacterium fortuitum

<400> SEQUENCE: 56
tccgtcccgt cgtggcggcg atcaaggagt tcttcggaac gtcgcagctg tcgcagttca 60
tggatcagaa caacccgctg tcgggtctga cccacaagcg tcgtctgtcg gcgctgggcc 120

-continued

```
ccggcggtct gtcccgtgag cgcgccggcc ttgaggtccg cgacgtccac tcgtcgcact    180

acggccgcat gtgtccgatc gagacccctg agggtccgaa catcggtctg atcggttcgc    240

tttcggtgta cgcgcgggtc aacccgttcg gtttcatcga gaccccgtac cgcaaggtcg    300

tcgacggtgt ggtcaccgat cakatckact acctgaccgc cgacgaggag gaccgccacg    360

tcgtggcgca ggccaactcg ccgatcgacc cggacggccg gttcaccgag gaccgcgtga    420

tggttcgtcg taagggcggc gaggtcgaga atgtggcccc gtccgacgtc gactacatgg    480

acgtctcgcc gcgccagatg gtgtccgtcg cgaccgcgat gatcccgttc ctcgagcacg    540

acgacgccaa ccgcgccctg atgggtgcca acatgcagcg ccaggcggtt ccgctggtgc    600

gcagcgaggc cccgctggtc ggtacc                                          626
```

<210> SEQ ID NO 57
<211> LENGTH: 705
<212> TYPE: DNA
<213> ORGANISM: Mycobacterium smegmatis

<400> SEQUENCE: 57

```
cccaggacgt ggaggcgatc acaccgcaga ccctgatcaa catccgcccc gtcgtggcgg     60

cgatcaagga gttcttcggc accagccagc tgtcgcagtt catggaccag aacaacccgc    120

tgtcgggtct gacccacaag cgtcgtctgt cggcgctggg ccccggcggt ctgtcccgtg    180

agcgcgccgg ccttgaggtc cgcgacgtgc actccagcca ctacggccgc atgtgcccga    240

tcgagacccc tgagggtccg aacatcggtc tgatcggctc gctgtcggtg tacgcccggg    300

tcaacccgtt cggcttcatc gagacgcctt accgcaaggt tgtcgacggt gtggtcagcg    360

accagatcga ctacctgacc gccgacgagg aggaccgcca cgtcgtggcg caggccaact    420

cgccgatcga caccgacggt cgcttcaccg aggaccgcgt gatggtccgc cgtaagggtg    480

gcgaggtcga gaacgtggcc ccgtccgacg tcgactacat ggacgtctca ccgcgccaga    540

tggtgtctgt cgcgaccgcg atgatcccgt tcctcgagca cgacgacgcc aaccgtgccc    600

tgatgggtgc caacatgcag cgccaggcag ttccgctggt acgcagcgag gccccgctgg    660

tcggtaccgg tatggagctg cgcgcggcga tcgacgcggc gacgt                     705
```

<210> SEQ ID NO 58
<211> LENGTH: 687
<212> TYPE: DNA
<213> ORGANISM: Mycobacterium chelonae

<400> SEQUENCE: 58

```
ggaggcgatc acaccgcaga ccctgatcaa catccgtccc gtcgtggcgg cgatcaagga     60

gttcttcggc accagccagc tgtcgcagtt catggaccag aacaacccgc tgtcgggtct    120

gacccacaag cgtcgcctgt cggcgctggg ccccggcggt ctgtcccgtg agcgtgccgg    180

ccttgaggtc cgcgacgtgc actccagcca ctacggccgc atgtgcccga tcgagacccc    240

tgagggtccg aacatcggtc tgatcggttc gctgtcggtg tacgcccggg tcaacccgtt    300

cggcttcatc gagacgccgt accgcaaggt cgtcgacggt gtggtctccg accagatcga    360

ctacctgacc gccgacgagg aggaccgcca cgtcgtggcg caggccaact cgccgatcga    420

cgcggacggc agcttcaccg aggatcgcgt gatggtccgc cgtaagggtg gcgaggtcga    480

gaacgtggcc ccgtccgacg tcgactacat ggacgtctcg ccgcgccaga tggtgtctgt    540

cgcgaccgcg atgatcccgt tcctcgagca cgacgacgcc aaccgcgccc tgatgggtgc    600

caacatgcag cgccaggcgg ttccgctggt gcgcagcgag gccccgctgg tcggtaccgg    660
```

-continued catggagttg cgcgcggcga tcgacgc 687

<210> SEQ ID NO 59
<211> LENGTH: 687
<212> TYPE: DNA
<213> ORGANISM: Mycobacterium fortuitum

<400> SEQUENCE: 59
ggaggcgatc acaccgcaga ccctgatcaa catccgtccc gtcgtggcgg cgatcaagga 60
gttcttcgga acgtcgcagc tgtcgcagtt catggatcag aacaacccgc tgtcgggtct 120
gacccacaag cgtcgtctgt cggcgctggg ccccggcggt ctgtcccgtg agcgcgccgg 180
ccttgaggtc cgcgacgtcc actcgtcgca ctacggccgc atgtgcccga tcgagacccc 240
tgagggtccg aacatcggtc tgatcggttc gctttcggtg tacgcgcggg tcaacccgtt 300
cggtttcatc gagaccccgt accgcaaggt cgtcgacggt gtggtcaccg aycagatcga 360
ctacctgacc gccgacgagg aggaccgcca cgtcgtggcg caggccaact cgccgatcga 420
cccggacggc cggttcaccg aggaccgcgt gatggttcgc cgtaagggcg gcgaggtcga 480
gaacgtggcc ccgtccgacg tcgactacat ggacgtctcg ccgcgccaga tggtgtccgt 540
cgcgaccgcg atgatcccgt tcctcgagca cgacgacgcc aaccgtgccc tgatgggtgc 600
caacatgcag cgccaggcgg ttccgctggt gcgcagcgag gccccgctgg tcggtaccgg 660
tatggagctg cgcgcggcga tcgacgc 687

<210> SEQ ID NO 60
<211> LENGTH: 687
<212> TYPE: DNA
<213> ORGANISM: Mycobacterium fortuitum

<400> SEQUENCE: 60
ggaggcgatc acaccgcaga ccctgatcaa catccgcccc gtcgtggcgg cgatcaagga 60
gttcttcggc accagccagc tgtcgcagtt catggaccag aacaacccgc tgtcgggtct 120
gacccacaag cgtcgtctgt cggcgctggg ccccggcggt ctgtcccgtg agcgcgccgg 180
ccttgaggtc cgcgacgtgc actccagcca ctacggccgc atgtgcccga tcgagacccc 240
tgagggtccg aacatcggtc tgatcggctc gctgtcggtg tacgcccggg tcaacccgtt 300
cggcttcatc gagacgcctt accgcaaggt tgtcgacggt gtggtcagcg accagatcga 360
ctacctgacc gccgacgagg aggaccgcca cgtcgtggcg caggccaact cgccgatcga 420
caccgacggt cgcttcaccg aggaccgcgt gatggtccgc cgtaagggtg gcgaggtcga 480
gaacgtggcc ccgtccgacg tcgactacat ggacgtctca ccgcgccaga tggtgtctgt 540
cgcgaccgcg atgatcccgt tcctcgagca cgacgacgcc aaccgtgccc tgatgggtgc 600
caacatgcag cgccaggcag ttccgctggt acgcagcgag gccccgctgg tcggtaccgg 660
tatggagctg cgcgcggcga tcgacgc 687

<210> SEQ ID NO 61
<211> LENGTH: 687
<212> TYPE: DNA
<213> ORGANISM: Mycobacterium fortuitum

<400> SEQUENCE: 61
ggaggcgatc acaccgcaga ccctgatcaa catccgtccc gtcgtggcgg cgatcaagga 60
gttcttcgga acgtcgcagc tgtcgcagtt catggatcag aacaacccgc tgtcgggtct 120

-continued

```
gacccacaag cgtcgtctgt cggcgctggg ccccggcggt ctgtcccgtg agcgcgccgg    180

ccttgaggtc cgcgacgtcc actcgtcgca ctacggccgc atgtgcccga tcgagacccc    240

tgagggtccg aacatcggtc tgatcggttc gctttcggtg tacgcgcggg tcaacccgtt    300

cggtttcatc gagaccccgt accgcaaggt cgtcgacggt gtggtcaccg atcagatcga    360

ctacctgacc gccgacgagg aggaccgcca cgtcgtggcg caggccaact cgccgatcga    420

cccggacggc cggttcaccg aggaccgcgt gatggttcgt cgtaagggcg gcgaggtcga    480

gaacgtggcc ccgtccgacg tcgactacat ggacgtctcg ccgcgccaga tggtgtccgt    540

cgcgaccgcg atgatcccgt tcctcgagca cgacgacgcc aaccgcgccc tgatgggtgc    600

caacatgcag cgccaggcgg ttccgctggt gcgcagcgag gccccgctgg tcggtaccgg    660

tatggagctg cgcgcggcga tcgacgc                                        687
```

```
<210> SEQ ID NO 62
<211> LENGTH: 687
<212> TYPE: DNA
<213> ORGANISM: Mycobacterium fortuitum

<400> SEQUENCE: 62

ggaggcgatc acaccgcaga ccctgatcaa catccgtccc gtcgtggcgg cgatcaagga     60

gttcttcgga acgtcgcagc tgtcgcagtt catggatcag aacaacccgc tgtcgggtct    120

gacccacaag cgtcgtctgt cggcgctggg ccccggcggt ctgtcccgtg agcgcgccgg    180

ccttgaggtc cgcgacgtcc actcgtcgca ctacggccgc atgtgcccga tcgagacccc    240

tgagggtccg aacatcggtc tgatcggttc gctttcggtg tacgcgcggg tcaacccgtt    300

cggtttcatc gagaccccgt accgcaaggt cgtcgacggt gtggtcaccg atcagatcga    360

ctacctgacc gccgacgagg aggaccgcca cgtcgtggcg caggccaact cgccgatcga    420

cccggacggc cggttcaccg aggaccgcgt gatggttcgt cgtaagggcg gcgaggtcga    480

gaacgtggcc ccgtccgacg tcgactacat ggacgtctcg ccgcgccaga tggtgtccgt    540

cgcgaccgcg atgatcccgt tcctcgagca cgacgacgcc aaccgcgccc tgatgggtgc    600

caacatgcag cgccaggcgg ttccgctggt gcgcagcgag gccccgctgg tcggtaccgg    660

tatggagctg cgcgcggcga tcgacgc                                        687
```

```
<210> SEQ ID NO 63
<211> LENGTH: 687
<212> TYPE: DNA
<213> ORGANISM: Mycobacterium fortuitum

<400> SEQUENCE: 63

ggaggcgatc acaccgcaga ccctgatcaa catccgtccc gtcgtggcgg cgatcaagga     60

gttcttcgga acgtcgcagc tgtcgcagtt catggatcag aacaacccgc tgtcgggtct    120

gacccacaag cgtcgtctgt cggcgctggg ccccggcggt ctgtcccgtg agcgcgccgg    180

ccttgaggtc cgcgacgtcc actcgtcgca ctacggccgc atgtgtccga tcgagacccc    240

tgagggtccg aacatcggtc tgatcggttc gctttcggtg tacgcgcggg tcaacccgtt    300

cggtttcatc gagaccccgt accgcaaggt cgtcgacggt gtggtcaccg atcagatcga    360

ctacctgacc gccgacgagg aggaccgcca cgtcgtggcg caggccaact cgccgatcga    420

cccggacggc cggttcaccg aggaccgcgt gatggttcgt cgtaagggcg gcgaggtcga    480

gaacgtggcc ccgtccgacg tcgactacat ggacgtctcg ccgcgccaga tggtgtccgt    540

cgcgaccgcg atgatcccgt tcctcgagca cgacgacgcc aaccgcgccc tgatgggtgc    600
```

-continued

```
caacatgcag cgccaggcgg ttccgctggt gcgcagcgag gccccgctgg tcggtaccgg    660

tatggagctg cgcgcggcga tcgacgc                                        687
```

<210> SEQ ID NO 64
<211> LENGTH: 626
<212> TYPE: DNA
<213> ORGANISM: Mycobacterium fortuitum

<400> SEQUENCE: 64

```
tccgtccggt cgttgccgcg atcaaggagt tcttcggaac cagccagctg tcgcagttca     60

tggaccagaa caacccgctc tccggtctca cccacaagcg ccgcctctcg gcgctggggc    120

cgggcggtct gtcccgtgag cgcgccggtc tggaagttcg tgacgtgcac ccgtcgcact    180

acggccggat gtgcccgatc gagacgccgg aagggccgaa catcggtctg atcggttcac    240

tgtcggtgta cgcccgggtc aacccgttcg ggttcatcga gacgccctac cgcaaggtgg    300

tcgacggggt cgtttccgac gagatccact acctgaccgc cgacgaggag gaccgccacg    360

tcgtggcgca ggccaactcg ccgatcgacg cgcagggccg cttcgtcgag ccgcgcgtgc    420

tggtccgccg gaaggcgggc gaggtcgagt acgtgccctc gtcagaggtg gactacatgg    480

acgtgtcgcc gcgccagatg gtgtcggtgg ccaccgcgat gattccgttc ctcgagcacg    540

atgacgccaa ccgcgccttg atgggtgcca acatgcagcg scaggcggtc ccgctggtgc    600

gcagcgaggc accgctggtc ggtacc                                         626
```

<210> SEQ ID NO 65
<211> LENGTH: 705
<212> TYPE: DNA
<213> ORGANISM: Mycobacterium gordonae

<400> SEQUENCE: 65

```
cccaggacgt ggaggcgatc acaccgcaga ccctgatcaa catccggccg gtcgtcgccg     60

cgatcaagga gttcttcggc accagccagc tctcgcagtt catggaccag aacaacccgc    120

tgtcgggtct gacccacaag cgtcgtctgt cggcgctggg gccgggtggt ctgtcccgtg    180

agcgtgcggg tctggaagta cgtgacgtgc acccgtcgca ctacggccgc atgtgcccga    240

tcgagacgcc ggaaggcccg aacatcggcc tgatcggttc gctgtcggtg tacgcgcggg    300

tcaacccgtt cggcttcatc gagacgcctt atcggaaggt ggtggatgga gtcgtttctg    360

acgagatcca ctacctcacc gccgacgagg aggaccgcca cgtggtggcg caggccaact    420

cgccgatcga cgagagcggc cggtttgctg agccgcgcgt tctggtccgc cgcaaggcgg    480

gcgaggtgga gtacgtgccc tcgtccgagg tggactacat ggacgtctcg ccgcgccaga    540

tggtgtcggt ggccaccgcg atgattccgt tcctcgaaca cgacgacgcc aaccgtgccc    600

tgatgggtgc caacatgcag cgccaggcgg ttccgctggt gcgcagcgag gcaccgctgg    660

tgggcaccgg catggagttg cgcgcggcga tcgacgcggc gacgt                    705
```

<210> SEQ ID NO 66
<211> LENGTH: 705
<212> TYPE: DNA
<213> ORGANISM: Mycobacterium gordonae
<220> FEATURE:
<221> NAME/KEY: modified_base
<222> LOCATION: (90)...(90)
<223> OTHER INFORMATION: n = g,a,c or t

<400> SEQUENCE: 66

-continued

```
cccaggacgt ggaggcgatc acaccgcaga ccctgatcaa catccggccg gtcgtcgccg    60
cgatcaagga gttcttcggc accagccagn tctcgcagtt catggaccag aacaacccgc   120
tgtcgggtct gacccacaag cgtcgtctgt cggcgctggg gccgggtggt ctgtcccgtg   180
agcgtgcggt gctggaagta cgtgacgtgc acccgtcgca ctacggccgc atgtgcccga   240
tcgagacgcc ggaaggcccg aacatcggcc tgatcggttc gctgtcggtg tacgcgcggg   300
tcaacccgtt cggcttcatc gagacgcctt atcggaaggt ggtggatgga gtcgtttctg   360
acgagatcca ctacctaacc gccgacgagg aggaccgcca cgtggtggcg caggccaact   420
cgccgatcga cgagagcggc cggtttgctg agccgcgcgt tctggtccgc cgcaaggcgg   480
gcgaggtgga gtacgtgccc tcgtccgagg tggactacat ggacgtctcg ccgcgccaga   540
tggtgtcggt ggccaccgcg atgattccgt tcctcgaaca cgacgacgcc aaccgtgccc   600
tgatgggtgc caacatgcag cgccaggcgg ttccgctggt gcgcagcgag gcaccgctgg   660
tgggcaccgg catggagttg cgcgcggcga tcgacgcggc gacgt                   705
```

<210> SEQ ID NO 67
<211> LENGTH: 705
<212> TYPE: DNA
<213> ORGANISM: Mycobacterium gordonae

<400> SEQUENCE: 67

```
cccaggacgt ggaggcgatc acaccgcaga ccctgatcaa catccggccg gtcgtcgccg    60
cgatcaagga gttcttcggc accagccagc tctcgcagtt catggaccag aacaacccgc   120
tttcgggcct cacccacaag cgtcgtctgt cggcgctggg gcccggcggt ctgtcccgtg   180
agcgggccgg cctggaggtc cgtgacgtcc acccgtcgca ctacggccgc atgtgcccga   240
tcgagactcc ggaaggcccc aacatcggcc tgatcggctc actgtcggtg tacgcgcggg   300
tgaacccgtt cggcttcatc gagacgccgt atagacgagt ggtgagcgga gttgtcacgg   360
atgagatcca ctacctcacc gccgacgagg aggaccgcca cgtcgtggcg caggccaact   420
cgccgatcga cgagaacggc cggtttgtcg agccgcgcgt tctggtccgc cgcaaggcgg   480
gcgaggtgga gtacgtgccc tcgtccgagg tcgactacat ggacgtctcg ccgcgccaga   540
tggtgtcggt ggccaccgcc atgattccgt tcctcgagca cgacgacgcc aaccgtgccc   600
tgatgggtgc caacatgcag cgccaggcgg ttccgctggt ccgcagcgar gcgccgctgg   660
tgggtaccgg catggagttg cgcgcggcga tcgacgcggc gacgt                   705
```

<210> SEQ ID NO 68
<211> LENGTH: 705
<212> TYPE: DNA
<213> ORGANISM: Mycobacterium gordonae

<400> SEQUENCE: 68

```
cccaggacgt ggaggcgatc acaccgcaga ccctgatcaa catccggccg gtcgtggccg    60
cgatcaagga gttcttcggc accagccagc tgtcgcagtt catggaccag aacaacccgc   120
tgtcgggtct gacccacaag cgtcgcctgt cggcgctggg gccgggtggt ctgtcccgtg   180
agcgtgccgg cctggaggtc cgtgacgtcc acccgtcgca ctacggccgc atgtgcccga   240
tcgagacccc ggaaggcccg aacatcggcc tgatcggctc gctgtcggtg tacgcgcggg   300
tcaacccgtt cgggttcatc gagacgccgt accgcaaggt ggtggaaggt gtcgtctccg   360
acgaaatcca ctacctgacc gccgacgagg aggaccgcca cgtggtggcg caggccaact   420
cgccgatcga cgagagcggt cggttcgtcg agccacgcgt tctggtccgc cggaaggcgg   480
```

-continued gcgaggtcga gtacgtgcct tcgtccgagg tggactacat ggacgtctcg ccgcgccaga 540
tggtgtcggt ggccaccgcg atgattccgt tcctcgagca cgacgacgcc aaccgcgccc 600
tgatgggtgc caacatgcag cgccaggcgg ttccgctggt gcgcagcgar gcaccgctgg 660
tgggcaccgg tatggaattg cgcgcggcga tcgacgcggc gacgt 705

<210> SEQ ID NO 69
<211> LENGTH: 705
<212> TYPE: DNA
<213> ORGANISM: Mycobacterium gordonae

<400> SEQUENCE: 69
cccaggacgt ggaggcgatc acaccgcaga ccctgatcaa catccggccg gtcgtcgccg 60
cgatcaagga gttcttcggc accagccagc tctcgcagtt catggaccag aacaacccgc 120
tttcgggcct cacccacaag cgtcgtctgt cggcgctggg gcccggcggt ctgtcccgtg 180
agcgggccgg cctggaggtc cgtgacgtcc acccgtcgca ctacggccgc atgtgcccga 240
tcgagactcc ggaaggcccc aacatcggcc tgatcggctc actgtcggtg tacgcgcggg 300
tgaacccgtt cggcttcatc gagacgccgt atagacgagt ggtgagcgga gttgtcacgg 360
atgagatcca ctacctcacc gccgacgagg aggaccgcca cgtcgtggcg caggccaact 420
cgccgatcga cgagaacggc cggttcgtcg agccgcgcgt tctggtccgc cgcaaggcgg 480
gcgaggtgga gtacgtgccc tcgtccgagg tcgactacat ggacgtctcg ccgcgccaga 540
tggtgtcggt ggccaccgcc atgattccgt tcctcgagca cgacgacgcc aaccgtgccc 600
tgatgggtgc caacatgcag cgccaggcgg ttccgctggt gcgcagcgag gcgccgctgg 660
tgggtaccgg catggagttg cgcgcggcga tcgacgcggc gacgt 705

<210> SEQ ID NO 70
<211> LENGTH: 705
<212> TYPE: DNA
<213> ORGANISM: Mycobacterium gordonae

<400> SEQUENCE: 70
cccaggacgt ggaggcgatc acaccgcaga ccctgatcaa catccggccg gtcgtcgctg 60
cgatcaagga gttcttcggc accagccagc tctcgcagtt catggaccag aacaacccgc 120
tttcgggcct cacccacaag cgtcgtctgt cggcgctggg gcccggcggt ctgtcccgtg 180
agcgggccgg cctggaggtc cgtgacgtcc acccgtcgca ctacggccgc atgtgcccga 240
tcgagactcc ggaaggcccg aacatcggcc tgatcggctc gctgtcggtg tacgcgcggg 300
tgaacccgtt cggcttcatc gagacgccgt accgcgaggt ggtcgacggt gtggtgacgg 360
acgagatcca ctacctcacc gccgacgagg aggaccgcca cgtcgtggcg caggccaact 420
cgccgatcga cgagaacggc cgcttcgtcg agccgcgcgt tctggtccgc cgcaaggcgg 480
gcgaggtgga gtacgtgccc tcgtccgagg tggactacat ggacgtctcg ccgcgccaga 540
tggtgtcggt ggccaccgcg atgattccgt tcctcgagca cgacgacgcc aaccgtgccc 600
tgatgggtgc caacatgcag cgccaggcgg ttccgctggt ccgcagcgag gcgccgctgg 660
tgggtaccgg catggagttg cgcgcggcga tcgacgcggc gacgt 705

<210> SEQ ID NO 71
<211> LENGTH: 705
<212> TYPE: DNA
<213> ORGANISM: Mycobacterium gordonae -continued

<400> SEQUENCE: 71
cccaggacgt ggaggcgatc acaccgcaga ccctgatcaa catccggccg gtcgtcgccg 60
cgatcaagga gttcttcggc accagccagc tctcgcagtt catggaccag aacaacccgc 120
tgtcgggtct gacccacaag cgtcgtctgt cggcgctggg gccgggtggt ctgtcccgtg 180
agcgtgcggg tctggaagta cgtgacgtgc acccgtcgca ctacggccgc atgtgcccga 240
tcgagacgcc ggaaggcccg aacatcggcc tgatcggttc gctgtcggtg tacgcgcggg 300
tcaacccgtt cggcttcatc gagacgcctt atcggaaggt ggtggatgga gtcgtttctg 360
acgagatcca ctacctcacc gccgacgagg aggaccgcca cgtggtggcg caggccaact 420
cgccgatcga cgagagcggc cggtttgctg agccgcgcgt tctggtccgc cgcaaggcgg 480
gcgaggtgga gtacgtgccc tcgtccgagg tggactacat ggacgtctcg ccgcgccaga 540
tggtgtcggt ggccaccgcg atgattccgt tcctcgaaca cgacgacgcc aaccgtgccc 600
tgatgggtgc caacatgcag cgccaggcgg ttccgctggt gcgcagcgag gcaccgctgg 660
tgggcaccgg catggagttg cgcgcggcga tcgacgcggc gacgt 705

<210> SEQ ID NO 72
<211> LENGTH: 705
<212> TYPE: DNA
<213> ORGANISM: Mycobacterium gordonae

<400> SEQUENCE: 72
cccaggacgt ggaggcgatc acaccgcaga ccctgatcaa catccggccg gtcgtcgccg 60
cgatcaagga gttcttcggc accagccagc tctcgcagtt catggaccag aacaacccgc 120
tgtcgggtct gacccacaag cgtcgtctgt cggcgctggg gccgggtggt ctgtcccgtg 180
agcgtgcggg tctggaagta cgtgacgtgc acccgtcgca ctacggccgc atgtgcccga 240
tcgagacgcc ggaaggcccg aacatcggcc tgatcggttc gctgtcggtg tacgcgcggg 300
tcaacccgtt cggcttcatc gagacgcctt atcggaaggt ggtggatgga gtcgtttctg 360
acgagatcca ctacctcacc gccgacgagg aggaccgcca cgtggtggcg caggccaact 420
cgccgatcga cgagagcggc cggtttgctg agccgcgcgt tctggtccgc cgcaaggcgg 480
gcgaggtgga gtacgtgccc tcgtccgagg tggactacat ggacgtctcg ccgcgccaga 540
tggtgtcggt ggccaccgcg atgattccgt tcctcgaaca cgacgacgcc aaccgtgccc 600
tgatgggtgc caacatgcag cgccaggcgg ttccgctggt gcgcagcgag gcaccgctgg 660
tgggcaccgg catggagttg cgcgcggcga tcgacgcggc gacgt 705

<210> SEQ ID NO 73
<211> LENGTH: 705
<212> TYPE: DNA
<213> ORGANISM: Mycobacterium gordonae
<220> FEATURE:
<221> NAME/KEY: modified_base
<222> LOCATION: (690)...(690)
<223> OTHER INFORMATION: n = g,a,c or t

<400> SEQUENCE: 73
cccaggacgt ggaggcgatc acaccgcaga ccctgatcaa catccggccg gtcgtcgccg 60
cgatcaagga gttcttcggc accagccagc tctcgcagtt catggaccag aacaacccgc 120
tttcgggcct cacccacaag cgtcgtctgt cggcgctggg gcccggcggt ctgtcccgtg 180
agcgggccgg cctggaggtc cgtgacgtcc acccgtcgca ctacggccgc atgtgcccga 240
tcgagactcc ggaaggcccg aacatcggcc tgatcggctc gctgtcggtg tacgcgcggg 300

-continued

```
tgaacccgtt cggcttcatc gagacgccgt accgcgaggt ggtcgacggt gtggtgacgg    360
acgagatcca ctacctcacc gccgacgagg aggaccgcca cgtcgtggcg caggccaact    420
cgccgatcga cgagaacggc cgcttcgtcg agccgcgcgt tctggtccgc cgcaaggcgg    480
gcgaggtgga gtacgtgccc tcgtccgagg tggactacat ggacgtctcg ccgcgccaga    540
tggtgtcggt ggccaccgcg atgattccgt tcctcgaaca cgacgacgcc aaccgtgccc    600
tgatgggtgc caacatgcag cgccaggcgg ttccgctggt ccgcagcgag gcgccgctgg    660
tgggtaccgg catggagttg cgcgcggcgn tcgacgcggc gacgt                    705
```

<210> SEQ ID NO 74
<211> LENGTH: 705
<212> TYPE: DNA
<213> ORGANISM: Mycobacterium gordonae

<400> SEQUENCE: 74

```
cccaggacgt ggaggcgatc acaccgcaga ccctgatcaa catccggccg gtcgtcgccg     60
cgatcaagga gttcttcggc accagccagc tctcgcagtt catggaccag aacaacccgc    120
tgtcgggtct gacccacaag cgtcgtctgt cggcgctggg gccgggtggt ctgtcccgtg    180
agcgtgcggg tctggaagta cgtgacgtgc acccgtcgca ctacggccgc atgtgcccga    240
tcgagacgcc ggaaggcccg aacatcggcc tgatcggttc gctgtcggtg tacgcgcggg    300
tcaacccgtt cggcttcatc gagacgcctt atcggaaggt ggtggatgga gtcgtttctg    360
acgagatcca ctacctcacc gccgacgagg aggaccgcca cgtggtggcg caggccaact    420
cgccgatcga cgagagcggc cggtttgctg agccgcgcgt tctggtccgc cgcaaggcgg    480
gcgaggtgga gtacgtgccc tcgtccgagg tggactacat ggacgtctcg ccgcgccaga    540
tggtgtcggt ggccaccgcg atgattccgt tcctcgaaca cgacgacgcc aaccgtgccc    600
tgatgggtgc caacatgcag cgccaggcgg ttccgctggt gcgcagcgag gcaccgctgg    660
tgggcaccgg catggagttg cgcgcggcga tcgacgcggc gacgt                    705
```

<210> SEQ ID NO 75
<211> LENGTH: 705
<212> TYPE: DNA
<213> ORGANISM: Mycobacterium gordonae

<400> SEQUENCE: 75

```
cccaggacgt ggaggcgatc acaccgcaga ccctgatcaa catccggccg gtcgtcgccg     60
cgatcaagga gttcttcggc accagccagc tctcgcagtt catggaccag aacaacccgc    120
tgtcgggtct gacccacaag cgtcgtctct cggcgctggg gccgggtggt ctgtcccgtg    180
agcgcgccgg tctggaggtc cgtgacgtcc acccgtcgca ctacggccgc atgtgcccga    240
tcgagacccc ggaaggtccg aacatcggcc tgatcggctc gctgtcggtg tacgcgcggg    300
tcaacccgtt cggcttcatc gagacgccgt accgggaggt tgtggacggg gtcgtcacag    360
acgagatcca ctacctgacc gccgacgagg aggaccgcca cgtggtggcg caggccaact    420
cgccgatcga cgagaacggc cggtttgtcg agccgcgcgt tctggtccgc cgcaaggcgg    480
gcgaggtgga gtacgtgccc tcgtccgagg tggactacat ggacgtctcg ccgcgccaga    540
tggtgtcggt ggccaccgcg atgatcccgt tcctcgagca cgacgacgcc aaccgtgccc    600
tgatgggcgc caacatgcag cgccaggcgg ttccgctggt gcgtagcgar gcgccgctgg    660
tgggcaccgg catggagctg cgcgcggcga tcgacgcggc gacgt                    705
```

-continued

<210> SEQ ID NO 76
<211> LENGTH: 705
<212> TYPE: DNA
<213> ORGANISM: Mycobacterium gordonae

<400> SEQUENCE: 76
cccaggacgt ggaggcgatc acaccgcaga ccctgatcaa catccggccg gtcgtcgccg 60
cgatcaagga gttcttcggc accagccagc tctcgcagtt catggaccag aacaacccgc 120
tgtcgggtct gacccacaag cgtcgtctgt cggcgctggg gccgggtggt ctgtcccgtg 180
agcgtgcggg tctggaagta cgtgacgtgc acccgtcgca ctacggccgc atgtgcccga 240
tcgagacgcc ggaaggcccg aacatcggcc tgatcggttc gctgtcggtg tacgcgcggg 300
tcaacccgtt cggcttcatc gagacgcctt atcggaaggt ggtggatgga gtcgtttctg 360
acgagatcca ctacctcacc gccgacgagg aggaccgcca cgtggtggcg caggccaact 420
cgccgatcga cgagagcggc cggtttgctg agccgcgcgt tctggtccgc cgcaaggcgg 480
gcgaggtgga gtacgtgccc tcgtccgagg tggactacat ggacgtctcg ccgcgccaga 540
tggtgtcggt ggccaccgcg atgattccgt tcctcgaaca cgacgacgcc aaccgtgccc 600
tgatgggtgc caacatgcag cgccaggcgg ttccgctggt gcgcagcgag gcaccgctgg 660
tgggcaccgg catggagttg cgcgcggcga tcgacgcggc gacgt 705

<210> SEQ ID NO 77
<211> LENGTH: 705
<212> TYPE: DNA
<213> ORGANISM: Mycobacterium gordonae

<400> SEQUENCE: 77
cccaggacgt ggaggcgatc acaccgcaga ccctgatcaa catccggccg gtcgtcgccg 60
cgatcaagga gttcttcggc accagccagc tgtcgcagtt catggaccag aacaacccgc 120
tgtcgggtct gactcacaag cgtcgtctgt cggcgctggg gcctggcggt ctgtcacgtg 180
agcgcgccgg cctggaagtc cgtgacgtcc acccgtcgca ctacggccgg atgtgcccga 240
tcgagacccc ggaaggcccg aacatcggcc tgatcggctc gctgtcggtg tacgcgcggg 300
tcaacccgtt cggcttcatc gagacgcctt atcggaaggt ggtcgacggt gtggtctccg 360
atgagatcca ctacctgacc gccgacgaag gagaccccca cgtggtggcg caggccaact 420
cgccgatcga cgagagcggc cggtttgccg agccgcgcgt tctggtccgc cgcaaggcgg 480
gcgaggtcga gtacgtcccg tcgtccgagg tggactacat ggacgtctcg ccgcgccaga 540
tggtgtcggt ggccaccgcg atgattccgt tcctcgagca cgacgacgcc aaccgtgccc 600
tgatgggtgc caacatgcag cgccaggcgg ttccgctggt gcgcagcgag gcaccgctgg 660
tgggcaccgg tatggagttg cgcgcggcga tcgacgcggc gacgt 705

<210> SEQ ID NO 78
<211> LENGTH: 705
<212> TYPE: DNA
<213> ORGANISM: Mycobacterium gordonae
<220> FEATURE:
<221> NAME/KEY: modified_base
<222> LOCATION: (688)...(688)
<223> OTHER INFORMATION: n = g,a,c or t
<220> FEATURE:
<221> NAME/KEY: modified_base
<222> LOCATION: (701)...(701)
<223> OTHER INFORMATION: n = g,a,c or t
<220> FEATURE:
<221> NAME/KEY: modified_base -continued
<222> LOCATION: (704)...(705)
<223> OTHER INFORMATION: n = g,a,c or t

<400> SEQUENCE: 78
cccaggacgt ggaggcgatc acaccgcaga ccctgatcaa catccggccg gtcgtcgccg 60
cgatcaagga gttcttcggc accagccagc tctcgcagtt catggaccag aacaacccgc 120
tgtcgggtct gacccacaag cgtcgtctgt cggcgctggg gccgggtggt ctgtcccgtg 180
agcgtgcggg tctggaagta cgtgacgtgc acccgtcgca ctacggccgc atgtgcccga 240
tcgagacgcc ggaaggcccg aacatcggcc tgatcggttc gctgtcggtg tacgcgcggg 300
tcaacccgtt cggcttcatc gagacgcctt atcggaaggt ggtggatgga gtcgtttctg 360
acgagatcca ctacctcacc gccgacgagg aggaccgcca cgtggtggcg caggccaact 420
cgccgatcga cgagagcggc cggtttgctg agccgcgcgt tctggtccgc cgcaaggcgg 480
gcgaggtgga gtacgtgccc tcgtccgagg tggactacat ggacgtctcg ccgcgccaga 540
tggtgtcggt ggccaccgcg atgattccgt tcctcgaaca cgacgacgcc aaccgtgccc 600
tgatgggtgc caacatgcag cgccaggcgg ttccgctggt gcgcagcgag gcaccgctgg 660
tgggcaccgg catggagttg cgcgcggnga tcgacgcggc nacnn 705

<210> SEQ ID NO 79
<211> LENGTH: 705
<212> TYPE: DNA
<213> ORGANISM: Mycobacterium gordonae

<400> SEQUENCE: 79
cccaggacgt ggaggcgatc acaccgcaga ccctgatcaa catccggccg gtcgtcgccg 60
cgatcaagga gttcttcggc accagccagc tctcgcagtt catggaccag aacaaccccc 120
tgtcgggtct cacccacaag cggcgtctgt cggcgctcgg gccgggtggt ctgtcgcgtg 180
agcgtgcggg tctggaagtc cgtgacgtcc acccgtcgca ctacggccgc atgtgcccga 240
tcgagacccc ggaaggtccg aacatcggcc tgatcggctc gctgtcggtg tacgcgcggg 300
tcaacccgtt cggcttcatc gagacgcctt atagacgcgt cgtcagcgga gttgtcacgg 360
atgagatcca ctacctgacc gccgacgagg aggaccgcca cgtggtggcg caggccaact 420
cgccgctggc cggtgcttct cactttgctg agccgcgcgt tctggtccgc cgcaaggcgg 480
gcgaggtgga gtacgttccg tcgtccgagg tggactacat ggacgtctcg ccgcgccaga 540
tggtgtcggt ggccaccgcg atgattccgt tcctcgagca cgacgacgcc aaccgtgccc 600
tgatgggcgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 80
<211> LENGTH: 687
<212> TYPE: DNA
<213> ORGANISM: Mycobacterium gordonae

<400> SEQUENCE: 80
ggaggcgatc acaccgcaga ccctgatcaa catccggccg gtcgtcgccg cgatcaagga 60
gttcttcggc accagccagc tctcgcagtt catggaccag aacaacccgc tgtcgggtct 120
gacccacaag cgtcgtctgt cggcgctggg gccgggtggt ctgtcccgtg agcgtgcggg 180
tctggaagta cgtgacgtgc acccgtcgca ctacggccgc atgtgcccga tcgagacgcc 240
ggaaggcccg aacatcggcc tgatcggttc gctgtcggtg tacgcgcggg tcaacccgtt 300

-continued

```
cggcttcatc gagacgcctt atcggaaggt ggtggatgga gtcgtttctg acgagatcca    360

ctacctcacc gccgacgagg aggaccgcca cgtggtggcg caggccaact cgccgatcga    420

cgagagcggc cggtttgctg agccgcgcgt tctggtccgc cgcaaggcgg gcgaggtgga    480

gtacgtgccc tcgtccgagg tggactacat ggacgtctcg ccgcgccaga tggtgtcggt    540

ggccaccgcg atgattccgt tcctcgaaca cgacgacgcc aaccgtgccc tgatgggtgc    600

caacatgcag cgccaggcgg ttccgctggt gcgcagcgag gcaccgctgg tgggcaccgg    660

catggagttg cgcgcggcga tcgacgc                                         687
```

<210> SEQ ID NO 81
<211> LENGTH: 687
<212> TYPE: DNA
<213> ORGANISM: Mycobacterium gordonae

<400> SEQUENCE: 81

```
ggaggcgatc acaccgcaga ccctgatcaa catccggccg gtcgtcgccg cgatcaagga     60

gttcttcggc accagccagc tctcgcagtt catggaccag aacaacccgc tctcgggtct    120

gacccacaag cgtcgtctgt cggcgctggg tccgggtggt ctgtcccgtg agcgcgccgg    180

tctggaggtc cgtgacgtcc acccgtcgca ctacggccgc atgtgcccga tcgagacccc    240

ggaaggtccg aacatcggcc tgatcggctc gctgtcggtg tacgcgcggg tcaacccgtt    300

cggcttcatc gagacgccgt accgggaggt tgtggacggg gtcgttacag acgagatcca    360

ctacctgacc gccgacgagg aggaccgcca cgtggtggcg caggccaact cgccgatcga    420

cgagagcggc cggtttgtcg agccgcgcgt tctggtccgc cgcaaggcgg gcgaggtgga    480

gtacgtgccc tcgtccgagg tggactacat ggacgtctcg ccgcgccaga tggtgtcggt    540

ggccaccgcg atgatcccgt tcctcgagca cgacgacgcc aaccgtgccc tgatgggcgc    600

caacatgcag cgccaggcgg ttccgctggt gcgcagcgag gcgccgctgg tgggtaccgg    660

catggagctg cgcgcggcga tcgacgc                                         687
```

<210> SEQ ID NO 82
<211> LENGTH: 687
<212> TYPE: DNA
<213> ORGANISM: Mycobacterium gordonae

<400> SEQUENCE: 82

```
ggaggcgatc acaccgcaga ccctgatcaa catccggccg gtcgtcgccg cgatcaagga     60

gttcttcggc accagccagc tctcgcagtt catggaccag aacaacccgc tgtcgggtct    120

gacccacaag cgtcgtctgt cggcgctggg gccgggtggt ctgtcccgtg agcgtgcggg    180

tctggaagta cgtgacgtgc acccgtcgca ctacggccgc atgtgcccga tcgagacgcc    240

ggaaggcccg aacatcggcc tgatcggttc gctgtcggtg tacgcgcggg tcaacccgtt    300

cggcttcatc gagacgcctt atcggaaggt ggtggatgga gtcgtttctg acgagatcca    360

ctacctcacc gccgacgagg aggaccgcca cgtggtggcg caggccaact cgccgatcga    420

cgagagcggc cggtttgctg agccgcgcgt tctggtccgc cgcaaggcgg gcgaggtgga    480

gtacgtgccc tcgtccgagg tggactacat ggacgtctcg ccgcgccaga tggtgtcggt    540

ggccaccgcg atgattccgt tcctcgaaca cgacgacgcc aaccgtgccc tgatgggtgc    600

caacatgcag cgccaggcgg ttccgctggt gcgcagcgag gcaccgctgg tgggcaccgg    660

catggagttg cgcgcggcga tcgacgc                                         687
```

-continued

<210> SEQ ID NO 83
<211> LENGTH: 687
<212> TYPE: DNA
<213> ORGANISM: Mycobacterium gordonae
<220> FEATURE:
<221> NAME/KEY: modified_base
<222> LOCATION: (47)...(47)
<223> OTHER INFORMATION: n = g,a,c or t
<220> FEATURE:
<221> NAME/KEY: modified_base
<222> LOCATION: (64)...(64)
<223> OTHER INFORMATION: n = g,a,c or t

<400> SEQUENCE: 83
ggaggcgatc acaccgcaga ctctgatcaa catccggccc gtcgtcnccg cgatcaagga 60
gttnttcggc accagccagc tctcgcagtt catggaccag aacaacccgc tgtccggttt 120
gacgcacaag aggcgtctgt ccgcgctggg gccgggtggt ctgtcccgtg agcgggccgg 180
cctggaggtc cgtgacgtgc acccgtcgca ctacggccgg atgtgcccga tcgagacccc 240
ggaaggtccg aacatcggtc tgatcgggtc gctgtcggtg tacgcgcggg tcaacccgtt 300
cgggttcatc gagacgccct atcggaaggt ggtggacggg gtcgtctcgg atgagatcca 360
ctacctgacc gccgacgagg aggaccgcca cgtcgtggcg caggccaact cgccgatcga 420
cgagaacggc cgcttcgtcg agccgcgtgt gctggtccgc cggaaggcgg gcgaggtgga 480
gtacgtgccg tcgtccgagg tggactacat ggacgtctcg ccgcgccaga tggtgtcggt 540
ggccacggcc atgattccgt tcctcgagca cgacgacgcc aaccgtgccc tgatgggcgc 600
caacatgcag cgccaggcgg ttccgctggt gcgtagcgag gcgccgttgg tgggcaccgg 660
gatggagttg cgcgcggcga tcgacgc 687

<210> SEQ ID NO 84
<211> LENGTH: 705
<212> TYPE: DNA
<213> ORGANISM: Mycobacterium gordonae

<400> SEQUENCE: 84
cccaggacgt ggaggcgatc acaccgcaga ccctgatcaa catccggccg gtcgtcgccg 60
cgatcaagga gttcttcggc accagccagc tgagccagtt catggaccag aacaacccgc 120
tgtccggtct gacccacaag cgccgcctct cggcgctggg ccccggcggt ctgtcccgtg 180
agcgcgccgg cctggaggtc cgtgacgtcc acccctcgca ctacggccgg atgtgcccga 240
tcgagacccc ggagggtccc aacatcggtc tgatcggctc gctgtcggtg tacgcgcggg 300
tgaacccgtt cgggttcatc gagaccccgt accgcaaggt ggtcgacggt gtggtcaccg 360
acgagatcca ctacctgacc gccgacgagg aggaccgcca cgtcgtggcg caggccaact 420
cgccgatcga cgccaagggc cggttcgagg agtcgcgcgt gctggtccgc cggaaggcgg 480
gcgaggtcga gtacgtgccc tcgtccgagg tggactacat ggacgtgtca ccgcgccaga 540
tggtgtcggt ggccaccgcg atgatcccgt tcctcgagca cgatgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 85
<211> LENGTH: 705
<212> TYPE: DNA
<213> ORGANISM: Mycobacterium intracellulare

<400> SEQUENCE: 85

-continued

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccgtt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480

gcgaggtcga gtacgtgccc tcgtccgagg tggactacat ggacgtgtca ccgcgccaga    540

tggtgtcggt ggccaccgcg atgatcccgt tcctcgagca cgatgacgcc aaccgtgccc    600

tgatgggcgc caacatgcag cgccaagcgg ttccgctggt gcgcagcgag gcgccgctgg    660

tgggcaccgg catggagctg cgcgcggcga tcgacgcggc gacgt                    705
```

<210> SEQ ID NO 86
<211> LENGTH: 705
<212> TYPE: DNA
<213> ORGANISM: Mycobacterium intracellulare

<400> SEQUENCE: 86

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccgtt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480

gcgaggtcga gtacgtgccc tcgtccgagg tggactacat ggacgtgtca ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 87
<211> LENGTH: 705
<212> TYPE: DNA
<213> ORGANISM: Mycobacterium intracellulare

<400> SEQUENCE: 87

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccgtt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480
```

-continued

```
gcgaggtcga gtacgtgccc tcgtccgagg tggactacat ggacgtgtcg ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 88
<211> LENGTH: 705
<212> TYPE: DNA
<213> ORGANISM: Mycobacterium intracellulare

<400> SEQUENCE: 88

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccgtt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 89
<211> LENGTH: 705
<212> TYPE: DNA
<213> ORGANISM: Mycobacterium intracellulare

<400> SEQUENCE: 89

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccctt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480

gcgaggtcga gtacgtgccc tcgtccgagg tggactacat ggacgtctcg ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 90
<211> LENGTH: 705
<212> TYPE: DNA
<213> ORGANISM: Mycobacterium intracellulare -continued

<400> SEQUENCE: 90
cccaggacgt ggaggcgatc acaccgcaga ccctgatcaa catccggccg gtcgtcgccg 60
cgatcaagga gttcttcggc accagccagc tgagccagtt catggaccag aacaacccgc 120
tgtccggtct gacccacaag cgccgcctct cggcgctggg ccccggcggt ctgtcccgtg 180
agcgcgccgg cctggaggtc cgtgacgtcc acccctcgca ctacggccgg atgtgcccga 240
tcgagacccc ggagggtccc aacatcggtc tgatcggctc gctgtcggtg tacgcgcggg 300
tgaacccgtt cgggttcatc gagaccccgt accgcaaggt ggtcgacggt gtggtcaccg 360
acgagatcca ctacctgacc gccgacgagg aggaccgcca cgtcgtggcg caggccaact 420
cgccgatcga cgccaagggc cggttcgagg agtcgcgcgt gctggtccgc cggaaggcgg 480
gcgaggtcga gtacgtgccc tcgtccgagg tggactacat ggacgtgtcg ccgcgccaga 540
tggtgtcggt ggccaccgcg atgatcccgt tcctcgagca cgatgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 91
<211> LENGTH: 705
<212> TYPE: DNA
<213> ORGANISM: Mycobacterium intracellulare

<400> SEQUENCE: 91
cccaggacgt ggaggcgatc acaccgcaga ccctgatcaa catccggccg gtcgtcgccg 60
cgatcaagga gttcttcggc accagccagc tgagccagtt catggaccag aacaacccgc 120
tgtccggtct gacccacaag cgccgcctct cggcgctggg ccccggcggt ctgtcccgtg 180
agcgcgccgg cctggaggtc cgtgacgtcc acccctcgca ctacggccgg atgtgcccga 240
tcgagacccc ggagggtccc aacatcggtc tgatcggctc gctgtcggtg tacgcgcggg 300
tgaacccctt cgggttcatc gagaccccgt accgcaaggt ggtcgacggt gtggtcaccg 360
acgagatcca ctacctgacc gccgacgagg aggaccgcca cgtcgtggcg caggccaact 420
cgccgatcga cgccaagggc cggttcgagg agtcgcgcgt gctggtccgc cggaaggcgg 480
gcgaggtcga gtacgtgccc tcgtccgagg tggactacat ggacgtctcg ccgcgccaga 540
tggtgtcggt ggccaccgcg atgatcccgt tcctcgagca cgatgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 92
<211> LENGTH: 705
<212> TYPE: DNA
<213> ORGANISM: Mycobacterium intracellulare

<400> SEQUENCE: 92
cccaggacgt ggaggcgatc acaccgcaga ccctgatcaa catccggccg gtcgtcgccg 60
cgatcaagga gttcttcggc accagccagc tgagccagtt catggaccag aacaacccgc 120
tgtccggtct gacccacaag cgccgcctct cggcgctggg ccccggcggt ctgtcccgtg 180
agcgcgccgg cctggaggtc cgtgacgtcc acccctcgca ctacggccgg atgtgcccga 240
tcgagacccc ggagggtccc aacatcggtc tgatcggctc gctgtcggtg tacgcgcggg 300
tgaacccgtt cgggttcatc gagaccccgt accgcaaggt ggtcgacggt gtggtcaccg 360
acgagatcca ctacctgacc gccgacgagg aggaccgcca cgtcgtggcg caggccaact 420

-continued

```
cgccgatcga cgccaagggc cggttcgagg agtcgcgcgt gctggtccgc cggaaggcgg    480

gcgaggtcga gtacgtgccc tcgtccgagg tggactacat ggacgtgtcg ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 93
<211> LENGTH: 705
<212> TYPE: DNA
<213> ORGANISM: Mycobacterium intracellulare

<400> SEQUENCE: 93

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccgtt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480

gcgaggtcga gtacgtgccc tcgtccgagg tggactacat ggacgtgtca ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 94
<211> LENGTH: 705
<212> TYPE: DNA
<213> ORGANISM: Mycobacterium intracellulare

<400> SEQUENCE: 94

```
cccaggacgt ggaggcgatc acaccgcaga ccctgatcaa catccggccg gtcgtcgccg     60

cgatcaagga gttcttcggc accagccagc tgagccagtt catggaccag aacaacccgc    120

tgtccggtct gacccacaag cgccgcctct cggcgctggg ccccggcggt ctgtcccgtg    180

agcgcgccgg cctggaggtc cgtgacgtcc acccctcgca ctacggccgg atgtgcccga    240

tcgagacccc ggagggtccc aacatcggtc tgatcggctc gctgtcggtg tacgcgcggg    300

tgaacccgtt cgggttcatc gagaccccgt accgcaaggt ggtcgacggt gtggtcaccg    360

acgagatcca ctacctgacc gccgacgagg aggaccgcca cgtcgtggcg caggccaact    420

cgccgatcga cgccaagggc cggttcgagg agtcgcgcgt gctggtccgc cggaaggcgg    480

gcgaggtcga gtacgtgccc tcgtccgagg tggactacat ggacgtgtca ccgcgccaga    540

tggtgtcggt ggccaccgcg atgatcccgt tcctcgagca cgatgacgcc aaccgtgccc    600

tgatgggcgc caacatgcag cgccaggcgg ttccgctggt gcgcagcgag gcgccgctgg    660

tgggcaccgg catggagctg cgcgcggcga tcgacgcggc gacgt                    705
```

<210> SEQ ID NO 95
<211> LENGTH: 705
<212> TYPE: DNA

-continued

<213> ORGANISM: Mycobacterium intracellulare

<400> SEQUENCE: 95
cccaggacgt ggaggcgatc acaccgcaga ccctgatcaa catccggccg gtcgtcgccg 60
cgatcaagga gttcttcggc accagccagc tgagccagtt catggaccag aacaacccgc 120
tgtccggtct gacccacaag cgccgcctct cggcgctggg ccccggcggt ctgtcccgtg 180
agcgcgccgg cctggaggtc cgtgacgtcc acccctcgca ctacggccgg atgtgcccga 240
tcgagacccc ggagggtccc aacatcggtc tgatcggctc gctgtcggtg tacgcgcggg 300
tgaacccgtt cgggttcatc gagaccccgt accgcaaggt ggtcgacggt gtggtcaccg 360
acgagatcca ctacctgacc gccgacgagg aggaccgcca cgtcgtggcg caggccaact 420
cgccgatcga cgccaagggc cggttcgagg agtcgcgcgt gctggtccgc cggaaggcgg 480
gcgaggtcga gtacgtgccc tcgtccgagg tggactacat ggacgtgtca ccgcgccaga 540
tggtgtcggt ggccaccgcg atgatcccgt tcctcgagca cgatgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 96
<211> LENGTH: 705
<212> TYPE: DNA
<213> ORGANISM: Mycobacterium intracellulare

<400> SEQUENCE: 96
cccaggacgt ggaggcgatc acaccgcaga ccctgatcaa catccggccg gtcgtcgccg 60
cgatcaagga gttcttcggc accagccagc tgagccagtt catggaccag aacaacccgc 120
tgtccggtct gacccacaag cgccgcctct cggcgctggg ccccggcggt ctgtcccgtg 180
agcgcgccgg cctggaggtc cgtgacgtcc acccctcgca ctacggccgg atgtgcccga 240
tcgagacccc ggagggtccc aacatcggtc tgatcggctc gctgtcggtg tacgcgcggg 300
tgaacccgtt cgggttcatc gagaccccgt accgcaaggt ggtcgacggt gtggtcaccg 360
acgagatcca ctacctgacc gccgacgagg aggaccgcca cgtcgtggcg caggccaact 420
cgccgatcga cgccaagggc cggttcgagg agtcgcgcgt gctggtccgc cggaaggcgg 480
gcgaggtcga gtacgtgccc tcgtccgagg tggactacat ggacgtgtcg ccgcgccaga 540
tggtgtcggt ggccaccgcg atgatcccgt tcctcgagca cgatgacgcc aaccgtgccc 600
tgatgggcgc caacatgcag cgccaggcgg ttccgctggt gcgcagcgag gcgccgctgg 660
tgggcaccgg catggagctg cgcgcggcga tcgacgcggc gacgt 705

<210> SEQ ID NO 97
<211> LENGTH: 687
<212> TYPE: DNA
<213> ORGANISM: Mycobacterium avium

<400> SEQUENCE: 97
ggaggcgatc acaccgcaga ccctgatcaa catccggccg gtcgtcgccg cgatcaagga 60
gttcttcggc accagccagc tgagccagtt catggaccag aacaacccgc tgtccggtct 120
gacccacaag cgccgcctct cggcgctggg ccccggcggt ctgtcccgtg agcgcgccgg 180
cctggaggtc cgtgacgtcc acccctcgca ctacggccgg atgtgcccga tcgagacccc 240
ggagggtccc aacatcggtc tgatcggctc gctgtcggtg tacgcgcggg tgaacccctt 300
cgggttcatc gagaccccgt accgcaaggt ggtcgacggt gtggtcaccg acgagatcca 360

-continued

```
ctacctgacc gccgacgagg aggaccgcca cgtcgtggcg caggccaact cgccgatcga    420

cgccaagggc cggttcgagg agtcgcgcgt gctggtccgc cggaaggcgg gcgaggtcga    480

gtacgtgccc tcgtccgagg tggactacat ggacgtctcg ccgcgccaga tggtgtcggt    540

ggccaccgcg atgatcccgt tcctcgagca cgatgacgcc aaccgtgccc tgatgggcgc    600

caacatgcag cgccaggcgg ttccactggt gcgcagcgag gcgccgctgg tgggcaccgg    660

catggagctg cgcgcggcga tcgacgc                                        687
```

<210> SEQ ID NO 98
<211> LENGTH: 687
<212> TYPE: DNA
<213> ORGANISM: Mycobacterium avium complex (MAC)

<400> SEQUENCE: 98

```
ggaggcgatc acaccgcaga ccctgatcaa catccggccg gtcgtcgccg cgatcaagga     60

gttcttcggc accagccagc tgagccagtt catggaccag aacaacccgc tgtccggtct    120

gacccacaag cgccgcctct cggcgctggg ccccggcggt ctgtcccgtg agcgcgccgg    180

cctggaggtc cgtgacgtcc acccctcgca ctacggccgg atgtgcccga tcgagacccc    240

ggagggtccc aacatcggtc tgatcggctc gctgtcggtg tacgcgcggg tgaacccctt    300

cgggttcatc gagaccccgt accgcaaggt ggtcgacggt gtggtcaccg acgagatcca    360

ctacctgacc gccgacgagg aggaccgcca cgtcgtggcg caggccaact cgccgatcga    420

cgccaagggc cggttcgagg agtcgcgcgt gctggtccgc cggaaggcgg gcgaggtcga    480

gtacgtgccc tcgtccgagg tggactacat ggacgtctcg ccgcgccaga tggtgtcggt    540

ggccaccgcg atgatcccgt tcctcgagca cgatgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                        687
```

<210> SEQ ID NO 99
<211> LENGTH: 687
<212> TYPE: DNA
<213> ORGANISM: Mycobacterium avium complex (MAC)

<400> SEQUENCE: 99

```
ggaggcgatc acaccgcaga ccctgatcaa catccggccg gtcgtcgccg cgatcaagga     60

gttcttcggc accagccagc tgagccagtt catggaccag aacaacccgc tgtccggtct    120

gacccacaag cgccgcctct cggcgctggg ccccggcggt ctgtcccgtg agcgcgccgg    180

cctggaggtc cgtgacgtcc acccctcgca ctacggccgg atgtgcccga tcgagacccc    240

ggagggtccc aacatcggtc tgatcggctc gctgtcggtg tacgcgcggg tgaacccgtt    300

cgggttcatc gagaccccgt accgcaaggt ggtcgacggt gtggtcaccg acgagatcca    360

ctacctgacc gccgacgagg aggaccgcca cgtcgtggcg caggccaact cgccgatcga    420

cgccaagggc cggttcgagg agtcgcgcgt cctggtccgc cggaaggcgg gcgaggtcga    480

gtacgtgccc tcgtccgagg tggactacat ggacgtgtcg ccgcgccaga tggtgtcggt    540

ggccaccgcg atgatcccgt tcctcgagca cgatgacgcc aaccgtgccc tgatgggcgc    600

caacatgcag cgccaggcgg ttccgctggt gcgcagcgag gcgccgctgg tgggcaccgg    660

catggagctg cgcgcggcga tcgacgc                                        687
```

<210> SEQ ID NO 100

-continued

<211> LENGTH: 687
<212> TYPE: DNA
<213> ORGANISM: Mycobacterium avium complex (MAC)

<400> SEQUENCE: 100
ggaggcgatc acaccgcaga ccctgatcaa catccggccg gtcgtcgccg cgatcaagga 60
gttcttcggc accagccagc tgagccagtt catggaccag aacaacccgc tgtccggtct 120
gacccacaag cgccgcctct cggcgctggg ccccggcggt ctgtcccgtg agcgcgccgg 180
cctggaggtc cgtgacgtcc acccctcgca ctacggccgg atgtgcccga tcgagacccc 240
ggagggtccc aacatcggtc tgatcggctc gctgtcggtg tacgcgcggg tgaacccgtt 300
cgggttcatc gagaccccgt accgcaaggt ggtcgacggt gtggtcaccg acgagatcca 360
ctacctgacc gccgacgagg aggaccgcca cgtcgtggcg caggccaact cgccgatcga 420
cgccaagggc cggttcgagg agtcgcgcgt gctggtccgc cggaaggcgg gcgaggtcga 480
gtacgtgccc tcgtccgagg tggactacat ggacgtgtcg ccgcgccaga tggtgtcggt 540
ggccaccgcg atgatcccgt tcctcgagca cgatgacgcc aaccgtgccc tgatgggcgc 600
caacatgcag cgccaggcgg ttccgctggt gcgcagcgag gcgccgctgg tgggcaccgg 660
catggagctg cgcgcggcga tcgacgc 687

<210> SEQ ID NO 101
<211> LENGTH: 705
<212> TYPE: DNA
<213> ORGANISM: Mycobacterium kansasii

<400> SEQUENCE: 101
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240
tcgagacccc ggagggtccc aacatcggcc tgatcggctc gctgtcggtg tacgcacggg 300
tcaacccgtt cggcttcatc gagacgccgt accgcaaggt gatcgacggt ctcgttactg 360
atgagatcca ctacttgacg gccgacgagg aggaccgcca cgtcgtggca caggccaact 420
cgccgatcga cgctgagggc cggttcgtcg agccgcgcgt gctggtgcgc cgcaaggccg 480
gcgaggtcga gtacgtggcc tcgtcggagg tggactacat ggacgtctcg ccgcgccaga 540
tggtgtcggt ggccacggcc atgattccgt tcctcgagca cgacgacgcc aaccgggctc 600
tgatgggtgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 102
<211> LENGTH: 705
<212> TYPE: DNA
<213> ORGANISM: Mycobacterium kansasii

<400> SEQUENCE: 102
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtt cgtgacgtgc acccgtcgca ctacggccgc atgtgcccga 240
tcgagacccc ggagggtccc aacatcggcc tgatcggctc gctgtcggtg tacgcacggg 300

-continued

```
tcaacccgtt cggcttcatc gagacgccgt accgcaaggt gatcgacggt ctcgttactg    360
atgagatcca ctacttgacg gccgacgagg aggaccgcca cgtcgtggca caggccaact    420
cgccgatcga cgctgagggc cggttcgtcg agccgcgcgt gctggtgcgc cgcaaggccg    480
gcgaggtcga gtacgtggcc tcgtcggagg tggactacat ggacgtctcg ccgcgccaga    540
tggtgtcggt ggccacggcc atgattccgt tcctcgagca cgacgacgcc aaccgggctc    600
tgatgggtgc caacatgcag cgccaggcgg ttccgctggt gcgcagcgag gcgccgctgg    660
tgggcaccgg catggagttg cgcgcggcga tcgacgcggc gacgt                    705
```

<210> SEQ ID NO 103
<211> LENGTH: 705
<212> TYPE: DNA
<213> ORGANISM: Mycobacterium kansasii

<400> SEQUENCE: 103

```
cccaggacgt ggaggcgatc acaccgcaga cactgatcaa catccgcccg gtggtcgccg     60
ccatcaagga gttcttcggc accagccagc tctcccagtt catggaccag aacaacccgc    120
tgtcgggcct cacccacaag cgccggcttt cggcgctggg gccgggcggt ctgtcccggg    180
agcgtgccgg gctggaagtg cgtgacgtgc acccgtcgca ctacggccgc atgtgcccga    240
tcgagacccc ggagggtccc aacatcggcc tgatcggctc gctgtcggtg tacgcacggg    300
tcaacccgtt cggcttcatc gagacgccgt accgcaaggt gatcgacggt ctcgttactg    360
atgagatcca ctacttgacg gccgacgagg aggaccgcca cgtcgtggca caggccaact    420
cgccgatcga cgctgagggc cggttcgtcg agccgcgcgt gctggtgcgc cgcaaggccg    480
gcgaggtcga gtacgtggcc tcgtcggagg tggactacat ggacgtctcg ccgcgccaga    540
tggtgtcggt ggccacggcc atgattccgt tcctcgagca cgacgacgcc aaccgggctc    600
tgatgggtgc caacatgcag cgccaggcgg ttccgctggt gcgcagcgag gcgccgctgg    660
tgggcaccgg catggagttg cgcgcggcga tcgacgcggc gacgt                    705
```

<210> SEQ ID NO 104
<211> LENGTH: 705
<212> TYPE: DNA
<213> ORGANISM: Mycobacterium kansasii

<400> SEQUENCE: 104

```
cccaggacgt ggaggcgatc acaccgcaga cactgatcaa catccgcccg gtggtcgccg     60
ccatcaagga gttcttcggc accagccagc tctcccagtt catggaccag aacaacccgc    120
tgtcgggcct cacccacaag cgccggcttt cggcgctggg gccgggcggt ctgtcccggg    180
agcgtgccgg gctggaagtg cgtgacgtgc acccgtcgca ctacggccgc atgtgcccga    240
tcgagacccc ggagggtccc aacatcggcc tgatcggctc gctgtcggtg tacgcacggg    300
tcaacccgtt cggcttcatc gagacgccgt accgcaaggt gatcgacggt ctcgttactg    360
atgagatcca ctacttgacg gccgacgagg aggaccgcca cgtcgtggca caggccaact    420
cgccgatcga cgctgagggc cggttcgtcg agccgcgcgt gctggtgcgc cgcaaggccg    480
gcgaggtcga gtacgtggcc tcgtcggagg tggactacat ggacgtctcg ccgcgccaga    540
tggtgtcggt ggccacggcc atgattccgt tcctcgagca cgacgacgcc aaccgggctc    600
tgatgggtgc caacatgcag cgccaggcgg ttccgctggt gcgcagcgag gcgccgctgg    660
tgggcaccgg catggagttg cgcgcggcga tcgacgcggc gacgt                    705
```

-continued

<210> SEQ ID NO 105
<211> LENGTH: 705
<212> TYPE: DNA
<213> ORGANISM: Mycobacterium kansasii

<400> SEQUENCE: 105
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240
tcgagacccc ggagggtccc aacatcggcc tgatcggctc gctgtcggtg tacgcacggg 300
tcaacccgtt cggcttcatc gagacgccgt accgcaaggt gatcgacggt ctcgttactg 360
atgagatcca ctacttgacg gccgacgagg aggaccgcca cgtcgtggca caggccaact 420
cgccgatcga cgctgagggc cggttcgtcg agccgcgcgt gctggtgcgc cgcaaggccg 480
gcgaggtcga gtacgtggcc tcgtcggagg tggactacat ggacgtctcg ccgcgccaga 540
tggtgtcggt ggccacggcc atgattccgt tcctcgagca cgacgacgcc aaccgggctc 600
tgatgggtgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 106
<211> LENGTH: 705
<212> TYPE: DNA
<213> ORGANISM: Mycobacterium kansasii

<400> SEQUENCE: 106
cccaggacgt ggaggcgatc acaccgcaga cactgatcaa catccgcccg gtggtcgccg 60
ccatcaagga gttcttcggc accagccagc tgtcgcagtt catggaccag aacaacccgt 120
tgtcgggcct gacccacaag cgccggcttt cggcgctggg gccgggcggt ctgtcccgtg 180
agcgtgccgg cctggaagtg cgtgacgtgc acccttcgca ctacggccgg atgtgcccga 240
tcgagacccc ggagggtccc aacatcggcc tgatcggatc gctgtcggtg tacgcgcggg 300
tcaacccgtt cggcttcatc gagacgccgt accggaaggt gatcgacggg ctggtcaccg 360
atgagatcca ctacctgacg gccgacgaag aggaccgcca cgtcgtggca caggccaact 420
cgccgatcga cgctgacggc cgctttgtcg agccgcgcgt tctggtgcgc cgcaaggcgg 480
gcgaggtcga atacgtcgcc tcctccgagg tggactacat ggacgtctcg ccacgccaaa 540
tggtgtcggt ggccaccgcg atgatcccgt tcctcgagca cgacgacgcc aaccgggcac 600
tgatgggcgc caacatgcag cgtcaggcgg ttccgctggt acgcagcgag gcgccgctgg 660
tgggcaccgg catggagttg cgcgcggcga tcgacgcggc gacgt 705

<210> SEQ ID NO 107
<211> LENGTH: 705
<212> TYPE: DNA
<213> ORGANISM: Mycobacterium kansasii

<400> SEQUENCE: 107
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240

-continued tcgagacccc ggagggtccc aacatcggcc tgatcggctc gctgtcggtg tacgcacggg 300
tcaacccgtt cggcttcatc gagacgccgt accgcaaggt gatcgacggt ctcgttactg 360
atgagatcca ctacttgacg gccgacgagg aggaccgcca cgtcgtggca caggccaact 420
cgccgatcga cgctgagggc cggttcgtcg agccgcgcgt gctggtgcgc cgcaaggccg 480
gcgaggtcga gtacgtggcc tcgtcggagg tggactacat ggacgtctcg ccgcgccaga 540
tggtgtcggt ggccacggcc atgattccgt tcctcgagca cgacgacgcc aaccgggctc 600
tgatgggtgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 108
<211> LENGTH: 705
<212> TYPE: DNA
<213> ORGANISM: Mycobacterium kansasii

<400> SEQUENCE: 108
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240
tcgagacccc ggagggtccc aacatcggcc tgatcggctc gctgtcggtg tacgcacggg 300
tcaacccgtt cggcttcatc gagacgccgt accgcaaggt gatcgacggt ctcgttactg 360
atgagatcca ctacttgacg gccgacgagg aggaccgcca cgtcgtggca caggccaact 420
cgccgatcga cgctgagggc cggttcgtcg agccgcgcgt gctggtgcgc cgcaaggccg 480
gcgaggtcga gtacgtggcc tcgtcggagg tggactacat ggacgtctcg ccgcgccaga 540
tggtgtcggt ggccacggcc atgattccgt tcctcgagca cgacgacgcc aaccgggctc 600
tgatgggtgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 109
<211> LENGTH: 626
<212> TYPE: DNA
<213> ORGANISM: Mycobacterium kansasii

<400> SEQUENCE: 109
tccgcccggt ggtcgccgcc atcaaggagt tcttcggcac cagccagctc tcccagttca 60
tggaccagaa caacccgctg tcgggcctca cccacaagcg ccggctttcg gcgctggggc 120
cgggcggtct gtcccgggag cgtgccgggc tggaagtgcg tgacgtgcac ccgtcgcact 180
acggccgcat gtgcccgatc gagaccccgg agggtcccaa catcggcctg atcggctcgc 240
tgtcggtgta cgcacgggtc aacccgttcg gcttcatcga gacgccgtac cgcaaggtga 300
tcgacggtct cgttactgat gagatccact acttgacggc cgacgaggag gaccgccacg 360
tcgtggcaca ggccaactcg ccgatcgacg ctgagggccg gttcgtcgag ccgcgcgtgc 420
tggtgcgccg caaggccggc gaggtcgagt acgtggcctc gtcggaggtg gactacatgg 480
acgtctcgcc gcgccagatg gtgtcggtgg ccacggccat gattccgttc ctcgagcacg 540
acgacgccaa ccgggctctg atgggtgcca acatgcagcg ccaggcggtt ccgctggtgc 600
gcagcgaggc gccgctggtg ggcacc 626

-continued

<210> SEQ ID NO 110
<211> LENGTH: 705
<212> TYPE: DNA
<213> ORGANISM: Mycobacterium kansasii

<400> SEQUENCE: 110
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240
tcgagacccc ggagggtccc aacatcggcc tgatcggctc gctgtcggtg tacgcacggg 300
tcaacccgtt cggcttcatc gagacgccgt accgcaaggt gatcgacggt ctcgttactg 360
atgagatcca ctacttgacg gccgacgagg aggaccgcca cgtcgtggca caggccaact 420
cgccgatcga cgctgagggc cggttcgtcg agccgcgcgt gctggtgcgc cgcaaggccg 480
gcgaggtcga gtacgtggcc tcgtcggagg tggactacat ggacgtctcg ccgcgccaga 540
tggtgtcggt ggccacggcc atgattccgt tcctcgagca cgacgacgcc aaccgggctc 600
tgatgggtgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 111
<211> LENGTH: 705
<212> TYPE: DNA
<213> ORGANISM: Mycobacterium kansasii

<400> SEQUENCE: 111
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240
tcgagacccc ggagggtccc aacatcggcc tgatcggctc gctgtcggtg tacgcacggg 300
tcaacccgtt cggcttcatc gagacgccgt accgcaaggt gatcgacggt ctcgttactg 360
atgagatcca ctacttgacg gccgacgagg aggaccgcca cgtcgtggca caggccaact 420
cgccgatcga cgctgagggc cggttcgtcg agccgcgcgt gctggtgcgc cgcaaggccg 480
gcgaggtcga gtacgtggcc tcgtcggagg tggactacat ggacgtctcg ccgcgccaga 540
tggtgtcggt ggccacggcc atgattccgt tcctcgagca cgacgacgcc aaccgggctc 600
tgatgggtgc caacatgcag cgccaggcgg ttccgctggt gcgcagcgag gcgccgctgg 660
tgggcaccgg catggagttg cgcgcggcga tcgacgcggc gacgt 705

<210> SEQ ID NO 112
<211> LENGTH: 705
<212> TYPE: DNA
<213> ORGANISM: Mycobacterium kansasii

<400> SEQUENCE: 112
cccaggacgt ggaggcgatc acaccgcaga cactgatcaa catccgcccg gtggtcgccg 60
ccatcaagga gttcttcggc accagccagc tctcccagtt catggaccag aacaacccgc 120
tgtcgggcct cacccacaag cgccggcttt cggcgctggg gccgggcggt ctgtcccggg 180
agcgtgccgg gctggaagtg cgtgacgtgc acccgtcgca ctacggccgc atgtgcccga 240

-continued

```
tcgagacccc ggagggtccc aacatcggcc tgatcggctc gctgtcggtg tacgcacggg    300

tcaacccgtt cggcttcatc gagacgccgt accgcaaggt gatcgacggt ctcgttactg    360

atgagatcca ctacttgacg gccgacgagg aggaccgcca cgtcgtggca caggccaact    420

cgccgatcga cgctgagggc cggttcgtcg agccgcgcgt gctggtgcgc cgcaaggccg    480

gcgaggtcga gtacgtggcc tcgtcggagg tggactacat ggacgtctcg ccgcgccaga    540

tggtgtcggt ggccacggcc atgattccgt tcctcgagca cgacgacgcc aaccgggctc    600

tgatgggtgc caacatgcag cgccaggcgg ttccgctggt gcgcagcgag gcgccgctgg    660

tgggcaccgg catggagttg cgcgcggcga tcgacgcggc gacgt                    705
```

```
<210> SEQ ID NO 113
<211> LENGTH: 705
<212> TYPE: DNA
<213> ORGANISM: Mycobacterium kansasii

<400> SEQUENCE: 113

cccaggacgt ggaggcgatc acaccgcaga cactgatcaa catccgcccg gtggtcgccg     60

ccatcaagga gttcttcggc accagccagc tctcccagtt catggaccag aacaacccgc    120

tgtcgggcct cacccacaag cgccggcttt cggcgccggg gccgggcggt ctgtcccggg    180

agcgtgccgg gctggaagtg cgtgacgtgc acccgtcgca ctacggccgc atgtgcccga    240

tcgagacccc ggagggtccc aacatcggcc tgatcggctc gctgtcggtg tacgcacggg    300

tcaacccgtt cggcttcatc gagacgccgt accgcaaggt gatcgacggt ctcgttactg    360

atgagatcca ctacttgacg gccgacgagg aggaccgcca cgtcgtggca caggccaact    420

cgccgatcga cgctgagggc cggttcgtcg agccgcgcgt gctggtgcgc cgcaaggccg    480

gcgaggtcga gtacgtggcc tcgtcggagg tggactacat ggacgtctcg ccgcgccaga    540

tggtgtcggt ggccacggcc atgattccgt tcctcgagca cgacgacgcc aaccgggctc    600

tgatgggtgc caacatgcag cgccaggcgg ttccgctggt gcgcagcgag gcgccgctgg    660

tgggcaccgg catggagttg cgcgcggcga tcgacgcggc gacgt                    705
```

```
<210> SEQ ID NO 114
<211> LENGTH: 705
<212> TYPE: DNA
<213> ORGANISM: Mycobacterium kansasii

<400> SEQUENCE: 114

cccaggacgt ggaggcgatc acaccgcaga cactgatcaa catccgcccg gtggtcgccg     60

ccatcaagga gttcttcggc accagccagc tctcccagtt catggaccag aacaacccgc    120

tgtcgggcct cacccacaag cgccggcttt cggcgctggg gccgggcggt ctgtcccggg    180

agcgtgccgg gctggaagtg cgtgacgtgc acccgtcgca ctacggccgc atgtgcccga    240

tcgagacccc ggagggtccc aacatcggcc tgatcggctc gctgtcggtg tacgcacggg    300

tcaacccgtt cggcttcatc gagacgccgt accgcaaggt gatcgacggt ctcgttactg    360

atgagatcca ctacttgacg gccgacgagg aggaccgcca cgtcgtggca caggccaact    420

cgccgatcga cgctgagggc cggttcgtcg agccgcgcgt gctggtgcgc cgcaaggccg    480

gcgaggtcga gtacgtggcc tcgtcggagg tggactacat ggacgtctcg ccgcgccaga    540

tggtgtcggt ggccacggcc atgattccgt tcctcgagca cgacgacgcc aaccgggctc    600

tgatgggtgc caacatgcag cgccaggcgg ttccgctggt gcgcagcgag gcgccgctgg    660
```

-continued

```
tgggcaccgg catggagttg cgcgcggcga tcgacgcggc gacgt                 705


<210> SEQ ID NO 115
<211> LENGTH: 705
<212> TYPE: DNA
<213> ORGANISM: Mycobacterium kansasii

<400> SEQUENCE: 115

cccaggacgt ggaggcgatc acaccgcaga cactgatcaa catccgcccg gtggtcgccg    60

ccatcaagga gttcttcggc accagccagc tctcccagtt catggaccag aacaacccgc   120

tgtcgggcct cacccacaag cgccggcttt cggcgctggg gccgggcggt ctgtcccggg   180

agcgtgccgg gctggaagtg cgtgacgtgc acccgtcgca ctacggccgc atgtgcccga   240

tcgagacccc ggagggtccc aacatcggcc tgatcggctc gctgtcggtg tacgcacggg   300

tcaacccgtt cggcttcatc gagacgccgt accgcaaggt gatcgacggt ctcgttactg   360

atgagatcca ctacttgacg gccgacgagg aggaccgcca cgtcgtggca caggccaact   420

cgccgatcga cgctgagggc cggttcgtcg agccgcgcgt gctggtgcgc cgcaaggccg   480

gcgaggtcga gtacgtggcc tcgtcggagg tggactacat ggacgtctcg ccgcgccaga   540

tggtgtcggt ggccacggcc atgattccgt tcctcgagca cgacgacgcc aaccgggctc   600

tgatgggtgc caacatgcag cgccaggcgg ttccgctggt gcgcagcgag gcgccgctgg   660

tgggcaccgg catggagttg cgcgcggcga tcgacgcggc gacgt                 705


<210> SEQ ID NO 116
<211> LENGTH: 687
<212> TYPE: DNA
<213> ORGANISM: Mycobacterium kansasii

<400> SEQUENCE: 116

ggaggcgatc acaccgcaga cactgatcaa catccgcccg gtggtcgccg ccatcaagga    60

gttcttcggc accagccagc tctcccagtt catggaccag aacaacccgc tgtcgggcct   120

cacccacaag cgccggcttt cggcgctggg gccgggcggt ctgtcccggg agcgtgccgg   180

gctggaagtg cgtgacgtgc acccgtcgca ctacggccgc atgtgcccga tcgagacccc   240

ggagggtccc aacatcggcc tgatcggctc gctgtcggtg tacgcacggg tcaacccgtt   300

cggcttcatc gagacgccgt accgcaaggt gatcgacggt ctcgttactg atgagatcca   360

ctacttgacg gccgacgagg aggaccgcca cgtcgtggca caggccaact cgccgatcga   420

cgctgagggc cggttcgtcg agccgcgcgt gctggtgcgc cgcaaggccg gcgaggtcga   480

gtacgtggcc tcgtcggagg tggactacat ggacgtctcg ccgcgccaga tggtgtcggt   540

ggccacggcc atgattccgt tcctcgagca cgacgacgcc aaccgggctc tgatgggtgc   600

caacatgcag cgccaggcgg ttccgctggt gcgcagcgag gcgccgctgg tgggcaccgg   660

catggagttg cgcgcggcga tcgacgc                                       687


<210> SEQ ID NO 117
<211> LENGTH: 687
<212> TYPE: DNA
<213> ORGANISM: Mycobacterium kansasii

<400> SEQUENCE: 117

ggaggcgatc acaccgcaga cactgatcaa catccgcccg gtggtcgccg ccatcaagga    60

gttcttcggc accagccagc tctcccagtt catggaccag aacaacccgc tgtcgggcct   120

cacccacaag cgccggcttt cggcgctggg gccgggcggt ctgtcccggg agcgtgccgg   180
```

-continued

```
gctggaagtg cgtgacgtgc acccgtcgca ctacggccgc atgtgcccga tcgagacccc    240
ggagggtccc aacatcggcc tgatcggctc gctgtcggtg tacgcacggg tcaacccgtt    300
cggcttcatc gagacgccgt accgcaaggt gatcgacggt ctcgttactg atgagatcca    360
ctacttgacg gccgacgagg aggaccgcca cgtcgtggca caggccaact cgccgatcga    420
cgctgagggc cggttcgtcg agccgcgcgt gctggtgcgc cgcaaggccg gcgaggtcga    480
gtacgtggcc tcgtcggagg tggactacat ggacgtctcg ccgcgccaga tggtgtcggt    540
ggccacggcc atgattccgt tcctcgagca cgacgacgcc aaccgggctc tgatgggtgc    600
caacatgcag cgccaggcgg ttccgctggt gcgcagcgag gcgccgctgg tgggcaccgg    660
catggagttg cgcgcggcga tcgacgc                                        687
```

```
<210> SEQ ID NO 118
<211> LENGTH: 687
<212> TYPE: DNA
<213> ORGANISM: Mycobacterium kansasii

<400> SEQUENCE: 118
```

```
ggaggcgatc acaccgcaga cactgatcaa catccgcccg gtggtcgccg ccatcaagga     60
gttcttcggc accagccagc tctcccagtt catggaccag aacaacccgc tgtcgggcct    120
cacccacaag cgccggcttt cggcgctggg gccgggcggt ctgtcccggg agcgtgccgg    180
gctggaagtg cgtgacgtgc acccgtcgca ctacggccgc atgtgcccga tcgagacccc    240
ggagggtccc aacatcggcc tgatcggctc gctgtcggtg tacgcacggg tcaacccgtt    300
cggcttcatc gagacgccgt accgcaaggt gatcgacggt ctcgttactg atgagatcca    360
ctacttgacg gccgacgagg aggaccgcca cgtcgtggca caggccaact cgccgatcga    420
cgctgagggc cggttcgtcg agccgcgcgt gctggtgcgc cgcaaggccg gcgaggtcga    480
gtacgtggcc tcgtcggagg tggactacat ggacgtctcg ccgcgccaga tggtgtcggt    540
ggccacggcc atgattccgt tcctcgagca cgacgacgcc aaccgggctc tgatgggtgc    600
caacatgcag cgccaggcgg ttccgctggt gcgcagcgag gcgccgctgg tgggcaccgg    660
catggagttg cgcgcggcga tcgacgc                                        687
```

```
<210> SEQ ID NO 119
<211> LENGTH: 687
<212> TYPE: DNA
<213> ORGANISM: Mycobacterium kansasii

<400> SEQUENCE: 119
```

```
ggaggcgatc acaccgcaga cactgatcaa catccgcccg gtggtcgccg ccatcaagga     60
gttcttcggc accagccagc tctcccagtt catggaccag aacaacccgc tgtcgggcct    120
cacccacaag cgccggcttt cggcgctggg gccgggcggt ctgtcccggg agcgtgccgg    180
gctggaagtg cgtgacgtgc acccgtcgca ctacggccgc atgtgcccga tcgagacccc    240
ggagggtccc aacatcggcc tgatcggctc gctgtcggtg tacgcacggg tcaacccgtt    300
cggcttcatc gagacgccgt accgcaaggt gatcgacggt ctcgttactg atgagatcca    360
ctacttgacg gccgacgagg aggaccgcca cgtcgtggca caggccaact cgccgatcga    420
cgctgagggc cggttcgtcg agccgcgcgt gctggtgcgc cgcaaggccg gcgaggtcga    480
gtacgtggcc tcgtcggagg tggactacat ggacgtctcg ccgcgccaga tggtgtcggt    540
ggccacggcc atgattccgt tcctcgagca cgacgacgcc aaccgggctc tgatgggtgc    600
```

-continued caacatgcag cgccaggcgg ttccgctggt gcgcagcgag gcgccgctgg tgggcaccgg 660
catggagttg cgcgcggcga tcgacgc 687

<210> SEQ ID NO 120
<211> LENGTH: 699
<212> TYPE: DNA
<213> ORGANISM: Mycobacterium malmoense

<400> SEQUENCE: 120
ggaggcgatc acaccgcaga cgctgatcaa catccggccg gtggtcgccg cgatcaagga 60
gttcttcggc accagccagc tgtcgcagtt catggaccag aacaacccgc tgtcggggct 120
gacccacaag cgccggctgt cggcgctggg cccgggtggt ctgtcgcgtg agcgtgccgg 180
cttggaggtc cgtgacgtgc acccgtcgca ctacggccgg atgtgcccga tcgagacccc 240
ggagggtccg aacatcggcc tgatcggttc gctgtcggtg tacgcgcggg tcaatccgtt 300
cgggttcatc gagacgcctt atcggaaggt tgtggacggt gtcgttactg acgagatcgt 360
ctacctgacc gccgacgagg aggaccgcca cgtcgtggcg caggccaact cgccgaccag 420
acccaacgag gccggtgccg aggttttcga agaggggcgt gtcctggttc gccgcaaggc 480
gggcgaggtg gagtacgtgc ccagctccga ggtggactac atggacgtct cgccgcggca 540
gatggtgtcc gtggccaccg ccatgattcc gttcctcgag cacgacgacg ccaaccgtgc 600
cctgatgggc gccaacatgc agcgccaggc ggttccgctg gtgcgcagcg aggcgccgct 660
ggtgggcacc ggcatggagc tgcgcgcggc gatcgacgc 699

<210> SEQ ID NO 121
<211> LENGTH: 699
<212> TYPE: DNA
<213> ORGANISM: Mycobacterium malmoense

<400> SEQUENCE: 121
ggaggcgatc acaccgcaga cgctgatcaa catccggccg gtggtcgccg cgatcaagga 60
gttcttcggc accagccagc tgtcgcagtt catggaccag aacaacccgc tgtcggggct 120
gacccacaag cgccggctgt cggcgctggg cccgggtggt ctgtcgcgtg agcgtgccgg 180
cttggaggtc cgtgacgtgc acccgtcgca ctacggccgg atgtgcccga tcgagacccc 240
ggagggtccg aacatcggcc tgatcggttc gctgtcggtg tacgcgcggg tcaatccgtt 300
cgggttcatc gagacgcctt atcggaaggt tgtggacggt gtcgttactg acgagatcgt 360
ctacctgacc gccgacgagg aggaccgcca cgtcgtggcg caggccaact cgccgaccag 420
acccaacgag gccggtgccg aggttttcga agaggggcgt gtcctggttc gccgcaaggc 480
gggcgaggtg gagtacgtgc ccagctccga ggtggactac atggacgtct cgccgcggca 540
gatggtgtcc gtggccaccg ccatgattcc gttcctcgag cacgacgacg ccaaccgtgc 600
cctgatgggc gccaacatgc agcgccaggc ggttccgctg gtgcgcagcg aggcgccgct 660
ggtgggcacc ggcatggagc tgcgcgcggc gatcgacgc 699

<210> SEQ ID NO 122
<211> LENGTH: 699
<212> TYPE: DNA
<213> ORGANISM: Mycobacterium malmoense

<400> SEQUENCE: 122
ggaggcgatc acaccgcaga cgctgatcaa catccggccg gtggtcgccg cgatcaagga 60
gttcttcggc accagccagc tgtcgcagtt catggaccag aacaacccgc tgtcggggct 120

-continued

```
gacccacaag cgccggctgt cggcgctggg cccgggtggt ctgtcgcgtg agcgtgccgg    180

cttggaggtc cgtgacgtgc acccgtcgca ctacggccgg atgtgcccga tcgagacccc    240

ggagggtccg aacatcggcc tgatcggttc gctgtcggtg tacgcgcggg tcaatccgtt    300

cgggttcatc gagacgcctt atcggaaggt tgtggacggt gtcgttactg acgagatcgt    360

ctacctgacc gccgacgagg aggaccgcca cgtcgtggcg caggccaact cgccgaccag    420

acccaacgag gccggtgccg aggttttcga agaggggcgt gtcctggttc gccgcaaggc    480

gggcgaggtg gagtacgtgc ccagctccga ggtggactac atggacgtct cgccgcggca    540

gatggtgtcc gtggccaccg ccatgattcc gttcctcgag cacgacgacg ccaaccgtgc    600

cctgatgggc gccaacatgc agcgccaggc ggttccgctg gtgcgcagcg aggcgccgct    660

ggtgggcacc ggcatggagc tgcgcgcggc gatcgacgc                           699
```

<210> SEQ ID NO 123
<211> LENGTH: 699
<212> TYPE: DNA
<213> ORGANISM: Mycobacterium malmoense

<400> SEQUENCE: 123

```
ggaggcgatc acaccgcaga cgctgatcaa catccggccg gtggtcgccg cgatcaagga     60

gttcttcggc accagccagc tgtcgcagtt catggaccag aacaacccgc tgtcggggct    120

gacccacaag cgccggctgt cggcgctggg cccgggtggt ctgtcgcgtg agcgtgccgg    180

cttggaggtc cgtgacgtgc acccgtcgca ctacggccgg atgtgcccga tcgagacccc    240

ggagggtccg aacatcggcc tgatcggttc gctgtcggtg tacgcgcggg tcaatccgtt    300

cgggttcatc gagacgcctt atcggaaggt tgtggacggt gtcgttactg acgagatcgt    360

ctacctgacc gccgacgagg aggaccgcca cgtcgtggcg caggccaact cgccgaccag    420

acccaacgag gccggtgccg aggttttcga agaggggcgt gtcctggttc gccgcaaggc    480

gggcgaggtg gagtacgtgc ccagctccga ggtggactac atggacgtct cgccgcggca    540

gatggtgtcc gtggccaccg ccatgattcc gttcctcgag cacgacgacg ccaaccgtgc    600

cctgatgggc gccaacatgc agcgccaggc ggttccgctg gtgcgcagcg aggcgccgct    660

ggtgggcacc ggcatggagc tgcgcgcggc gatcgacgc                           699
```

<210> SEQ ID NO 124
<211> LENGTH: 699
<212> TYPE: DNA
<213> ORGANISM: Mycobacterium malmoense

<400> SEQUENCE: 124

```
ggaggcgatc acaccgcaga cgctgatcaa catccggccg gtggtcgccg cgatcaagga     60

gttcttcggc accagccagc tgtcgcagtt catggaccag aacaacccgc tgtcggggct    120

gacccacaag cgccggctgt cggcgctggg cccgggtggt ctgtcgcgtg agcgtgccgg    180

cttggaggtc cgtgacgtgc acccgtcgca ctacggccgg atgtgcccga tcgagacccc    240

ggagggtccg aacatcggcc tgatcggttc gctgtcggtg tacgcgcggg tcaatccgtt    300

cgggttcatc gagacgcctt atcggaaggt tgtggacggt gtcgttactg acgagatcgt    360

ctacctgacc gccgacgagg aggaccgcca cgtcgtggcg caggccaact cgccgaccag    420

acccaacgag gccggtgccg aggttttcga agaggggcgt gtcctggttc gccgcaaggc    480

gggcgaggtg gagtacgtgc ccagctccga ggtggactac atggacgtct cgccgcggca    540
```

-continued gatggtgtcc gtggccaccg ccatgattcc gttcctcgag cacgacgacg ccaaccgtgc 600
cctgatgggc gccaacatgc agcgccaggc ggttccgctg gtgcgcagcg aggcgccgct 660
ggtgggcacc ggcatggagc tgcgcgcggc gatcgacgc 699

<210> SEQ ID NO 125
<211> LENGTH: 699
<212> TYPE: DNA
<213> ORGANISM: Mycobacterium malmoense

<400> SEQUENCE: 125
ggaggcgatc acaccgcaga cgctgatcaa catccggccg gtggtcgccg cgatcaagga 60
gttcttcggc accagccagc tgtcgcagtt catggaccag aacaacccgc tgtcggggct 120
gacccacaag cgccggctgt cggcgctggg cccgggtggt ctgtcgcgtg agcgtgccgg 180
cttggaggtc cgtgacgtgc acccgtcgca ctacggccgg atgtgcccga tcgagacccc 240
ggagggtccg aacatcggcc tgatcggttc gctgtcggtg tacgcgcggg tcaatccgtt 300
cgggttcatc gagacgcctt atcggaaggt tgtggacggt gtcgttactg acgagatcgt 360
ctacctgacc gccgacgagg aggaccgcca cgtcgtggcg caggccaact cgccgaccag 420
acccaacgag gccggtgccg aggttttcga agaggggcgt gtcctggttc gccgcaaggc 480
gggcgaggtg gagtacgtgc ccagctccga ggtggactac atggacgtct cgccgcggca 540
gatggtgtcc gtggccaccg ccatgattcc gttcctcgag cacgacgacg ccaaccgtgc 600
cctgatgggc gccaacatgc agcgccaggc ggttccgctg gtgcgcagcg aggcgccgct 660
ggtgggcacc ggcatggagc tgcgcgcggc gatcgacgc 699

<210> SEQ ID NO 126
<211> LENGTH: 699
<212> TYPE: DNA
<213> ORGANISM: Mycobacterium malmoense

<400> SEQUENCE: 126
ggaggcgatc acaccgcaga cgctgatcaa catccggccg gtggtcgccg cgatcaagga 60
gttcttcggc accagccagc tgtcgcagtt catggaccag aacaacccgc tgtcggggct 120
gacccacaag cgccggctgt cggcgctggg cccgggtggt ctgtcgcgtg agcgtgccgg 180
cttggaggtc cgtgacgtgc acccgtcgca ctacggccgg atgtgcccga tcgagacccc 240
ggagggtccg aacatcggcc tgatcggttc gctgtcggtg tacgcgcggg tcaatccgtt 300
cgggttcatc gagacgcctt atcggaaggt tgtggacggt gtcgttactg acgagatcgt 360
ctacctgacc gccgacgagg aggaccgcca cgtcgtggcg caggccaact cgccgaccag 420
acccaacgag gccggtgccg aggttttcga agaggggcgt gtcctggttc gccgcaaggc 480
gggcgaggtg gagtacgtgc ccagctccga ggtggactac atggacgtct cgccgcggca 540
gatggtgtcc gtggccaccg ccatgattcc gttcctcgag cacgacgacg ccaaccgtgc 600
cctgatgggc gccaacatgc agcgccaggc ggttccgctg gtgcgcagcg aggcgccgct 660
ggtgggcacc ggcatggagc tgcgcgcggc gatcgacgc 699

<210> SEQ ID NO 127
<211> LENGTH: 687
<212> TYPE: DNA
<213> ORGANISM: Mycobacterium marinum

<400> SEQUENCE: 127
ggaggcgatc acaccgcaga cgttgatcaa catccgtccg gtcgttgccg cgatcaagga 60

-continued gttcttcgga accagccagc tgtcgcagtt catggaccag aacaacccgc tctccggtct 120
cacccacaag cgccgcctct cggcgctggg gccgggcggt ctgtcccgtg agcgcgccgg 180
tctggaagtt cgtgacgtgc acccgtcgca ctacggccgg atgtgcccga tcgagacgcc 240
ggaagggccg aacatcggtc tgatcggttc actgtcggtg tacgcccggg tcaacccgtt 300
cgggttcatc gagacgccct accgcaaggt ggtcgacggg gtcgtttccg acgagatcca 360
ctacctgacc gccgacgagg aggaccgcca cgtcgtggcg caggccaact cgccgatcga 420
cgcgcagggc cgcttcgtcg agccgcgcgt gctggtccgc cggaaggcgg gcgaggtcga 480
gtacgtgccc tcgtcagagg tggactacat ggacgtgtcg ccgcgccaga tggtgtcggt 540
ggccaccgcg atgattccgt tcctcgagca cgatgacgcc aaccgcgccc tgatgggtgc 600
caacatgcag cgccaggcgg tcccgctggt gcgcagcgag gcaccgctgg tcggtaccgg 660
tatggagttg cgcgcggcga tcgacgc 687

<210> SEQ ID NO 128
<211> LENGTH: 687
<212> TYPE: DNA
<213> ORGANISM: Mycobacterium marinum

<400> SEQUENCE: 128
ggaggcgatc acaccgcaga cgttgatcaa catccgtccg gtcgttgccg cgatcaagga 60
gttcttcgga accagccagc tgtcgcagtt catggaccag aacaacccgc tctccggtct 120
cacccacaag cgccgcctct cggcgctggg gccgggcggt ctgtcccgtg agcgcgccgg 180
tctggaagtt cgtgacgtgc acccgtcgca ctacggccgg atgtgcccga tcgagacgcc 240
ggaagggccg aacatcggtc tgatcggttc actgtcggtg tacgcccggg tcaacccgtt 300
cgggttcatc gagacgccct accgcaaggt ggtcgacggg gtcgtttccg acgagatcca 360
ctacctgacc gccgacgagg aggaccgcca cgtcgtggcg caggccaact cgccgatcga 420
cgcgcagggc cgcttcgtcg agccgcgcgt gctggtccgc cggaaggcgg gcgaggtcga 480
gtacgtgccc tcgtcagagg tggactacat ggacgtgtcg ccgcgccaga tggtgtcggt 540
ggccaccgcg atgattccgt tcctcgagca cgatgacgcc aaccgcgccc tgatgggtgc 600
caacatgcag cgccaggcgg tcccgctggt gcgcagcgag gcaccgctgg tcggtaccgg 660
tatggagttg cgcgcggcga tcgacgc 687

<210> SEQ ID NO 129
<211> LENGTH: 687
<212> TYPE: DNA
<213> ORGANISM: Mycobacterium marinum

<400> SEQUENCE: 129
ggaggcgatc acaccgcaga cgctgatcaa catccgtccg gtcgttgccg cgatcaagga 60
gttcttcgga accagccagc tgtcgcagtt catggaccag aacaacccgc tctccggtct 120
cacccacaag cgccgcctct cggcgctggg gccgggcggt ctgtcccgtg agcgcgccgg 180
tctggaagtt cgtgacgtgc acccgtcgca ctacggccgg atgtgcccga tcgagacgcc 240
ggaagggccg aacatcggtc tgatcggttc actgtcggtg tacgcccggg tcaacccgtt 300
cgggttcatc gagacgccct accgcaaggt ggtcgacggg gtcgtttccg acgagatcca 360
ctacctgacc gccgacgagg aggaccgcca cgtcgtggcg caggccaact cgccgatcga 420
cgcgcagggc cgcttcgtcg agccgcgcgt gctggtccgc cggaaggcgg gcgaggtcga 480

-continued

```
gtacgtgccc tcgtcagagg tggactacat ggacgtgtcg ccgcgccaga tggtgtcggt    540

ggccaccgcg atgattccgt tcctcgagca cgatgacgcc aaccgcgccc tgatgggtgc    600

caacatgcag cgccaggcgg tcccgctggt gcgcagcgag gcaccgctgg tcggtaccgg    660

tatggagttg cgcgcggcga tcgacgc                                        687
```

<210> SEQ ID NO 130
<211> LENGTH: 687
<212> TYPE: DNA
<213> ORGANISM: Mycobacterium marinum

<400> SEQUENCE: 130

```
ggaggcgatc acaccgcaga cgctgatcaa catccgtccg gtcgttgccg cgatcaagga     60

gttcttcgga accagccagc tgtcgcagtt catggaccag aacaacccgc tctccggtct    120

cacccacaag cgccgcctct cggcgctggg gccgggcggt ctgtcccgtg agcgcgccgg    180

tctggaagtt cgtgacgtgc acccgtcgca ctacggccgg atgtgcccga tcgagacgcc    240

ggaagggccg aacatcggtc tgatcggttc actgtcggtg tacgcccggg tcaacccgtt    300

cgggttcatc gagacgccct accgcaaggt ggtcgacggg gtcgtttccg acgagatcca    360

ctacctgacc gccgacgagg aggaccgcca cgtcgtggcg caggccaact cgccgatcga    420

cgcgcagggc cgcttcgtcg agccgcgcgt gctggtccgc cggaaggcgg gcgaggtcga    480

gtacgtgccc tcgtcagagg tggactacat ggacgtgtcg ccgcgccaga tggtgtcggt    540

ggccaccgcg atgattccgt tcctcgagca cgatgacgcc aaccgcgccc tgatgggtgc    600

caacatgcag cgccaggcgg tcccgctggt gcgcagcgag gcaccgctgg tcggtaccgg    660

tatggagttg cgcgcggcga tcgacgc                                        687
```

<210> SEQ ID NO 131
<211> LENGTH: 687
<212> TYPE: DNA
<213> ORGANISM: Mycobacterium marinum

<400> SEQUENCE: 131

```
ggaggcgatc acaccgcaga cgctgatcaa catcsgtccg gtcgttgccg cgatcaagga     60

gttcttcgga accagccagc tgtcgcagtt catggaccag aacaacccgc tctccggtct    120

cacccacaag cgccgcctct cggcgctggg gccgggcggt ctgtcccgtg agcgcgccgg    180

tctggaagtt cgtgacgtgc acccgtcgca ctacggccgg atgtgcccga tcgagacgcc    240

ggaagggccg aacatcggtc tgatcggttc actgtcggtg tacgcccggg tcaacccgtt    300

cgggttcatc gagacgccct accgcaaggt ggtcgacggg gtcgtttccg acgagatcca    360

ctacctgacc gccgacgagg aggaccgcca cgtcgtggcg caggccaact cgccgatcga    420

cgcgcagggc cgcttcgtcg agccgcgcgt gctggtccgc cggaaggcgg gcgaggtcga    480

gtacgtgccc tcgtcagagg tggactacat ggacgtgtcg ccgcgccaga tggtgtcggt    540

ggccaccgcg atgattccgt tcctcgagca cgatgacgcc aaccgcgccc tgatgggtgc    600

caacatgcag cgccaggcgg tcccgctggt gcgcagcgag gcaccgctgg tcggtaccgg    660

tatggagttg cgcgcggcga tcgacgc                                        687
```

<210> SEQ ID NO 132
<211> LENGTH: 626
<212> TYPE: DNA
<213> ORGANISM: Mycobacterium mucogenicum

<400> SEQUENCE: 132

-continued

```
tccgtcccgt cgtggcggcg atcaaggagt tcttcggtac gtcgcagctg tcgcagttca     60
tggaccagaa caacccgctg tcgggtctga cccacaagcg tcgtctgtcg gcgctgggcc    120
ccggtggtct gtcccgtgag cgcgccggcc tcgaggtccg cgacgtccac tcgtcgcact    180
acggccgcat gtgcccgatc gagacccctg aaggcccgaa catcggtctg atcggctcgc    240
tgtcggtgta cgcgcgggtg aacccgttcg gcttcatcga gaccccgtac cgcaaggtcg    300
tcgacggcat cgtcaccgat cagatcgact acctgaccgc cgacgaggag gaccgccacg    360
tcgtggcgca ggccaactcg ccgctggacg cgaacggcca cttcaccgag gagaagatcc    420
tcgtccgtcg taagggcggc gaggtcgagt tcgtctcggc gaacgacgtc gactacatgg    480
acgtctcgcc gcgccagatg gtgtcggtcg cgaccgcgat gatcccgttc ctggagcacg    540
acgacgccaa ccgcgccctc atgggtgcga acatgcagcg tcaggcggtt ccgctggtgc    600
gcagcgaggc cccgctggtc ggtacc                                         626
```

<210> SEQ ID NO 133
<211> LENGTH: 626
<212> TYPE: DNA
<213> ORGANISM: Mycobacterium mucogenicum

<400> SEQUENCE: 133

```
tccgtcccgt cgtggcggcg atcaaggagt tcttcggcac gtcgcagctg tcgcagttca     60
tggaccagaa caacccgctg tcgggtctga cccacaagcg tcgtctgtcg gcgctgggcc    120
ccggtggtct gtcccgtgag cgcgccggcc tcgaggtccg cgacgtccac tcgtcgcact    180
acggccgcat gtgcccgatc gagaccccgg aaggcccgaa catcggtctg atcggctcgc    240
tgtcggtgta cgcacgggtc aacccgttcg gcttcatcga gaccccgtac cgcaaggtcg    300
tcgacggcat cgtcaccgat cagatcgact acctgaccgc cgacgaggag gaccgccacg    360
tcgtggcgca ggccaactcg ccgctggacg cgaacggcca cttcaccgag gagaagatcc    420
tcgtccgtcg taagggcggc gaggtcgagt tcgtctcggc gaacgacgtc gactacatgg    480
acgtctcgcc gcgccagatg gtgtcggtcg cgaccgcgat gatcccgttc ctcgagcacg    540
acgacgccaa ccgcgccctg atgggtgcga acatgcagcg tcaggcggtt ccgctggtgc    600
gcagcgaggc cccgctggtc ggtacc                                         626
```

<210> SEQ ID NO 134
<211> LENGTH: 626
<212> TYPE: DNA
<213> ORGANISM: Mycobacterium mucogenicum

<400> SEQUENCE: 134

```
tccgtcccgt cgtggcggcg atcaaggagt tcttcggcac gtcgcagctg tcgcagttca     60
tggaccagaa caacccgctg tcgggtctga cccacaagcg tcgtctgtcg gcgctgggcc    120
ccggtggtct gtcccgtgag cgcgccggcc tcgaggtccg cgacgtccac tcgtcgcact    180
acggccgcat gtgcccgatc gagaccccgg aaggcccgaa catcggtctg atcggctcgc    240
tgtcggtgta cgcacgggtc aacccgttcg gcttcatcga gaccccgtac cgcaaggtcg    300
tcgacggcat cgtcaccgat cagatcgact acctgaccgc cgacgaggag gaccgccacg    360
tcgtggcgca ggccaactcg ccgctggacg cgaacggcca cttcaccgag gagaagatcc    420
tcgtccgtcg taagggcggc gaggtcgagt tcgtctcggc gaacgacgtc gactacatgg    480
acgtctcgcc gcgccagatg gtgtcggtcg cgaccgcgat gatcccgttc ctcgagcacg    540
```

-continued

```
acgacgccaa ccgcgccctg atgggtgcga acatgcagcg tcaggcggtt ccgctggtgc    600

gcagcgaggc cccgctggtc ggtacc                                         626
```

<210> SEQ ID NO 135
<211> LENGTH: 626
<212> TYPE: DNA
<213> ORGANISM: Mycobacterium mucogenicum
<220> FEATURE:
<221> NAME/KEY: modified_base
<222> LOCATION: (8)...(8)
<223> OTHER INFORMATION: n = g,a,c or t

<400> SEQUENCE: 135

```
tccgtccngt cgtggcggcg atcaaggagt tcttcggcac gtcgcagctg tcgcagttca     60

tggaccagaa caacccgctg tcgggtctga cccacaagcg tcgtctgtcg gcgctgggcc    120

ccggtggtct gtcccgtgag cgcgccggcc tcgaggtccg cgacgtccac tcgtcgcact    180

acggccgcat gtgcccgatc gagaccccgg aaggcccgaa catcggtctg atcggctcrc    240

tgtcggtgta cgcacgggtc aacccgttcg gcttcatcga gaccccgtac cgcaaggtcg    300

tcgacggcat cgtcaccgat cagatcgact acctgaccgc cgacgaggag gaccgccacg    360

tcgtggcgca ggccaactcg ccgctggacg cgaacggcca cttcaccgag gagaagatcc    420

tcgtccgtcg taagggcggc gaggtcgagt tcgtctcggc gaacgacgtc gactacatgg    480

acgtctcgcc gcgccagatg gtgtcggtcg cgaccgcgat gatcccgttc ctcgagcacg    540

acgacgccaa ccgcgccctg atgggtgcga acatgcagcg tcaggcggtt ccgctggtgc    600

gcagcgaggc cccgctggtc ggtacc                                         626
```

<210> SEQ ID NO 136
<211> LENGTH: 626
<212> TYPE: DNA
<213> ORGANISM: Mycobacterium mucogenicum

<400> SEQUENCE: 136

```
tccgtcccgt cgtggcggcg atcaaggagt tcttcggcac gtsgcagctg tcgcagttca     60

tggaccagaa caacccgctg tcgggtctga cccacaagcg tcgtctgtcg gcgctgggcc    120

ccggtggtct gtcccgtgag cgcgccggcc tcgaggtycg cgacgtccac tcgtcgcact    180

acggccgcat gtgcccgatc gagaccccgg aaggcccgaa catcggtctg atcggctcrc    240

tgtcggtgta cgcacgggtc aacccgttcg gcttcatcga gaccccgtac cgcaaggtcg    300

tcgacggcat cgtcaccgat cagatcgact acctgaccgc cgacgaggag gaccgccacg    360

tcgtggcgca ggccaactcg ccgctggacg cgaacggcca cttcaccgag gagaagatcc    420

tcgtccgtcg taagggcggc gaggtcgagt tcgtctcggc gaacgacgtc gactacatgg    480

acgtctcgcc gcgccagatg gtgtcggtcg cgaccgcgat gatcccgttc ctcgagcacg    540

acgacgccaa ccgcgccctg atgggtgcga acatgcagcg tcaggcggtt ccgctggtgc    600

gcagcgaggc cccgctggtc ggtacc                                         626
```

<210> SEQ ID NO 137
<211> LENGTH: 687
<212> TYPE: DNA
<213> ORGANISM: Mycobacterium nonchromagenicum

<400> SEQUENCE: 137

```
ggaggcgatc acaccgcaga ccctgatcaa catccgcccg gtggtcgccg cgatcaagga     60

gttcttcggc accagccagc tctcccagtt catggaccag aacaacccgt tgtcgggtct    120
```

-continued

```
gacccacaag cgccgcctgt cggcgctggg accgggcggt ctgtcgcgtg agcgggccgg    180

cctggaagtt cgtgacgtgc acccgtccca ctacggccgg atgtgtccga tcgagacccc    240

ggaaggcccg aacatcggtc tgatcgggtc gctgtcggtg tacgcgcggg tcaacccgtt    300

cggtttcatc gagacgccct accgcaaggt cgtggacggg gtcgtcaccg acgagatcca    360

ctacctgacc gccgacgagg aggaccgcca cgtcgtggcg caggccaact cgccgctgga    420

ggaggacggg cacttcaccg aggaccgggt tctggttcgt cgtaagggtg gtgaggtcga    480

gtacgtgtcg tccgccgagg tcgactacat ggacgtctca ccgcgccaga tggtgtcggt    540

ggccacggcc atgattccgt tcctcgagca cgacgacgcc aaccgtgccc tgatgggcgc    600

caacatgcag cgccaggcgg ttccgctggt gcgcagtgag gcgccgctgg tgggtaccgg    660

catggagctg cgcgcggcga tcgacgc                                        687
```

<210> SEQ ID NO 138
<211> LENGTH: 687
<212> TYPE: DNA
<213> ORGANISM: Mycobacterium nonchromagenicum

<400> SEQUENCE: 138

```
ggaggcgatc acaccgcaga ccctgatcaa catccgcccg gtggtcgccg cgatcaagga     60

gttcttcggc accagccagc tctcccagtt catggaccag aacaacccgt tgtcgggtct    120

gacccacaag cgccgcctgt cggcgctggg accgggcggt ctgtcgcgtg agcgggccgg    180

cctggaagtt cgtgacgtgc acccgtccca ctacggccgg atgtgtccga tcgagacccc    240

ggaaggcccg aacatcggtc tgatcgggtc gctgtcggtg tacgcgcggg tcaacccgtt    300

cggtttcatc gagacgccct accgcaaggt cgtggacggg gtcgtcaccg acgagatcca    360

ctacctgacc gccgacgagg aggaccgcca cgtcgtggcg caggccaact cgccgctgga    420

ggaggacggc cacttcaccg aggaccgggt tctggttcgc cgtaagggtg gcgaggtcga    480

gtacgtctcg tccgccgagg tcgactacat ggacgtctca ccgcgccaga tggtgtcggt    540

ggccacggcc atgatcccgt tcctcgagca cgacgacgcc aaccgtgccc tgatgggcgc    600

caacatgcag cgccaggcgg ttccgctggt gcgcagtgag gcgccgctgg tgggtaccgg    660

catggagctg cgcgcggcga tcgacgc                                        687
```

<210> SEQ ID NO 139
<211> LENGTH: 687
<212> TYPE: DNA
<213> ORGANISM: Mycobacterium nonchromagenicum

<400> SEQUENCE: 139

```
ggaggcgatc acaccgcaga ccctgatcaa catccgtccg gtggtcgccg cgatcaagga     60

gttcttcggc accagccagc tctcccagtt catggaccag aacaacccgt tgtcgggtct    120

gacccacaag cgccgcctgt cggcgctggg accgggcggt ctgtcgcgtg agcgggccgg    180

cctggaagtt cgtgacgtgc acccgtccca ctacggccgg atgtgtccga tcgagacccc    240

ggaaggcccg aacatcggtc tgatcgggtc gctgtcggtg tacgcgcggg tcaacccgtt    300

cggtttcatc gagacgccct accgcaaggt cgtggacggg gtcgtcaccg acgagatcca    360

ctacctgacc gccgacgagg aggaccgcca cgttgtggcg caggccaact cgccgctgga    420

ggaggacggc cacttcaccg aggaccgggt tctggttcgt cgtaagggtg gtgaggtcga    480

gtacgtctcg tccgccgagg tcgactacat ggacgtctca ccgcgccaga tggtgtcggt    540
```

-continued

```
ggccacggcc atgattccgt tcctcgagca cgacgacgcc aaccgtgccc tgatgggcgc    600

caacatgcag cgccaggcgg ttccgctggt gcgcagtgag gcgccgctgg tgggtaccgg    660

catggagctg cgcgcggcga tcgacgc                                        687
```

<210> SEQ ID NO 140
<211> LENGTH: 687
<212> TYPE: DNA
<213> ORGANISM: Mycobacterium nonchromagenicum

<400> SEQUENCE: 140

```
ggaggcgatc acaccgcaga ccctgatcaa catccgtccg gtggtcgccg cgatcaagga     60

gttcttcggc accagccagc tctcccagtt catggaccag aacaacccgt tgtcgggtct    120

gacccacaag cgccgcctgt cggcgctggg accgggcggt ctgtcgcgtg agcgggccgg    180

cctggaagtt cgtgacgtgc acccgtccca ctacggccgg atgtgtccga tcgagacccc    240

ggaaggcccg aacatcggtc tgatcgggtc gctgtcggtg tacgcgcggg tcaacccgtt    300

cggtttcatc gagacgccct accgcaaggt cgtggacggg gtcgtcaccg acgagatcca    360

ctacctgacc gccgacgagg aggaccgcca cgttgtggcg caggccaact cgccgctgga    420

ggaggacggc cacttcaccg aggaccgggt tctggttcgt cgtaagggtg gtgaggtcga    480

gtacgtctcg tccgccgagg tcgactacat ggacgtctca ccgcgccaga tggtgtcggt    540

ggccacggcc atgattccgt tcctcgagca cgacgacgcc aaccgtgccc tgatgggcgc    600

caacatgcag cgccaggcgg ttccgctggt gcgcagtgag gcgccgctgg tgggtactgg    660

catggagctg cgcgcggcga tcgacgc                                        687
```

<210> SEQ ID NO 141
<211> LENGTH: 687
<212> TYPE: DNA
<213> ORGANISM: Mycobacterium nonchromagenicum

<400> SEQUENCE: 141

```
ggaggcgatc acaccgcaga ccctgatcaa catccgcccg gtggtcgccg cgatcaagga     60

gttcttcggc accagccagc tctcccagtt catggaccag aacaacccgt tgtcgggtct    120

gacccacaag cgccgcctgt cggcgctggg accgggcggt ctgtcgcgtg agcgggccgg    180

cctggaagtt cgtgacgtgc acccgtccca ctacggccgg atgtgtccga tcgagacccc    240

ggaaggcccg aacatcggtc tgatcgggtc gctgtcggtg tacgcgcggg tcaacccgtt    300

cggtttcatc gagacgccct accgcaaggt cgtggacggg gtcgtcaccg acgagatcca    360

ctacctgacc gccgacgagg aggaccgcca cgtcgtggcg caggccaact cgccgctgga    420

ggaggacggc cacttcaccg aggaccgggt tctggttcgt cgtaagggtg gtgaggtcga    480

gtacgtgtcg tccgccgagg tcgactacat ggacgtctca ccgcgccaga tggtgtcggt    540

ggccacggcc atgattccgt tcctcgagca cgacgacgcc aaccgtgccc tgatgggcgc    600

caacatgcag cgccaggcgg ttccgctggt gcgcagtgag gcgccgctgg tgggtaccgg    660

catggagctg cgcgcggcga tcgacgc                                        687
```

<210> SEQ ID NO 142
<211> LENGTH: 687
<212> TYPE: DNA
<213> ORGANISM: Mycobacterium terrae

<400> SEQUENCE: 142

```
ggaggcgatc acaccgcaga ccctgatcaa catccgcccg gtggtcgccg cgatcaagga     60
```

-continued

```
gttcttcggc accagccagc tctcccagtt catggaccag aacaacccgc tgtcgggtct    120

gacccacaag cgccggctgt cggcgctggg gcccggtggt ctgtcccgtg agcgcgccgg    180

cctggaagtt cgtgacgtgc acccgagcca ctacggccgg atgtgtccga tcgagacccc    240

ggaaggcccg aacatcggtc tgatcgggtc gctgtcggtg tacgcgcggg tgaacccgtt    300

cggcttcatc gagacgccct accgcaaggt ggtcgacggt gtcgtcagcg acgagatcca    360

ctacctgacc gccgacgagg aggaccgcca cgtcgtggcg caggccaact cgccgctgga    420

ggacgacggc cggttcgccg aggaacgagt tctggtgcgc cgcaagggcg gcgaggtcga    480

gtacgtgtcg tcggccgagg ttgactacat ggacgtctcg ccgcgccaga tggtgtcggt    540

ggccacggcc atgattccgt tcctcgagca cgacgacgcc aaccgtgccc tgatgggcgc    600

caacatgcag cgtcaggcgg ttccgctggt gcgcagcgag gcgccgctgg tgggcaccgg    660

catggagctg cgcgcggcga tcgacgc                                        687
```

<210> SEQ ID NO 143
<211> LENGTH: 705
<212> TYPE: DNA
<213> ORGANISM: Mycobacterium scrofulaceum

<400> SEQUENCE: 143

```
cccaggacgt ggaggcgatc acaccgcaga ccctgatcaa catccggccg gtcgtggccg     60

cgatcaagga gttcttcggc accagccagc tctcgcagtt catggaccag aacaacccgc    120

tgtcgggcct gacccacaag cgccgcctgt cggcgctggg cccgggtggt ctgtcccgcg    180

agcgggccgg gctggaggtc cgggacgtgc acccgtcgca ctacggccgg atgtgcccga    240

tcgagacccc ggagggtccc aacatcggtc tgatcggctc gctgtcggtg tacgcgcggg    300

tcaacccgtt cggcttcatc gagacgccgt accgcaaggt ggtcgacggt gtggtcaccg    360

acgagatcca ctacctgacc gccgacgagg aggaccgtca cgtcgtggcg caggccaact    420

cgccgatcga cgcgagcggc cggttcgagg agtcgcgcgt cctggtccgc cggaaggcgg    480

gcgaggtcga gtacgtgccg tcgtccgagg tggactacat ggacgtgtcg ccgcgccaga    540

tggtgtcggt ggccaccgcc atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagttg cgcgcggcga tcgacgcggc gacgt                    705
```

<210> SEQ ID NO 144
<211> LENGTH: 705
<212> TYPE: DNA
<213> ORGANISM: Mycobacterium scrofulaceum

<400> SEQUENCE: 144

```
cccaggacgt ggaggcgatc acaccgcaga ccctgatcaa catccggccg gtcgtggccg     60

cgatcaagga gttcttcggc accagccagc tctcgcagtt catggaccag aacaacccgc    120

tgtcgggcct gacccacaag cgccgcctgt cggcgctggg cccgggtggt ctgtcccgcg    180

agcgggccgg gctggaggtc cgggacgtgc acccgtcgca ctacggccgg atgtgcccga    240

tcgagacccc ggagggtccc aacatcggtc tgatcggctc gctgtcggtg tacgcgcggg    300

tcaacacgtt cggcttcatc gagacgccgt accgcaaggt ggtcgacggt gtggtcaccg    360

acgagatcca ctacctgacc gccgacgagg aggaccgtca cgtcgtggcg caggccaact    420

cgccgatcga cgcgagcggc cggttcgagg agtcgcgcgt cctggtccgc cggaaggcgg    480
```

-continued

```
gcgaggtcga gtacgtgccg tcgtccgagg tggactacat ggacgtgtcg ccgcgccaga    540

tggtgtcggt ggccaccgcc atgatcccgt tcctcgagca cgacgacgcc aaccgtgccc    600

tgatgggcgc caacatgcag cgccaggcgg ttccgctggt gcgcagcgag gcgccgctgg    660

tgggcaccgg catggagttg cgcgcggcga tcgacgcggc gacgt                    705
```

<210> SEQ ID NO 145
<211> LENGTH: 687
<212> TYPE: DNA
<213> ORGANISM: Mycobacterium scrofulaceum

<400> SEQUENCE: 145

```
ggaggcgatc acaccgcaga ccctgatcaa catccggccg gtggtggccg cgatcaagga     60

gttcttcggc accagccagc tctcccagtt catggaccag aacaacccgc tgtcgggtct    120

gacccacaag cgccgcctgt cggcgctggg cccgggcggt ctgtcccgtg agcgggccgg    180

cctcgaggtg cgcgacgtgc acccgtcgca ctacggccgg atgtgcccga tcgagacccc    240

ggagggtccc aacatcggcc tgatcggctc gctgtcggtg tacgcgcggg tcaacccgtt    300

cgggttcatc gagacgccgt accgcaaggt cgtcgacggt gtggtcaccg acgagatcca    360

ctacctgacc gccgacgagg aggaccgcca cgtcgtggcg caggccaact cgccgatcga    420

cgcgagcggc cggttcgagg agtcgcgcgt gctggtccgc cggaaggccg gcgaggtcga    480

gtacgtgccg tcgtccgagg tggactacat ggacgtgtcg ccgcgccaga tggtgtcggt    540

ggccaccgcc atgatcccgt tcctcgagca cgacgacgcc aaccgtgccc tgatgggcgc    600

caacatgcag cgccaggcgg tcccgctggt gcgcagcgag gcgccgctgg tgggcaccgg    660

catggagttg cgcgcggcga tcgacgc                                        687
```

<210> SEQ ID NO 146
<211> LENGTH: 687
<212> TYPE: DNA
<213> ORGANISM: Mycobacterium scrofulaceum

<400> SEQUENCE: 146

```
ggaggcgatc acaccgcaga ccctgatcaa catccggccg gtcgtggccg cgatcaagga     60

gttcttcggc accagccagc tctcgcagtt catggaccag aacaacccgc tgtcgggcct    120

gacccacaag cgccgcctgt cggcgctggg cccgggtggt ctgtcccgcg agcgggccgg    180

gctggaggtc cgggacgtgc acccgtcgca ctacggccgg atgtgcccga tcgagacccc    240

ggagggtccc aacatcggtc tgatcggctc gctgtcggtg tacgcgcggg tcaacccgtt    300

cggcttcatc gagacgccgt accgcaaggt ggtcgacggt gtggtcaccg acgagatcca    360

ctacctgacc gccgacgagg aggaccgtca cgtcgtggcg caggccaact cgccgatcga    420

cgcgagcggc cggttcgagg agtcgcgcgt cctggtccgc cggaaggcgg gcgaggtcga    480

gtacgtgccg tcgtccgagg tggactacat ggacgtgtcg ccgcgccaga tggtgtcggt    540

ggccaccgcc atgatcccgt tcctcgagca cgacgacgcc aaccgtgccc tgatgggcgc    600

caacatgcag cgccaggcgg ttccgctggt gcgcagcgag gcgccgctgg tgggcaccgg    660

catggagttg cgcgcggcga tcgacgc                                        687
```

<210> SEQ ID NO 147
<211> LENGTH: 687
<212> TYPE: DNA
<213> ORGANISM: Mycobacterium scrofulaceum

<400> SEQUENCE: 147

-continued

```
ggaggcgatc acaccgcaga cgctgatcaa catccggccg gtcgtcgccg cgatcaagga    60
gttcttcggc accagccagc tctcccagtt catggaccag aacaacccgc tgtcgggtct   120
gacgcacaag cgccgcctgt cggcgctggg ccccggcggt ctgtcccgtg agcgggccgg   180
gctggaggtc cgcgacgtgc acccgtcgca ctacggccgg atgtgcccga tcgagacccc   240
ggaggggccg aacatcggtc tgatcggctc gctgtcggtg tacgcccggg tcaacccgtt   300
cggcttcatc gagaccccgt accgcaaggt ggtcgacggt gtggtcaccg acgagattca   360
ctacctgacc gccgacgagg aggaccgcca cgtggtggcg caggccaact cgccgatcga   420
cgcgaacggc cggttcgagg agtcgcgcgt cctggtccgc cggaaggcgg gcgaggtcga   480
gtacgtgccg tcgtccgagg tggactacat ggacgtgtcg ccgcgccaga tggtgtcggt   540
ggccaccgcc atgatcccgt tcctcgagca cgacgacgcc aaccgtgccc tgatgggcgc   600
caacatgcag cgtcaggcgg ttccgctggt gcgcagcgag gcgccgctgg tgggcaccgg   660
catggagctg cgcgcggcga tcgacgc                                       687
```

<210> SEQ ID NO 148
<211> LENGTH: 687
<212> TYPE: DNA
<213> ORGANISM: Mycobacterium scrofulaceum

<400> SEQUENCE: 148

```
ggaggcgatc acaccgcaga ccctgatcaa catccggccg gtcgtggccg cgatcaagga    60
gttcttcggc accagccagc tctcgcagtt catggaccag aacaacccgc tgtcgggcct   120
gacccacaag cgccgcctgt cggcgctggg cccgggtggt ctgtcccgcg agcgggccgg   180
gctggaggtc cgggacgtgc acccgtcgca ctacggccgg atgtgcccga tcgagacccc   240
ggagggtccc aacatcggtc tgatcggctc gctgtcggtg tacgcgcggg tcaacccgtt   300
cggcttcatc gagacgccgt accgcaaggt ggtcgacggt gtggtcaccg acgagatcca   360
ctacctgacc gccgacgagg aggaccgtca cgtcgtggcg caggccaact cgccgatcga   420
cgcgagcggc cggttcgagg agtcgcgcgt cctggtccgc cggaaggcgg gcgaggtcga   480
gtacgtgccg tcgtccgagg tggactacat ggacgtgtcg ccgcgccaga tggtgtcggt   540
ggccaccgcc atgatcccgt tcctcgagca cgacgacgcc aaccgtgccc tgatgggcgc   600
caacatgcag cgccaggcgg ttccgctggt gcgcagcgag gcgccgctgg tgggcaccgg   660
catggagttg cgcgcggcga tcgacgc                                       687
```

<210> SEQ ID NO 149
<211> LENGTH: 687
<212> TYPE: DNA
<213> ORGANISM: Mycobacterium scrofulaceum

<400> SEQUENCE: 149

```
ggaggcgatc acaccgcaga ccctgatcaa catccgtccg gtcgtggcgg cgatcaagga    60
gttcttcggc accagccagc tgtcgcagtt catggaccag aacaacccgc tgtcgggtct   120
gacccacaag cgccgcctct cggcgctggg acccggtggt ctgtcccgtg agcgtgcggg   180
cctcgaggtc cgtgacgtac acccgtcgca ctacggccgg atgtgtccga tcgaaacccc   240
ggaggggccg aacatcggtc tgatcgggtc gctgtcggtg tacgcccggg tcaacccgtt   300
cgggttcatc gagacgccgt accgcaaggt tgtcgacggt gtggtcaccg acgagatcga   360
gtacctgacc gccgacgagg aggaccgcca cgtcgtggcg caggccaact cgccgatcga   420
```

-continued

```
cgccgacggg cgcttcgaag agtcgcgtgt gctggttcgc cgcaaggcgg gcgaggtcga    480

gtacgtgccg tcgtccgagg tggactacat ggacgtgtcg ccgcgccaga tggtgtcggt    540

cgccacggcg atgatcccgt tcctcgagca cgacgacgcc aaccgcgccc tgatgggtgc    600

caacatgcag cgccaggcgg ttccgctggt gcgcagcgag gcaccgctgg tgggcaccgg    660

gatggagttg cgcgcggcga tcgacgc                                        687
```

<210> SEQ ID NO 150
<211> LENGTH: 687
<212> TYPE: DNA
<213> ORGANISM: Mycobacterium scrofulaceum

<400> SEQUENCE: 150

```
ggaggcgatc acaccgcaga ccctgatcaa catccgtccg gtcgtggcgg cgatcaagga     60

gttcttcggc accagccagc tctcgcagtt catggaccag aacaacccgc tgtcgggtct    120

tacccacaag cgccgcctgt cggcgctggg gccgggcggt ctgtcccgtg agcgggcggg    180

cctcgaggtc cgcgatgtgc acccgtcgca ctacggccgg atgtgtccga tcgagacccc    240

cgagggtccg aacatcggtc tgatcgggtc gctatcggtg tacgcgcggg tcaacccgtt    300

cgggttcatc gagacgccgt accgcaaggt tgtcgacggt gtggtcaccg acgagatcga    360

gtacctgacc gccgacgagg aggaccgcca cgtcgtggcg caggccaact cgccgatcga    420

ccccgacggc cgcttcgaag agtcgcgcgt gctggttcgc cgtaaggcgg gcgaggtcga    480

atacgtgccg tcgtccgagg tggactacat ggacgtgtcg ccgcgccaga tggtgtcggt    540

ggcgaccgcg atgatcccgt tcctcgaaca cgacgacgcc aaccgtgccc tgatgggtgc    600

caacatgcag cgccaggcgg ttccgctggt acgcagcgag gccccgctgg tcggcaccgg    660

gatggagctg cgcgcggcga tcgacgc                                        687
```

<210> SEQ ID NO 151
<211> LENGTH: 687
<212> TYPE: DNA
<213> ORGANISM: Mycobacterium scrofulaceum

<400> SEQUENCE: 151

```
ggaggcgatc acaccgcaga ccctgatcaa catccgtccg gtcgtggcgg cgatcaagga     60

gttcttcggc accagccagc tctcgcagtt catggaccag aacaacccgc tgtcgggtct    120

tacccacaag cgccgcctgt cggcgctggg gccgggcggt ctgtcccgtg agcgggcggg    180

cctcgaggtc cgcgatgtgc acccgtcgca ctacggccgg atgtgtccga tcgagacccc    240

cgagggtccg aacatcggtc tgatcgggtc gctatcggtg tacgcgcggg tcaacccgtt    300

cgggttcatc gagacgccgt accgcaaggt tgtcgacggt gtggtcaccg acgagatcga    360

gtacctgacc gccgacgagg aggaccgcca cgtcgtggcg caggccaact cgccgatcga    420

ccccgacggc cgcttcgaag agtcgcgcgt gctggttcgc cgtaaggcgg gcgaggtcga    480

atacgtgccg tcgtccgagg tggactacat ggacgtgtcg ccgcgccaga tggtgtcggt    540

ggcgaccgcg atgatcccgt tcctcgaaca cgacgacgcc aaccgtgccc tgatgggtgc    600

caacatgcag cgccaggcgg ttccgctggt acgcagcgag gccccgctgg tcggcaccgg    660

gatggagctg cgcgcggcga tcgacgc                                        687
```

<210> SEQ ID NO 152
<211> LENGTH: 687
<212> TYPE: DNA
<213> ORGANISM: Mycobacterium scrofulaceum -continued

<400> SEQUENCE: 152
ggaggcgatc acaccgcaga ccctgatcaa catccgtccg gtcgtggcgg cgatcaagga 60
gttcttcggc accagccagc tctcgcagtt catggaccag aacaacccgc tgtcgggtct 120
cacccacaag cgccgcctgt cggcgctggg gccgggcggt ctgtcccgtg agcgggcggg 180
cctcgaggtc cgagacgtgc acccgtcgca ctacggccgg atgtgtccga tcgagacccc 240
cgagggtccg aacatcggtc tgatcgggtc gctgtcggtg tacgcgcggg tcaacccgtt 300
cgggttcatc gagacgccgt accgcaaggt tgtcgacggt gtggttaccg acgagatcga 360
gtacctgacc gccgacgagg aggaccgcca cgtggtggcg caggccaact cgccgatcga 420
cgccgacggc cgcttcgaag agtcgcgcgt actggttcgc cgtaaggcgg gcgaggtcga 480
gtacgtgccg tcgtccgagg tggactacat ggacgtgtcg ccgcgccaga tggtgtcggt 540
ggcgaccgcg atgatcccgt tcctcgagca cgacgacgcc aaccgtgccc tgatgggtgc 600
caacatgcag cgccaggcgg ttccgctggt acgcagcgag gccccgctgg tcggcaccgg 660
gatggagctg cgcgcggcga tcgacgc 687

<210> SEQ ID NO 153
<211> LENGTH: 705
<212> TYPE: DNA
<213> ORGANISM: Mycobacterium smegmatis

<400> SEQUENCE: 153
cccaggacgt ggaggcgatc acaccgcaga ccctgatcaa catccgtccc gtcgtggcgg 60
cgatcaagga gttcttcggc accagccagc tgtcgcagtt catggaccag aacaacccgc 120
tgtcgggtct gacccacaag cgtcgtcttt cggcgctggg ccccggcggt ctgtcccgtg 180
agcgcgctgg cctcgaggtc cgcgacgtgc accccagcca ctacggccgc atgtgcccga 240
tcgagacccc tgagggtccc aacatcggtc tgatcggttc gctgtcggtg tacgcccgcg 300
tgaacccgtt cggcttcatc gagacgccgt accgcaaggt cgagaacggt gtggtcaccg 360
accagatcga ctacctgacc gccgacgagg aggaccgcca cgtcgtggcg caggccaact 420
cgccgaccga cgagaacggc cgcttcaccg aggaccgcgt catggtccgc aagaagggcg 480
gcgaggtcga gttcgtctcc gccgaccagg tggactacat ggacgtctcg ccgcgccaga 540
tggtgtcggt cgctacggcc atgatcccgt tcctcgagca cgacgacgcc aaccgcgccc 600
tgatgggtgc caacatgcag cgccaggcgg ttccgctggt gcgcagcgag gcaccgctgg 660
tgggtaccgg tatggaactg cgcgcggcga tcgacgcggc gacgt 705

<210> SEQ ID NO 154
<211> LENGTH: 626
<212> TYPE: DNA
<213> ORGANISM: Mycobacterium smegmatis
<220> FEATURE:
<221> NAME/KEY: modified_base
<222> LOCATION: (9)...(9)
<223> OTHER INFORMATION: n = g,a,c or t

<400> SEQUENCE: 154
tccgtccgnt cgtggcggcg atcaaggagt tcttcggaac gtcgcagctg tcgcagttca 60
tggaccagaa caacccgctg tccggtctga cccacaagcg ccgcctgtcg gcgctgggcc 120
cgggtggtct gtcccgtgag cgcgccggcc tggaggtccg cgacgtgcac tccagccact 180
acggccggat gtgcccgatc gagaccccgg aaggcccgaa catcggcctg atcggttcgc 240

-continued

```
tgtcggtgta cgcgcgggtc aacccgttcg ggttcatcga gaccccgtac cgcaaggtga    300

tcgacggcca ggtcagcgat cagatcgact acctcaccgc cgacgaggag gaccgccaca    360

tcgtggcgca ggccaactcg ccgctcgacg acgagggccg gttcaccgag gacaagatcc    420

tcgtccgccg taagggcggc gaggtcgagt tcgtcgcggc caccgaggtg gactacatgg    480

acgtctcgcc gcgccagatg gtgtcggtcg cgacggcgat gatcccgttc ctcgagcacg    540

acgacgccaa ccgtgccctg atgggtgcca acatgcagcg ccaggcggtt ccgctggtcc    600

gcagcgaggc cccgctggtc ggcacc                                          626
```

<210> SEQ ID NO 155
<211> LENGTH: 705
<212> TYPE: DNA
<213> ORGANISM: Mycobacterium smegmatis

<400> SEQUENCE: 155

```
cccaggacgt ggaggcgatc acaccgcaga ccctgatcaa catccgcccc gtcgtggcgg     60

cgatcaagga gttcttcggc accagccagc tgtcgcagtt catggaccag aacaacccgc    120

tgtcgggtct gacccacaag cgtcgtctgt cggcgctggg cccgggcggt ctgtcccgtg    180

agcgcgccgg cctggaggtc cgcgacgtgc actccagcca ctacggccgg atgtgcccga    240

tcgagacccc ggaaggcccg aacatcggcc tgatcggttc gctgtcggtg tacgcgcggg    300

tgaacccgtt cggtttcatc gagaccccgt accgcaaggt cgtcgacggt gtcatcaccg    360

accagatcga ctacctgacc gccgacgagg aggaccgcca cgtcgtggcg caggccaact    420

cgccgatcga cgacaacggc cggttcaccg aggaccgcgt gctggtgcgc cgcaagggtg    480

gcgaggtcga gttcgtctcc gccaccgagg tggactacat ggacgtctcg ccgcgccaga    540

tggtgtcggt cgcgacggcg atgatcccgt tcctcgagca cgacgacgcc aaccgtgcct    600

tgatgggtgc caacatgcag cgccaggccg ttccgctggt gcgcagcgag gccccgctgg    660

tcggcaccgg tatggagctg cgcgcggcga tcgacgcggc gacgt                     705
```

<210> SEQ ID NO 156
<211> LENGTH: 705
<212> TYPE: DNA
<213> ORGANISM: Mycobacterium smegmatis

<400> SEQUENCE: 156

```
cccaggacgt ggaggcgatc acaccgcaga ccctgatcaa catccgtccc gtcgtggcgg     60

cgatcaagga gttcttcggc accagccagc tgtcgcagtt catggaccag aacaacccgc    120

tgtcgggtct gacccacaag cgtcgtcttt cggcgctggg ccccggcggt ctgtcccgtg    180

agcgcgccgg cctcgaggtc cgcgacgtgc accccagcca ctacggccgc atgtgcccga    240

tcgagacccc tgagggtccc aacatcggtc tgatcggttc gctgtcggtg tacgcccgcg    300

tgaacccgtt cggcttcatc gagacgcctt accgcaaggt cgagaacggt gtggtcaccg    360

accagatcga ctacctgacc gccgacgagg aggaccgcca cgtcgtggcg caggccaact    420

cgccgaccga cgagaacggc cgcttcaccg aggaccgcgt catggtccgc aagaagggcg    480

gcgaggtcga gttcgtctcc gccgaccagg tggactacat ggacgtctcg ccgcgccaga    540

tggtgtcggt cgctacggcc atgatcccgt tcctcgagca cgacgacgcc aaccgcgccc    600

tgatgggtgc caacatgcag cgccaggcgg ttccgctggt gcgcagcgag gcaccgctgg    660

tgggtaccgg tatggaactg cgcgcggcga tcgacgcggc gacgt                     705
```

-continued

<210> SEQ ID NO 157
<211> LENGTH: 705
<212> TYPE: DNA
<213> ORGANISM: Mycobacterium gordonae
<220> FEATURE:
<221> NAME/KEY: modified_base
<222> LOCATION: (688)...(688)
<223> OTHER INFORMATION: n = g,a,c or t
<220> FEATURE:
<221> NAME/KEY: modified_base
<222> LOCATION: (700)...(701)
<223> OTHER INFORMATION: n = g,a,c or t
<220> FEATURE:
<221> NAME/KEY: modified_base
<222> LOCATION: (704)...(705)
<223> OTHER INFORMATION: n = g,a,c or t

<400> SEQUENCE: 157
cccaggacgt ggaggcgatc acaccgcaga ccctgatcaa catccggccc gtcgtcgccg 60
cgatcaagga gttcttcggc accagccagc tctcgcagtt catggaccag aacaacccgc 120
tctccggtct gacgcacaag cggcgtctgt ccgctttggg gccgggcggt ctgtcccgtg 180
agcgggccgg gctggaggtc cgtgacgtgc acccgtcgca ctacggccgg atgtgcccga 240
tcgagacccc ggagggtccg aatatcggtc tgatcgggtc gctgtcggtg tacgcacggg 300
tcaacccgtt cgggttcatc gagacgccgt atagacgcgt cgtcagcgga gttgtcacgg 360
atgagatcca ctacctgacc gccgacgagg aggaccgcca cgtcgtggcg caggccaact 420
cgccgatcga cgccgacgga cggttcgtcg agggacgcgt cctggtccgc cgcaaggcgg 480
gcgaggtcga gtacgtgccc tcctccgagg tggactacat ggacgtgtcg ccgcgccaga 540
tggtgtcggt ggccaccgcg atgattccgt tcctcgagca cgacgacgcc aaccgcgccc 600
tgatgggtgc caacatgcag cgccaggcgg ttccgctggt gcgcagcgag gcaccgctgg 660
tgggtaccgg tatggagttg cgcgcggnga tcgacgcggn nacnn 705

<210> SEQ ID NO 158
<211> LENGTH: 687
<212> TYPE: DNA
<213> ORGANISM: Mycobacterium smegmatis

<400> SEQUENCE: 158
ggaggcgatc acaccgcaga ccctgatcaa catccgtccc gtcgtggcgg cgatcaagga 60
gttcttcggc accagccagc tgtcgcagtt catggaccag aacaacccgc tgtcgggtct 120
gacccacaag cgtcgtcttt cggcgctggg ccccggcggt ctgtcccgtg agcgcgccgg 180
cctcgaggtc cgcgacgtgc accccagcca ctacggccgc atgtgcccga tcgagacccc 240
tgagggtccc aacatcggtc tgatcggttc gctgtcggtg tacgcccgcg tgaacccgtt 300
cggcttcatc gagacgccgt accgcaaggt cgagaacggt gtggtcaccg accagatcga 360
ctacctgacc gccgacgagg aggaccgcca cgtcgtggcg caggccaact cgccgaccga 420
cgagaacggc cgcttcaccg aggaccgcgt catggtccgc aagaagggcg gcgaggtcga 480
gttcgtctcc gccgaccagg tggactacat ggacgtctcg ccgcgccaga tggtgtcggt 540
cgccacggcc atgatcccgt tcctcgagca cgacgacgcc aaccgcgccc tgatgggtgc 600
caacatgcag cgccaggcgg ttccgctggt gcgcagcgag gcaccgctgg tgggtaccgg 660
tatggaactg cgcgcggcga tcgacgc 687

<210> SEQ ID NO 159
<211> LENGTH: 687
<212> TYPE: DNA

-continued

<213> ORGANISM: Mycobacterium szulgai

<400> SEQUENCE: 159
ggaggcgatc acaccgcaga ccctgatcaa catccggccc gtcgtcgccg cgatcaagga 60
gttcttcggc accagccagc tctcgcagtt catggaccag aacaacccgc tctccggtct 120
gacgcacaag cggcgtctgt ccgctttggg gccgggcggt ctgtcccgtg agcgggccgg 180
gctggaggtc cgtgacgtgc acccgtcgca ctacggccgg atgtgcccga tcgagacccc 240
ggagggtccg aatatcggtc tgatcgggtc gctgtcggtg tacgcacggg tcaacccgtt 300
cgggttcatc gagacgccgt atagacgcgt cgtcagcgga gttgtcacgg atgagatcca 360
ctacctgacc gccgacgagg aggaccgcca cgtcgtggcg caggccaact cgccgatcga 420
cgccgacgga cggttcgtcg agggacgtgt cctggtccgc cgcaaggcgg gcgaggtcga 480
gtacgtgccc tcctccgagg tggactacat ggacgtgtcg ccgcgccaga tggtgtcggt 540
ggccaccgcg atgattccgt tcctcgagca cgacgacgcc aaccgcgccc tgatgggtgc 600
caacatgcag cgccaggcgg ttccgctggt gcgcagcgag gcaccgctgg tgggtaccgg 660
tatggagttg cgcgcggcga tcgacgc 687

<210> SEQ ID NO 160
<211> LENGTH: 687
<212> TYPE: DNA
<213> ORGANISM: Mycobacterium szulgai

<400> SEQUENCE: 160
ggaggcgatc acaccgcaga ccctgatcaa catccggccc gtcgtcgccg cgatcaagga 60
gttcttcggc accagccagc tctcgcagtt catggaccag aacaacccgc tctccggtct 120
gacgcacaag cggcgtctgt ccgctttggg gccgggcggt ctgtcccgtg agcgggccgg 180
gctggaggtc cgtgacgtgc acccgtcgca ctacggccgg atgtgcccga tcgagacccc 240
ggagggtccg aatattggtc tgatcgggtc gctgtcggtg tacgcacggg tcaacccgtt 300
cgggttcatc gagacgccgt atagacgcgt cgtcagcgga gttgtcacgg atgagatcca 360
ctacctgacc gccgacgagg aggaccgcca cgtcgtggcg caggccaact cgccgatcga 420
cgccgacgga cggttcgtcg agggacgtgt cctggtccgc cgcaaggcgg gcgaggtcga 480
gtacgtgccc tcctccgagg tggactacat ggacgtgtcg ccgcgccaga tggtgtcggt 540
ggccaccgcg atgattccgt tcctcgagca cgacgacgcc aaccgcgccc tgatgggtgc 600
caacatgcag cgccaggcgg ttccgctggt gcgcagcgag gcaccgctgg tgggtaccgg 660
tatggagttg cgcgcggcga tcgacgc 687

<210> SEQ ID NO 161
<211> LENGTH: 687
<212> TYPE: DNA
<213> ORGANISM: Mycobacterium szulgai

<400> SEQUENCE: 161
ggaggcgatc acaccgcaga ccctgatcaa catccggccc gtcgtcgccg cgatcaagga 60
gttcttcggc accagccagc tctcgcagtt catggaccag aacaacccgc tctccggtct 120
gacgcacaag cggcgtctgt ccgctctggg gccgggcggt ctgtcccgtg agcgggccgg 180
gctggaggtc cgtgacgtgc acccgtcgca ctacggccgg atgtgcccga tcgagacccc 240
ggagggtccg aatatcggtc tgatcgggtc gctgtcggtg tacgcacggg tcaacccgtt 300
cgggttcatc gagacgccgt atagacgcgt cgtcagcgga gttgtcacgg atgagatcca 360

-continued

```
ctacctgacc gccgacgagg aggaccgcca cgtcgtggcg caggccaact cgccgatcga    420
cgccgacgga cggttcgtcg agggacgcgt cctggtccgc cgcaaggcgg gcgaggtcga    480
gtacgtgccc tcctccgagg tggactacat ggacgtgtcg ccgcgccaga tggtgtcggt    540
ggccaccgcg atgattccgt tcctcgagca cgacgacgcc aaccgcgccc tgatgggtgc    600
caacatgcag cgccaggcgg ttccgctggt gcgcagcgag gcaccgctgg tgggtaccgg    660
tatggagttg cgcgcggcga tcgacgc                                         687
```

<210> SEQ ID NO 162
<211> LENGTH: 687
<212> TYPE: DNA
<213> ORGANISM: Mycobacterium szulgai

<400> SEQUENCE: 162

```
ggaggcgatc acaccgcaga ccctgatcaa catccggccc gtcgtcgccg cgatcaagga     60
gttcttcggc accagccagc tctcgcagtt catggaccag aacaacccgc tctccggtct    120
gacgcacaag cggcgtctgt ccgctctggg gccgggcggt ctgtcccgtg agcgggccgg    180
gctggaggtc cgtgacgtgc acccgtcgca ctacggccgg atgtgcccga tcgagacccc    240
ggagggtccg aatatcggtc tgatcgggtc gctgtcggtg tacgcacggg tcaacccgtt    300
cgggttcatc gagacgccgt atagacgcgt cgtcagcgga gttgtcacgg atgagatcca    360
ctacctgacc gccgacgagg aggaccgcca cgtcgtggcg caggccaact cgccgatcga    420
cgccgacgga cggttcgtcg agggacgcgt cctggtccgc cgcaaggcgg gcgaggtcga    480
gtacgtgccc tcctccgagg tggactacat ggacgtgtcg ccgcgccaga tggtgtcggt    540
ggccaccgcg atgattccgt tcctcgagca cgacgacgcc aaccgcgccc tgatgggtgc    600
caacatgcag cgccaggcgg ttccgctggt gcgcagcgag gcaccgctgg tgggtaccgg    660
tatggagttg cgcgcggcga tcgacgc                                         687
```

<210> SEQ ID NO 163
<211> LENGTH: 687
<212> TYPE: DNA
<213> ORGANISM: Mycobacterium szulgai

<400> SEQUENCE: 163

```
ggaggcgatc acaccgcaga ccctgatcaa catccggccc gtcgtcgccg cgatcaagga     60
gttcttcggc accagccagc tctcgcagtt catggaccag aacaacccgc tctccggtct    120
gacgcacaag cggcgtctgt ccgctttggg gccgggcggt ctgtcccgtg agcgggccgg    180
gctggaggtc cgtgacgtgc acccgtcgca ctacggccgg atgtgcccga tcgagacccc    240
ggagggtccg aatatcggtc tgatcgggtc gctgtcggtg tacgcacggg tcaacccgtt    300
cgggttcatc gagacgccgt atagacgcgt cgtcagcgga gttgtcacgg atgagatcca    360
ctacctgacc gccgacgagg aggaccgcca cgtcgtggcg caggccaact cgccgatcga    420
cgccgacgga cggttcgtcg agggacgtgt cctggtccgc cgcaaggcgg gcgaggtcga    480
gtacgtgccc tcctccgagg tggactacat ggacgtgtcg ccgcgccaga tggtgtcggt    540
ggccaccgcg atgattccgt tcctcgagca cgacgacgcc aaccgcgccc tgatgggtgc    600
caacatgcag cgccaggcgg ttccgctggt gcgcagcgag gcaccgctgg tgggtaccgg    660
tatggagttg cgcgcggcga tcgacgc                                         687
```

<210> SEQ ID NO 164

-continued

<211> LENGTH: 687
<212> TYPE: DNA
<213> ORGANISM: Mycobacterium terrae

<400> SEQUENCE: 164
ggaggcgatc acaccgcaga ccctgatcaa catccgcccg gtggtcgccg cgattaagga 60
gttcttcggc accagccagc tctcgcagtt catggaccag aacaacccgc tgtcgggtct 120
gacccacaag cgccggctgt cggcgctggg cccgggtggt ctgtcccgtg aacgggccgg 180
gcttgaggtc cgtgacgtgc acccgtccca ctacggccgg atgtgtccga tcgagacccc 240
ggagggtccg aacatcggtc tgatcggctc gctggcgact tacgcgcggg tcaacccgtt 300
cgggttcatc gaaaccccgt accgcaaggt caacgacggt gtggtcagcg atgagatcgt 360
ctacctgacc gccgacgagg aggaccgcca cgtcgtggcg caggccaact cgccgctgga 420
ggacgacaat cgcttcaccg aggaccgggt tctggtgcgc cgcaagggcg gcgaggtcga 480
gtacgtgtcg tcggccgagg tcgactacat ggacgtctcg ccgcgccaga tggtgtcggt 540
ggccacggcc atgatcccgt tcctggagca cgacgacgcc aaccgggccc tgatgggtgc 600
caacatgcag cgtcaggcgg ttcccctggt gcgcagcgag gcgccgctgg tgggcaccgg 660
catggagctg cgcgcggcga tcgacgc 687

<210> SEQ ID NO 165
<211> LENGTH: 687
<212> TYPE: DNA
<213> ORGANISM: Mycobacterium terrae

<400> SEQUENCE: 165
ggaggcgatc acaccgcaga ccttgatcaa catccgcccg gtggtcgccg cgatcaagga 60
gttcttcggc accagccagc tctcgcagtt catggaccag aacaacccgc tgtcgggtct 120
gacccacaag cgccggctgt cggcgctggg cccgggtggt ctgtcccgtg agcgggccgg 180
gcttgaggtc cgtgacgtgc acccgtccca ctacggccgg atgtgtccga tcgagacccc 240
ggagggtccg aacatcggtc tgatcggctc gctggcgact tacgcgcggg tcaacccgtt 300
cgggttcatc gaaaccccgt accgcaaggt caacgacggt gtggtcagcg atgagatcgt 360
ctacctgacc gccgacgagg aggaccgcca cgtcgtggcg caggccaact cgccgctgga 420
ggacgacaat cgcttcaccg aggaccgggt tctggtgcgc cgcaagggcg gcgaggtcga 480
gtacgtgtcg tcggccgagg tcgactacat ggacgtctcg ccgcgccaga tggtgtcggt 540
ggccacggcc atgatcccgt tcctggagca cgacgacgcc aaccgggccc tgatgggtgc 600
caacatgcag cgtcaggcgg ttcccctggt gcgcagcgag gcgccgctgg tgggcaccgg 660
catggagctg cgcgcggcga tcgacgc 687

<210> SEQ ID NO 166
<211> LENGTH: 687
<212> TYPE: DNA
<213> ORGANISM: Mycobacterium terrae

<400> SEQUENCE: 166
ggaggcgatc acaccgcaga ccctgatcaa catccgcccg gtggtcgccg cgatcaagga 60
gttcttcggc accagccagc tctcgcagtt catggaccag aacaacccgc tgtcgggtct 120
gacccacaag cgccggctgt cggcgctggg cccgggtggt ctgtcccgtg agcgggccgg 180
gcttgaggtc cgtgacgtgc acccgtccca ctacggccgg atgtgtccga tcgagacccc 240
ggagggtccg aacatcggtc tgatcggctc gctggcgacc tacgcgcggg tcaacccgtt 300

-continued

```
cggggttcatc gaaaccccgt accgcaaggt caacgacggt gtggtcagcg atgagatcgt    360

ctacctgacc gccgacgagg aggaccgcca cgtcgtggcg caggccaact cgccgctgga    420

ggacgacagt cgcttcgccg aggaccgagt tctggtgcgc cgcaagggcg gtgaggtcga    480

gtacgtgtcg tcggccgagg tcgactacat ggacgtctcg ccgcgccaga tggtgtcggt    540

ggccacggcc atgatcccgt tcctggagca cgacgacgcc aaccgtgccc tgatgggcgc    600

caacatgcag cgtcaggcgg ttcccctggt gcgcagcgag gcgccgctgg tgggcaccgg    660

catggagctg cgcgcggcga tcgacgc                                         687
```

<210> SEQ ID NO 167
<211> LENGTH: 687
<212> TYPE: DNA
<213> ORGANISM: Mycobacterium triplex
<220> FEATURE:
<221> NAME/KEY: modified_base
<222> LOCATION: (139)...(139)
<223> OTHER INFORMATION: n = g,a,c or t

<400> SEQUENCE: 167

```
ggaggcgatc acaccgcaga ccctgatcaa catccgtccc gtcgtggccg cgatcaagga     60

gttcttcggc accagccagc tgtcccagtt catggaccag aacaacccgc tgtccgggct    120

cacccacaag cgccgcctnt cggcgctggg gccgggcggt ctgtcgcgtg agcgcgcggg    180

cctcgaggtt cgtgacgtgc acccgtcgca ctacggccgg atgtgcccga tcgagacccc    240

cgagggtccg aacatcggtc tgatcggttc gctgtcggtg tacgcgcggg tcaacccgtt    300

cgggttcatc gagacgccgt accgcaaggt ggtcgacggt gtggtcaccg amcaratcga    360

ctasctgrcc gccgacgagg aggaccgcca cgtcgtggcg caggccaact cgccgatcga    420

cgccgacggc cggttcgagg agtcgcgtgt cctggtccgc cggaaggcgg gcgaggtcga    480

gtacgtgccg tcgtccgagg tcgactacat ggacgtgtcg ccgcgccaga tggtgtcggt    540

ggccacggcc atgatcccgt tcctcgagca cgacgacgcc aaccgtgccc tgatgggcgc    600

caacatgcag cgccaggcgg ttccgctggt gcgcagcgag gcgccgctgg tcggtaccgg    660

tatggagctg cgcgcggcga tcgacgc                                         687
```

<210> SEQ ID NO 168
<211> LENGTH: 705
<212> TYPE: DNA
<213> ORGANISM: Mycobacterium xenopi

<400> SEQUENCE: 168

```
cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600
```

-continued

```
tgatgggcgc gaacatgcag cgccaggccg ttccgttggt gcgtagcgag gcaccgctgg    660

tgggcaccgg gatggaattg cgcgcggcga tcgacgcggc gacgt                    705
```

```
<210> SEQ ID NO 169
<211> LENGTH: 705
<212> TYPE: DNA
<213> ORGANISM: Mycobacterium xenopi

<400> SEQUENCE: 169

cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705
```

```
<210> SEQ ID NO 170
<211> LENGTH: 705
<212> TYPE: DNA
<213> ORGANISM: Mycobacterium xenopi

<400> SEQUENCE: 170

cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtakcgag gcaccgctgg    660

tgggcaccgg gatggaattg cgcgcggcga tcgacgcggc gacgt                    705
```

```
<210> SEQ ID NO 171
<211> LENGTH: 705
<212> TYPE: DNA
<213> ORGANISM: Mycobacterium xenopi

<400> SEQUENCE: 171

cccaggacgt ggaggcgatc acaccgcaga ccttgatcaa catccgcccc gtggtggccg     60

cgatcaagga gttcttcggc accagccagc tctcgcagtt catggatcag aacaacccgc    120
```

-continued

```
tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705
```

<210> SEQ ID NO 172
<211> LENGTH: 705
<212> TYPE: DNA
<213> ORGANISM: Mycobacterium xenopi

<400> SEQUENCE: 172

```
cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705
```

<210> SEQ ID NO 173
<211> LENGTH: 705
<212> TYPE: DNA
<213> ORGANISM: Mycobacterium xenopi

<400> SEQUENCE: 173

```
cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540
```

-continued

```
tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705


<210> SEQ ID NO 174
<211> LENGTH: 705
<212> TYPE: DNA
<213> ORGANISM: Mycobacterium xenopi

<400> SEQUENCE: 174

cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705


<210> SEQ ID NO 175
<211> LENGTH: 705
<212> TYPE: DNA
<213> ORGANISM: Mycobacterium xenopi

<400> SEQUENCE: 175

cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705


<210> SEQ ID NO 176
<211> LENGTH: 705
<212> TYPE: DNA
<213> ORGANISM: Mycobacterium xenopi

<400> SEQUENCE: 176

cccaggacgt ggaggcgatc acaccgcaga ccttgatcaa catccgcccc gtggtggccg     60
```

-continued

```
cgatcaagga gttcttcggc accagccagc tctcgcagtt catggatcag aacaacccgc    120
tgtcggggct cacccacaag cggcggctct cggcgcttgg tccgggcggt ctgtcgcgcg    180
agcgggccgg gctggaggtc cgtgacgtgc actcgagcca ctacggccgg atgtgcccga    240
tcgaaacccc ggagggcccg aacatcggtt tgatcggctc gctgtcggtg tacgcgcggg    300
tcaacccgta cgggttcatt gagacgcctt accgcaaggt ggtcaacggc gtggtcaccg    360
acgagatcgt gtacctgacc gccgacgagg aggaccgcca tgtggtggcg caggccaact    420
cgccgatcga cgaggatggc cgcttcaccg agccgcgggt gctggtgcgc cgcaagggtg    480
gggaggtcga gtacgtgtcc tcctccgagg tggactacat ggacgtctcg ccgcgccaga    540
tggtgtcggt ggccaccgcg atgatcccgt tcctcgagca cgacgacgcc aaccgcgcgt    600
tgatgggcgc gaacatgcag cgccaggccg ttccgttggt gcgtagcgag gcaccgctgg    660
tgggcaccgg gatggaattg cgcgcggcga tcgacgcggc gacgt                    705
```

<210> SEQ ID NO 177
<211> LENGTH: 705
<212> TYPE: DNA
<213> ORGANISM: Mycobacterium xenopi

<400> SEQUENCE: 177

```
cccaggacgt ggaggcgatc acaccgcaga ccttgatcaa catccgcccc gtggtggccg     60
cgatcaagga gttcttcggc accagccagc tctcgcagtt catggatcag aacaacccgc    120
tgtcggggct cacccacaag cggcggctct cggcgcttgg tccgggcggt ctgtcgcgcg    180
agcgggccgg gctggaggtc cgtgacgtgc actcgagcca ctacggccgg atgtgcccga    240
tcgaaacccc ggagggcccg aacatcggtt tgatcggctc gctgtcggtg tacgcgcggg    300
tcaacccgta cgggttcatt gagacgcctt accgcaaggt ggtcaacggc gtggtcaccg    360
acgagatcgt gtacctgacc gccgacgagg aggaccgcca tgtggtggcg caggccaact    420
cgccgatcga cgaggatggc cgcttcaccg agccgcgggt gctggtgcgc cgcaagggtg    480
gggaggtcga gtacgtgtcc tcctccgagg tggactacat ggacgtctcg ccgcgccaga    540
tggtgtcggt ggccaccgcg atgatcccgt tcctcgagca cgacgacgcc aaccgcgcgt    600
tgatgggcgc gaacatgcag cgccaggccg ttccgttggt gcgtagcgag gcaccgctgg    660
tgggcaccgg gatggaattg cgcgcggcga tcgacgcggc gacgt                    705
```

<210> SEQ ID NO 178
<211> LENGTH: 705
<212> TYPE: DNA
<213> ORGANISM: Mycobacterium xenopi

<400> SEQUENCE: 178

```
cccaggacgt ggaggcgatc acaccgcaga ccttgatcaa catccgcccc gtggtggccg     60
cgatcaagga gttcttcggc accagccagc tctcgcagtt catggatcag aacaacccgc    120
tgtcggggct cacccacaag cggcggctct cggcgcttgg tccgggcggt ctgtcgcgcg    180
agcgggccgg gctggaggtc cgtgacgtgc actcgagcca ctacggccgg atgtgcccga    240
tcgaaacccc ggagggcccg aacatcggtt tgatcggctc gctgtcggtg tacgcgcggg    300
tcaacccgta cgggttcatt gagacgcctt accgcaaggt ggtcaacggc gtggtcaccg    360
acgagatcgt gtacctgacc gccgacgagg aggaccgcca tgtggtggcg caggccaact    420
cgccgatcga cgaggatggc cgcttcaccg agccgcgggt gctggtgcgc cgcaagggtg    480
```

-continued

```
gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705
```

<210> SEQ ID NO 179
<211> LENGTH: 705
<212> TYPE: DNA
<213> ORGANISM: Mycobacterium xenopi

<400> SEQUENCE: 179

```
cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705
```

<210> SEQ ID NO 180
<211> LENGTH: 705
<212> TYPE: DNA
<213> ORGANISM: Mycobacterium xenopi

<400> SEQUENCE: 180

```
cccaggacgt ggaggcgatc acaccgcaga ccttgatcaa catccgcccc gtggtggccg     60

cgatcaagga gttcttcggc accagccagc tctcgcagtt catggatcag aacaacccgc    120

tgtcggggct cacccacaag cggcggctct cggcgcttgg tccgggcggt ctgtcgcgcg    180

agcgggccgg gctggaggtc cgtgacgtgc actcgagcca ctacggccgg atgtgcccga    240

tcgaaacccc ggagggcccg aacatcggtt tgatcggctc gctgtcggtg tacgcgcggg    300

tcaacccgta cgggttcatt gagacgcctt accgcaaggt ggtcaacggc gtggtcaccg    360

acgagatcgt gtacctgacc gccgacgagg aggaccgcca tgtggtggcg caggccaact    420

cgccgatcga cgaggatggc cgcttcaccg agccgcgggt gctggtgcgc cgcaagggtg    480

gggaggtcga gtacgtgtcc tcctccgagg tggactacat ggacgtctcg ccgcgccaga    540

tggtgtcggt ggccaccgcg atgatcccgt tcctcgagca cgacgacgcc aaccgcgcgt    600

tgatgggcgc gaacatgcag cgccaggccg ttccgttggt gcgtagcgag gcaccgctgg    660

tgggcaccgg gatggaattg cgcgcggcga tcgacgcggc gacgt                    705
```

<210> SEQ ID NO 181
<211> LENGTH: 705
<212> TYPE: DNA
<213> ORGANISM: Mycobacterium sp. unique MAC#4

<400> SEQUENCE: 181

-continued

```
cccaggacgt ggaggcgatc acaccgcaga cgctgatcaa catccgtccg gtcgtcgccg     60
cgatcaagga gttcttcggc accagccagc tgtcgcagtt catggaccag aacaacccgc    120
tgtcgggcct gacccacaag cgccgcctgt cggcgctggg cccgggcggt ctgtcccgtg    180
agcgcgccgg cctcgaggtc cgcgacgtgc acccgtcgca ctacggccgc atgtgcccga    240
tcgagacccc ggagggtccg aacatcggtc tgatcggctc gctgtcggtg tacgcgaggg    300
tcaacccgtt cggcttcatc gagacgccgt accgcaaggt ggtcgacggt gtggtcagcg    360
acgagatcgt gtacctgacc gccgacgagg aggaccgcca cgtggtggcg caggccaact    420
cgccgatcga cgccgacggc cggttcgtcg agggccgcgt cctggtccgc cgcaaggcgg    480
gcgaggtcga gtacgtgccc tcgtccgagg tggactacat ggacgtgtcg ccgcgccaga    540
tggtgtcggt ggccacggcc atgatcccgt tcctcgagca cgacgacgcc aaccgtgccc    600
tgatgggcgc caacatgcag cgccaggcgg ttccgctggt gcgcagcgag gcgccgctgg    660
tgggcaccgg catggagctg cgcgcggcga tcgacgcggc gacgt                    705
```